US009701746B2

(12) United States Patent
Franks et al.

(10) Patent No.: US 9,701,746 B2
(45) Date of Patent: Jul. 11, 2017

(54) METHODS OF TREATING NEUROPATHIC PAIN WITH SPECIFIC BINDING MEMBERS FOR NGF

(71) Applicant: MedImmune Limited, Cambridge (GB)

(72) Inventors: Ruth Franks, Cambridge (GB); Andrew Grier Buchanan, Cambridge (GB); Albert George Thom, Cambridge (GB); Fraser Ewing Welsh, Cambridge (GB); Philip Antony Bland-Ward, Cambridge (GB); Matthew Alexander Sleeman, Cambridge (GB); Carl Anthony Matthews, Cambridge (GB); Celia Patricia Hart, Cambridge (GB); Jon Eric Hawkinson, South San Francisco, CA (US)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 15/131,825

(22) Filed: Apr. 18, 2016

(65) Prior Publication Data

US 2016/0297878 A1 Oct. 13, 2016

Related U.S. Application Data

(62) Division of application No. 11/814,668, filed as application No. PCT/GB2006/000238 on Jan. 24, 2006, now Pat. No. 9,315,571.

(60) Provisional application No. 60/645,587, filed on Jan. 24, 2005.

(51) Int. Cl.
*A61K 39/395* (2006.01)
*C07K 16/22* (2006.01)
*C07K 14/48* (2006.01)
*A61K 39/00* (2006.01)

(52) U.S. Cl.
CPC .......... *C07K 16/22* (2013.01); *A61K 39/3955* (2013.01); *C07K 14/48* (2013.01); *A61K 2039/505* (2013.01); *C07K 2317/21* (2013.01); *C07K 2317/33* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | WO 92/09631 A1 | 6/1992 |
|---|---|---|
| WO | WO 00/73344 A2 | 12/2000 |
| WO | WO 01/27279 A1 | 4/2001 |
| WO | WO 01/44300 A2 | 6/2001 |
| WO | WO 01/64247 A2 | 7/2001 |
| WO | WO 01/78698 A2 | 10/2001 |
| WO | WO 02/096458 A1 | 12/2002 |
| WO | WO 03/030833 A2 | 4/2003 |
| WO | WO 03/102136 A2 | 12/2003 |
| WO | WO 2004/032852 A2 | 4/2004 |
| WO | WO 2004/032870 A2 | 4/2004 |
| WO | WO 2004/050683 A2 | 6/2004 |
| WO | WO 2004/058184 A2 | 7/2004 |
| WO | WO 2005/019266 A2 | 3/2005 |

OTHER PUBLICATIONS

Brown, M., et al., "Tolerance to Single, but Not Multiple, Amino Acid Replacements in Antibody VH DRR2," J. Immunol. 156(9):3285-3291 (1996).
Foot, J., et al., "Antibody Framework Residues Affecting the Conformation of the Hypervariable Loops," J. Mol. Biol. 224:487-499 (1992).
Winter, G., et al., "Humanized Antibodies," Immunology Today 14(6):243 (1993).
Hongo, et al. "Antibody Binding Regions on Human Nerve Growth Factor Identified by Homolog-and Alanine Scanning Mutagenesis" Hybridoma, Liebert, 193(3): 215-227, 2000.
Koizumi, et al., "K-252a: a specific inhibitor of the action of nerve growth factor on PC 12 cells" J. Neuroscience 8(2): 715-721.1998.
Okishio, et al., "Establishment of Monoclonal Antibodies Against Human Nerve Growth Factor" Biochemical and Biophysical Research Communications, vol. 196, Issue. 3, Nov. 15, 1993, pp. 1474-1480.
Ro, Long-Sun, et al. "Effect of NGF and anti-NGF on Neuropathic Pain in Rats Following Chronic Constriction Injury of the Sciatic Nerve" PAIN, vol. 79, No. 2-3, Feb. 1999 (Feb. 1999), pp. 265-274.
Warren, S.L., et al., "Inhibition of Biological Activity of Mouse Beta-Nerve Growth Factor by Monoclonal Antibody." Science. Nov. 21, 1980, vol. 210, No. 4472, Nov. 21, 1980 (Nov. 21, 1980), pp. 910-912.
Brennan, T.J., et al. "Role of Nerve Growth Factor in a Rat Model for Postoperative Pain," Society for Neuorscience Abstracts 28th Annual Meeting, Los Angeles, CA, Nov. 7-12, 1998, 24(1):880. Abstract No. 349.4 (1998).
Leem, J.W. et al., "Anti-NGF Treatment Suppresses Abnormal Pain Behaviors Induced After Spinal Cord Injury in the Rat" 30th Annual Meeting of the Society of Neuroscience, New Orleans, LA, Nov. 4-9, 2000, Society for Neuroscience Abstracts 26(2): 1690, Abstract No. 633.1 (2000).
Little, M., et al., "Of Mice and Men: Hybridoma and Recombinant Antibodies," Review. Immunology Today, Elsevier Science Limited, vol. 21, No. 8, 364-369, Aug. 2000.

*Primary Examiner* — Robert C Hayes

(57) ABSTRACT

Specific binding members for Nerve Growth Factor (NGF), in particular anti-NGF antibody molecules, especially human antibody molecules, and especially those that neutralize NGF activity. Methods for using anti-NGF antibody molecules in diagnosis or treatment of NGF related disorders, including pain, asthma, chronic obstructive pulmonary disease, pulmonary fibrosis, other diseases of airway inflammation, diabetic neuropathy, cardiac arrhythmias, HIV, arthritis, psoriasis and cancer.

6 Claims, 12 Drawing Sheets

*P<0.05 and **P<0.01 c.f. CAT-001 null isotype antibody control (n=13-16 animals per group)

METHODS OF TREATING NEUROPATHIC PAIN WITH SPECIFIC BINDING MEMBERS FOR NGF

This application is a Divisional of U.S. application Ser. No. 11/814,668, filed on Jul. 24, 2007, said application Ser. No. 11/814,668 is a U.S. National Stage application of International Application No. PCT/GB2006/000238, filed on Jan. 24, 2006, said International Application No. PCT/GB2006/000238 claims benefit under 35 U.S.C. §119(e) to U.S. Provisional Application No. 60/645,587, filed Jan. 24, 2005. Each of the above listed applications is incorporated by reference herein in its entirety for all purposes.

REFERENCE TO THE SEQUENCE LISTING

This application incorporates by reference a Sequence Listing submitted with this application as text file entitled Sequence Listing, created on Apr. 18, 2016, and having a size of 253 kilobytes.

The present invention relates to specific binding members, in particular anti-NGF antibody molecules, especially human antibody molecules, and especially those that neutralise NGF (Nerve Growth Factor) activity. It further relates to methods for using anti-NGF antibody molecules in diagnosis or treatment of NGF related disorders, including pain, asthma, chronic obstructive pulmonary disease, pulmonary fibrosis, other diseases of airway inflammation, diabetic neuropathy, cardiac arrhythmias, HIV, arthritis, psoriasis and cancer.

The present invention provides antibody molecules of particular value in binding and neutralising NGF, and thus of use in any of a variety of therapeutic treatments, as indicated by the experimentation contained herein and further by the supporting technical literature.

Nerve growth factor (β-NGF, commonly known as NGF) plays a well-known pivotal role in the development of the nervous system. In the adult, however, NGF plays a more restricted role, where it promotes the health and survival of a subset of central and peripheral neurons (Huang & Reichardt, 2001). NGF also contributes to the modulation of the functional characteristics of these neurons. As part of this latter process, NGF exerts tonic control over the sensitivity, or excitability, of nociceptors (Priestley et al., 2002; Bennett, 2001). These peripheral neurons sense and transmit to the central nervous system the various noxious stimuli that ultimately give rise to perceptions of pain (nociception). Thus, agents that reduce levels of NGF may possess utility as analgesic therapeutics.

The societal cost of inadequately treated pain further supports the potential utility of analgesics based on anti-NGF activity. That is, despite the existence and widespread use of numerous pain medications, a clear need exists for new analgesics. Pain is one of the most common symptoms for which medical assistance is sought and is the primary complaint of half of all patients visiting a physician. The high cost of pain to society is well documented. In the U.S., for example, chronic pain afflicts some 34 million Americans. Pain results in 50 million workdays lost each year. Direct medical costs attributed to back pain, arthritic pain, and migraine amount to $40 billion annually alone. The total prescription pain medication market is approximately $15 billion per year (Pleuvry & Pleuvry).

As these statistics imply, a substantial percentage of pain sufferers fail to receive adequate pain relief. As a consequence, a large medical need remains for safe and effective analgesics with novel mechanisms of action (Pleuvry & Pleuvry).

Therapeutic agents that reduce the tissue levels or inhibit the effects of secreted NGF have the potential to be just such novel analgesics. Subcutaneous injections of NGF itself produce pain in humans and animals. Thus, injected NGF causes a rapid thermal hyperalgesia, followed by delayed thermal hyperalgesia and mechanical allodynia (Petty et al., 1994; McArthur et al., 2000). Endogenously secreted NGF is similarly pro-nociceptive. Tissue-injury-induced release of NGF and its subsequent action in the periphery plays a major role in the induction of thermal hyperalgesia through the process of 'peripheral sensitization' (Mendell & Arvanian, 2002). Tissue injury promotes the release of pro-nociceptive and pro-inflammatory cytokines, which, in turn, induce the release of NGF from keratinocytes and fibroblasts. This released NGF acts directly on nociceptors to induce painful or nociceptive states within minutes of the noxious insult. This NGF also acts indirectly to induce and maintain nociceptive/pain states. It triggers mast cell degranulation, releasing pro-nociceptive agents such as histamine and serotonin and, importantly, more NGF, and can also stimulate sympathetic nerve terminals to release pro-nociceptive neurotransmitters, such as noradrenaline (Ma & Woolf, 1997).

Tissue levels of NGF are elevated in CFA- and carrageenan-injected animals (Ma & Woolf, 1997; Amann & Schuligoi, 2000). Moreover, increased levels of NGF have been documented in patients suffering from rheumatoid arthritis (Aloe & Tuveri, 1997) or cystitis (Lowe et al., 1997). In rodents, peripheral nerve injury increases the expression of NGF mRNA in macrophages, fibroblasts, and Schwann cells (Heumann et al., 1987). Over-expression of NGF in transgenic mice results in enhanced neuropathic pain behavior following nerve injury above that of wild-type mice (Ramer et al., 1998). Over hours and days, elevated NGF levels play a role in promoting 'central sensitization'—the enhancement of neurotransmission at synapses in the nociceptive pathways of the spinal cord. Central sensitization results in persistent and chronic hyperalgesia and allodynia. This process is thought to involve internalization of complexes of NGF and its high affinity receptor, trkA (tyrosine receptor kinase A). Retrograde transport of these complexes to nociceptor cell bodies in the dorsal root ganglia (DRG) potentiates secretion of nociceptive neuropeptides (e.g., substance P, CGRP), PKC activation, and NMDA receptor activation in the dorsal horn of the spinal cord (Sah et al., 2003)—all processes that promote the sensitization of the nociceptive pathways. NGF also plays a role in the up-regulation and re-distribution of voltage-dependent and ligand-gated ion channels, including sodium channel subtypes and the capsaicin receptor, VR1 (Mamet et al., 1999; Fjell et al., 1999; Priestley et al., 2002). The altered activities and/or expression of transmitters, receptors, and ion channels underlie the increased sensitivity and excitability of nociceptors associated with neuropathic pain states.

NGF can also promote the sprouting of sympathetic neurons and the formation of aberrant innervation of nociceptive neurons. This innervation is thought to contribute to the induction and maintenance of chronic nociceptive/pain states, such as sympathetically maintained pain, or complex regional pain syndrome (Ramer et al., 1999).

NGF-induced nociception/pain is mediated by the high affinity NGF receptor, trkA (tyrosine receptor kinase A) (Sah, et al., 2003). About 40-45% of nociceptor cell bodies in DRGs express trkA. These are the cell bodies of the small diameter fibers, or C-fibers, that also express the secreted pro-nociceptive peptides, substance P and CGRP. These fibers terminate in laminae I and II of the dorsal horn, where they transfer to the central nervous system the noxious stimuli sensed by peripheral nociceptors. Mutations or deletions in the trkA gene produce a phenotype characterized by loss of pain sensation both in humans (Indo, 2002) and in trkA knock-out mice (de Castro et al., 1998). Significantly, the expression of trkA is up-regulated in animals subjected to models of arthritic (Pozza et al., 2000) or cystitic pain (Qiao & Vizzard, 2002), or the inflammatory pain induced by injection of complete Freund's adjuvant (CFA) or carrageenan into the paw (Cho et al., 1996).

NGF also binds to the p75 neurotrophin receptor. The role of the p75 receptor is dependent on its cellular environment and the presence of other receptors with which it is believed to play an accessory or co-receptor function. Interaction between the trkA and p75 receptors results in the formation of high affinity binding sites for NGF. The importance of such receptor interactions in NGF-mediated pain signalling is not clear, but recent studies have implicated the p75 receptor in cellular processes that may be relevant (Zhang & Nicol, 2004). However, whilst p75 receptor knockout mice display elevated thresholds to noxious stimuli, they remain responsive to the hyperalgesic effects of NGF, suggesting that trkA receptors alone are sufficient to mediate these effects (Bergmann et al., 1998).

The evidence cited above indicates that NGF-mediated processes are responsible for the induction of acute pain, short-term pain, persistent nociceptive pain, and persistent or chronic neuropathic pain. Thus, anti-NGF agents are indicated as having utility as effective analgesics for treating sufferers of any or all of these various pain states.

One such anti-NGF agent is trkA-Fc, which acts as a decoy or scavenger to bind up, and thereby inactivate, endogenous NGF. TrkA-Fc is a fusion protein consisting of the NGF binding region of trkA linked to a constant domain fragment (Fc) of an IgG antibody. TrkA-Fc produces hypoalgesia in naïve animals, decreases nociceptor responses, and decreases sprouting of unmyelinated pain-sensing neurons (Bennett et al., 1998).

Antisera raised against NGF can also reduce NGF levels when injected locally or systemically. Both anti-NGF antisera and trkA-Fc attenuate carrageenan- or CFA-induced inflammatory paw pain (Koltzenberg et al., 1999) and inflamed bladder responses in rats (Jaggar et al., 1999). Anti-NGF antiserum blocks heat and cold hyperalgesia, reverses established thermal hyperalgesia, and prevents collateral sprouting in the chronic constriction injury (CCI) model of neuropathic pain (Woolf, 1996; Ro et al., 1999). Small molecule inhibitors of the trkA-NGF interaction have also been reported. In rats, the NGF-trkA inhibitor ALE-0540 reduces hyperalgesia in a thermally-induced inflammatory pain model and in the formalin test of acute and persistent pain (Owolabi et al., 1999). ALE-0540 also reduces mechanical allodynia in the sciatic nerve injury model of neuropathic pain (Owolabi et al., 1999).

Therapeutic antibodies in general hold out the promise of a degree of target selectivity within a family of closely related receptors, receptor ligands, channels, or enzymes that is rarely attainable with small molecule drugs. NGF-mediated pain is particularly well suited to safe and effective treatment with antibodies because NGF levels increase in the periphery in response to noxious stimuli and antibodies have low blood-brain barrier permeability. Whilst polyclonal antibodies have been shown to be effective in animal models of pain, anti-NGF monoclonal antibodies are more likely to be successfully developed as human therapeutics due to the advantages in manufacturing and characterizing a consistent, well-defined, chemical, entity. The anti-nociceptive effects of mouse anti-NGF monoclonal antibodies (Sammons et al., 2000) have been reported, but the amino acid sequences of these antibodies were not provided.

Recent evidence suggests that NGF promotes other pathologies in addition to pain. Thus, anti-NGF antibodies may also possess utility for treating other NGF-mediated diseases, including but not limited to asthma, chronic obstructive pulmonary disease, pulmonary fibrosis, other diseases of airway inflammation (Hoyle, 2003; Lommatzch et al., 2003), diabetic neuropathy (Yasuda et al., 2003), cardiac arrhythmias (WO04/032852), HIV (Garaci et al., 2003), arthritis, psoriasis and cancer (Nakagawara, 2001).

WO02/096458 relates to anti-NGF antibodies, in particular mouse monoclonal antibody 911, and use of such antibodies in treatment of various NGF-related disorders, including pain, asthma, arthritis and psoriasis. It states that the antibody 911 had no adverse effect on the immune system in an experimental mouse model of allergy. These antibodies were also described by Hongo et al., 2000.

WO04/032870 describes the pain-reducing effect of the mouse monoclonal NGF antibody mab 911 and humanized NGF antibody E3 in experimental models of post-operative pain. E3 differs from human heavy chain gamma2a constant region by 2 amino acids.

WO04/032852 describes methods for preventing sudden cardiac death and for treatment of cardiac arryhthmias using NGF antagonists.

WO 01/78698 describes the use of polyclonal antiserum to NGF to treat chronic visceral pain.

The present invention provides specific binding members for NGF, preferably human NGF. Thus, a specific binding member of the invention may bind human NGF or non-human NGF (e.g. non-human primate NGF and/or rat NGF and/or mouse NGF).

Specific binding members of the invention may be antibodies to human NGF, especially human antibodies, which may be cross-reactive with non-human NGF, including non-human primate NGF and/or mouse NGF and/or rat NGF.

A specific binding member in accordance with the present invention preferably neutralises NGF. Neutralisation means reduction or inhibition of biological activity of NGF, e.g. reduction or inhibition of NGF binding to one or more of its receptors (preferably TrkA). The reduction in biological activity may be partial or total. The degree to which an antibody neutralises NGF is referred to as its neutralising potency. Potency may be determined or measured using one or more assays known to the skilled person and/or as described or referred to herein, for example:

"FLIPR" calcium mobilisation assay (see Example 2 herein)
PC12 survival assay (see Example 5 herein)
TF-1 proliferation assay (see Example 6 herein)
Receptor binding inhibition assay (see Example 9 herein).
  Assays and potencies are described in more detail elsewhere herein.

Specific binding members of the present invention may be optimised for neutralising potency. Generally potency optimisation involves mutating the sequence of a selected specific binding member (normally the variable domain sequence of an antibody) to generate a library of specific binding members, which are then assayed for potency and the more potent specific binding members are selected. Thus selected "potency-optimised" specific binding members tend to have a higher potency than the specific binding member from which the library was generated. Nevertheless, high potency specific binding members may also be obtained without optimisation, for example a high potency specific binding member may be obtained directly from an initial screen e.g. a biochemical neutralisation assay. The present invention provides both potency-optimised and non-optimised specific binding members, as well as methods for potency optimisation from a selected specific binding member. The present invention thus allows the skilled person to generate specific binding members having high potency.

A specific binding member in accordance with the present invention preferably exhibits antihyperalgesic and/or anti-allodynic activity, e.g. inhibits carrageenan-induced thermal hyperalgesia.

In some embodiments, a specific binding member of the invention comprises an antibody molecule. In other embodiments, a specific binding member of the invention comprises an antigen-binding site within a non-antibody molecule, e.g. a set of CDRs in a non-antibody protein scaffold, as discussed further below.

In various aspects and embodiments of the invention there is provided the subject-matter of the claims included below.

Preferred embodiments within the present invention are antibody molecules, whether whole antibody (e.g. IgG, such as IgG4) or antibody fragments (e.g. scFv, Fab, dAb). Preferably, an antibody molecule of the invention is a human antibody molecule. Antibody molecules comprising antibody antigen-binding sites are provided, as are antibody VH and VL domains. Within VH and VL domains are provided complementarity determining regions, ("CDRs"), and framework regions, ("FRs"), to form VH or VL domains as the case may be. An antibody antigen-binding site may consist of an antibody VH domain and/or a VL domain. All VH and VL sequences, CDR sequences, sets of CDRs and sets of HCDRs and sets of LCDRs disclosed herein represent aspects and embodiments of the invention. A "set of CDRs" comprises CDR1, CDR2 and CDR3. Thus, a set of HCDRs means HCDR1, HCDR2 and HCDR3, and a set of LCDRs means LCDR1, LCDR2 and LCDR3. Unless otherwise stated, a "set of CDRs" includes HCDRs and LCDRs.

Examples of antibody VH and VL domains and CDRs according to the present invention are as listed in the appended sequence listing.

A number of antibody lineages are disclosed herein, defined with reference to sequences, e.g. a set of CDR sequences, optionally with one or more, e.g. one or two, or two substitutions. The preferred parent lineage is the 1021E5 lineage. The 1021E5 lineage includes the preferred antibody molecule 1133C11 and other antibody molecules of the "1133C11 lineage", including 1252A5. Also within the 1021E5 parent lineage are antibody molecules 1165D4, 1230H7 and 1152H5. The present inventors have identified the 1021E5, 1083H4 and especially the 1133C11 lineages as providing human antibody antigen-binding sites against NGF that are of particular value.

The 1133C11 lineage is defined with reference to a set of six CDR sequences of 1133C11 as follows: HCDR1 SEQ ID NO: 193, HCDR2 SEQ ID NO: 194, HCDR3 SEQ ID NO: 195, LCDR1 SEQ ID NO: 198, LCDR2 SEQ ID NO: 199, and LCDR3 SEQ ID NO: 200. The set of CDRs wherein the HCDR1 has the amino acid sequence of SEQ ID NO: 193, the HCDR2 has the amino acid sequence of SEQ ID NO: 194, the HCDR3 has the amino acid sequence of SEQ ID NO: 195, the LCDR1 has the amino acid sequence of SEQ ID NO: 198, the LCDR2 has the amino acid sequence of SEQ ID NO: 199, and the LCDR3 has the amino acid sequence of SEQ ID NO: 200, are herein referred to as the "1133C11 set of CDRs". The HCDR1, HCDR2 and HCDR3 within the 1133C11 set of CDRs are referred to as the "1133C11 set of HCDRs" and the LCDR1, LCDR2 and LCDR3 within the 1133C11 set of CDRs are referred to as the "1133C11 set of LCDRs". A set of CDRs with the 1133C11 set of CDRs, 1133C11 set of HCDRs or 1133C11 LCDRs, or one or two substitutions therein, is said to be of the 1133C11 lineage.

Other preferred lineages and sets of CDRs are defined with reference to the analogous CDRs as set out anywhere herein, including as preferred embodiments the sets of CDRs disclosed in Table 2a (with SEQ ID NOS as set out in Table 2b). Table 2a and Table 2b show sets of CDRs (HCDRs and LCDRs) from optimised clones derived from clone 1021E5, illustrating how the CDR sequences of the optimised clones differ from those of 1021E5. A set of CDRs from Table 2a/2b includes a set of HCDRs and/or a set of LCDRs from any clone illustrated in the Table, optionally including 1021E5 itself.

Sets of CDRs of these are provided, as indicated, as are sets of CDRs with the disclosed sequences containing one or two amino acid substitutions.

The present invention also provides specific binding members and antibody molecules comprising the defined sets of CDRs, set of HCDRs or set of LCDRs, as disclosed herein, and sets of CDRs of with one or two substitutions within the disclosed set of CDRs. The relevant set of CDRs is provided within an antibody framework or other protein scaffold, e.g. fibronectin or cytochrome B (Koide et al., 1998; Nygren et al., 1997), as discussed below. Preferably antibody framework regions are employed. For example, one or more CDRs or a set of CDRs of an antibody may be grafted into a framework (e.g. human framework) to provide an antibody molecule or different antibody molecules. For example, an antibody molecule may comprise CDRs of an antibody of the 1021E5 lineage and framework regions of human germline gene segment sequences. An antibody of a lineage may be provided with a set of CDRs within a framework which may be subject to "germlining", where one or more residues within the framework are changed to match the residues at the equivalent position in the most similar human germline framework (e.g. DP10 from the VH1 family) or a framework of the λ1 family e.g. DPL5. Thus, antibody framework regions are preferably germline and/or human.

The invention provides an isolated human antibody specific for NGF, having a VH domain comprising a set of HCDRs in a human germline framework comprising DP10. Normally the specific binding member also has a VL domain comprising a set of LCDRs, preferably in a human germline framework comprising a Vλ1, e.g. DPL5. Preferably, the CDRs are a set of CDRs disclosed herein.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

In one aspect, the present invention provides a specific binding member for NGF, comprising an antibody antigen-binding site which is composed of a human antibody VH domain and a human antibody VL domain and which comprises a set of CDRs, wherein the VH domain comprises HCDR1, HCDR2 and HCDR3 and the VL domain comprises LCDR1, LCDR2 and LCDR3, wherein the HCDR1 has the amino acid sequence of SEQ ID NO: 193, the HCDR2 has the amino acid sequence of SEQ ID NO: 194, the HCDR3 has the amino acid sequence of SEQ ID NO: 195, the LCDR1 has the amino acid sequence of SEQ ID NO: 198, the LCDR2 has the amino acid sequence of SEQ ID NO: 199, and the LCDR3 has the amino acid sequence of SEQ ID NO: 200; or wherein the set of CDRs contains one or two amino acid substitutions compared with this set of CDRs.

Thus, the invention provides a specific binding member for NGF, comprising an antibody antigen-binding site which is composed of a human antibody VH domain and a human antibody VL domain and which comprises a set of CDRs, wherein the set of CDRs is the 1133C11 set of CDRs or other set of CDRs disclosed herein, or a set of CDRs containing one or two substitutions compared with the 1133C11 set of CDRs or other set of CDRs disclosed herein.

In preferred embodiments, the one or two substitutions are at one or two of the following residues within the CDRs of the VH and/or VL domains, using the standard numbering of Kabat (1991).
31, 34 in HCDR1
51, 55, 56, 57, 58, 65 in HCDR2
96 in HCDR3
26, 27, 27A, 27B, 28, 29, 30 in LCDR1
56 in LCDR2
90, 94 in LCDR3.

In preferred embodiments one or two substitutions are made at one or two of the following residues within the 1133C11 set of CDRs in accordance with the identified groups of possible substitute residues:

| Position of substitution | Substitute Residue selected from the group consisting of |
|---|---|
| 31 in HCDR1: | A |
| 34 in HCDR1: | V |
| 51 in HCDR2: | V |
| 55 in HCDR2: | N |
| 56 in HCDR2: | A |
| 57 in HCDR2: | V |
| 58 in HCDR2: | S |
| 65 in HCDR2: | D |
| 96 in HCDR3: | N |
| 26 in LCDR1: | T |
| 26 in LCDR1: | G |
| 27 in LCDR1: | N |
| 27 in LCDR1: | R |
| 27A in LCDR1: | T |
| 27A in LCDR1: | P |
| 27B in LCDR1: | D |
| 28 in LCDR1: | T |
| 29 in LCDR1: | E |
| 30 in LCDR1: | D |
| 56 in LCDR2: | T |
| 90 in LCDR3: | A |
| 94 in LCDR3: | G. |

Residue 29E within LCDR1 is a particularly preferred embodiment.

Preferred embodiments have the 1133C11 or 1252A5, 1152H5, 1165D4, 1230H7 or 1021E5 set of CDRs.

In one embodiment an isolated specific binding member comprises a set of CDRs which contains the 1133C11 set of CDRs with the amino acid sequence FNSALIS (SEQ ID NO: 532) or the amino acid sequence MISSLQP (SEQ ID NO: 533), substituted for the amino acid sequence LNPSLTA (SEQ ID NO: 531) within HCDR3.

Any set of HCDRs of the lineages disclosed herein can be provided in a VH domain that is used as a specific binding member alone or in combination with a VL domain. A VH domain may be provided with a set of HCDRs of a 1133C11, 1021E5 or other lineage antibody, e.g. a set of HCDRs as illustrated in Table 2a/2b, and if such a VH domain is paired with a VL domain, then the VL domain may be provided with a set of LCDRs of a 1133C11, 1021E5 or other lineage antibody, e.g. a set of LCDRs as illustrated in Table 2a/2b. A pairing of a set of HCDRs and a set of LCDRs may be as shown in Table 2a/2b, providing an antibody antigen-binding site comprising a set of CDRs as shown in Table 2a/2b.

The VH and VL domain frameworks comprise framework regions, one or more of which may be a germlined framework region, normally human germline. The VH domain framework is preferably human heavy chain germ-line framework and the VL domain framework is preferably human light chain germ-line framework. Framework regions of the heavy chain domain may be selected from the VH-1 family, and a preferred VH-1 framework is a DP-10 framework. Framework regions of the light chain may be selected from the λ1 family, and a preferred framework is DPL5.

One or more CDRs may be taken from the 1252A5 VH or VL domain and incorporated into a suitable framework. This is discussed further herein. 1252A5 HCDRs 1, 2 and 3 are shown in SEQ ID NO: 393, 394, 395 respectively. 1252A5 LCDRs 1, 2 and 3 are shown in SEQ ID NO: 398, 399, 400, respectively.

All this applies the same for other CDRs and sets of CDRs as disclosed herein, especially for 1152H5, 1165D4 and 1230H7.

Embodiments of the present invention employ the antibody VH and/or VL domain of an antibody molecule of the 1021E5 lineage, e.g. the antibody molecule 1021E5. A specific binding member comprising an antibody antigen-binding site comprising such a VH and/or VL domain is also provided by the present invention.

Preferred embodiments are as follows:
A VH domain, VL domain, set of HCDRs, set of LCDRs, or set of CDRs of: 1126F1 (VH SEQ ID NO: 102; VL SEQ ID NO: 107), 1126G5 (VH SEQ ID NO: 112; VL SEQ ID NO: 117), 1126H5 (VH SEQ ID NO: 122; VL SEQ ID NO: 127), 1127D9 (VH SEQ ID NO: 132; VL SEQ ID NO: 137), 1127F9 (VH SEQ ID NO: 142; VL SEQ ID NO: 147), 1131D7 (VH SEQ ID NO: 152; VL SEQ ID NO: 157), 1131H2 (VH SEQ ID NO: 162; VL SEQ ID NO: 167), 1132A9 (VH SEQ ID NO: 172; VL SEQ ID NO: 177), 1132H9 (VH SEQ ID NO: 182; VL SEQ ID NO: 187), 1133C11 (VH SEQ ID NO: 192; VL SEQ ID NO: 197), 1134D9 (VH SEQ ID NO: 202; VL SEQ ID NO: 207), 1145D1 (VH SEQ ID NO: 212; VL SEQ ID NO: 217), 1146D7 (VH SEQ ID NO: 222; VL SEQ ID NO: 227), 1147D2 (VH SEQ ID NO: 232; VL SEQ ID NO: 237), 1147G9 (VH SEQ ID NO: 242; VL SEQ ID NO: 247), 1150F1 (VH SEQ ID NO: 252; VL SEQ ID NO: 257), 1152H5 (VH SEQ ID NO: 262; VL SEQ ID NO: 267), 1155H1 (VH SEQ ID NO: 272; VL SEQ ID NO: 277), 1158A1 (VH SEQ ID NO: 282; VL SEQ ID NO: 287), 1160E3 (VH SEQ ID NO: 292; VL SEQ ID NO: 297), 1165D4 (VH SEQ ID NO: 302; VL SEQ ID NO: 307), 1175H8 (VH SEQ ID NO: 312; VL SEQ ID NO: 317), 1211G10 (VH SEQ ID NO: 322; VL SEQ ID NO: 327), 1214A1 (VH SEQ ID NO: 332; VL SEQ ID NO: 337), 1214D10 (VH SEQ ID NO: 342; VL SEQ ID NO: 347), 1218H5 (VH SEQ ID NO: 352; VL SEQ ID NO: 357), and 1230H7 (VH SEQ ID NO: 362; VL SEQ ID NO: 367).

Still further preferred are a VH domain, VL domain, set of HCDRs, set of LCDRs, or set of CDRs of 1083H4 (VH SEQ ID NO: 22; VL SEQ ID NO: 27), 1227H8 (VH SEQ ID NO: 372; VL SEQ ID NO: 377) and 1230D8 (VH SEQ ID NO: 382; VL SEQ ID NO: 387).

In a highly preferred embodiment, a VH domain is provided with the amino acid sequence of SEQ ID NO: 192, this being termed "1133C11 VH domain". In a further highly preferred embodiment, a VL domain is provided with the amino acid sequence of SEQ ID NO: 197, this being termed "1133C11 VL domain". A highly preferred antibody antigen-binding site provided in accordance with the present invention is composed of the 1133C11 VH domain, SEQ ID NO: 192, and the 1133C11 VL domain, SEQ ID NO: 197. This antibody antigen-binding site may be provided within any desired antibody molecule format, e.g. scFv, Fab, IgG, IgG4 etc., as is discussed further elsewhere herein.

In a further highly preferred embodiment, a VH domain is provided with the amino acid sequence of SEQ ID NO: 392, this being termed "1252A5 VH domain". In a further highly preferred embodiment, a VL domain is provided with the amino acid sequence of SEQ ID NO: 397, this being termed "1252A5 VL domain". A highly preferred antibody antigen-binding site provided in accordance with the present invention is composed of the 1252A5 VH domain, SEQ ID NO: 392, and the 1252A5 VL domain, SEQ ID NO: 397. This antibody antigen-binding site may be provided within any desired antibody molecule format, e.g. scFv, Fab, IgG, IgG4 etc., as is discussed further elsewhere herein.

In a further highly preferred embodiment, the present invention provides an IgG4 antibody molecule comprising the 1252A5 VH domain, SEQ ID NO: 392, and the 1252A5 VL domain, SEQ ID NO: 397. This is termed herein "1252A5 IgG4".

Other IgG or other antibody molecules comprising the 1252A5 VH domain, SEQ ID NO: 392, and/or the 1252A5 VL domain, SEQ ID NO: 397, are provided by the present invention, as are other antibody molecules comprising the 1252A5 set of HCDRs (SEQ ID NOS: 393, 394 and 395) within an antibody VH domain, and/or the 1252A5 set of LCDRs (SEQ ID NOS: 398, 399 and 400) within an antibody VL domain.

As noted, the present invention provides a specific binding member which binds human NGF and which comprises the 1252A5 VH domain (SEQ ID NO: 392) and/or the 1252A5 VL domain (SEQ ID NO: 397). Properties of such a specific binding member are disclosed herein.

Generally, a VH domain is paired with a VL domain to provide an antibody antigen-binding site, although as discussed further below a VH domain alone may be used to bind antigen. In one preferred embodiment, the 1252A5 VH domain (SEQ ID NO: 392) is paired with the 1252A5 VL domain (SEQ ID NO: 397), so that an antibody antigen-binding site is formed comprising both the 1252A5 VH and VL domains. Analogous embodiments are provided for the other VH and VL domains disclosed herein. In other embodiments, the 1252A5 VH is paired with a VL domain other than the 1252A5 VL. Light-chain promiscuity is well established in the art. Again, analogous embodiments are provided by the invention for the other VH and VL domains disclosed herein.

Variants of the VH and VL domains and CDRs of the present invention, including those for which amino acid sequences are set out herein, and which can be employed in specific binding members for NGF can be obtained by means of methods of sequence alteration or mutation and screening. Such methods are also provided by the present invention.

In accordance with further aspects of the present invention there is provided a specific binding member which competes for binding to antigen with any specific binding member which both binds the antigen and comprises a specific binding member, VH and/or VL domain disclosed herein, or HCDR3 disclosed herein, or variant of any of these. Competition between binding members may be assayed easily in vitro, for example using ELISA and/or by tagging a specific reporter molecule to one binding member which can be detected in the presence of one or more other untagged binding members, to enable identification of specific binding members which bind the same epitope or an overlapping epitope.

Thus, a further aspect of the present invention provides a specific binding member comprising a human antibody antigen-binding site that competes with an antibody molecule, for example especially 1252A5 or other preferred scFv and/or IgG4, for binding to NGF. In further aspects the present invention provides a specific binding member comprising a human antibody antigen-binding site which competes with an antibody antigen-binding site for binding to NGF, wherein the antibody antigen-binding site is composed of a VH domain and a VL domain, and wherein the VH and VL domains comprise a set of CDRs of the 1133C11, 1021E5, 1252A5 or other lineage, disclosed herein.

Various methods are available in the art for obtaining antibodies against NGF and which may compete with a 1252A5 or other antibody molecule, an antibody molecule with a 1252A5 or other set of CDRs, or an antibody molecule with a set of CDRs of 1252A5 or other lineage, for binding to NGF.

In a further aspect, the present invention provides a method of obtaining one or more specific binding members able to bind the antigen, the method including bringing into contact a library of specific binding members according to the invention and said antigen, and selecting one or more specific binding members of the library able to bind said antigen.

The library may be displayed on particles or molecular complexes, e.g. replicable genetic packages such as yeast, bacterial or bacteriophage (e.g. T7) particles, or covalent, ribosomal or other in vitro display systems, each particle or molecular complex containing nucleic acid encoding the antibody VH variable domain displayed on it, and optionally also a displayed VL domain if present.

Following selection of specific binding members able to bind the antigen and displayed on bacteriophage or other library particles or molecular complexes, nucleic acid may be taken from a bacteriophage or other particle or molecular complex displaying a said selected specific binding member. Such nucleic acid may be used in subsequent production of a specific binding member or an antibody VH or VL variable domain by expression from nucleic acid with the sequence of nucleic acid taken from a bacteriophage or other particle or molecular complex displaying a said selected specific binding member.

An antibody VH variable domain with the amino acid sequence of an antibody VH variable domain of a said selected specific binding member may be provided in isolated form, as may a specific binding member comprising such a VH domain.

Ability to bind NGF may be further tested, also ability to compete with e.g. 1252A5 (e.g. in scFv format and/or IgG format, e.g. IgG4) for binding to NGF. Ability to neutralise NGF may be tested, as discussed further below.

A specific binding member according to the present invention may bind NGF with the affinity of a 1252A5 or other antibody molecule, e.g. scFv, or preferably 1252A5 or other IgG4, or with an affinity that is better.

A specific binding member according to the present invention may neutralise NGF with the potency of a 1252A5 or other antibody molecule, e.g. scFv, or preferably 1252A5 or other IgG4, or with a potency that is better.

Binding affinity and neutralisation potency of different specific binding members can be compared under appropriate conditions.

The antibodies of the present invention have a number of advantages over existing commercially available anti-NGF antibodies. For example, the present invention provides human or germlined antibodies, which are expected to display a lower degree of immunogenicity when chronically or repeatedly administered to humans for therapeutic or diagnostic use. Further, the present invention provides antibodies that are more potent neutralisers of NGF and therefore a desired therapeutic or diagnostic effect may be achieved using less antibody material. In addition, in one embodiment of the invention, the potency for inhibition of the NGF/TrKA receptor interaction is greater than that observed for inhibition of the NGF/p75 receptor interaction. This may confer advantages over other apparently non-selective NGF antagonist treatments in this regard, either in the magnitude or nature of the therapeutic effect achieved, or in reducing undesirable side effects.

The invention also provides heterogeneous preparations comprising anti-NGF antibody molecules. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

In further aspects, the invention provides an isolated nucleic acid which comprises a sequence encoding a specific binding member, VH domain and/or VL domains according to the present invention, and methods of preparing a specific binding member, a VH domain and/or a VL domain of the invention, which comprise expressing said nucleic acid under conditions to bring about production of said specific binding member, VH domain and/or VL domain, and recovering it.

A further aspect of the present invention provides nucleic acid, generally isolated, encoding an antibody VH variable domain and/or VL variable domain disclosed herein.

Another aspect of the present invention provides nucleic acid, generally isolated, encoding a VH CDR or VL CDR sequence disclosed herein, especially a VH CDR selected from: 1133C11 (VH CDR1 SEQ ID NO: 193, VH CDR2 SEQ ID NO: 194, and VH CDR3 SEQ ID NO: 195), 1152H5(VH CDR1 SEQ ID NO: 263, VH CDR2 SEQ ID NO: 264, and VH CDR3 SEQ ID NO: 265), and 1252A5 (VH CDR1 SEQ ID NO: 393, VH CDR2 SEQ ID NO: 394, and VH CDR3 SEQ ID NO: 395), or a VL CDR selected from: 1133C11(VL CDR1 SEQ ID NO: 198, VL CDR2 SEQ ID NO: 199, and VL CDR3 SEQ ID NO: 200), 1152H5 (VL CDR1 SEQ ID NO: 268, VL CDR2 SEQ ID NO: 269, and VL CDR3 SEQ ID NO: 270), and 1252A5 (VL CDR1 SEQ ID NO: 398, VL CDR2 SEQ ID NO: 399, and VL CDR3 SEQ ID NO: 400), most preferably 1252A5 VH CDR3 (SEQ ID NO: 395). Nucleic acid encoding the 1252A5 set of CDRs, nucleic acid encoding the 1252A5 set of HCDRs and nucleic acid encoding the 1252A5 set of LCDRs are also provided by the present invention, as are nucleic acids encoding individual CDRs, HCDRs, LCDRs and sets of CDRs, HCDRs, LCDRs of the 1252A5, 1133C11 or 1021E5 lineage.

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and specific binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Further aspects of the present invention provide for compositions containing specific binding members of the invention, and their use in methods of inhibiting or neutralising NGF, including methods of treatment of the human or animal body by therapy.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention. Conditions treatable in accordance with the present invention include any in which NGF plays a role, especially pain, asthma, chronic obstructive pulmonary disease, pulmonary fibrosis, other diseases of airway inflammation, diabetic neuropathy, HIV, cardiac arrhythmias, arthritis, psoriasis and cancer.

These and other aspects of the invention are described in further detail below.

TERMINOLOGY

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

NGF

NGF (also known as beta-NGF) is nerve growth factor. In the context of the present invention, NGF is normally human NGF, although it may be non-human NGF (e.g. non-human primate NGF and/or rat NGF and/or mouse NGF). NGF is also referred to in places as "the antigen".

NGF used in an assay described herein is normally human, rat or mouse NGF, but NGF from another non-human animal could be used, e.g. non-human primate NGF.

Pain

This describes, as is well known in the art, sensation of pain, and may encompass one or more, or all, of the following:

hyperalgesia (exaggerated pain response to a normally painful stimulus);

allodynia (sensation of pain caused by a stimulus that is not normally painful);

spontaneous sensation of pain caused by any mechanism in the absence of any apparent external influence;

pain evoked by physical stimuli, such as heat, warmth, cold, pressure, vibration, static or dynamic touch, or body posture and movement;

somatic and visceral pain caused by any mechanism, for example, trauma, infection, inflammation, metabolic disease, stroke or neurological disease.

Pain may for example be acute pain, short-term pain, persistent nociceptive pain, or persistent or chronic neuropathic pain.

Specific Binding Member

This describes a member of a pair of molecules that have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. The present invention is concerned with antigen-antibody type reactions.

A specific binding member normally comprises a molecule having an antigen-binding site. For example, a specific binding member may be an antibody molecule or a non-antibody protein that comprises an antigen-binding site. An antigen binding site may be provided by means of arrangement of CDRs on non-antibody protein scaffolds such as fibronectin or cytochrome B etc. (Haan & Maggos, 2004; Koide et al., 1998; Nygren et al., 1997), or by randomising or mutating amino acid residues of a loop within a protein scaffold to confer binding specificity for a desired target. Scaffolds for engineering novel binding sites in proteins have been reviewed in detail by Nygren et al. (1997). Protein scaffolds for antibody mimics are disclosed in WO/0034784 in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein.

An advantage of a non-antibody protein scaffold is that it may provide an antigen-binding site in a scaffold molecule that is smaller and/or easier to manufacture than at least some antibody molecules. Small size of a specific binding member may confer useful physiological properties such as an ability to enter cells, penetrate deep into tissues or reach targets within other structures, or to bind within protein cavities of the target antigen.

Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site having specificity for binding the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides small proteins having intra-molecular disulphide bonds.

In addition to antibody sequences and/or an antigen-binding site, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or a targeting moiety or enzyme (e.g. via a peptidyl bond or linker). For example, a specific binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by scaffolds such as fibronectin or cytochrome B (Haan & Maggos, 2004; Koide et al., 1998; Nygren et al., 1997), the structure for carrying a CDR or a set of CDRs of the invention will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to (Kabat, et al., 1987, and updates thereof, now available on the Internet (http://immuno.bme.nwu.edu or find "Kabat" using any search engine).

Antibody Molecule

This describes an immunoglobulin whether natural or partly or wholly synthetically produced. The term also covers any polypeptide or protein comprising an antibody antigen-binding site. Antibody fragments that comprise an antibody antigen-binding site are molecules such as Fab, scFv, Fv, dAb, Fd; and diabodies.

It is possible to take monoclonal and other antibodies and use techniques of recombinant DNA technology to produce other antibodies or chimeric molecules that retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any specific binding member or substance having an antibody antigen-binding site with the required specificity. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide are therefore included. Cloning and expression of chimeric antibodies are described in EP-A- and EP-A-0125023, and a large body of subsequent literature.

Further techniques available in the art of antibody engineering have made it possible to isolate human and humanised antibodies. For example, human hybridomas can be made as described by Kontermann & Dubel (2001). Phage display, another established technique for generating specific binding members has been described in detail in many publications such as Kontermann & Dubel (2001) and WO92/01047 (discussed further below). Transgenic mice in which the mouse antibody genes are inactivated and functionally replaced with human antibody genes while leaving intact other components of the mouse immune system, can be used for isolating human antibodies (Mendez et al., 1997).

Synthetic antibody molecules may be created by expression from genes generated by means of oligonucleotides synthesized and assembled within suitable expression vectors, for example as described by Knappik et al. (2000) or Krebs et al. (2001).

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, 1989; McCafferty et al., 1990; Holt et al., 2003), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988); (viii) bispecific single chain Fv dimers (PCT/US92/09965) and (ix) "diabodies", multivalent or multispecific fragments constructed by gene fusion (WO94/13804; Holliger et al., 1993). Fv, scFv or diabody molecules may be stabilised by the incorporation of disulphide bridges linking the VH and VL domains (Reiter et al., 1996). Minibodies comprising a scFv joined to a CH3 domain may also be made (Hu et al., 1996).

A dAb (domain antibody) is a small monomeric antigen-binding fragment of an antibody, namely the variable region of an antibody heavy or light chain (Holt et al., 2003). VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A specific binding member of the present invention may be a dAb comprising a VH or VL domain substantially as set out herein, or a VH or VL domain comprising a set of CDRs substantially as set out herein.

Where bispecific antibodies are to be used, these may be conventional bispecific antibodies, which can be manufactured in a variety of ways (Holliger & Winter, 1993), e.g. prepared chemically or from hybrid hybridomas, or may be any of the bispecific antibody fragments mentioned above. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against NGF, then a library can be made where the other arm is varied and an antibody of appropriate specificity selected. Bispecific whole antibodies may be made by knobs-into-holes engineering (Ridgeway et al., 1996).

Antigen-Binding Site

This describes the part of a molecule that binds to and is complementary to all or part of the target antigen. In an antibody molecule it is referred to as the antibody antigen-binding site, and comprises the part of the antibody that specifically binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

Isolated

This refers to the state in which specific binding members of the invention, or nucleic acid encoding such binding members, will generally be in accordance with the present invention. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

DETAILED DESCRIPTION

As noted above, a specific binding member in accordance with the present invention preferably neutralises NGF. The degree to which an antibody neutralises NGF is referred to as its neutralising potency.

Potency is normally expressed as an IC50 value, in nM unless otherwise stated. IC50 is the median inhibitory concentration of an antibody molecule. In functional assays, IC50 is the concentration that reduces a biological response by 50% of its maximum. In ligand-binding studies, IC50 is the concentration that reduces receptor binding by 50% of maximal specific binding level.

IC50 may be calculated by plotting % biological response (represented e.g. by calcium ion mobilisation in a FLIPR assay, by survival in a PC12 assay, or by proliferation in a TF-1 proliferation assay) or % specific receptor binding as a function of the log of the specific binding member concentration, and using a software program such as Prism (GraphPad) to fit a sigmoidal function to the data to generate IC50 values, for example as described in Example 2, 5, 6 or 9 herein.

A specific binding member in accordance with the present invention preferably inhibits human NGF-evoked intracellular calcium mobilisation in cells expressing TrkA receptor, e.g. cells recombinantly transfected with a TrkA gene, for instance HEK cells. In a "FLIPR" calcium mobilisation assay as described in Example 2 herein, a specific binding member according to the invention preferably has a potency (IC50) for neutralising human NGF of or less than 600, 100, 90, 80, 70, 60, 50, 40, 30, 20 or 10 nM. Normally, a specific binding member of the invention has a potency of 5 nM or less, preferably 2.5 nM or less, more preferably 1 nM or less. In particularly preferred embodiments, the potency is 0.5 nM or less, e.g. 0.4 nM or less; 0.3 nM or less; 0.2 nM or less; or 0.15 nM or less. In some embodiments, the potency may be about 0.1 nM.

Potency may be between 0.1-100 nM, 0.1-50 nM, 0.1-10 nM, or 0.1-1.0 nM. For example, potency may be 0.1-5.0 nM, 0.2-5.0 nM, 0.3-5.0 nM, or 0.3-0.4 nM.

In some embodiments of the invention, the neutralising potency of a non potency-optimised specific binding member in a HEK cell assay as described herein is about 1.8 to 560 nM for human NGF and/or about 2.9 to 620 nM for rat NGF. In some embodiments, the neutralizing potency of potency-optimised binding members in HEK cell assays as described herein are about 0.12 to 120 nM for human NGF, about 0.11 to 37 nM for rat NGF and about 0.11 to 71 nM for mouse NGF. However, these are examples only and higher potencies may be achieved. Although potency optimisation may be used to generate higher potency specific binding members from a given specific binding member, it is also noted that high potency specific binding members may be obtained even without potency optimisation.

A specific binding member in accordance with the present invention preferably inhibits NGF-maintained serum-deprived PC12 cell survival. The neutralising potency of a specific binding member of the present invention in a PC12 survival assay for human NGF as described herein in Example 5 is generally 1500 nM or less, and is preferably 50 nM or less, or 10 nM or less. As explained above and as demonstrated herein, potency-optimisation may be used to achieve higher anti-NGF potencies. Preferably, a specific binding member has a potency of or less than 5 nM, 4 nM, 3 nM, 2 nM, 1.5 nM, 1 nM or 0.5 nM. In some embodiments, potency is about 0.1 nM or more, 0.2 nM or more. Thus, potency may be between 0.1 or 0.2 nM and 0.5, 1.5, 5 or 50 nM.

In some embodiments of the invention, the neutralizing potency of a potency optimised specific binding member in a PC12 survival assay as described herein is about 0.2 to 670 nM for human NGF and is about 0.2 to 54 nM for rat NGF.

A specific binding member in accordance with the present invention preferably inhibits NGF-stimulated TF-1 cell proliferation. The neutralising potency of a specific binding member (normally a potency-optimised specific binding member) of the present invention in a TF-1 proliferation assay for human NGF as described herein in Example 6 is generally 5 nM or less, preferably 1 nM or less. Preferably, a specific binding member of the invention has a potency of or less than 0.7, 0.6, 0.5, 0.45, 0.4, 0.3, 0.2 or 0.1 nM for human NGF. For example, potency may be between 0.05-0.1 nm, 0.05-0.2 nM, 0.05-0.3 nM, 0.05-0.4 nM, or 0.05-0.5 nM.

In some embodiments of the invention, the neutralizing potency of a potency optimised specific binding member in a TF-1 proliferation assay as described herein is about 0.08 to 0.7 nM for human NGF, about 0.07 to 1.9 nM for rat NGF and about 0.07 to 1.4 nM for mouse NGF.

A specific binding member in accordance with the present invention preferably inhibits NGF binding to a TrkA and/or p75 receptor, preferably a human TrkA and/or p75 receptor. The invention also extends more generally to a specific binding member that preferentially blocks NGF binding to TrkA receptor over NGF binding to p75 receptor. The neutralising potency of a specific binding member (normally a potency-optimised specific binding member) of the present invention in a TrkA receptor binding assay as described herein in Example 9 is generally 2.5 nM or less, preferably 1 nM or less for neutralising human NGF. Preferably, a specific binding member of the invention has a potency of or less than 0.5, 0.4, 0.3, 0.2, 0.1 or 0.075 nM for neutralising human NGF binding to TrkA. For example, potency may be between 0.05-0.1 nm, 0.05-0.2 nM, 0.05-0.3 nM, 0.05-0.4 nM, or 0.05-0.5 nM.

The neutralising potency of a specific binding member (normally a potency-optimised specific binding member) of the present invention in a p75 receptor binding assay as described herein in Example 9 is generally 1.5 nM or less, preferably 1 nM or less for neutralising human NGF. Preferably, a specific binding member of the invention has a potency of or less than 0.9, 0.8, 0.7, 0.6, 0.5, 0.4, 0.3, 0.2 or 0.1 nM for neutralising human NGF binding to p75. For example, potency may be between 0.1-0.2 nM, 0.1-0.3 nM, 0.1-0.4 nM, 0.1-0.5 nM, or 0.1-0.6 nM.

Some preferred specific binding members according to the present invention inhibit NGF (e.g. human and/or rat NGF) binding to TrkA receptor preferentially over NGF binding to p75 receptor. Accordingly, in some embodiments a specific binding member of the invention has a lower binding inhibition constant, Ki, for inhibition of NGF (e.g. human and/or rat NGF) binding to TrkA than for NGF binding to p75. Ki may be calculated using the formula set out in Example 9. Alternatively, binding inhibition constants can be expressed as pKi, which can be calculated as $-\log_{10} Ki$. Thus, a specific binding member of the invention preferably has a higher pKi value for inhibition of NGF binding to TrkA than to p75.

Preferably, a specific binding member according to the invention binds human NGF and/or rat NGF with an affinity of or less than 1, 0.8, 0.7, 0.6, 0.5, 0.4, 0.3 or 0.2 nM. For example, a specific binding member may bind human NGF with an affinity of about 0.25-0.44 nM and rat NGF with an affinity of about 0.25-0.70 nM.

As noted above, variants of antibody molecules disclosed herein may be produced and used in the present invention. Following the lead of computational chemistry in applying multivariate data analysis techniques to the structure/property-activity relationships (Wold, et al. 1984) quantitative activity-property relationships of antibodies can be derived using well-known mathematical techniques such as statistical regression, pattern recognition and classification (Norman et al. 1998; Kandel & Backer, 1995; Krzanowski, 2000; Witten & Frank, 1999; Denison (Ed), 2002; Ghose & Viswanadhan). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites (Chothia et al. 1992; Al-Lazikani, et al. 1997). These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions (Chothia et al. and Al-Lazikani et al., supra).

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule (Chothia, et al. 1986) using any freely available or commercial package such as WAM (Whitelegg & Rees, 2000). A protein visualisation and analysis software package such as Insight II (Accelerys, Inc.) or Deep View (Guex & Peitsch, 1997) may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and specific binding members generally are available in the art. Variant sequences may be made, with substitutions that may or may not be predicted to have a minimal or beneficial effect on activity, and tested for ability to bind and/or neutralise NGF and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs.

Preferably alterations do not result in loss of function, so a specific binding member comprising a thus-altered amino acid sequence preferably retains an ability to bind and/or neutralise NGF. More preferably, it retains the same quantitative binding and/or neutralising ability as a specific binding member in which the alteration is not made, e.g. as measured in an assay described herein. Most preferably, the specific binding member comprising a thus-altered amino acid sequence has an improved ability to bind or neutralise NGF.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Preferred numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. (Voet & Voet, 1995). Those amino acid residues that are derivatised at their N-alpha position will only be located at the N-terminus of an amino-acid sequence. Normally in the present invention an amino acid is an L-amino acid, but in some embodiments it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and specific binding members of the invention may comprise non-natural or non-standard amino acids described above. In some embodiments non-standard amino acids (e.g. D-amino acids) may be incorporated into an amino acid sequence during synthesis, while in other embodiments the non-standard amino acids may be introduced by modification or replacement of the "original" standard amino acids after synthesis of the amino acid sequence.

Use of non-standard and/or non-naturally occurring amino acids increases structural and functional diversity, and can thus increase the potential for achieving desired NGF binding and neutralising properties in a specific binding member of the invention. Additionally, D-amino acids and analogues have been shown to have better pharmacokinetic profiles compared with standard L-amino acids, owing to in vivo degradation of polypeptides having L-amino acids after administration to an animal.

As noted above, a CDR amino acid sequence substantially as set out herein is preferably carried as a CDR in a human antibody variable domain or a substantial portion thereof. The HCDR3 sequences substantially as set out herein represent preferred embodiments of the present invention and it is preferred that each of these is carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A CDR sequence of the invention (e.g. CDR3) may be introduced into a repertoire of variable domains lacking a CDR (e.g. CDR3), using recombinant DNA technology.

For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 or any of a subsequent large body of literature, including Kay, Winter & McCafferty (1996), so that suitable specific binding members may be selected. A repertoire may consist of from anything from $10^4$ individual members upwards, for example from $10^6$ to $10^8$ or $10^{10}$ members. Other suitable host systems include yeast display, bacterial display, T7 display, ribosome display and covalent display.

Analogous shuffling or combinatorial techniques are also disclosed by Stemmer (1994), who describes the technique in relation to a β-lactamase gene but observes that the approach may be used for the generation of antibodies.

A further alternative is to generate novel VH or VL regions carrying CDR-derived sequences of the invention using random mutagenesis of one or more selected VH and/or VL genes to generate mutations within the entire variable domain. Such a technique is described by Gram et al. (1992), who used error-prone PCR. In preferred embodiments one or two amino acid substitutions are made within a set of HCDRs and/or LCDRs.

Another method that may be used is to direct mutagenesis to CDR regions of VH or VL genes. Such techniques are disclosed by Barbas et al. (1994) and Schier et al. (1996).

All the above-described techniques are known as such in the art and the skilled person will be able to use such techniques to provide specific binding members of the invention using routine methodology in the art.

A further aspect of the invention provides a method for obtaining an antibody antigen-binding site specific for NGF antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen-binding site specific for NGF antigen and optionally with one or more preferred properties, preferably ability to neutralise NGF activity. Said VL domain may have an amino acid sequence which is substantially as set out herein.

An analogous method may be employed in which one or more sequence variants of a VL domain disclosed herein are combined with one or more VH domains.

In a preferred embodiment, 1252A5 VH domain (SEQ ID NO: 392) may be subject to mutation to provide one or more VH domain amino acid sequence variants, optionally combined with 1252A5 VL (SEQ ID NO: 397).

A further aspect of the invention provides a method of preparing a specific binding member specific for NGF antigen, which method comprises:
(a) providing a starting repertoire of nucleic acids encoding a VH domain which either include a CDR3 to be replaced or lack a CDR3 encoding region;
(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
(c) expressing the nucleic acids of said product repertoire;
(d) selecting a specific binding member specific for NGF; and
(e) recovering said specific binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a specific binding member or specific binding members specific for NGF.

In a preferred embodiment, one or more of 1252A5 HCDR1 (SEQ ID NO: 393), HCDR2 (SEQ ID NO: 394) and HCDR3 (SEQ ID NO: 395), or the 1252A5 set of HCDRs, may be employed, and/or one or more of 1252A5 LCDR1 (SEQ ID NO: 398), LCDR2 (SEQ ID NO: 399) and LCDR3 (SEQ ID NO: 400) or the 1252A5 set of LCDRs may be employed.

In other analogous embodiments 1152H5, 1165D4 or 1230H7 is substituted for 1252A5.

Similarly, other VH and VL domains, sets of CDRs and sets of HCDRs and/or sets of LCDRs disclosed herein may be employed.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single specific binding domains, these domains may be used to screen for complementary domains capable of forming a two-domain specific binding member able to bind NGF.

This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof, preferably human antibody constant regions or parts thereof. For example, a VL domain may be attached at its C-terminal end to antibody light chain constant domains including human Cκ or Cλ chains, preferably Cλ chains. Similarly, a specific binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG4 is preferred. IgG4 is preferred because it does not bind complement and does not create effector functions. Any synthetic or other constant region variant that has these properties and stabilizes variable regions is also preferred for use in embodiments of the present invention.

Specific binding members of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin that may be detected via binding to a specific cognate detectable moiety, e.g. labelled avidin.

Specific binding members of the present invention are designed to be used in methods of diagnosis or treatment in human or animal subjects, preferably human.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Clinical indications in which an anti-NGF antibody may be used to provide therapeutic benefit include pain, asthma, chronic obstructive pulmonary disease, pulmonary fibrosis, other diseases of airway inflammation, diabetic neuropathy, arthritis, psoriasis, cardiac arrhythmias, HIV and cancer. As already explained, anti-NGF treatment is indicated for all these diseases.

Anti-NGF treatment may be given orally, by injection (for example, subcutaneously, intravenously, intraperitoneal or intramuscularly), by inhalation, by the intravesicular route (instillation into the urinary bladder), or topically (for example intraocular, intranasal, rectal, into wounds, on skin). The route of administration can be determined by the physicochemical characteristics of the treatment, by special considerations for the disease or by the requirement to optimise efficacy or to minimise side-effects.

It is envisaged that anti-NGF treatment will not be restricted to use in the clinic. Therefore, subcutaneous injection using a needle free device is also preferred.

Combination treatments may be used to provide significant synergistic effects, particularly the combination of an anti-NGF specific binding member with one or more other drugs. A specific binding member according to the present invention may be provided in combination or addition to short or long acting analgesic, anti-inflammatory, anti-allergic, anti-asthmatic, anti-fibrotic, antiviral, chemotherapeutic agents and immunotherapeutic agents.

Combination treatment with one or more short or long acting analgesics and/or anti-inflammatory agents, such as opioids and non-steroid anti-inflammatory drugs (NSAIDs), may be employed for treatment of conditions characterized by pain and/or inflammation for example rheumatoid arthritis or post-surgical pain. Antibodies of the present invention can also be used in combination with anti-asthma, anti-allergic, or anti-fibrotic therapies, such as inhaled beta adrenoceptor agonists, steroids, cytokine antagonists, or other novel therapeutic approaches for treatment of asthma, allergic asthma, other allergic conditions, or any condition characterized by abnormal fibrosis. Antibodies of the present invention may also be used in combination with anti-infective agents, for example antiviral agents for the treatment of HIV infection.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors, and may depend on the severity of the symptoms and/or progression of a disease being treated. Appropriate doses of antibody are well known in the art; see Ledermann et al. (1991) and Bagshawe (1991). Specific dosages indicated herein, or in the Physician's Desk Reference (2003) as appropriate for the type of medicament being administered, may be used. A therapeutically effective amount or suitable dose of a specific binding member of the invention can be determined by comparing its in vitro activity and in vivo activity in an animal model. Methods for extrapolation of effective dosages in mice and other test animals to humans are known.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 100 µg to 1 g for systemic applications, and 1 µg to 1 mg for topical applications. Typically, the antibody will be a whole antibody, preferably the IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. In preferred embodiments of the present invention, treatment is periodic, and the period between administrations is about two weeks or more, preferably about three weeks or more, more preferably about four weeks or more, or about once a month. In other preferred embodiments of the invention, treatment may be given before, and/or after surgery, and more preferably, may be administered or applied directly at the anatomical site of surgical treatment.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated.

Specific binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-NGF will depend upon the intended route of delivery: for example, formulations for pulmonary delivery may consist of particles with physical properties that ensure penetration into the deep lung upon inhalation; topical formulations may include viscosity modifying agents, which prolong the time that the drug is resident at the site of action. In certain embodiments, the specific binding member may be prepared with a carrier that will protect the specific binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art. See, e.g., Robinson, 1978.

The present invention provides a method comprising causing or allowing binding of a specific binding member as provided herein to NGF. As noted, such binding may take place in vivo, e.g. following administration of a specific binding member, or nucleic acid encoding a specific binding member, or it may take place in vitro, for example in ELISA, Western blotting, immunocytochemistry, immuno-precipitation, affinity chromatography, or cell based assays such as a TF-1 assay.

The amount of binding of specific binding member to NGF may be determined. Quantitation may be related to the amount of the antigen in a test sample, which may be of diagnostic interest.

A kit comprising a specific binding member or antibody molecule according to any aspect or embodiment of the present invention is also provided as an aspect of the present invention. In a kit of the invention, the specific binding member or antibody molecule may be labelled to allow its reactivity in a sample to be determined, e.g. as described further below. Components of a kit are generally sterile and in sealed vials or other containers. Kits may be employed in diagnostic analysis or other methods for which antibody molecules are useful. A kit may contain instructions for use of the components in a method, e.g. a method in accordance with the present invention. Ancillary materials to assist in or to enable performing such a method may be included within a kit of the invention.

The reactivities of antibodies in a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes, which catalyse reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring antigen levels in a competition assay, that is to say a method of measuring the level of antigen in a sample by employing a specific binding member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a specific binding member according to the invention for example in a biosensor system.

The mode of determining binding is not a feature of the present invention and those skilled in the art are able to choose a suitable mode according to their preference and general knowledge.

As noted, in various aspects and embodiments, the present invention extends to a specific binding member that competes for binding to NGF with any specific binding member defined herein, e.g. 1252A5 IgG4. Competition between binding members may be assayed easily in vitro, for example by tagging a specific reporter molecule to one binding member which can be detected in the presence of other untagged binding member(s), to enable identification of specific binding members which bind the same epitope or an overlapping epitope.

Competition may be determined for example using ELISA in which NGF is immobilised to a plate and a first tagged binding member along with one or more other untagged binding members is added to the plate. Presence of an untagged binding member that competes with the tagged binding member is observed by a decrease in the signal emitted by the tagged binding member.

In testing for competition a peptide fragment of the antigen may be employed, especially a peptide including or consisting essentially of an epitope of interest. A peptide having the epitope sequence plus one or more amino acids at either end may be used. Specific binding members according to the present invention may be such that their binding for antigen is inhibited by a peptide with or including the sequence given. In testing for this, a peptide with either sequence plus one or more amino acids may be used.

Specific binding members that bind a specific peptide may be isolated for example from a phage display library by panning with the peptide(s).

The present invention further provides an isolated nucleic acid encoding a specific binding member of the present invention. Nucleic acid may include DNA and/or RNA. In a preferred aspect, the present invention provides a nucleic acid that codes for a CDR or set of CDRs or VH domain or VL domain or antibody antigen-binding site or antibody molecule, e.g. scFv or IgG4, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG4 as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, plant cells, yeast and baculovirus systems and transgenic plants and animals. The expression of antibodies and antibody fragments in prokaryotic cells is well established in the art. For a review, see for example Plückthun (1991). A common, preferred bacterial host is E. coli.

Expression in eukaryotic cells in culture is also available to those skilled in the art as an option for production of a specific binding member for example Chadd & Chamow (2001), Andersen & Krummen (2002), Larrick & Thomas (2001). Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al., 1988 and Ausubel et al., 1999.

Thus, a further aspect of the present invention provides a host cell containing nucleic acid as disclosed herein. Such a host cell may be in vitro and may be in culture. Such a host cell may be in vivo. In vivo presence of the host cell may allow intracellular expression of the specific binding members of the present invention as "intrabodies" or intracellular antibodies. Intrabodies may be used for gene therapy.

A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a specific binding member or polypeptide as above.

Aspects and embodiments of the present invention will now be illustrated, by way of example, with reference to the following experimentation and the accompanying drawings, in which:

FIG. 1A and FIG. 1B show concentration-inhibition curves for antibody neutralisation of human and rat NGF in the human TrkA receptor calcium mobilisation assay.

Human IgG4 NGF antibodies were compared with the commercial NGF antibodies G1131, Mab5260Z, and MAB256 for inhibition of intracellular calcium mobilisation evoked by nM NGF. Data points indicate results from a single experiment and are mean±sd of triplicate determinations for each antibody concentration.

FIG. 2A, FIG. 2B and FIG. 2C show inhibition of intracellular calcium mobilisation in HEK-293 cells recombinantly expressing the human TrkA receptor. Potency-optimised human IgG4 antibodies were evaluated for inhibition of responses evoked by 1 nM human, rat, and mouse NGF. Data points indicate results from a single experiment and are mean±sd of triplicate determinations for each antibody concentration.

FIG. 3A and FIG. 3B show the inhibitory effect of human IgG4 NGF antibodies in the PC12 cell survival assay. Cell survival was maintained by the presence of 1 nM human NGF or rat NGF. Data indicate mean±sd for triplicate determinations from a single experiment.

FIG. 4A, FIG. 4B and FIG. 4C show inhibition of NGF-mediated TF-cell proliferation by germline and non-germline human IgG4 NGF antibodies, and the reference NGF antibody, MAB256. Cells were stimulated with 200 pM human NGF, rat NGF, or mouse NGF. Data represent the mean±sem of triplicate determinations from a single experiment.

Figure 8A:
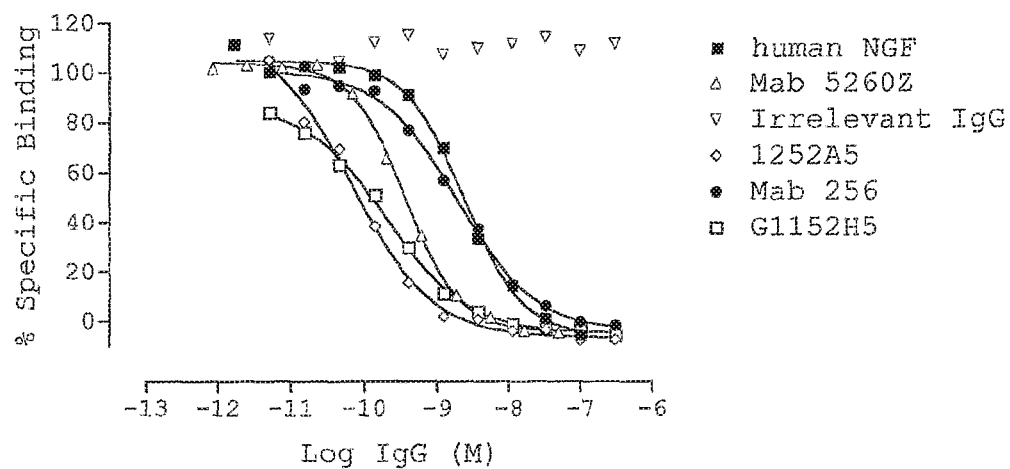
Figure 8B:
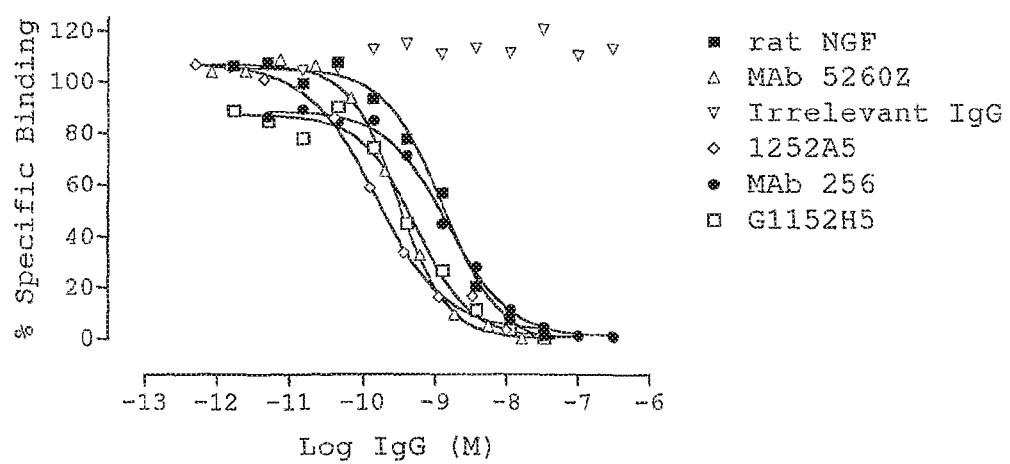

FIG. 8A and FIG. 8B show concentration-dependent inhibition of human or rat $^{125}$I-NGF binding to TrkA receptor fusion protein, by human IgG4 or reference antibodies. The concentration of radiolabelled NGF in each assay well was approximately 150 pM. Data indicate the result of a single experiment. See also Tables 6 and 7.

Figure 9A:
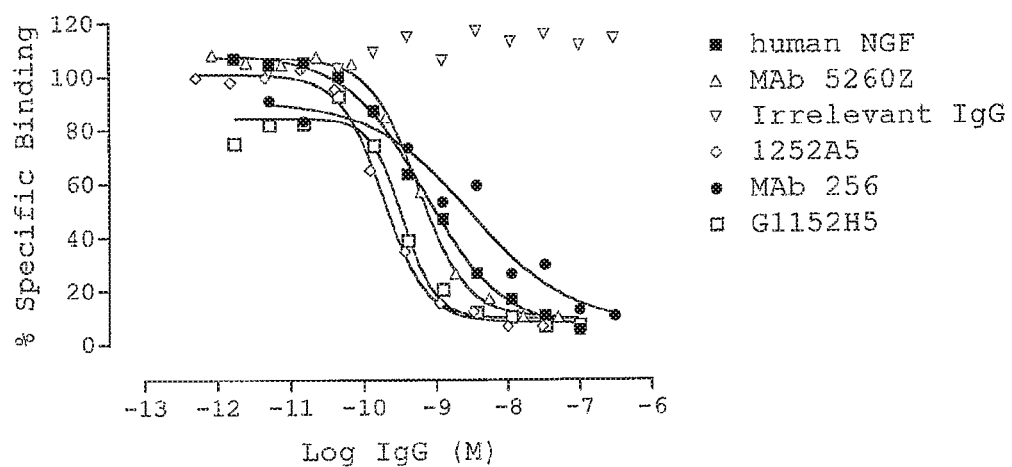
Figure 9B:
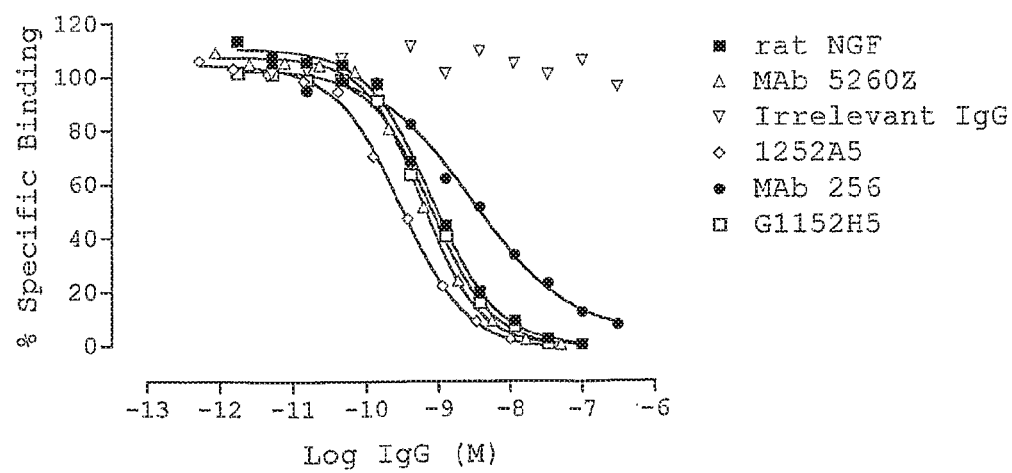

FIG. 9A and FIG. 9B show concentration-dependant inhibition of human or rat $^{125}$I-NGF binding to p75 receptor fusion protein, by human IgG4 or reference antibodies. The concentration of radiolabelled NGF in each assay well was approximately 150 pM. Data indicate the result of a single experiment. See also Tables 8 and 9.

Figure 10:
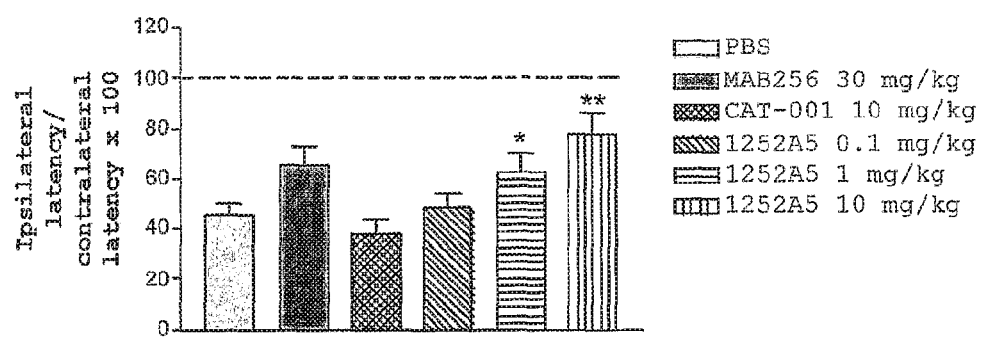

FIG. 10 shows dose-related inhibition of carrageenan-induced thermal hyperalgesia in the mouse, 48 h after systemic administration of the human IgG4 anti-NGF, 1252A5.

EXAMPLE 1

Isolation of Anti-NGF scFv
ScFv Antibody Repertoire

Three large single chain Fv (scFv) human antibody libraries cloned into a phagemid vector, were used for selections. The libraries were derived from (A) spleen lymphocytes (Hutchings, 2001), (B) a combination of peripheral blood lymphocytes, tonsil B cells and bone marrow B cells (Vaughan et al., 1996) and (C) the light chains and VH CDR3 regions of A combined with the framework of the DP47 germline heavy chain.

Selection of scFv

The phage selection procedure used was essentially as described in Hutchings, supra. ScFv that recognised NGF were isolated from phage display libraries in a series of selection cycles on human and rat NGF. In brief, unmodified antigen was coated to Nunc Maxisorb tubes. Phage were incubated on the antigen in a total volume of 500 µl for 1 h prior to washing to remove unbound phage. Bound phage were then rescued as described by Vaughan et al., supra and the selection process repeated. To assist the isolation of human/rodent cross-reactive scFv alternate rounds of selection were performed on the respective species isoforms of NGF. A maximum of four rounds of selection was performed with any one library using this alternating isoform selection strategy. Either human or rat β-NGF were used as the initial antigen for first round selections.

Outputs from rounds 2-4 were prioritised for biochemical screening based on the percentage of NGF-specific clones isolated and the sequence diversity of these clones. The percentage of NGF-specific clones was determined in each case by phage ELISA. Sequence diversity was determined by DNA sequencing.

Phage ELISA Protocol

Cultures of phage transduced bacteria were prepared in 1 ml 2×TY medium containing 100 µg/ml ampicillin and 50 µg/ml kanamycin with shaking at 30° C. for 16 h. Phage supernatant was prepared by centrifugation of the culture (10 min at 3000 rpm) and blocking with 3% w/v milk powder in PBS for 1 h. Blocked phage were then added to plates previously coated with (1 µg/ml) antigen or irrelevant antigen. Plates were washed between each step with three rinses in PBS-Tween 20 (0.1% v/v) followed by three rinses in PBS. Bound phage were detected by incubation with horseradish peroxidase (HRP)/anti-M13 conjugate (Amersham UK) diluted 1:5000 in 3% w/v milk powder PBS for 1 h, and developed by incubation with tetramethylbenzidine (TMB) substrate (Sigma). The colorimetric reaction was stopped after an appropriate period by adding 0.5M sulphuric acid. Absorbance readings were taken at 450 nm. Clones which bound specifically to the antigen were identified as having a signal on the antigen greater than or equal to 5× that on the irrelevant antigen.

DNA Sequencing

Double stranded DNA template for sequencing was obtained by PCR of scFv using the primers FDTETSEQ24 (TTTGTCGTCTTTCCAGACGTTAGT—SEQ ID NO: 534) and PUCreverse (AGCGGATAACAATTTCA-CACAGG—SEQ ID NO: 535). Excess primer and dNTPs from the primary PCR were removed using Macherey-Nagel Nucleofast 96 well PCR plates (Millipore) according to the manufacturer's recommendations. VH genes were sequenced with primer Lseq (GATTACGCCAAGCTTTG-GAGC SEQ ID NO: 536). VL genes were sequenced with primer MYC Seq 10 (CTCTTCTGAGATGAGTTTTTG SEQ ID NO: 537). Each reaction mixture contained 20-40 ng DNA, 3-20 pmol primer and 4 µl Big Dye Terminator V3.0 (Applied Biosystems, UK) in a volume of 20 µl. Sequencing reactions consisted of 25 cycles of 96° C. 10 s; 50° C., 5 s; 60° C., 4 min. Samples were run and analysed on an Applied Biosystems 3700 DNA Analyser. Areas of ambiguity were analysed manually using Continuity software developed in-house (Cambridge Antibody Technology, UK) and SeqEd DNA sequence manipulation software (Applied Biosystems, UK).

Biochemical Screen for NGF-Neutralising scFv

The output from the phage selection process was further screened to identify clones that inhibited NGF binding to a TrkA receptor extracellular domain fusion protein.

Crude scFv samples were prepared from periplasmic lysates of E. coli TG-1 bacteria transfected with selected phage for evaluation in the binding assay. Nunc Maxisorb 96 well plates were coated overnight with human TrkA receptor extracellular domain fusion protein (R&D Systems; coating concentration; human NGF assay, 0.25 nM; rat NGF assay, 1 nM). Assay plates were washed with PBS/Tween 20, blocked for 2 h using 1% bovine serum albumin (BSA) in PBS, and washed again. ScFv samples were preincubated for 30 min with 1 nM human or rat recombinant β-NGF (R&D Systems) in 1% BSA. Samples were transferred in a volume of 100 µl to assay plates and incubated for 60 min at room temperature. Plates were washed and NGF that remained bound to the plates was labelled using 0.3 µg/ml of either anti-human NGF biotin (Peprotech) or anti-rat NGF biotin (R&D Systems) diluted in 1% BSA, followed by incubation for 60 min at room temperature. Biotin-labelled anti-NGF was detected using the DELFIA (Wallac) time-resolved fluorescence detection system. Briefly, plates were washed and 100 µl streptavidin $Eu^{3+}$ added to each well, diluted 1/1000 in DELFIA assay buffer. Plates were incubated for a further 60 min at room temperature and washed with DELFIA wash buffer, followed by addition of 100 µl DELFIA enhancement solution to each well. Plates were read using a Wallac Victor fluorimetric plate reader (excitation wavelength 314 nm; emission wavelength 615 nm).

Clones that inhibited both human and rat NGF binding by more than 70% as periplasmic lysate scFv preparations were re-evaluated as purified scFv in the binding assay. Purified scFv preparations were prepared as described in Example 3 of WO01/66754. Protein concentrations of purified scFv preparations were determined using the BCA method (Pierce). Re-assay highlighted the following scFv antibodies that were potent neutralisers of human and rat NGF binding to the human TrkA receptor extracellular domain fusion protein:

1064F8 (VH SEQ ID NO: 2; VL SEQ ID NO: 7),
1022E3 (VH SEQ ID NO: 12; VL SEQ ID NO: 17),
1083H4 (VH SEQ ID NO: 22; VL SEQ ID NO: 27),
1021E5 (VH SEQ ID NO: 32; VL SEQ ID NO: 37),
1033G9 (VH SEQ ID NO: 42; VL SEQ ID NO: 47),
1016A8 (VH SEQ ID NO: 52; VL SEQ ID NO: 57),
1028F8 (VH SEQ ID NO: 62; VL SEQ ID NO: 67),
1033B2 (VH SEQ ID NO: 72; VL SEQ ID NO: 77),
1024C4 (VH SEQ ID NO: 82; VL SEQ ID NO: 87), and
1057F11 (VH SEQ ID NO: 92; VL SEQ ID NO: 97).

EXAMPLE 2

Expression of Human IgG4 Antibodies and In Vitro Functional Evaluation of NGF-Neutralising Potency The NGF-neutralising scFv 1064F8, 1022E3, 1083H4, 1021E5, 1033G9, 1016A8, 1028F8, 1033B2, 1024C4, and 1057F11 were reformatted as human IgG4 antibodies and assayed for NGF neutralising potency in a whole-cell assay system.

IgG Conversion

Vectors were constructed for the most potent scFv clones to allow re-expression as whole antibody human IgG4, essentially as described by Persic et al. (1997). EBNA-293 cells maintained in conditioned medium were co-transfected with constructs expressing heavy and light chain domains. Whole antibody was purified from the medium using protein A affinity chromatography (Amersham Pharmacia). The purified antibody preparations were sterile filtered and stored at 4° C. in phosphate buffered saline (PBS) prior to in vitro potency evaluation. Protein concentration was determined spetrophotometrically according to Mach et al. (1992).

FLIPR Assay of Intracellular Calcium Mobilisation

The potency and efficacy of anti-human IgGs for neutralising NGF were determined in a cell-based fluorescent calcium-mobilisation assay. The potency of human antibodies was compared with mouse anti-human NGF (MAB256; R&D Systems), rat anti-mouse NGF (G1131; Promega), and mouse anti-mouse NGF (MAB5260Z; Chemicon). Anti-NGF IgGs were co-incubated with recombinant human β-NGF (Calbiochem, 480275) or recombinant rat β-NGF (R&D Systems, 556-NG-100). The complex was then added to HEK293 cells expressing recombinant human TrkA receptors loaded with the calcium sensitive dye, Fluo-4, and then $Ca^{2+}$-dependent fluorescence was monitored.

HEK cells (peak-S, Edge Biosystems) transfected with recombinant human TrkA (obtained from M. Chao, Skirball Institute, NY) were grown in Dulbecco's Modified Eagle's Medium (MEM, Cellgro, MT10-017-CV) supplemented with 10% fetal bovine serum (Hyclone, SH30071.03), 1.5 µg/ml puromycin (Edge Biosystems, 80018) and 1% penicillin-streptomycin. Confluent cells were harvested by dislodging the cells with Dulbecco's phosphate buffered saline (DPBS), and then loaded with loading buffer containing 6 µM Fluo-4 (Molecular Probes) at 37° C. for 1.5 h in the presence of an anion transport inhibitor (2.5 mM probenecid in 1% FBS/MEM). After washing the cells once with assay buffer (2.5 mM probenecid in 0.1% BSA Hank's/HEPES), the cells were plated on poly-D-lysine coated, clear bottom 96-well plates (Costar 25 #3904) at approximately 60,000 cells/well in 120 µl. The cells were incubated in the dark for 30 min at room temperature, and the plates were then centrifuged at 1,200 rpm (290×g) for 5 min. Prior to testing, the plates were pre-warmed at 35° C. for 20 min. Test IgGs were assayed at 7 concentrations in triplicate wells. Thirty-five microliters of 10× anti-NGF IgG and equal amounts of 10 nM human-, rat- or mouse 2.5S NGF were pre-incubated at room temperature for approximately 1 h. Plates containing the pre-complexed IgGs and plates containing 100 µl/well assay buffer were pre-warmed at 35° C. for 20 min before testing on the Fluorometric Imaging Plate Reader (FLIPR; Molecular Devices). Following the addition of 80 µl/well assay buffer to the cell plate and incubation for 5 min at 35° C., 50 µl/well of diluted anti-human IgG/NGF complex was added to the cell plate in the FLIPR with continuous monitoring of the $Ca^{2+}$-dependent fluorescence. The NGF-induced fluorescence was calculated as the difference between the baseline fluorescence intensity just prior to NGF addition and highest fluorescence intensity attained in 2 minutes following NGF addition. The average of triplicate NGF-induced fluorescence values in the absence of antibody was defined as 100% calcium mobilisation. In the presence of antibody, the average±SD of triplicate NGF-induced fluorescence values was calculated as a percent of control calcium mobilisation. The percent of control calcium mobilisation values were plotted as function of the log of the IgG concentration. IC50 values were calculated by fitting the sigmoidal dose-response (variable slope) function using Prism (GraphPad).

All antibodies tested displayed concentration-related inhibition of human NGF-evoked intracellular calcium mobilisation. The rank order of potency for neutralisation of human NGF was 1064F8>1022E3>1083H4≥1033G9≥

Figure 1A:
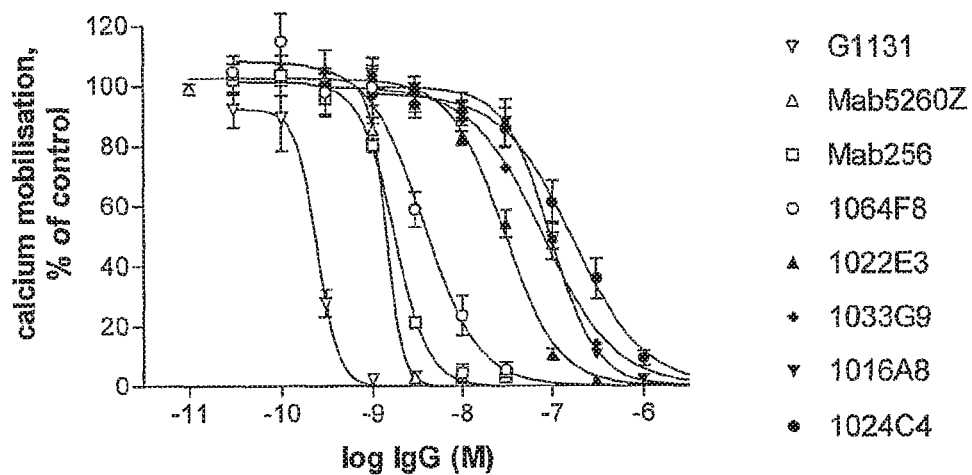
Figure 1B:
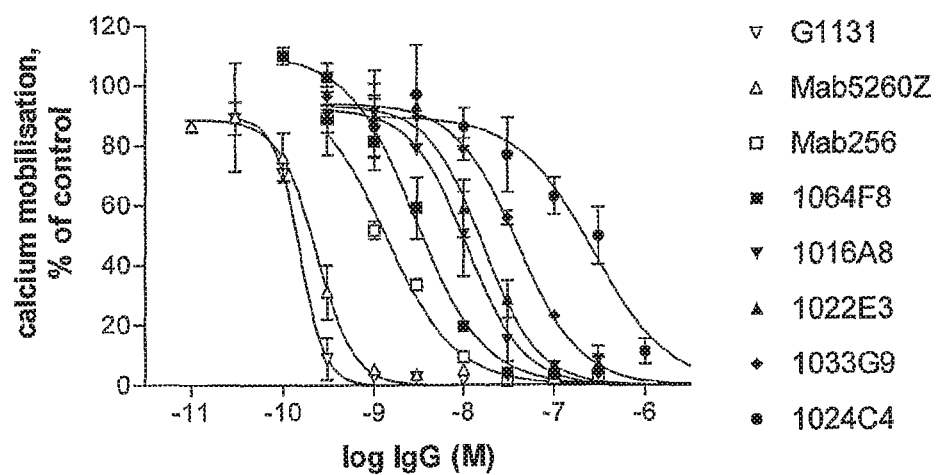

1016A8≥1028F8≥1021E5≥1033B2>>1024C4>>1057F11 (Table 1). Five antibodies were further evaluated for functional neutralisation of rat NGF, and these were approximately equipotent against both species isoforms (FIGS. 1A and 1B; Table 1).

EXAMPLE 3

Isolation of Optimised Human IgG4 NGF Antibodies
Ribosome Display scFv Potency Optimisation Large ribosome display libraries were created and selected for scFv that specifically recognised recombinant human NGF (R&D Systems), essentially as described in Hanes et al. (2000). Initially, the clones 1064F8, 1022E3, 1083H4, 1021E5, 1033G9, 1016A8, 1028F8, 1033B2, and 1024C4 were converted to ribosome display format, where the templates were subsequently used for library creation. The clone 1057F11 was not chosen for potency optimisation, and therefore a ribosome display template was not made for this antibody. On the DNA level, a T7 promoter was added at the 5'-end for efficient transcription to mRNA. On the mRNA level, the construct contained a prokaryotic ribosome-binding site (Shine-Dalgarno sequence). At the 3'end of the single chain, the stop codon was removed and a portion of gIII was added to act as a spacer (Hanes et al., supra).

Ribosome display libraries derived from 1064F8, 1022E3, 1083H4, 1021E5, 1033G9, 1016A8, 1028F8, 1033B2, and 1024C4 were created by mutagenesis of the scFv HCDR3. PCR reactions were performed with non-proof reading Taq polymerase. Affinity-based selections were performed whereby, following incubation with the library, biotinylated human NGF was coupled to streptavidin-coated paramagnetic beads (Dynal M280). Bound tertiary complexes (mRNA-ribosome-scFv) were recovered by magnetic separation whilst unbound complexes were washed away. The mRNA encoding the bound scFv were then rescued by RT-PCR as described in Hanes et al., (supra) and the selection process repeated with decreasing concentrations (100 nM-10 pM over five rounds) of biotinylated human NGF present during the selection.

Error-prone PCR was also used to further increase library size. An error rate of 7.2 mutations per 1,000 bp was employed (Diversify™, Clontech) during the selection regime. Error-prone PCR reactions were performed before selections commenced at rounds three and four using biotinylated human NGF concentrations of 1 nM and 0.1 nM, respectively.

A representative proportion of scFv from the output of selection rounds three, four and five were ligated into pCantab6 vector (Vaughan et al., 1996) and cloned in the TG1 strain of E. coli. A sample of these scFv was DNA sequenced as described in Example 1 to confirm sequence diversity of the output before screening in vitro for NGF neutralising activity. Clones were screened as unpurified scFv in the NGF/TrkA receptor extracellular domain fusion protein binding assay, as described in Example 1. The concentration of the periplasmic lysate scFv preparations in the assays was reduced to 0.5%-5% of the final assay volume, and clones that inhibited both human and rat NGF binding>95% were isolated for further study. In this way a panel of potency-optimised, cross-reactive NGF neutralisers was isolated. Surprisingly, the most potent NGF neutralisers were derived from the parent clones 1021E5 and 1083H4, which were not the most potent of the parent antibodies.

Optimised clones were sequenced and reassayed as purified scFv to confirm potency before reformatting to human IgG4 as described in Example 2.

Antibodies derived from the parent clone 1021E5 (VH SEQ ID NO: 32; VL SEQ ID NO: 37) and converted to human IgG4 format were 1126F1 (VH SEQ ID NO: 102; VL SEQ ID NO: 107), 1126G5 (VH SEQ ID NO: 112; VL SEQ ID NO: 117), 1126H5 (VH SEQ ID NO: 122; VL SEQ ID NO: 127), 1127D9 (VH SEQ ID NO: 132; VL SEQ ID NO: 137), 1127F9 (VH SEQ ID NO: 142; VL SEQ ID NO: 147), 1131D7 (VH SEQ ID NO: 152; VL SEQ ID NO: 157), 1131H2 (VH SEQ ID NO: 162; VL SEQ ID NO: 167), 1132A9 (VH SEQ ID NO: 172; VL SEQ ID NO: 177), 1132H9 (VH SEQ ID NO: 182; VL SEQ ID NO: 187), 1133C11 (VH SEQ ID NO: 192; VL SEQ ID NO: 197), 1134D9 (VH SEQ ID NO: 202; VL SEQ ID NO: 207), 1145D1 (VH SEQ ID NO: 212; VL SEQ ID NO: 217), 1146D7 (VH SEQ ID NO: 222; VL SEQ ID NO: 227), 1147D2 (VH SEQ ID NO: 232; VL SEQ ID NO: 237), 1147G9 (VH SEQ ID NO: 242; VL SEQ ID NO: 247), 1150F1 (VH SEQ ID NO: 252; VL SEQ ID NO: 257), 1152H5 (VH SEQ ID NO: 262; VL SEQ ID NO: 267), 1155H1 (VH SEQ ID NO: 272; VL SEQ ID NO: 277), 1158A1 (VH SEQ ID NO: 282; VL SEQ ID NO: 287), 1160E3 (VH SEQ ID NO: 292; VL SEQ ID NO: 297), 1165D4 (VH SEQ ID NO: 302; VL SEQ ID NO: 307), 1175H8 (VH SEQ ID NO: 312; VL SEQ ID NO: 317), 1211G10 (VH SEQ ID NO: 322; VL SEQ ID NO: 327), 1214A1 (VH SEQ ID NO: 332; VL SEQ ID NO: 337), 1214D10 (VH SEQ ID NO: 342; VL SEQ ID NO: 347), 1218H5 (VH SEQ ID NO: 352; VL SEQ ID NO: 357), and 1230H7 (VH SEQ ID NO: 362; VL SEQ ID NO: 367).

Antibodies derived from the parent clone 1083H4 (VH SEQ ID NO: 22; VL SEQ ID NO: 27) and converted to human IgG4 format were 1227H8 (VH SEQ ID NO: 372; VL SEQ ID NO: 377) and 1230D8 (VH SEQ ID NO: 382; VL SEQ ID NO: 387).

Germlining Framework Regions of 1133C11 to Derive 1252A5 and Other 1021E5 Variants Examination of the VH and VL CDR sequence information for optimised clones derived from 1021E5 highlighted that a large proportion of these antibodies contained the amino acid sequence LNPSLTA (SEQ ID NO: 531) in VH CDR3 (i.e. amino acids 100A to 100G according to the Kabat numbering system). These clones are shown in Table 2a, highlighting how they vary in amino acid sequence in the VH and VL CDR regions, together with an estimate of their NGF neutralising potency when assayed as purified scFv. Of these clones, 1133C11 differed in CDR regions from 1021E5 only by the 7 consecutive amino acids 100A to 100G as described. Therefore, 1133C11 was chosen for germlining, first to confirm that potency was retained with the modified framework, and second to allow subsequent CDR mutations to be introduced, if desired, in order to generate further germline antibodies of interest from the same lineage.

The derived amino acid VH and VL sequences of 1133C11 were aligned to the known human germline sequences in the VBASE database (Tomlinson 25 [1997], MRC Centre for Protein Engineering, Cambridge, UK) and the closest germline identified. The closest germline for the VH of 1133C11 was identified as DP10, a member of the VH1 family. The 1133C11 VH has 5 amino acid changes from the DP10 germline within framework regions. The closest germline for the VL of 1133C11 was identified as DPL5, a member of the Vλ1 family. The 1133C11 VL has only 4 changes from the germline within framework regions. Framework regions of 1133C11 were returned to germline by site directed mutagenesis of the scFv to derive the scFv 1252A5 (VH SEQ ID NO: 392; VL SEQ ID NO: 397). This was converted to human IgG4 as described in Example 2. Germlining of other variants of 1021E5-derived clones was achieved by introducing CDR mutations onto the germlined 1252A5 IgG4 backbone. This method resulted in generation of the germlined antibodies G1152H5 (VH SEQ ID NO: 402; VL SEQ ID NO: 407), G1165D4 (VH SEQ ID NO: 412; VL SEQ ID NO: 417) and G1230H7 (VH SEQ ID NO: 422; VL SEQ ID NO: 427).

EXAMPLE 4

Figure 2A:
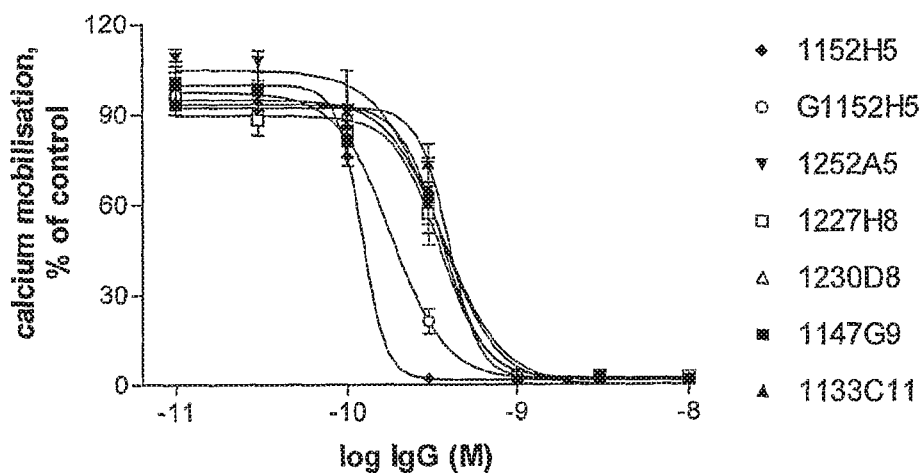
Figure 2B:
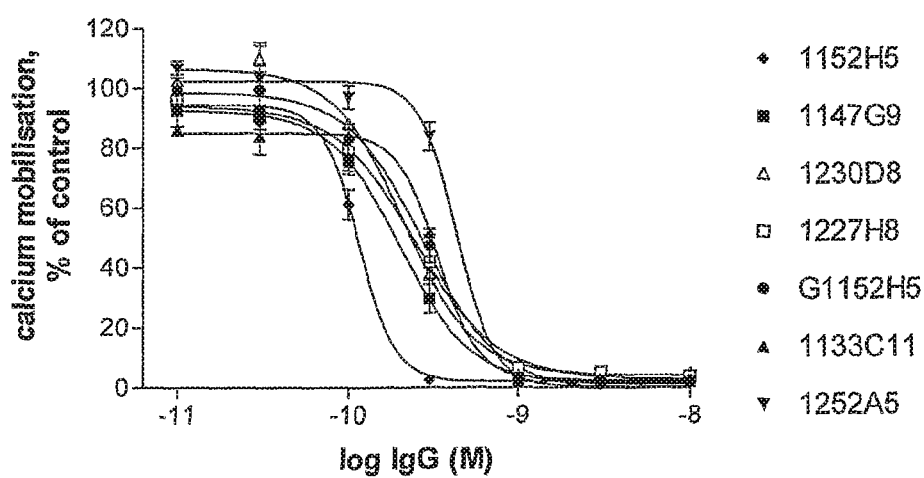
Figure 2C:
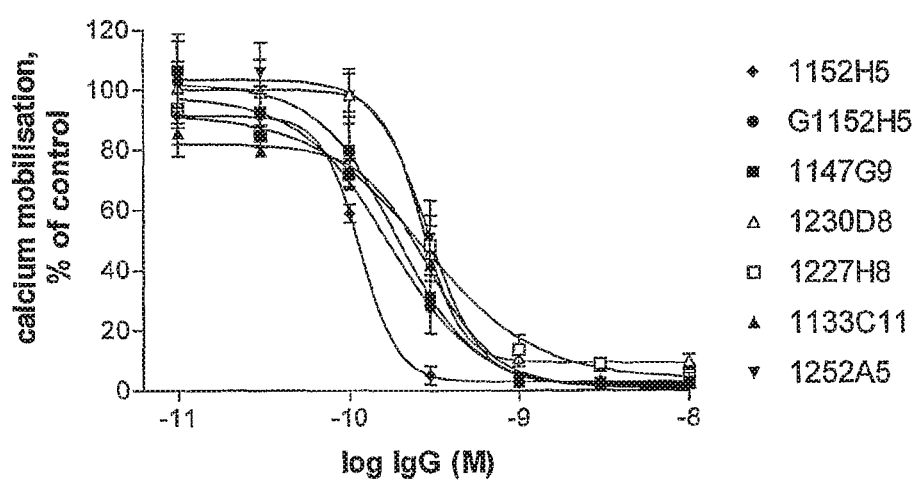

Evaluation of Optimised Human IgG4 Antibodies in the FLIPR Assay of Intracellular Calcium Mobilisation Optimised human IgG4 NGF antibodies were evaluated in an assay of NGF-evoked intracellular calcium mobilisation in cells recombinantly expressing the human TrkA receptor, as described in Example 2. Antibodies were assayed for neutralising activity against human, rat, and mouse NGF (FIGS. 2A, 2B, and 2C; Table 3).

Intracellular calcium mobilisation evoked by 1 nM NGF was inhibited by all optimised human antibodies tested. Optimised antibodies displayed subnanomolar IC50 values, in most cases representing greater than one hundredfold enhancement of NGF neutralising potency over the parent IgGs (Table 3). Neutralising potencies (IC50) of the germlined human IgG4 antibodies against the human, rat and mouse NGF isoforms were, respectively:

1252A5—0.33 nM, 0.29 nM, and 0.26 nM;
G1152H5—0.22 nM, 0.27 nM, and 0.18 nM;
G1165D4—0.32 nM, 0.33 nM, and 0.27 nM;
G1230H7—0.31 nM, 0.34 nM, and 0.25 nM.

These results highlight the efficiency and value of the ribosome display technique for antibody potency optimisation. A more conventional approach to antibody optimisation in the past has been to generate phage display libraries of variant scFv antibodies. This process is labour intensive and slower than the ribosome display method, which often means that only a single parent scFv is used as the starting point for library construction. The relative ease of generating ribosome display libraries allows multiple scFv parents to be optimised simultaneously and, as demonstrated in Example 3, this can lead to the isolation of highly potent antibodies derived from parent clones that would have been otherwise overlooked for optimisation.

EXAMPLE 5

Evaluation of Optimised Human IgG4 Antibodies in a PC12 Cell Survival Assay

In the PC12 assay, NGF maintains the survival of serum-deprived rat PC12 cells expressing native TrkA and p75 receptors for two days. Neutralising NGF antibodies reduce cell survival measured with AlamarBlue.

Rat pheochromocytoma PC12 cells were grown in RPMI 1640 (Cellgro, 18040181) supplemented with 5% fetal bovine serum (JRH, 12103-78P), 10% heat-inactivated donor horse serum (JRH, 12446-77P), and 1% penicillin-streptomycin. The cells were harvested by trituration, and then washed twice with serum-free RPMI 1640 containing 0.01% BSA (Sigma, A7030). Cells were plated in rat tail collagen (Biological Technology Institute, BT-274)-coated 96 well plates at 50,000 cells/well in 120 µl serum-free media with 0.01% BSA. Serial dilutions of 5× anti-human NGF IgGs were made using serum-free media and 40 µl/well was added to the cell plate. 40 µl/well 0.5 nM human β-NGF (Calbiochem, 480275) or rat recombinant NGF (R&D Systems, 556-NG-100) was added to the plate, and the total volume was brought up to with serum-free medium. Maximal cell death was defined by of serum-free medium in triplicate wells. 100% survival was defined by 40 µl/well serum-free media and 40 µl/well 0.5 nM NGF in triplicate wells. The plates were incubated at 37° C. in 5% $CO_2$ for 48 h.

To measure the cell viability, 22 µl/well AlamarBlue was added and the plates were read immediately to determine the background fluorescence in each well with a fluorometric plate reader (BMG) at 530 nm excitation wavelength and 590 nm emission wavelength. Following an incubation for 6~7 h at 37° C., the plate was re-read to determine total fluorescence. The Alamar blue fluorescence was calculated as the difference between the background and total fluorescence intensities. In the presence of antibody, the average±SD of triplicate fluorescence values was calculated as a percent of the average of triplicate 100% survival fluorescence values. The percent of control survival values were plotted as function of the log of the IgG concentration. $IC_{50}$ values were calculated by fitting the sigmoidal dose-response (variable slope) function using Prism (GraphPad).

Figure 3A:
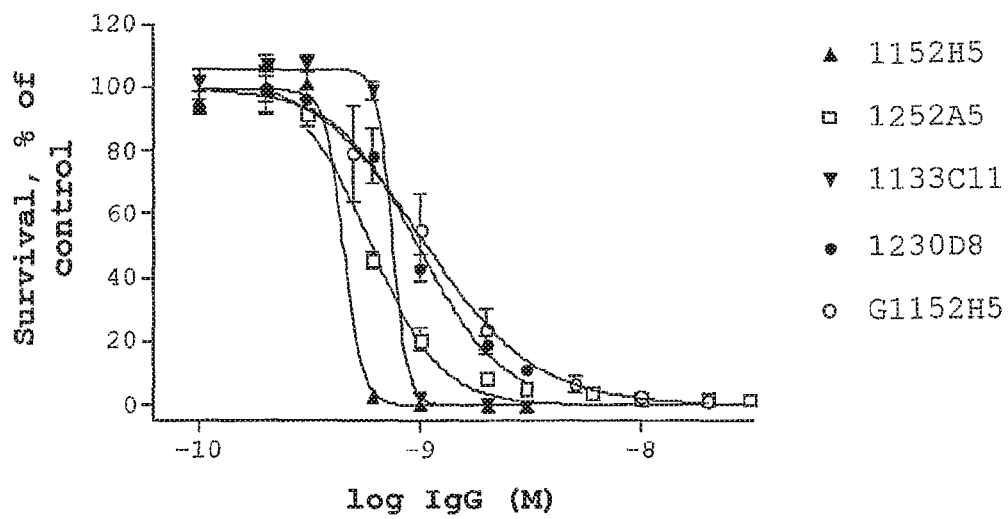
Figure 3B:
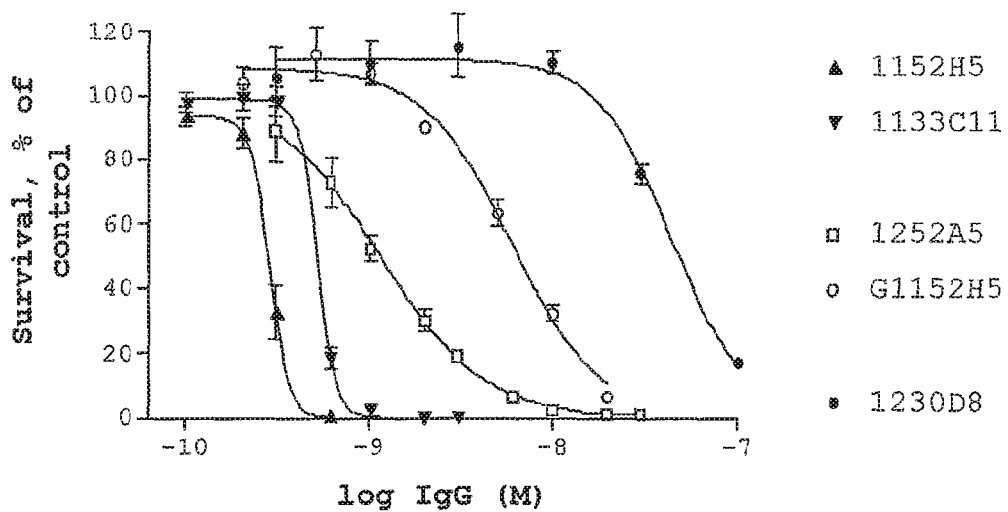

Results from the PC12 assay further confirmed the increased potency of optimised human IgG4 NGF antibodies over their parent IgGs. Antibodies inhibited human and rat NGF-maintained PC12 cell survival in a concentration-related manner (FIGS. 3A and 3B; Table 3). Germlining appeared to reduce the NGF neutralising potency of the test antibodies, particularly against the rat NGF isoform. For example, the mean IC50 of the germline antibody G1152H5 for inhibition of cell survival mediated by 1 nM human or rat NGF was 1.1 nM and 7.3 nM, respectively. In contrast, the mean $IC_{50}$ for neutralisation of 1 nM human or rat NGF by 1152H5 (ie non-germline antibody) was 0.40 nM and 0.38 nM, respectively.

EXAMPLE 6

NGF-Neutralising Activity in a TF-1 Cell Proliferation Assay

The TF-1 cell line is a human premyeloid cell line that can be stimulated to proliferate by exogenous growth factors and cytokines. TF-1 cells express the human TrkA receptor, and proliferate in response to activation with NGF. The TF-1 cell proliferation assay was used to further characterise the in vitro functional potency of neutralising human IgG4 NGF antibodies.

TF-1 cells were obtained from R&D Systems and maintained according to supplied protocols. Assay media comprised of RPMI-1640 with GLUTAMAX I (Invitrogen) containing 5% foetal bovine serum (Hyclone) and 1% sodium pyruvate (Sigma). Prior to each assay, TF-1 cells were pelleted by centrifugation at 300×g for 5 minutes, the media removed by aspiration and the cells resuspended in assay media. This process was repeated three times with cells resuspended at a final concentration of $10^5$/ml in assay media and 100 µl was added to each well of a 96 well flat bottomed tissue culture assay plate to give final cell density at 1×$10^4$/well. Test solutions of antibodies (in triplicate) were diluted to give a final assay concentration of 1 µg/ml in assay media and titrated 1:5 across assay plate. An irrelevant antibody (CAT-001) not directed at NGF, was used as a negative control. In addition, a reference monoclonal antibody MAB256 (R&D Systems) was used as a positive control. Fifty microliters of test antibodies were then added to each well followed by 50 µl of native purified murine (7S form; Invitrogen), rat (Sigma) or human (Sigma) NGF diluted to give a final assay concentration of 200 pM. Assay plates were incubated for 68 h at 37° C. in 5% $CO_2$ in a humidified chamber. Twenty microliters of tritiated thymidine (5.0 µCi/ml, NEN) was then added to each assay well and assay plates were returned to the incubator for a further 5 h. Cells were harvested onto 96 well glass fibre filter plates (Perkin Elmer) using a cell harvester. MicroScint 20™ (50 µl) was then added to each well of the filter plate and [$^3$H]-thymidine incorporation quantified using a Packard TopCount microplate liquid scintillation counter. In the presence of antibody, thymidine incorporation (quantified as counts per minute) was calculated as the difference between the average background (i.e. cells not exposed to NGF) and the average total (i.e. cells stimulated with NGF) counts per minute and expressed as a percent of maximum proliferation. The percent maximum proliferation was plotted as function of the log of the IgG concentration. IC50 values were calculated by fitting the sigmoidal dose (variable slope) function using GraphPad prism.

Figure 4A:
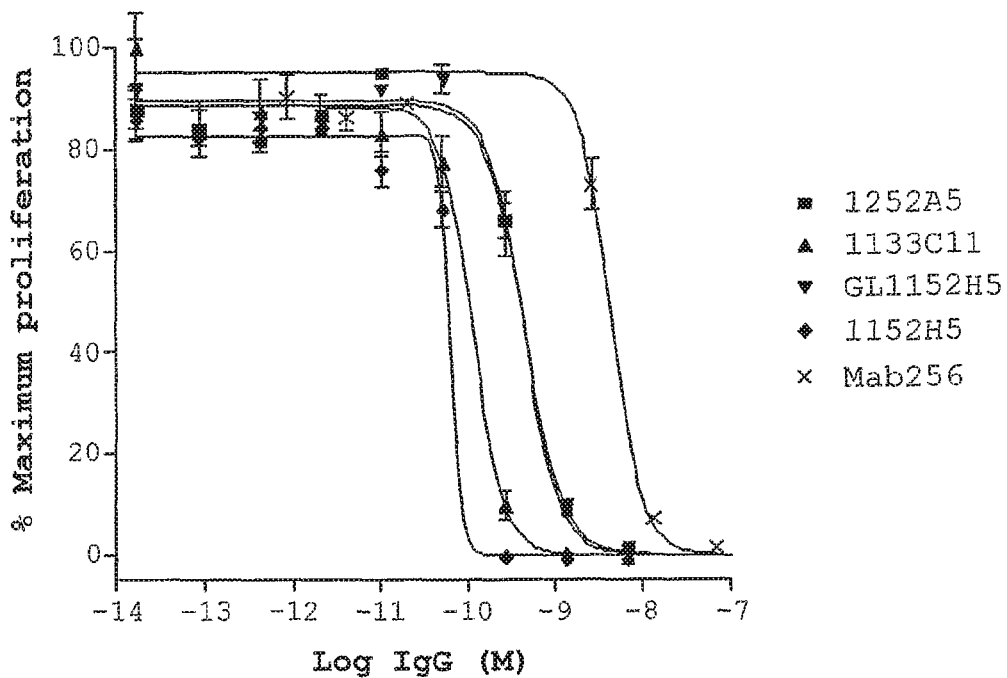
Figure 4B:
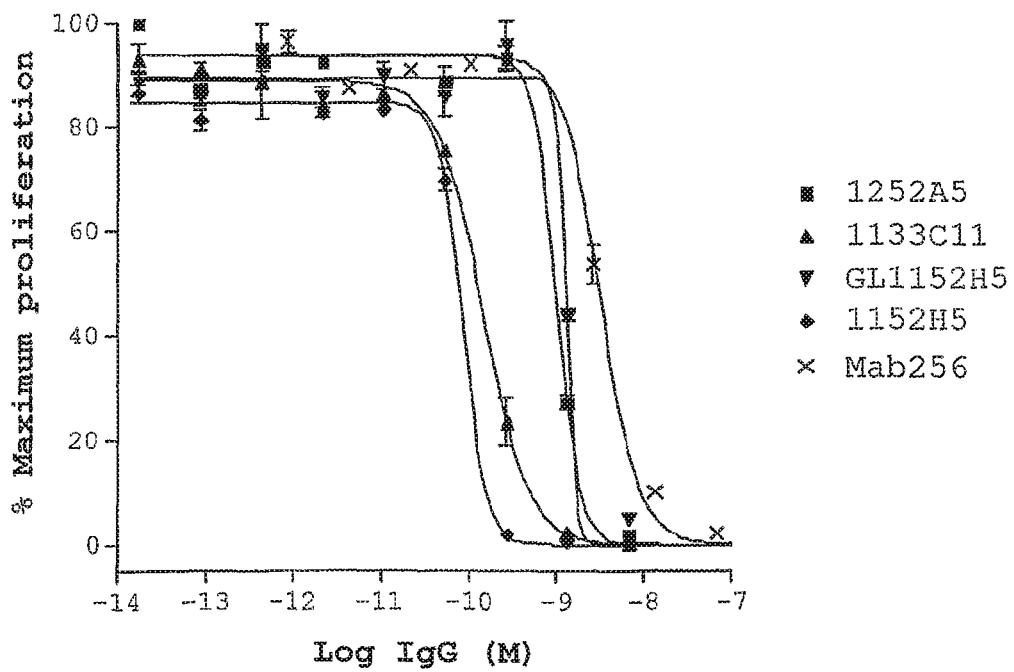
Figure 4C:
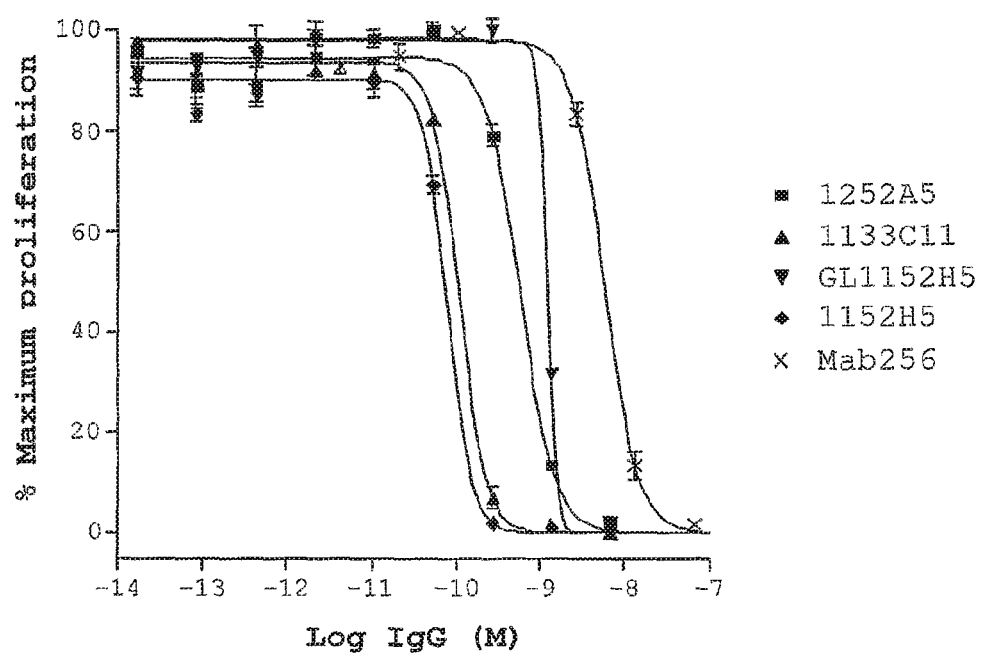

Human IgG4 NGF antibodies were potent inhibitors of TF-1 cell proliferation mediated by human, rat and mouse NGF isoforms (FIGS. 4A, 4B, and 4C). These results demonstrate that antibodies derived from the 1021E5 lineage can disrupt NGF signalling mediated by activation of native human NGF receptors in vitro. In accordance with the observed activity of human NGF antibodies in the PC12 cell survival assay (Example 5), non-germline antibodies were more potent than their germline counterparts in the TF-1 proliferation assay (Table 3). Based on mean IC50 data, the rank order of potency of the antibodies tested for inhibition of proliferation mediated by 200 pM human NGF was 1133C11>1152H5>1252A5=G1152H5>>MAB256.

EXAMPLE 7

Cross-Reactivity of Anti-NGF IgGs with Other Neurotrophins

ELISAs were performed to determine the cross-reactivity of the anti-NGF IgGs for other neurotrophins. The ELISAs consisted of coating plates with 100 ng/well human NGF (R&D systems, 256-GF), brain derived neurotrophic factor (BDNF; R&D systems, 248-BD), neurotrophin-3 (NT-3; R&D systems, 257-N3), or neurotrophin-4 (NT4; R&D systems, 257-N4) at room temperature for 5-6 h, followed by blocking the plates with 0.25% HSA at 4° C. overnight. Increasing concentrations of anti-NGF IgG, ranging from 0.03-10 nM, were incubated at room temperature for 2 h to allow binding to each neurotrophin. Anti-NGF IgGs were detected with a biotinylated anti-human polyclonal antibody (1:300) (Rockland 609-1602), streptavidin-linked alkaline phosphatase (1:1000), and fluorescent Substrate A. Positive controls demonstrating neurotrophin binding to the plate utilised commercial biotinylated anti-human polyclonal antibodies (R&D Systems anti-NGF BAF 256, anti-BDNF BAM 648, anti-NT-3 BAF 267, anti-NT-4 BAF 268), which were detected directly using streptavidin-linked alkaline phosphatase and subsequent addition of Substrate A. Non-specific binding was determined using wells coated with BSA instead of neurotrophin. Product development was followed over time from 0-60 min after addition of Substrate A. Anti-NGF IgG 1064F8 was used to optimise the assay. For 1064F8, there was linear product development for 15 min, which then leveled off with time, probably due to substrate depletion. Cross-reactivities were calculated as a percent of the specific binding to neurotrophin relative to NGF for all concentrations of IgG. For high affinity IgGs such as 1064F8, percent cross-reactivities were calculated using 15 min product development data. For low affinity IgGs such as 1016A8, percent cross-reactivities were calculated using 60 min product development data.

Figure 5:
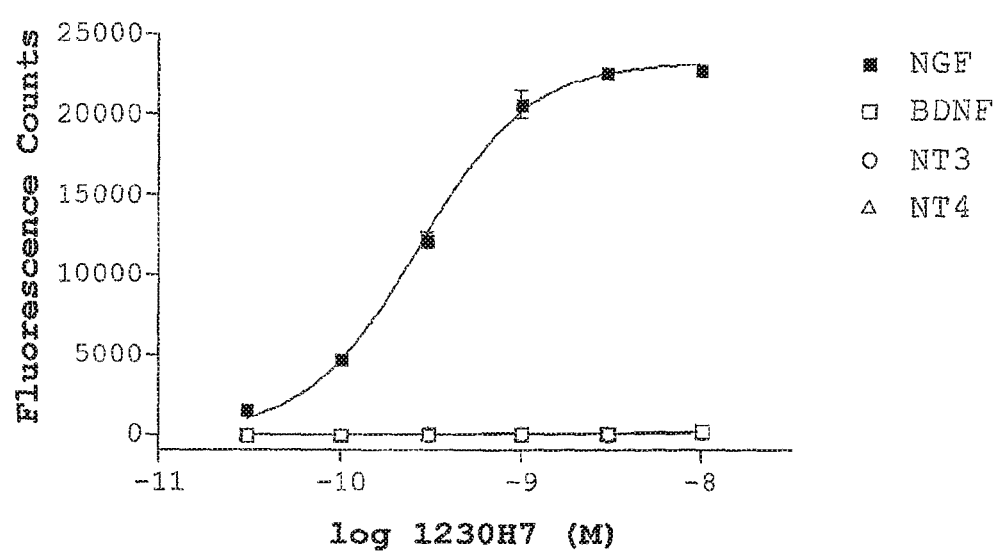
FIG. 5 shows the lack of cross-reactivity of the human IgG4 NGF antibody 1252A5 with the neurotrophins BDNF, NT-3 and NT-4. 100 ng neurotrophin was adsorbed per well. Each data point represents the mean±sd of triplicate determinations from a single experiment.

The cross-reactivities of seven human IgG4 NGF antibodies to BDNF, NT-3, and NT-4 relative to NGF were determined. At the concentrations tested, all seven antibodies showed negligible cross-reactivity (Table 4). For example, with 1252A5 the highest levels of cross-reactivity observed with NT-3, NT-4 and BDNF were 1.1%, 0.9% and 1.4%, respectively (FIG. 5).

EXAMPLE 8

Determination of the NGF-Binding Affinity of Human NGF Antibodies

The NGF-binding affinities of human IgG4 NGF antibodies were determined using a radioligand-binding assay format, performed at room temperature. Briefly, flashplates (Perkin Elmer SMP200) were coated with 100 µl/well of 2.2 µg/ml goat anti-human IgG (Sigma-Aldrich, UK) in phosphate buffered saline (PBS) for 1 h. Wells were washed with PBS and then blocked for 1 h with 200 µl/well PBS containing 3% w/v bovine serum albumin (BSA; Sigma-Aldrich, UK). Wells were washed with PBS and 10 ng of human NGF antibody was added to each well in a volume of 0.1 ml PBS containing 0.5% w/v BSA. Following incubation for 1 h plates were washed with PBS.

Radioiodinated human and rat NGF were obtained from Amersham UK (human $^{125}$I-NGF, Amersham cat. no. IM286; rat $^{125}$I-NGF, custom-labelled recombinant rat β-NGF purchased from R&D Systems, cat. no. 556-GF-100). Each $^{125}$I-NGF isoform was serially diluted in assay buffer (PBS containing 0.5% w/v BSA and 0.05% v/v Tween 20) and duplicate 100 µl samples were added to the assay plate to give a measure of 'total binding' over the concentration range 2 pM-15 nM. Non-specific binding (NSB) was determined at each $^{125}$I-NGF concentration by measuring binding in the presence of a large excess of non-radiolabelled NGF. NSB wells contained $^{125}$I-NGF (2 pM-15 nM) together with a final concentration of 500 nM unlabelled human β-NGF (R&D Systems Cat. No. 256-GF-100) or rat β-NGF (R&D Systems Cat. No. 556-GF-100), as appropriate. Plates were incubated overnight, and wells counted for 1 min on a gamma counter (TopCount NXT, Perkin Elmer). Specific binding was calculated according to the formula 'specific binding=total binding—non-specific binding'. Binding curves were plotted and binding parameters determined according to a one-site saturation binding model using Prism software (GraphPad Software Inc., USA).

Figure 6A:
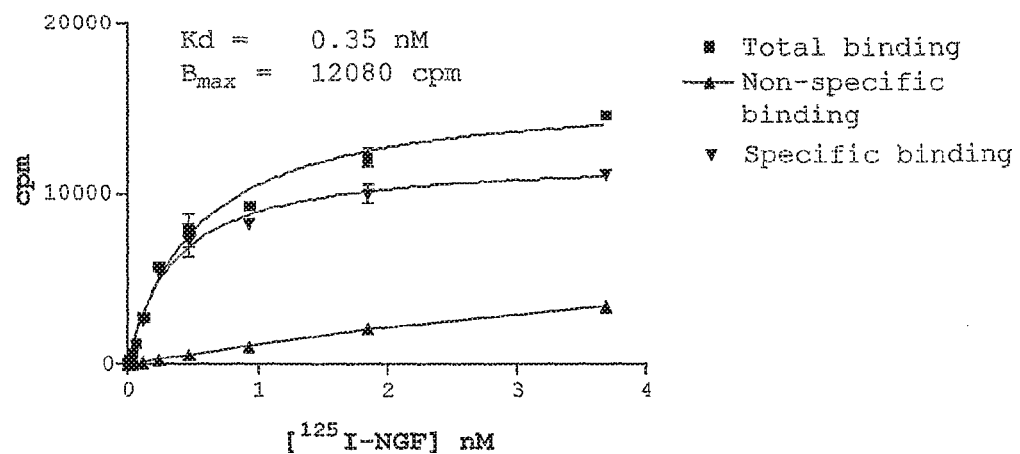
FIG. 6A and FIG. 6B show saturation binding curves for human $^{125}$I-NGF binding to the human IgG4 NGF antibodies 1252A5 and G1152H5. Calculated Kd values are 0.35 nM and 0.37 nM, respectively, and are the result of a single experiment.
Figure 6B:
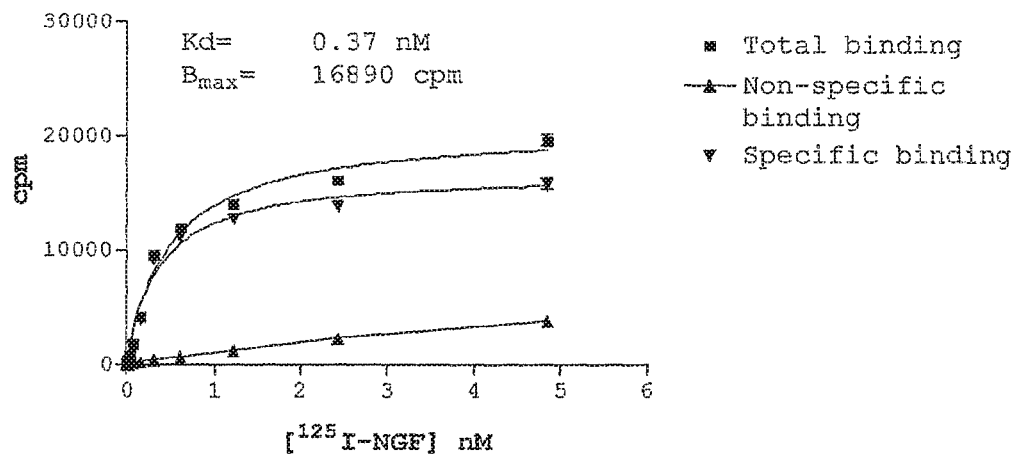
Figure 7A:
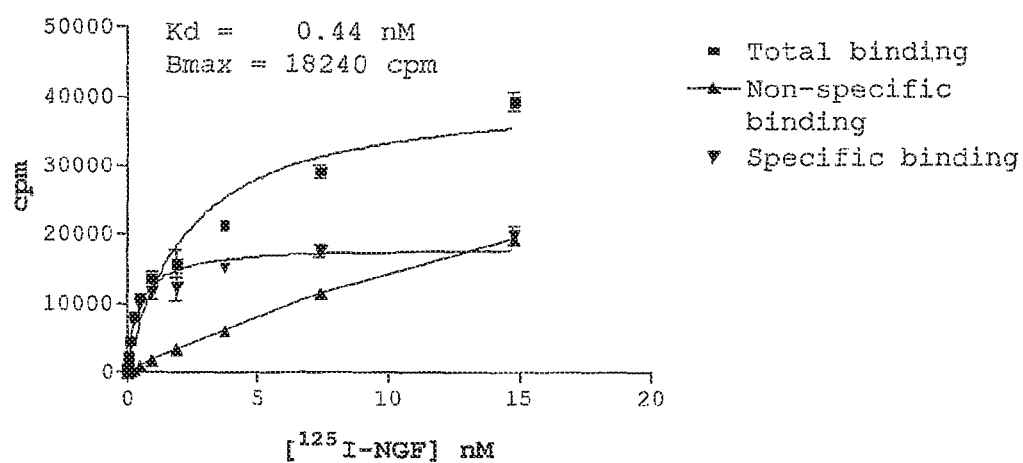
FIG. 7A and FIG. 7B show saturation binding curves for rat $^{125}$I-NGF binding to the human IgG4 NGF antibodies 1252A5 and G1152H5. Calculated Kd values are 0.44 nM and 0.50 nM, respectively, and are the result of a single experiment.
Figure 7B:
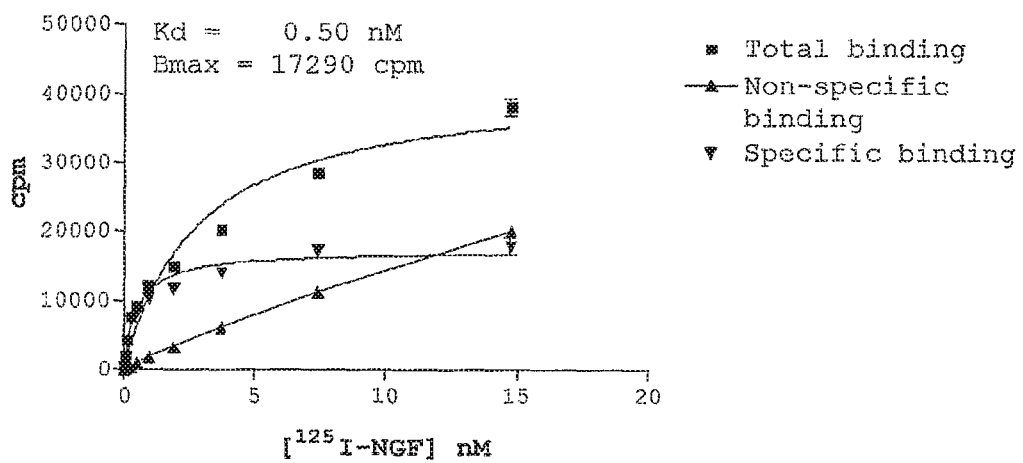

Human and rat $^{125}$I-NGF displayed saturable, high affinity binding to the human IgG4 NGF antibodies, 1252A5 and G1152H5 (FIGS. 6 and 7). Calculated Kd values for the binding interaction with human $^{125}$I-NGF were 0.35 nM for 1252A5, and 0.37 nM for G1152H5. Kd values for rat $^{125}$I-NGF binding were 0.44 nM for 1252A5 and 0.50 nM for G1152H5.

EXAMPLE 9

Determination of Ki Values for Inhibition of NGF Binding to Human TrkA and p75 Receptors Experiments were performed to determine whether the antibodies 1252A5 and G1152H5 display differential inhibition of NGF binding to TrkA and p75 receptors. Competition binding experiments were designed in order to calculate binding inhibition constant (Ki) values. $IC_{50}$s were calculated for antibody-mediated inhibition of radiolabelled human or rat NGF binding to human TrkA- or p75-receptor fusion proteins. Ki values were then derived using the Cheng-Prusoff equation.

Human TrkA and p75 receptor fusion proteins (R&D Systems) were diluted in Dulbecco's PBS (Gibco) to final concentrations of 10 nM and 0.6 nM, respectively. Maxisorp Nunc white 96 well microtitre plates (Nalge Nunc) were coated overnight at 4° C. with 100 µl/well of the diluted TrkA or p75 receptor solution. Plates were washed 3 times with PBS Tween 20, and then blocked with 200 µl/well 3% w/v bovine serum albumin (BSA) in PBS. Plates were washed after 1 h incubation at room temperature. Test antibodies were diluted to the desired concentration in assay buffer (0.5% w/v BSA and 0.05% v/v Tween 20 in PBS). An irrelevant antibody, not directed towards NGF, was used as a negative control whilst non-radiolabelled NGF was used as a reference inhibitor of radioligand binding. Duplicate wells were prepared for each concentration of test sample. Human or rat $^{125}$I-NGF (Amersham Biosciences) was diluted with assay buffer such that the final concentration in assay wells, when mixed with test sample, was 150 pM in a total assay volume of 100 µl. Assay plates were incubated at room temperature for 2 h before washing with PBS/Tween 20 to remove unbound 30 $^{125}$I-NGF. Bound radiolabel was quantified by addition of 100 µl/well Microscint 20 (Perkin Elmer) followed by counting using a Packard TopCount microplate liquid scintillation counter. Data were plotted and analysed using Graphpad Prism software to calculate IC50 values for each experiment, and to derive the corresponding Ki according to the Cheng-Prusoff equation;

$$Ki=IC_{50}/(1+D/Kd)$$

Where:
D=the NGF concentration in the assay (nominally 150 pM, but actual assay concentrations were determined for each experiment)
Kd=the affinity of NGF for the TrkA or p75 receptor under identical assay conditions. This was determined by saturation binding analysis of $^{125}$I-NGF binding to TrkA and p75 receptors in separate experiments.

All antibodies evaluated, except the human IgG4 control, inhibited human and rat $^{125}$I-NGF binding to human TrkA and p75 receptors (FIGS. 8 and 9; Table 5). Table 6 shows IC50 and Ki values calculated from data shown in FIG. 8A; Table 7 shows IC50 and Ki values calculated from data shown in FIG. 8B; Table 8 shows IC50 and Ki values calculated from data shown in FIG. 9A; Table 9 shows IC50 and Ki values calculated from data shown in FIG. 9B. Antibody 1252A5 consistently showed the greatest potency of $^{125}$I-NGF binding inhibition. Interestingly, binding inhibition constant values determined for 1252A5-mediated inhibition of NGF binding to TrkA and p75 receptors were significantly different. Thus, the calculated mean pKi for inhibition of human NGF binding to TrkA and p75 was 10.26±0.08 and 9.85±0.04, respectively (P<0.01, Student's T-test; both n=3). Calculated mean pKi for inhibition of rat NGF to TrkA and p75 receptors was 9.79±0.04 and 9.55±0.03, respectively (P<0.05, Student's T-test; both n=3). This result suggests that 1252A5 is a preferential inhibitor of the interaction between NGF and the TrkA receptor, and unexpectedly contrasts with the results obtained with G1152H5 for which there was no significant difference between corresponding pKi values (Table 5).

EXAMPLE 10

Antihyperalgesic Activity of Human IgG4 NGF Antibodies

The antihyperalgesic activity of NGF antibodies was evaluated in a mouse model of carrageenan-induced thermal hypersensitivity. Male mice (20-25 g body weight) were initially acclimatised to the test apparatus for 2 h. The following day, baseline measures of responsiveness to thermal stimulation of both hind paws were determined. A focussed heat source was applied to the plantar hind paw surface, and the latency to withdrawal was recorded, according to the method of Hargreaves et al. (1988). Baseline values were calculated as the mean of triplicate determinations for each paw, recorded 10 min apart. Mice then received an intraperitoneal injection of NGF-neutralising human IgG4 antibody or control isotype-matched null antibody in phosphate-buffered saline (PBS) vehicle. Twenty-four hours later, inflammatory hyperalgesia was induced by subplantar injection of carrageenan (2% w/v in PBS; 30 µl injection volume). After a further 24 h period, withdrawal latencies were again determined for inflamed and non-inflamed hind paws.

Thermal hyperalgesia observed 24 h after carrageenan injection was dose-dependently inhibited by pretreatment of mice with the human IgG4 NGF antibody 1252A5 (FIG. 10).

All documents cited are incorporated herein by reference.

REFERENCES

Al-Lazikani, et al. Journal Molecular Biology (1997) 273 (4), 927-948
Aloe, L. and Tuveri, M. A. (1997) Clin Exp Rheumatol, 15(4): 433-8.
Amann, R. and Schuligoi R. (2000) Neurosci Lett, 278(3): 173-6.
Andersen D C and Krummen L (2002) Current Opinion in Biotechnology 13: 117
Ausubel et al. eds., *Short Protocols in Molecular Biology: A Compendium of Methods from Current Protocols in Molecular Biology*, John Wiley & Sons, 4' edition 1999
Bagshawe K. D. et al. (1991) Antibody, Immunoconjugates and Radiopharmaceuticals 4: 915-922
Barbas et al., 1994, *Proc. Natl. Acad. Sci., USA*, 91:3809-3813
Bennett, D. L. et al. (1998) Eur J Neurosci, 10(4): 1282-91.
Bennett, D. L. (2001) Neuroscientist, 7(1): 13-7.
Bergmann I. et al., *Neurosci Lett.*, 255(2) 87-90, 1998
Bird et al, Science, 242, 423-426, 1988;
de Castro, F. et al. (1998) Eur J Neurosci, 10(1): 146-52.
Chadd H E and Chamow S M (2001) Current Opinion in Biotechnology 12: 188-194
Cho, H. J. et al. (1996) Brain Res, 716(1-2): 197-201.
Chothia, et al. Science, 223, 755-758 (1986)
Chothia C. et al. Journal Molecular Biology (1992) 227, 799-817 *Current Protocols in Molecular Biology*, Second Edition, Ausubel et al. eds., John Wiley & Sons, 1988
Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369
Fjell, J. et al. (1999) J Neurosci Res, 57(1): 39-47.
Garaci, E. et al. (2003) Proc Natl Acad Sci USA, 100(15): 8927-8932.
Ghose, Arup K. & Viswanadhan, Vellarkad N. Combinatorial Library Design and Evaluation Principles, Software, Tools, and Applications in Drug Discovery. ISBN: 0-8247-0487-8
Gram et al., 1992, *Proc. Natl. Acad. Sci., USA*, 89:3576-3580

Guex, N. and Peitsch, M. C. Electrophoresis (1997) 18, 2714-2723
Haan & Maggos (2004) BioCentury, 12(5): A1-A6
Hanes et al., *Methods in Enzymology,* 328: 24, (2000)
Hargreaves et al., *Pain,* 32: 77 (1988)
Heumann, R. et al. (1987) J Cell Biol, 104(6): 1623-31.
Holliger, P. and Winter G. Current Opinion Biotechnol 4, 446-449 1993
Holliger, P. et al, Proc. Natl. Acad. Sci. USA 90 6444-6448, 1993
Holt et al (2003) Trends in Biotechnology 21, 484-490
Hongo, J. S. et al. (2000) Hybridoma 19(3): 215-227.
Hoyle, G. W. (2003) Cytokine Growth Factor Rev, 14(6): 551-8.
Hu, S. et al, Cancer Res., 56, 3055-3061, 1996.
Huang, E. J. and Reichardt, L. F. (2001) Ann Rev Neurosci, 24: 677-736.
Huston et al, PNAS USA, 85, 5879-5883, 1988
Hutchings, in *Antibody Engineering*, Konterman and Dubel eds., Springer, Berlin, pp. 93-108 [2001]
Indo, Y. (2002) Clin Auton Res, 12 Suppl 1: 120-32.
Jagger, S. I. et al. (1999) Br J Anaesth, 83(3): 442-8.
Kabat, E. A. et al, Sequences of Proteins of Immunological Interest. 4th Edition. US Department of Health and Human Services. 1987
Kabat, E. A. et al. (1991) Sequences of Proteins of Immunological Interest, 5th Edition. US Department of Health and Human Services, Public Service, NIH, Washington.
Kandel, Abraham & Backer, Eric. Computer-Assisted Reasoning in Cluster Analysis. Prentice Hall P T R, (May 11, 1995), ISBN: 0133418847
Kay, B. K., Winter, J., and McCafferty, J. (1996) Phage Display of Peptides and Proteins: A Laboratory Manual, San Diego: Academic Press.
Knappik et al. J. Mol. Biol. (2000) 296, 57-86
Koide et al. (1998) Journal of Molecular Biology, 284: 1141-1151.
Koltzenburg, M. et al. (1999) Eur J Neurosci, 11(5): 1698-704.
Kontermann, R & Dubel, S, *Antibody Engineering*, Springer-Verlag New York, LLC; 2001, ISBN: 3540413545.
Krebs et al. Journal of Immunological Methods 254 2001 67-84
Krzanowski, Wojtek. Principles of Multivariate Analysis: A User's Perspective (Oxford Statistical Science Series, No 22 (Paper)). Oxford University Press; (December 2000), ISBN: 0198507089
Larrick J W and Thomas D W (2001) Current Opinion in Biotechnology 12:411-418.
Ledermann J. A. et al. (1991) Int. J. Cancer 47: 659-664
Lommatzsch, M. et al. (2003) Ann NY Acad Sci, 992: 241-9.
Lowe, E. M. et al. (1997) Br J Urol, 79(4): 572-577.
Ma, Q. P. and Woolf, C. J. (1997) Neuroreport, 8(4): 807-10.
Mach et al., *Analytical Biochemistry,* 200: 74, (1992)
Mamet, J. et al. (2003) J Biol Chem, 278(49): 48907-13.
Marks et al Bio/Technology, 1992, 10:779-783
McArthur, J. C. et al. (2000) Neurology, 54(5): 1080-8.
McCafferty et al (1990) Nature, 348, 552-554
Mendell, L. M. and Arvanian, V. L. (2002) Brain Res Rev, 40(1-3): 230-9.
Mendez, M. et al. (1997) Nature Genet, 15(2): 146-156.
Nakagawara, A. (2001) Cancer Lett, 169(2): 107-14.
Norman et al. Applied Regression Analysis. Wiley-Interscience; 3rd edition (April 1998) ISBN: 0471170828
Nygren et al. (1997) Current Opinion in Structural Biology, 7: 463-469.
Owolabi, J. B. et al. (1999) J Pharmacol Exp Ther, 289(3): 1271-6.
Persic et al., *Gene,* 187: 9, (1997)
Petty, B. G. et al. (1994) Ann Neurol, 36(2): 244-6.
Pleuvry B. & Pleuvry A., (2000) Analgesia: Markets and Therapies, ISBN 1860674143
Plückthun, A. Bio/Technology 9: 545-551 (1991)
Pozza, M., et al. (2000) J Rheumatol, 27(5): 1121-7.
Priestley, J. V. et al. (2002) Can J Physiol Pharmacol, 80(5): 495-505.
Qiao, L. Y. and Vizzard, M. A. (2002) J Comp Neurol, 454(2): 200-11.
Ramer, M. S. et al. (1998) Neurosci Lett, 251(1): 53-6.
Ramer, M. S. et al. (1999) Pain, Suppl 6: S111-20.
Reiter, Y. et al, Nature Biotech, 14, 1239-1245, 1996
Ridgeway, J. B. B. et al, Protein Eng., 9, 616-621, 1996
Ro, L. S. et al. (1999) Pain, 79(2-3): 264-74.
Robinson, J. R. ed., Sustained and Controlled Release Drug Delivery Systems, Marcel Dekker, Inc., New York, 1978
Sah, D. W. et al. (2003) Nat Rev Drug Discov, 2(6): 460-72.
Sambrook and Russell, *Molecular Cloning: a Laboratory Manual:* 3rd edition, 2001, Cold Spring Harbor Laboratory Press
Sammons, M. J. et al. (2000) Brain Res, 876(1-2): 48-54.
Schier et al., 1996, *J. Mol. Biol.* 263:551-567
Stemmer, *Nature,* 1994, 370:389-391
Vaughan et al., *Nature Biotechnology* 14 309-314, 1996.
Voet & Voet, *Biochemistry,* 2nd Edition, (Wiley) 1995.
Ward, E. S. et al., Nature 341, 544-546 (1989)
Wess, L. In: BioCentury, The Bernstein Report on BioBusiness, 12(42), A1-A7, 2004.
Whitelegg, N. R. u. and Rees, A. R (2000). Prot. Eng., 12, 815-824
Witten, Ian H. & Frank, Eibe. Data Mining: Practical Machine Learning Tools and Techniques with Java Implementations. Morgan Kaufmann; (Oct. 11, 1999), ISBN: 1558605525
Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)
Woolf, C. J. (1996) Philos Trans R Soc Lond B Biol Sci, 351(1338): 441-8.
Yasuda, H. et al. (2003) Prog Neurobiol, 69(4): 229-85.
Zhang Y H, Nicol G D. Neurosci Lett. 2004 Aug. 12; 366(2):187-92.

The invention claimed is:

1. A method of treating neuropathic pain, the method comprising administering an isolated specific binding member to a patient having neuropathic pain, wherein said isolated binding member comprises the 1252A5 VH domain of SEQ ID NO: 392 and the 1252A5 VL domain of SEQ ID NO: 397.

2. The method of claim 1, wherein said isolated specific binding member comprises an scFv antibody molecule.

3. The method of claim 1, wherein said isolated specific binding member comprises an antibody constant region.

4. The method of claim 1, wherein said isolated specific binding member is an IgG4 antibody.

5. A method of treating neuropathic pain, the method comprising administering a composition to a patient having neuropathic pain, wherein said composition comprises an isolated specific binding member comprising the 1252A5 VH domain of SEQ ID NO: 392 and the 1252A5 VL domain of SEQ ID NO: 397.

6. The method of claim 5, wherein the composition comprises a pharmaceutically acceptable excipient, vehicle or carrier.

* * * * *

UNITED STATES PATENT AND TRADEMARK OFFICE
CERTIFICATE OF CORRECTION

PATENT NO. : 9,701,746 B2
APPLICATION NO. : 15/131825
DATED : July 11, 2017
INVENTOR(S) : Ruth Franks et al.

Page 1 of 1

It is certified that error appears in the above-identified patent and that said Letters Patent is hereby corrected as shown below:

On the Title Page

Applicant: item (71), please replace "MedImmune Limited, Cambridge (GB)" with
-- MedImmune Limited, Cambridge (GB); Perrigo Pharma International Designated Activity Company, Dublin, IE --

Signed and Sealed this
Twenty-sixth Day of June, 2018

Andrei Iancu
*Director of the United States Patent and Trademark Office*

SEQUENCE LISTING

<160> NUMBER OF SEQ ID NOS: 537

<210> SEQ ID NO 1
<211> LENGTH: 396
<212> TYPE: DNA
<213> ORGANISM: Homo sapiens

```
<220> FEATURE:
<223> OTHER INFORMATION: 1064F8 VH nucleotide sequence

<400> SEQUENCE: 1
gaggtgcagc tggtgcagtc tggggctgag gtgaagaagc ctgggtcctc ggtgaaggtc      60
tcctgcaagg cttctggagg caccttcagc agctatgctt acacctgggt gcgacaggcc     120
cctggacaag gcttgagtg gatgggaggg atcgtcccca tctttggttc aacaaactac      180
gcacagaagt tccagggcag actcacgatt accgcgacg aattcacgag cacagcccat      240
atggagctga gcagcctgac atctgcggac acggccgtat attactgtgc gggaggcagt    300
gacttatatt gtagtggtgg taactgctac gggggcggtc actactacta ctacatggac     360
gtctgggggc aagggaccac ggtcaccgtc tcgagt                                396

<210> SEQ ID NO 2
<211> LENGTH: 132
<212> TYPE: PRT
<213> ORGANISM: Homo sapiens
<220> FEATURE:
<223> OTHER INFORMATION: 1064F8 VH amino acid sequence

<400> SEQUENCE: 2

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Tyr Thr Trp Val Arg Gln Ala Pro Gly Gln Gly Leu Glu Trp Met
        35                  40                  45

Gly Gly Ile Val Pro Ile Phe Gly Ser Thr Asn Tyr Ala Gln Lys Phe
    50                  55                  60

Gln Gly Arg Leu Thr Ile Thr Ala Asp Glu Phe Thr Ser Thr Ala His
65                  70                  75                  80

Met Glu Leu Ser Ser Leu Thr Ser Ala Asp Thr Ala Val Tyr Tyr Cys
                85                  90                  95

Ala Gly Gly Ser Asp Leu Tyr Cys Ser Gly Gly Asn Cys Tyr Gly Gly
            100                 105                 110

Gly His Tyr Tyr Tyr Tyr Met Asp Val Trp Gly Gln Gly Thr Thr Val
        115                 120                 125

Thr Val Ser Ser
    130

<210> SEQ ID NO 3
<211> LENGTH: 5
<212> TYPE: PRT
<213> ORGANISM: Homo sapiens
<220> FEATURE:
<223> OTHER INFORMATION: 1064F8 VH CDR1 amino acid sequence

<400> SEQUENCE: 3

Ser Tyr Ala Tyr Thr
1               5

<210> SEQ ID NO 4
<211> LENGTH: 17
<212> TYPE: PRT
<213> ORGANISM: Homo sapiens
<220> FEATURE:
<223> OTHER INFORMATION: 1064F8 VH CDR2 amino acid sequence
```

<400> SEQUENCE: 4

Gly Ile Val Pro Ile Phe Gly Ser Thr Asn Tyr Ala Gln Lys Phe Gln
1               5                   10                  15

Gly

<210> SEQ ID NO 5
<211> LENGTH: 23
<212> TYPE: PRT
<213> ORGANISM: Homo sapiens
<220> FEATURE:
<223> OTHER INFORMATION: 1064F8 VH CDR3 amino acid sequence

<400> SEQUENCE: 5

Gly Ser Asp Leu Tyr Cys Ser Gly Gly Asn Cys Tyr Gly Gly Gly His
1               5                   10                  15

Tyr Tyr Tyr Tyr Met Asp Val
            20

<210> SEQ ID NO 6
<211> LENGTH: 330
<212> TYPE: DNA
<213> ORGANISM: Homo sapiens
<220> FEATURE:
<223> OTHER INFORMATION: 1064F8 VL nucleotide sequence

<400> SEQUENCE: 6
tcgtctgagc tgactcagga ccctgctgtg tctgtggcct tgggacagac agtcaggatc        60
acttgcactg gaaccagcag tgacgttggt ggttataact atgtctcctg gtaccaacaa       120
cacccaggca aagcccccaa actcatgatt tatgagggca gtaagcggcc ctcaggggtt       180
tctaatcgct tctctggctc caagtctggc aacacggcct ccctgacaat ctctgggctc       240
caggctgagg acgaggctga ttattactgc agctcatata caaccaggag cactcgagtt       300
ttcggcggag ggaccaagct gaccgtccta                                        330

<210> SEQ ID NO 7
<211> LENGTH: 110
<212> TYPE: PRT
<213> ORGANISM: Homo sapiens
<220> FEATURE:
<223> OTHER INFORMATION: 1064F8 VL amino acid sequence

<400> SEQUENCE: 7

Ser Ser Glu Leu Thr Gln Asp Pro Ala Val Ser Val Ala Leu Gly Gln
1               5                   10                  15

Thr Val Arg Ile Thr Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu
            100                 105                 110

<210> SEQ ID NO 8
<211> LENGTH: 14

```
<212> TYPE: PRT
<213> ORGANISM: Homo sapiens
<220> FEATURE:
<223> OTHER INFORMATION: 1064F8 VL CDR1 amino acid sequence

<400> SEQUENCE: 8

Thr Gly Thr Ser Ser Asp Val Gly Gly Tyr Asn Tyr Val Ser
 1               5                  10

<210> SEQ ID NO 9
<211> LENGTH: 7
<212> TYPE: PRT
<213> ORGANISM: Homo sapiens
<220> FEATURE:
<223> OTHER INFORMATION: 1064F8 VL CDR2 amino acid sequence

<400> SEQUENCE: 9

Glu Gly Ser Lys Arg Pro Ser
 1               5

<210> SEQ ID NO 10
<211> LENGTH: 10
<212> TYPE: PRT
<213> ORGANISM: Homo sapiens
<220> FEATURE:
<223> OTHER INFORMATION: 1064F8 VL CDR3 amino acid sequence

<400> SEQUENCE: 10

Ser Ser Tyr Thr Thr Arg Ser Thr Arg Val
 1               5                  10

<210> SEQ ID NO 11
<211> LENGTH: 381
<212> TYPE: DNA
<213> ORGANISM: Homo sapiens
<220> FEATURE:
<223> OTHER INFORMATION: 1022E3 VH nucleotide sequence

<400> SEQUENCE: 11
caggtgcagc tggtgcagtc tggggctgag gtgaagaagc ctggggcctc agtgaaagtt      60
tcctgcaagg catctggata cagcttcatc aactactcta tgcactgggt gcgacaggcc     120
cctggacaag gacttgagtg gataggaata atcaatcctg gtggtgacag cacaaaatac     180
acacagaggt tccaggacag agtcaccatg acctgggaca cgtccacgag cacagtctac     240
atggacctca gcagcctgag atctgaggac acggccatct attactgtgc gagaggcctc     300 cacccc atcc ctatgatgtt agcgactatt aacccaattt ttgcctactg gggccaggga     360
accctggtca ccgtctcgag t                                                381

<210> SEQ ID NO 12
<211> LENGTH: 127
<212> TYPE: PRT
<213> ORGANISM: Homo sapiens
<220> FEATURE:
<223> OTHER INFORMATION: 1022E3 VH amino acid sequence

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Ile Asn Tyr
                20                  25                  30

Ser Met His Trp Val Arg Gln Ala Pro Gly Gln Gly Leu Glu Trp Ile
            35                  40                  45
```

```
Gly Ile Ile Asn Pro Gly Gly Asp Ser Thr Lys Tyr Thr Gln Arg Phe
        50                  55                  60
Gln Asp Arg Val Thr Met Thr Trp Asp Thr Ser Thr Ser Thr Val Tyr
 65                  70                  75                  80
Met Asp Leu Ser Ser Leu Arg Ser Glu Asp Thr Ala Ile Tyr Tyr Cys
                 85                  90                  95
Ala Arg Gly Leu His Pro Ile Pro Met Met Leu Ala Thr Ile Asn Pro
            100                 105                 110
Ile Phe Ala Tyr Trp Gly Gln Gly Thr Leu Val Thr Val Ser Ser
            115                 120                 125

<210> SEQ ID NO 13
<211> LENGTH: 5
<212> TYPE: PRT
<213> ORGANISM: Homo sapiens
<220> FEATURE:
<223> OTHER INFORMATION: 1022E3 VH CDR1 amino acid sequence

<400> SEQUENCE: 13

Asn Tyr Ser Met His
1               5

<210> SEQ ID NO 14
<211> LENGTH: 17
<212> TYPE: PRT
<213> ORGANISM: Homo sapiens
<220> FEATURE:
<223> OTHER INFORMATION: 1022E3 VH CDR2 amino acid sequence

<400> SEQUENCE: 14

Ile Ile Asn Pro Gly Gly Asp Ser Thr Lys Tyr Thr Gln Arg Phe Gln
1               5                   10                  15
Asp

<210> SEQ ID NO 15
<211> LENGTH: 18
<212> TYPE: PRT
<213> ORGANISM: Homo sapiens
<220> FEATURE:
<223> OTHER INFORMATION: 1022E3 VH CDR3 amino acid sequence

<400> SEQUENCE: 15

Gly Leu His Pro Ile Pro Met Met Leu Ala Thr Ile Asn Pro Ile Phe
1               5                   10                  15
Ala Tyr

<210> SEQ ID NO 16
<211> LENGTH: 330
<212> TYPE: DNA
<213> ORGANISM: Homo sapiens
<220> FEATURE:
<223> OTHER INFORMATION: 1022E3 VL nucleotide sequence

<400> SEQUENCE: 16
tcttctgagc tgactcagga ccctgctgta tctgtggcct tgggacagac agtcaggatc        60
acatgccgag agacagcct ccgaaactat tatgcaaact ggtaccagca gaagccggga       120
caggcccctg tacttgtcat ctatgatgaa aataagcggc cctcagggat cccagaccga       180
ttctctggct ccggctcagg gaacacagct tccttgacca tcaccggggc tcaggcggaa       240
gatgaggctg actatttctg caactcccgg gacacctttg gttacgttcg cgatgtgtta       300
ttcggcggag ggaccaaggt caccgtccta                                       330
```

```
<210> SEQ ID NO 17
<211> LENGTH: 110
<212> TYPE: PRT
<213> ORGANISM: Homo sapiens
<220> FEATURE:
<223> OTHER INFORMATION: 1022E3 VL amino acid sequence

<400> SEQUENCE: 17

Ser Ser Glu Leu Thr Gln Asp Pro Ala Val Ser Val Ala Leu Gly Gln
1               5                   10                  15

Thr Val Arg Ile Thr Cys Arg Gly Asp Ser Leu Arg Asn Tyr Tyr Ala
            20                  25                  30

Asn Trp Tyr Gln Gln Lys Pro Gly Gln Ala Pro Val Leu Val Ile Tyr
        35                  40                  45

Asp Glu Asn Lys Arg Pro Ser Gly Ile Pro Asp Arg Phe Ser Gly Ser
    50                  55                  60

Gly Ser Gly Asn Thr Ala Ser Leu Thr Ile Thr Gly Ala Gln Ala Glu
65                  70                  75                  80

Asp Glu Ala Asp Tyr Phe Cys Asn Ser Arg Asp Thr Phe Gly Tyr Val
                85                  90                  95

Arg Asp Val Leu Phe Gly Gly Gly Thr Lys Val Thr Val Leu
            100                 105                 110

<210> SEQ ID NO 18
<211> LENGTH: 11
<212> TYPE: PRT
<213> ORGANISM: Homo sapiens
<220> FEATURE:
<223> OTHER INFORMATION: 1022E3 VL CDR1 amino acid sequence

<400> SEQUENCE: 18

Arg Gly Asp Ser Leu Arg Asn Tyr Tyr Ala Asn
1               5                   10

<210> SEQ ID NO 19
<211> LENGTH: 7
<212> TYPE: PRT
<213> ORGANISM: Homo sapiens
<220> FEATURE:
<223> OTHER INFORMATION: 1022E3 VL CDR2 amino acid sequence

<400> SEQUENCE: 19

Asp Glu Asn Lys Arg Pro Ser
1               5

<210> SEQ ID NO 20
<211> LENGTH: 13
<212> TYPE: PRT
<213> ORGANISM: Homo sapiens
<220> FEATURE:
<223> OTHER INFORMATION: 1022E3 VL CDR3 amino acid sequence

<400> SEQUENCE: 20

Asn Ser Arg Asp Thr Phe Gly Tyr Val Arg Asp Val Leu
1               5                   10

<210> SEQ ID NO 21
<211> LENGTH: 375
<212> TYPE: DNA
<213> ORGANISM: Homo sapiens
<220> FEATURE:
<223> OTHER INFORMATION: 1083H4 VH nucleotide sequence
```

```
<400> SEQUENCE: 21
cagatgcagc tggtgcagtc tggggctgag gtgaagaaga ccgggtcctc agtgaaggtt      60
tcctgcaagg cttccggata caccttcgcc taccactacc tacactgggt gcgacaggcc    120
cctggacaag gcttgagtg gatgggaggg atcatcccta tctttggtac aacaaactac     180
gcacagaggt tccaggacag agtcacgatt accgcggacg agtccaccag cacagcctac    240
atggagttga gcagtctgag atctgaggac acggccgtct attactgtgc gagtgctgat    300
tacgtttggg ggagttatcg tcccgactgg tacttcgatc tctggggcag agggacaatg    360
gtcaccgtct cgagt                                                     375

<210> SEQ ID NO 22
<211> LENGTH: 125
<212> TYPE: PRT
<213> ORGANISM: Homo sapiens
<220> FEATURE:
<223> OTHER INFORMATION: 1083H4 VH amino acid sequence

<400> SEQUENCE: 22

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Ala Tyr His
            20                  25                  30

Tyr Leu His Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Arg Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ala Asp Tyr Val Trp Gly Ser Tyr Arg Pro Asp Trp Tyr Phe
            100                 105                 110

Asp Leu Trp Gly Arg Gly Thr Met Val Thr Val Ser Ser
        115                 120                 125

<210> SEQ ID NO 23
<211> LENGTH: 5
<212> TYPE: PRT
<213> ORGANISM: Homo sapiens
<220> FEATURE:
<223> OTHER INFORMATION: 1083H4 VH CDR1 amino acid sequence

<400> SEQUENCE: 23

Tyr His Tyr Leu His
1               5

<210> SEQ ID NO 24
<211> LENGTH: 17
<212> TYPE: PRT
<213> ORGANISM: Homo sapiens
<220> FEATURE:
<223> OTHER INFORMATION: 1083H4 VH CDR2 amino acid sequence

<400> SEQUENCE: 24

Gly Ile Ile Pro Ile Phe Gly Thr Thr Asn Tyr Ala Gln Arg Phe Gln
1               5                   10                  15

Asp
```

```
<210> SEQ ID NO 25
<211> LENGTH: 16
<212> TYPE: PRT
<213> ORGANISM: Homo sapiens
<220> FEATURE:
<223> OTHER INFORMATION: 1083H4 VH CDR3 amino acid sequence

<400> SEQUENCE: 25

Ala Asp Tyr Val Trp Gly Ser Tyr Arg Pro Asp Trp Tyr Phe Asp Leu
1               5                   10                  15

<210> SEQ ID NO 26
<211> LENGTH: 330
<212> TYPE: DNA
<213> ORGANISM: Homo sapiens
<220> FEATURE:
<223> OTHER INFORMATION: 1083H4 VL nucleotide sequence

<400> SEQUENCE: 26
cagtctgtgt tgacgcagcc gccctcagcg tctgggaccc ccggggcagag ggtcaccatc      60 tcttgttctg gaagcagctc caacatcggg agtaacactg taaactggta ccagcgactc     120
ccaggagcgg ccccccaact cctcatctac aataatgacc agcggccctc agggatccct     180
gaccgattct ctggctccaa gtctggcacc tcaggctccc tggtcatcag tgggctccag     240
tctgaagatg aggctgatta ctactgtgcg tcatgggatg acagtctgaa tggtcgggtg     300
ttcggcggag ggaccaagct gaccgtccta                                      330

<210> SEQ ID NO 27
<211> LENGTH: 110
<212> TYPE: PRT
<213> ORGANISM: Homo sapiens
<220> FEATURE:
<223> OTHER INFORMATION: 1083H4 VL amino acid sequence

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Arg Leu Pro Gly Ala Ala Pro Gln Leu Leu
            35                  40                  45

Ile Tyr Asn Asn Asp Gln Arg Pro Ser Gly Ile Pro Asp Arg Phe Ser
        50                  55                  60

Gly Ser Lys Ser Gly Thr Ser Gly Ser Leu Val Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Gly Arg Val Phe Gly Gly Gly Thr Lys Leu Thr Val Leu
            100                 105                 110

<210> SEQ ID NO 28
<211> LENGTH: 13
<212> TYPE: PRT
<213> ORGANISM: Homo sapiens
<220> FEATURE:
<223> OTHER INFORMATION: 1083H4 VL CDR1 amino acid sequence

<400> SEQUENCE: 28

Ser Gly Ser Ser Asn Ile Gly Ser Asn Thr Val Asn
1               5                   10
```

<210> SEQ ID NO 29
<211> LENGTH: 7
<212> TYPE: PRT
<213> ORGANISM: Homo sapiens
<220> FEATURE:
<223> OTHER INFORMATION: 1083H4 VL CDR2 amino acid sequence

<400> SEQUENCE: 29

Asn Asn Asp Gln Arg Pro Ser
1               5

<210> SEQ ID NO 30
<211> LENGTH: 11
<212> TYPE: PRT
<213> ORGANISM: Homo sapiens
<220> FEATURE:
<223> OTHER INFORMATION: 1083H4 VL CDR3 amino acid sequence

<400> SEQUENCE: 30

Ala Ser Trp Asp Asp Ser Leu Asn Gly Arg Val
1               5                   10

<210> SEQ ID NO 31
<211> LENGTH: 384
<212> TYPE: DNA
<213> ORGANISM: Homo sapiens
<220> FEATURE:
<223> OTHER INFORMATION: 1021E5 VH nucleotide sequence

<400> SEQUENCE: 31

```
gaagtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggaggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg actatgccgg gggtgaccac tactactacg atatggatgt ctggggccag     360
gggacaatgg tcaccgtctc gagt                                            384
```

<210> SEQ ID NO 32
<211> LENGTH: 128
<212> TYPE: PRT
<213> ORGANISM: Homo sapiens
<220> FEATURE:
<223> OTHER INFORMATION: 1021E5 VH amino acid sequence

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Tyr Ala Gly Gly Asp His Tyr Tyr
            100                 105                 110

Tyr Asp Met Asp Val Trp Gly Gln Gly Thr Met Val Thr Val Ser Ser
            115                 120                 125

<210> SEQ ID NO 33
<211> LENGTH: 5
<212> TYPE: PRT
<213> ORGANISM: Homo sapiens
<220> FEATURE:
<223> OTHER INFORMATION: 1021E5 VH CDR1 amino acid sequence

<400> SEQUENCE: 33

Thr Tyr Gly Ile Ser
1               5

<210> SEQ ID NO 34
<211> LENGTH: 17
<212> TYPE: PRT
<213> ORGANISM: Homo sapiens
<220> FEATURE:
<223> OTHER INFORMATION: 1021E5 VH CDR2 amino acid sequence

<400> SEQUENCE: 34

Gly Ile Ile Pro Ile Phe Asp Thr Gly Asn Ser Ala Gln Ser Phe Gln
1               5                   10                  15

Gly

<210> SEQ ID NO 35
<211> LENGTH: 19
<212> TYPE: PRT
<213> ORGANISM: Homo sapiens
<220> FEATURE:
<223> OTHER INFORMATION: 1021E5 VH CDR3 amino acid sequence

<400> SEQUENCE: 35

Ser Ser Arg Ile Tyr Asp Tyr Ala Gly Gly Asp His Tyr Tyr Tyr Asp
1               5                   10                  15

Met Asp Val

<210> SEQ ID NO 36
<211> LENGTH: 330
<212> TYPE: DNA
<213> ORGANISM: Homo sapiens
<220> FEATURE:
<223> OTHER INFORMATION: 1021E5 VL nucleotide sequence

<400> SEQUENCE: 36
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag cccccaaact cctcatttat gacaataata gcgaccctca gggattcct     180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 37
<211> LENGTH: 110
<212> TYPE: PRT
<213> ORGANISM: Homo sapiens
<220> FEATURE:
<223> OTHER INFORMATION: 1021E5 VL amino acid sequence

<400> SEQUENCE: 37

```
Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
        100                 105                 110

<210> SEQ ID NO 38
<211> LENGTH: 13
<212> TYPE: PRT
<213> ORGANISM: Homo sapiens
<220> FEATURE:
<223> OTHER INFORMATION: 1021E5 VL CDR1 amino acid sequence

<400> SEQUENCE: 38

Ser Gly Ser Ser Asn Ile Gly Asn Asn Tyr Val Ser
1               5                   10

<210> SEQ ID NO 39
<211> LENGTH: 7
<212> TYPE: PRT
<213> ORGANISM: Homo sapiens
<220> FEATURE:
<223> OTHER INFORMATION: 1021E5 VL CDR2 amino acid sequence

<400> SEQUENCE: 39

Asp Asn Asn Lys Arg Pro Ser
1               5

<210> SEQ ID NO 40
<211> LENGTH: 11
<212> TYPE: PRT
<213> ORGANISM: Homo sapiens
<220> FEATURE:
<223> OTHER INFORMATION: 1021E5 VL CDR3 amino acid sequence

<400> SEQUENCE: 40

Gly Thr Trp Asp Ser Ser Leu Ser Ala Trp Val
1               5                   10

<210> SEQ ID NO 41
<211> LENGTH: 366
<212> TYPE: DNA
<213> ORGANISM: Homo sapiens
<220> FEATURE:
<223> OTHER INFORMATION: 1033G9 VH nucleotide sequence

<400> SEQUENCE: 41
gaagtgcagc tggtgcagtc tggggctgag gtgaggaagc ctgggtcctc cgtgaaggtc      60
tcctgcaagg cttctggaga cacctccacc ttgtattcta tcaactgggt gcgacaggtc    120
cctggacaag gacttgagtg gatgggagcg atcatcccta tctttggttt aacagactac    180
gcacaggagt tccagggcag actcacgatt accgcggacg aatccacgaa cacagcctac    240
atggagctga ccggcctgag gtctgaggac acggccatat attattgtgc gagaaatctc    300
```

```
tttacaactc tcagctactg gtacttcgat ctctggggcc aaggaaccct ggtcaccgtc    360
tcgagt                                                              366
```

<210> SEQ ID NO 42
<211> LENGTH: 122
<212> TYPE: PRT
<213> ORGANISM: Homo sapiens
<220> FEATURE:
<223> OTHER INFORMATION: 1033G9 VH amino acid sequence

<400> SEQUENCE: 42

```
Glu Val Gln Leu Val Gln Ser Gly Ala Glu Val Arg Lys Pro Gly Ser
1               5                   10                  15

Ser Val Lys Val Ser Cys Lys Ala Ser Gly Asp Thr Ser Thr Leu Tyr
            20                  25                  30

Ser Ile Asn Trp Val Arg Gln Val Pro Gly Gln Gly Leu Glu Trp Met
        35                  40                  45

Gly Ala Ile Ile Pro Ile Phe Gly Leu Thr Asp Tyr Ala Gln Glu Phe
    50                  55                  60

Gln Gly Arg Leu Thr Ile Thr Ala Asp Glu Ser Thr Asn Thr Ala Tyr
65                  70                  75                  80

Met Glu Leu Thr Gly Leu Arg Ser Glu Asp Thr Ala Ile Tyr Tyr Cys
                85                  90                  95

Ala Arg Asn Leu Phe Thr Thr Leu Ser Tyr Trp Tyr Phe Asp Leu Trp
            100                 105                 110

Gly Gln Gly Thr Leu Val Thr Val Ser Ser
        115                 120
```

<210> SEQ ID NO 43
<211> LENGTH: 5
<212> TYPE: PRT
<213> ORGANISM: Homo sapiens
<220> FEATURE:
<223> OTHER INFORMATION: 1033G9 VH CDR1 amino acid sequence

<400> SEQUENCE: 43

```
Leu Tyr Ser Ile Asn
1               5
```

<210> SEQ ID NO 44
<211> LENGTH: 17
<212> TYPE: PRT
<213> ORGANISM: Homo sapiens
<220> FEATURE:
<223> OTHER INFORMATION: 1033G9 VH CDR2 amino acid sequence

<400> SEQUENCE: 44

```
Ala Ile Ile Pro Ile Phe Gly Leu Thr Asp Tyr Ala Gln Glu Phe Gln
1               5                   10                  15

Gly
```

<210> SEQ ID NO 45
<211> LENGTH: 13
<212> TYPE: PRT
<213> ORGANISM: Homo sapiens
<220> FEATURE:
<223> OTHER INFORMATION: 1033G9 VH CDR3 amino acid sequence

<400> SEQUENCE: 45

```
Asn Leu Phe Thr Thr Leu Ser Tyr Trp Tyr Phe Asp Leu
1               5                   10
```

<210> SEQ ID NO 46
<211> LENGTH: 324
<212> TYPE: DNA
<213> ORGANISM: Homo sapiens
<220> FEATURE:
<223> OTHER INFORMATION: 1033G9 VL nucleotide sequence

<400> SEQUENCE: 46

```
tcgtctgagc tgactcagga ccctgctgtg tctgtggcct tgggacagac agtcaggatc      60
acttgccaag agacagact cagaagctat tatgcaagct ggtaccagca gaagccagga     120
caggcccctg tacttgtcat ctatggtaaa aacaaccggc cctcagggat cccagaccga     180
ttctctggct ccagctcagg aaacacagct tccttgacca tcactggggc tcaggcggaa     240
gatgaggctg actattactg taactcccgg gacagcagtg gtaaccatgt ggtattcggc     300
ggagggaccc tgctgaccgt cctg                                             324
```

<210> SEQ ID NO 47
<211> LENGTH: 108
<212> TYPE: PRT
<213> ORGANISM: Homo sapiens
<220> FEATURE:
<223> OTHER INFORMATION: 1033G9 VL amino acid sequence

<400> SEQUENCE: 47

Ser Ser Glu Leu Thr Gln Asp Pro Ala Val Ser Val Ala Leu Gly Gln
1               5                   10                  15

Thr Val Arg Ile Thr Cys Gln Gly Asp Arg Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Leu Leu Thr Val Leu
            100                 105

<210> SEQ ID NO 48
<211> LENGTH: 11
<212> TYPE: PRT
<213> ORGANISM: Homo sapiens
<220> FEATURE:
<223> OTHER INFORMATION: 1033G9 VL CDR1 amino acid sequence

<400> SEQUENCE: 48

Gln Gly Asp Arg Leu Arg Ser Tyr Tyr Ala Ser
1               5                   10

<210> SEQ ID NO 49
<211> LENGTH: 7
<212> TYPE: PRT
<213> ORGANISM: Homo sapiens
<220> FEATURE:
<223> OTHER INFORMATION: 1033G9 VL CDR2 amino acid sequence

<400> SEQUENCE: 49

Gly Lys Asn Asn Arg Pro Ser
1               5

```
<210> SEQ ID NO 50
<211> LENGTH: 11
<212> TYPE: PRT
<213> ORGANISM: Homo sapiens
<220> FEATURE:
<223> OTHER INFORMATION: 1033G9 VL CDR3 amino acid sequence

<400> SEQUENCE: 50

Asn Ser Arg Asp Ser Ser Gly Asn His Val Val
1               5                   10

<210> SEQ ID NO 51
<211> LENGTH: 378
<212> TYPE: DNA
<213> ORGANISM: Homo sapiens
<220> FEATURE:
<223> OTHER INFORMATION: 1016A8 VH nucleotide sequence

<400> SEQUENCE: 51
gaggtccagc tggtgcagtc tggggctgag ctgaagaagc ctggggcctc agtgaaggtt      60
tcctgcaagg catctggata ccccttcacc agctactata tgcactgggt gcggcaggcc     120
cctggacaag gcttgagtg gatgggactt gttgatcctg aagatggtga acaatatac      180 gcagagaagt tccagggcag agtcaccata accgcggaca cgtctacaga cacagcctac     240
atggagctga gcagcctgag atctgaggac acggccgtgt attcctgtgc aacatccagt     300
cacaactatg gaccgcgtc ctactaccac tacggcatgg acgtctgggg caggggggaca    360 atggtcaccg tctcttca                                                   378

<210> SEQ ID NO 52
<211> LENGTH: 126
<212> TYPE: PRT
<213> ORGANISM: Homo sapiens
<220> FEATURE:
<223> OTHER INFORMATION: 1016A8 VH amino acid sequence

<400> SEQUENCE: 52

Glu Val Gln Leu Val Gln Ser Gly Ala Glu Leu Lys Lys Pro Gly Ala
1               5                   10                  15

Ser Val Lys Val Ser Cys Lys Ala Ser Gly Tyr Pro Phe Thr Ser Tyr
                20                  25                  30

Tyr Met His Trp Val Arg Gln Ala Pro Gly Gln Gly Leu Glu Trp Met
            35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Ser Cys
                85                  90                  95

Ala Thr Ser Ser His Asn Tyr Gly Thr Ala Ser Tyr Tyr His Tyr Gly
            100                 105                 110

Met Asp Val Trp Gly Arg Gly Thr Met Val Thr Val Ser Ser
        115                 120                 125

<210> SEQ ID NO 53
<211> LENGTH: 5
<212> TYPE: PRT
<213> ORGANISM: Homo sapiens
<220> FEATURE:
<223> OTHER INFORMATION: 1016A8 VH CDR1 amino acid sequence
```

<400> SEQUENCE: 53

Ser Tyr Tyr Met His
1               5

<210> SEQ ID NO 54
<211> LENGTH: 17
<212> TYPE: PRT
<213> ORGANISM: Homo sapiens
<220> FEATURE:
<223> OTHER INFORMATION: 1016A8 VH CDR2 amino acid sequence

<400> SEQUENCE: 54

Leu Val Asp Pro Glu Asp Gly Glu Thr Ile Tyr Ala Glu Lys Phe Gln
1               5                   10                  15

Gly

<210> SEQ ID NO 55
<211> LENGTH: 17
<212> TYPE: PRT
<213> ORGANISM: Homo sapiens
<220> FEATURE:
<223> OTHER INFORMATION: 1016A8 VH CDR3 amino acid sequence

<400> SEQUENCE: 55

Ser Ser His Asn Tyr Gly Thr Ala Ser Tyr Tyr His Tyr Gly Met Asp
1               5                   10                  15

Val

<210> SEQ ID NO 56
<211> LENGTH: 330
<212> TYPE: DNA
<213> ORGANISM: Homo sapiens
<220> FEATURE:
<223> OTHER INFORMATION: 1016A8 VL nucleotide sequence

<400> SEQUENCE: 56
cagtctgtgc tgactcagcc accctcagcg tctgggaccc ccgggcagag ggtcaccatc      60
tcttgttctg gaagcagctc aacatcggg agtaacactg taaactggta ccagcgactc     120
ccaggagcgg ccccccaact cctcatctac aataatgacc agcggccctc agggatccct    180
gaccgattct ctggctccaa gtctggcacc tcaggctccc tggtcatcag tgggctccag    240
tctgaagatg aggctgatta ctactgtgcg tcatgggatg acagtctgaa tggtcgggtg    300
ttcggcggag ggaccaagct gaccgtccta                                      330

<210> SEQ ID NO 57
<211> LENGTH: 110
<212> TYPE: PRT
<213> ORGANISM: Homo sapiens
<220> FEATURE:
<223> OTHER INFORMATION: 1016A8 VL amino acid sequence

<400> SEQUENCE: 57

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Arg Leu Pro Gly Ala Ala Pro Gln Leu Leu
            35                  40                  45

Ile Tyr Asn Asn Asp Gln Arg Pro Ser Gly Ile Pro Asp Arg Phe Ser
        50                  55                  60

Gly Ser Lys Ser Gly Thr Ser Gly Ser Leu Val Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Gly Arg Val Phe Gly Gly Gly Thr Lys Leu Thr Val Leu
            100                 105                 110

<210> SEQ ID NO 58
<211> LENGTH: 13
<212> TYPE: PRT
<213> ORGANISM: Homo sapiens
<220> FEATURE:
<223> OTHER INFORMATION: 1016A8 VL CDR1 amino acid sequence

<400> SEQUENCE: 58

Ser Gly Ser Ser Ser Asn Ile Gly Ser Asn Thr Val Asn
1               5                   10

<210> SEQ ID NO 59
<211> LENGTH: 7
<212> TYPE: PRT
<213> ORGANISM: Homo sapiens
<220> FEATURE:
<223> OTHER INFORMATION: 1016A8 VL CDR2 amino acid sequence

<400> SEQUENCE: 59

Asn Asn Asp Gln Arg Pro Ser
1               5

<210> SEQ ID NO 60
<211> LENGTH: 11
<212> TYPE: PRT
<213> ORGANISM: Homo sapiens
<220> FEATURE:
<223> OTHER INFORMATION: 1016A8 VL CDR3 amino acid sequence

<400> SEQUENCE: 60

Ala Ser Trp Asp Asp Ser Leu Asn Gly Arg Val
1               5                   10

<210> SEQ ID NO 61
<211> LENGTH: 366
<212> TYPE: DNA
<213> ORGANISM: Homo sapiens
<220> FEATURE:
<223> OTHER INFORMATION: 1028F8 VH nucleotide sequence

<400> SEQUENCE: 61
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attattggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagccggc     300
ggcagtggct ggttcgagaa ctggttcgac ccctggggcc ggggcaccct ggtcaccgtc     360
tcgagt                                                                366

<210> SEQ ID NO 62
<211> LENGTH: 122
<212> TYPE: PRT
<213> ORGANISM: Homo sapiens
<220> FEATURE:

<223> OTHER INFORMATION: 1028F8 VH amino acid sequence

<400> SEQUENCE: 62

Glu Val Gln Leu Leu Glu Ser Gly Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Gly Ser Gly Trp Phe Glu Asn Trp Phe Asp Pro Trp
            100                 105                 110

Gly Arg Gly Thr Leu Val Thr Val Ser Ser
        115                 120

<210> SEQ ID NO 63
<211> LENGTH: 5
<212> TYPE: PRT
<213> ORGANISM: Homo sapiens
<220> FEATURE:
<223> OTHER INFORMATION: 1028F8 VH CDR1 amino acid sequence

<400> SEQUENCE: 63

Ser Tyr Ala Met Ser
1               5

<210> SEQ ID NO 64
<211> LENGTH: 17
<212> TYPE: PRT
<213> ORGANISM: Homo sapiens
<220> FEATURE:
<223> OTHER INFORMATION: 1028F8 VH CDR2 amino acid sequence

<400> SEQUENCE: 64

Ala Ile Ile Gly Ser Gly Gly Ser Thr Tyr Tyr Ala Asp Ser Val Lys
1               5                   10                  15

Gly

<210> SEQ ID NO 65
<211> LENGTH: 13
<212> TYPE: PRT
<213> ORGANISM: Homo sapiens
<220> FEATURE:
<223> OTHER INFORMATION: 1028F8 VH CDR3 amino acid sequence

<400> SEQUENCE: 65

Ala Gly Gly Ser Gly Trp Phe Glu Asn Trp Phe Asp Pro
1               5                   10

<210> SEQ ID NO 66
<211> LENGTH: 324
<212> TYPE: DNA
<213> ORGANISM: Homo sapiens
<220> FEATURE:
<223> OTHER INFORMATION: 1028F8 VL nucleotide sequence

<400> SEQUENCE: 66

```
cagtctgtgc tgacgcagcc gccctctgtg tccgtgtccc caggacagac agccaccatc    60
acctgctctg gagacaattt ggaagataag tatgtttctt ggtatcaaca aaaggcaggc   120
cagtcccctg tgttggtcat ctttcaggat tctaagcggc cctcagagat ccctgagcga   180
ttctctggct ccaactcagg gaacacagcc actctaacca tcagcgggac cctgagtggg   240
gatgaggctg actattactg tcaggtgtgg gacgccggaa ttgacccttg ggctttcggc   300
ggagggacca agctgaccgt ccta                                          324
```

```
<210> SEQ ID NO 67
<211> LENGTH: 108
<212> TYPE: PRT
<213> ORGANISM: Homo sapiens
<220> FEATURE:
<223> OTHER INFORMATION: 1028F8 VL amino acid sequence

<400> SEQUENCE: 67
```

Gln Ser Val Leu Thr Gln Pro Pro Ser Val Ser Val Ser Pro Gly Gln
1               5                   10                  15

Thr Ala Thr Ile Thr Cys Ser Gly Asp Asn Leu Glu Asp Lys Tyr Val
            20                  25                  30

Ser Trp Tyr Gln Gln Lys Ala Gly Gln Ser Pro Val Leu Val Ile Phe
        35                  40                  45

Gln Asp Ser Lys Arg Pro Ser Glu Ile Pro Glu Arg Phe Ser Gly Ser
    50                  55                  60

Asn Ser Gly Asn Thr Ala Thr Leu Thr Ile Ser Gly Thr Leu Ser Gly
65                  70                  75                  80

Asp Glu Ala Asp Tyr Tyr Cys Gln Val Trp Asp Ala Gly Ile Asp Pro
                85                  90                  95

Trp Ala Phe Gly Gly Gly Thr Lys Leu Thr Val Leu
            100                 105

```
<210> SEQ ID NO 68
<211> LENGTH: 11
<212> TYPE: PRT
<213> ORGANISM: Homo sapiens
<220> FEATURE:
<223> OTHER INFORMATION: 1028F8 VL CDR1 amino acid sequence

<400> SEQUENCE: 68
```

Ser Gly Asp Asn Leu Glu Asp Lys Tyr Val Ser
1               5                   10

```
<210> SEQ ID NO 69
<211> LENGTH: 7
<212> TYPE: PRT
<213> ORGANISM: Homo sapiens
<220> FEATURE:
<223> OTHER INFORMATION: 1028F8 VL CDR2 amino acid sequence

<400> SEQUENCE: 69
```

Gln Asp Ser Lys Arg Pro Ser
1               5

```
<210> SEQ ID NO 70
<211> LENGTH: 11
<212> TYPE: PRT
<213> ORGANISM: Homo sapiens
<220> FEATURE:
<223> OTHER INFORMATION: 1028F8 VL CDR3 amino acid sequence

<400> SEQUENCE: 70
```

Gln Val Trp Asp Ala Gly Ile Asp Pro Trp Ala
1               5                   10

<210> SEQ ID NO 71
<211> LENGTH: 387
<212> TYPE: DNA
<213> ORGANISM: Homo sapiens
<220> FEATURE:
<223> OTHER INFORMATION: 1033B2 VH nucleotide sequence

<400> SEQUENCE: 71

```
caggtacagc tgcagcagtc aggggctgag gtgaagaagc ctgggtcctc ggtgaagctc    60
tcctgcaagg cttctggagg caccttcagc tcctttggta tcagctgggt gcggcaggcc   120
cctggacaag gcttgagtg gctgggaagg atcatccctt tccttggtcc agcggactac   180
gcacagaagt tccagggcag agtcacgatt accgcgacg aatccaggag cacagcgtac   240
atggaactga gcagcctgac atctgaggac acggccgtct atttctgtgc gagatccttc   300
tacgatattt tgacgggtta ttatgagggg gtcttctact actacatgga cgtctggggc   360
caagggacaa tggtcaccgt ctcgagt                                        387
```

<210> SEQ ID NO 72
<211> LENGTH: 129
<212> TYPE: PRT
<213> ORGANISM: Homo sapiens
<220> FEATURE:
<223> OTHER INFORMATION: 1033B2 VH amino acid sequence

<400> SEQUENCE: 72

Gln Val Gln Leu Gln Gln Ser Gly Ala Glu Val Lys Lys Pro Gly Ser
1               5                   10                  15

Ser Val Lys Leu Ser Cys Lys Ala Ser Gly Gly Thr Phe Ser Ser Phe
            20                  25                  30

Gly Ile Ser Trp Val Arg Gln Ala Pro Gly Gln Gly Leu Glu Trp Leu
        35                  40                  45

Gly Arg Ile Ile Pro Phe Leu Gly Pro Ala Asp Tyr Ala Gln Lys Phe
    50                  55                  60

Gln Gly Arg Val Thr Ile Thr Ala Asp Glu Ser Arg Ser Thr Ala Tyr
65                  70                  75                  80

Met Glu Leu Ser Ser Leu Thr Ser Glu Asp Thr Ala Val Tyr Phe Cys
                85                  90                  95

Ala Arg Ser Phe Tyr Asp Ile Leu Thr Gly Tyr Tyr Glu Gly Val Phe
            100                 105                 110

Tyr Tyr Tyr Met Asp Val Trp Gly Gln Gly Thr Met Val Thr Val Ser
        115                 120                 125

Ser

<210> SEQ ID NO 73
<211> LENGTH: 5
<212> TYPE: PRT
<213> ORGANISM: Homo sapiens
<220> FEATURE:
<223> OTHER INFORMATION: 1033B2 VH CDR1 amino acid sequence

<400> SEQUENCE: 73

Ser Phe Gly Ile Ser
1               5

<210> SEQ ID NO 74
<211> LENGTH: 17

```
<212> TYPE: PRT
<213> ORGANISM: Homo sapiens
<220> FEATURE:
<223> OTHER INFORMATION: 1033B2 VH CDR2 amino acid sequence

<400> SEQUENCE: 74

Arg Ile Ile Pro Phe Leu Gly Pro Ala Asp Tyr Ala Gln Lys Phe Gln
1               5                   10                  15

Gly

<210> SEQ ID NO 75
<211> LENGTH: 20
<212> TYPE: PRT
<213> ORGANISM: Homo sapiens
<220> FEATURE:
<223> OTHER INFORMATION: 1033B2 VH CDR3 amino acid sequence

<400> SEQUENCE: 75

Ser Phe Tyr Asp Ile Leu Thr Gly Tyr Tyr Glu Gly Val Phe Tyr Tyr
1               5                   10                  15

Tyr Met Asp Val
            20

<210> SEQ ID NO 76
<211> LENGTH: 330
<212> TYPE: DNA
<213> ORGANISM: Homo sapiens
<220> FEATURE:
<223> OTHER INFORMATION: 1033B2 VL nucleotide sequence

<400> SEQUENCE: 76
cagtctgtgc tgattcagcc tgcctccgtg tctgggtccc ctggacagtc gatcaccatc     60
tcctgcactg gaaccagcag tgacgttggt ggttataact atgtctcctg gtaccaacaa    120
cacccaggca agccccccaa actcatgatt tatgagggca gtaagcggcc ctcaggggtt    180
tctaatcgct tctctggctc caagtctggc aacacggcct ccctgacaat ctctgggctc    240
caggctgagg acgaggctga ttattactgc agctcatata accaggagag cactcgagtt    300
tttggcggag ggaccaagct gaccgtccta                                     330

<210> SEQ ID NO 77
<211> LENGTH: 110
<212> TYPE: PRT
<213> ORGANISM: Homo sapiens
<220> FEATURE:
<223> OTHER INFORMATION: 1033B2 VL amino acid sequence

<400> SEQUENCE: 77

Gln Ser Val Leu Ile Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu
```

<210> SEQ ID NO 78
<211> LENGTH: 14
<212> TYPE: PRT
<213> ORGANISM: Homo sapiens
<220> FEATURE:
<223> OTHER INFORMATION: 1033B2 VL CDR1 amino acid sequence

<400> SEQUENCE: 78

Thr Gly Thr Ser Ser Asp Val Gly Gly Tyr Asn Tyr Val Ser
1               5                   10

<210> SEQ ID NO 79
<211> LENGTH: 7
<212> TYPE: PRT
<213> ORGANISM: Homo sapiens
<220> FEATURE:
<223> OTHER INFORMATION: 1033B2 VL CDR2 amino acid sequence

<400> SEQUENCE: 79

Glu Gly Ser Lys Arg Pro Ser
1               5

<210> SEQ ID NO 80
<211> LENGTH: 10
<212> TYPE: PRT
<213> ORGANISM: Homo sapiens
<220> FEATURE:
<223> OTHER INFORMATION: 1033B2 VL CDR3 amino acid sequence

<400> SEQUENCE: 80

Ser Ser Tyr Thr Thr Arg Ser Thr Arg Val
1               5                   10

<210> SEQ ID NO 81
<211> LENGTH: 387
<212> TYPE: DNA
<213> ORGANISM: Homo sapiens
<220> FEATURE:
<223> OTHER INFORMATION: 1024C4 VH nucleotide sequence

<400> SEQUENCE: 81
caggtgcagc tgcaggagtc ggggggaggc gtggtccagc ctggggaggtc cctgagactc     60 tcctgtgcag cctctggatt cgccttcaaa agtatggcc tgcactgggt ccgccaggct    120
ccaggcaagg gctggagtg gtgggcgtt acttcttatg atggaagtaa aaattactat    180
gcagactccg tgaagggccg attcaccatc tccagagaca attccaagaa cacgctgtat    240
ctgcaagtga acagcctgag acctgaggac acggctgtct attactgtgc gaaagatggg    300
gaggtggggg atcttcacct agtacctttc cgtcaggact ccggtttgga cgtctggggc    360
agaggcaccc tggtcaccgt ctcgagt                                        387

<210> SEQ ID NO 82
<211> LENGTH: 129
<212> TYPE: PRT
<213> ORGANISM: Homo sapiens
<220> FEATURE:
<223> OTHER INFORMATION: 1024C4 VH amino acid sequence

<400> SEQUENCE: 82

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Ala Phe Lys Lys Tyr

```
                    20                  25                  30
Gly Leu His Trp Val Arg Gln Ala Pro Gly Lys Gly Leu Glu Trp Val
                35                  40                  45

Gly Val Thr Ser Tyr Asp Gly Ser Lys Asn Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Pro Glu Asp Thr Ala Val Tyr Tyr Cys
                85                  90                  95

Ala Lys Asp Gly Glu Val Gly Asp Leu His Leu Val Pro Phe Arg Gln
            100                 105                 110

Asp Ser Gly Leu Asp Val Trp Gly Arg Gly Thr Leu Val Thr Val Ser
                115                 120                 125

Ser

<210> SEQ ID NO 83
<211> LENGTH: 5
<212> TYPE: PRT
<213> ORGANISM: Homo sapiens
<220> FEATURE:
<223> OTHER INFORMATION: 1024C4 VH CDR1 amino acid sequence

<400> SEQUENCE: 83

Lys Tyr Gly Leu His
1               5

<210> SEQ ID NO 84
<211> LENGTH: 17
<212> TYPE: PRT
<213> ORGANISM: Homo sapiens
<220> FEATURE:
<223> OTHER INFORMATION: 1024C4 VH CDR2 amino acid sequence

<400> SEQUENCE: 84

Val Thr Ser Tyr Asp Gly Ser Lys Asn Tyr Tyr Ala Asp Ser Val Lys
1               5                   10                  15

Gly

<210> SEQ ID NO 85
<211> LENGTH: 20
<212> TYPE: PRT
<213> ORGANISM: Homo sapiens
<220> FEATURE:
<223> OTHER INFORMATION: 1024C4 VH CDR3 amino acid sequence

<400> SEQUENCE: 85

Asp Gly Glu Val Gly Asp Leu His Leu Val Pro Phe Arg Gln Asp Ser
1               5                   10                  15

Gly Leu Asp Val
            20

<210> SEQ ID NO 86
<211> LENGTH: 318
<212> TYPE: DNA
<213> ORGANISM: Homo sapiens
<220> FEATURE:
<223> OTHER INFORMATION: 1024C4 VL nucleotide sequence

<400> SEQUENCE: 86
cagtctgtgc tgactcagcc acccctcagtg tccgtgtccc caggacagac agccagcatc      60
acctgctctg gagataattt gggtgataaa tatgttcact ggtatcagca gaagccaggc     120
```

```
cagtcccctg tgctggtcac ttatcaagat accaagcgac cctcagggat ccctgaacga    180
ttctctggct ccaactctgg gaacacagcc actctgacca tcagcgggac ccaggctatg    240
gatgaggctg gctattactg tcaggcatgg gacagcagca ctgtggtatt cggcggaggg    300
accaagctga ccgtccta                                                  318
```

<210> SEQ ID NO 87
<211> LENGTH: 106
<212> TYPE: PRT
<213> ORGANISM: Homo sapiens
<220> FEATURE:
<223> OTHER INFORMATION: 1024C4 VL amino acid sequence

<400> SEQUENCE: 87

```
Gln Ser Val Leu Thr Gln Pro Pro Ser Val Ser Val Ser Pro Gly Gln
1               5                   10                  15

Thr Ala Ser Ile Thr Cys Ser Gly Asp Asn Leu Gly Asp Lys Tyr Val
            20                  25                  30

His Trp Tyr Gln Gln Lys Pro Gly Gln Ser Pro Val Leu Val Thr Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Gly Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 88
<211> LENGTH: 11
<212> TYPE: PRT
<213> ORGANISM: Homo sapiens
<220> FEATURE:
<223> OTHER INFORMATION: 1024C4 VL CDR1 amino acid sequence

<400> SEQUENCE: 88

```
Ser Gly Asp Asn Leu Gly Asp Lys Tyr Val His
1               5                   10
```

<210> SEQ ID NO 89
<211> LENGTH: 7
<212> TYPE: PRT
<213> ORGANISM: Homo sapiens
<220> FEATURE:
<223> OTHER INFORMATION: 1024C4 VL CDR2 amino acid sequence

<400> SEQUENCE: 89

```
Gln Asp Thr Lys Arg Pro Ser
1               5
```

<210> SEQ ID NO 90
<211> LENGTH: 9
<212> TYPE: PRT
<213> ORGANISM: Homo sapiens
<220> FEATURE:
<223> OTHER INFORMATION: 1024C4 VL CDR3 amino acid sequence

<400> SEQUENCE: 90

```
Gln Ala Trp Asp Ser Ser Thr Val Val
1               5
```

<210> SEQ ID NO 91
<211> LENGTH: 363
<212> TYPE: DNA
<213> ORGANISM: Homo sapiens
<220> FEATURE:
<223> OTHER INFORMATION: 1057F11 VH nucleotide sequence

<400> SEQUENCE: 91

```
gaggtgcagc tggtggagac tgggggaggc gtggtccagc ctgggacgtc cctgagactc      60
tcctgtgcag cgtctggatt caccttcagt agccatggca tgcactgggt ccgccaggct     120
ccaggccagg ggctggagtg ggtggcacat gcatggtctg atggaagtaa taaatattat     180
gcagactccc tgaagggccg attcaccatc tccagagaca attccaggaa cacgctgtat     240
ctgcagatga acagcctgag agccgaggac acggctgtat attactgtgc gagagatgga     300
cagcagctgg ccaactacgc tatggacgtc tggggcggg ggaccacggt caccgtctcg     360
agt                                                                   363
```

<210> SEQ ID NO 92
<211> LENGTH: 121
<212> TYPE: PRT
<213> ORGANISM: Homo sapiens
<220> FEATURE:
<223> OTHER INFORMATION: 1057F11 VH amino acid sequence

<400> SEQUENCE: 92

Glu Val Gln Leu Val Glu Thr Gly Gly Gly Val Val Gln Pro Gly Thr
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Gln Gly Leu Glu Trp Val
        35                  40                  45

Ala His Ala Trp Ser Asp Gly Ser Asn Lys Tyr Tyr Ala Asp Ser Leu
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Gln Leu Ala Asn Tyr Ala Met Asp Val Trp Gly
            100                 105                 110

Arg Gly Thr Thr Val Thr Val Ser Ser
        115                 120

<210> SEQ ID NO 93
<211> LENGTH: 5
<212> TYPE: PRT
<213> ORGANISM: Homo sapiens
<220> FEATURE:
<223> OTHER INFORMATION: 1057F11 VH CDR1 amino acid sequence

<400> SEQUENCE: 93

Ser His Gly Met His
1               5

<210> SEQ ID NO 94
<211> LENGTH: 17
<212> TYPE: PRT
<213> ORGANISM: Homo sapiens
<220> FEATURE:
<223> OTHER INFORMATION: 1057F11 VH CDR2 amino acid sequence

```
<400> SEQUENCE: 94

His Ala Trp Ser Asp Gly Ser Asn Lys Tyr Tyr Ala Asp Ser Leu Lys
1               5                   10                  15

Gly

<210> SEQ ID NO 95
<211> LENGTH: 12
<212> TYPE: PRT
<213> ORGANISM: Homo sapiens
<220> FEATURE:
<223> OTHER INFORMATION: 1057F11 VH CDR3 amino acid sequence

<400> SEQUENCE: 95

Asp Gly Gln Gln Leu Ala Asn Tyr Ala Met Asp Val
1               5                   10

<210> SEQ ID NO 96
<211> LENGTH: 321
<212> TYPE: DNA
<213> ORGANISM: Homo sapiens
<220> FEATURE:
<223> OTHER INFORMATION: 1057F11 VL nucleotide sequence

<400> SEQUENCE: 96
gacatccaga tgacccagtc tccatccttc ctgtctgcat ctgtaggaga cagagtcacc      60
atcacttgcc gggccagtca gggcattaac agttatttag cctggtatca gcaaatacca    120
gggaaagccc ctaacctcct gatctatgct gcatccactt tgcaaagtgg ggtcccatca    180
aggttcagcg gcagtggatc tgggacagaa ttcactctca caatcagcag cctgcagcct    240
gaagattttg cgacttatta ctgtcaacag cttaatactt accccttcac tttcggccct    300
gggactaagg tggaaatcaa a                                              321

<210> SEQ ID NO 97
<211> LENGTH: 107
<212> TYPE: PRT
<213> ORGANISM: Homo sapiens
<220> FEATURE:
<223> OTHER INFORMATION: 1057F11 VL amino acid sequence

<400> SEQUENCE: 97

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Asn Ser Tyr
            20                  25                  30

Leu Ala Trp Tyr Gln Gln Ile Pro Gly Lys Ala Pro Asn Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Thr Tyr Pro Phe
                85                  90                  95

Thr Phe Gly Pro Gly Thr Lys Val Glu Ile Lys
            100                 105

<210> SEQ ID NO 98
<211> LENGTH: 11
<212> TYPE: PRT
<213> ORGANISM: Homo sapiens
<220> FEATURE:
```

<223> OTHER INFORMATION: 1057F11 VL CDR1 amino acid sequence

<400> SEQUENCE: 98

Arg Ala Ser Gln Gly Ile Asn Ser Tyr Leu Ala
1               5                   10

<210> SEQ ID NO 99
<211> LENGTH: 7
<212> TYPE: PRT
<213> ORGANISM: Homo sapiens
<220> FEATURE:
<223> OTHER INFORMATION: 1057F11 VL CDR2 amino acid sequence

<400> SEQUENCE: 99

Ala Ala Ser Thr Leu Gln Ser
1               5

<210> SEQ ID NO 100
<211> LENGTH: 9
<212> TYPE: PRT
<213> ORGANISM: Homo sapiens
<220> FEATURE:
<223> OTHER INFORMATION: 1057F11 VL CDR3 amino acid sequence

<400> SEQUENCE: 100

Gln Gln Leu Asn Thr Tyr Pro Phe Thr
1               5

<210> SEQ ID NO 101
<211> LENGTH: 385
<212> TYPE: DNA
<213> ORGANISM: Homo sapiens
<220> FEATURE:
<223> OTHER INFORMATION: 1126F1 VH nucleotide sequence

<400> SEQUENCE: 101

```
gaggtgcagc tggtgcagac tggggctgag gtgaagaagc ctgggtcctc ggtgaaggtc    60
tcctgcaagg cttctggagg caccttcagc acctatggta tctcatgggt gcgacaggcc   120
cctggacaag gacttgagtg gataggaggg attattccta tctttgacac aggcaactct   180
gcacagagct tccagggcag agtcacgatt accgcgacg aatccacgag cacagcctac   240
atggaggtga gcagcctgag atctgacgac acggccgtat attattgtgc aagttcaagt   300
cgtatctacg acgccaaccg ccaggccgtc cctactacg atatggatgt ctggggccag   360
gggacaatgg tcaccgtctc ctcag                                          385
```

<210> SEQ ID NO 102
<211> LENGTH: 128
<212> TYPE: PRT
<213> ORGANISM: Homo sapiens
<220> FEATURE:
<223> OTHER INFORMATION: 1126F1 VH amino acid sequence

<400> SEQUENCE: 102

Glu Val Gln Leu Val Gln Thr Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Gly Ile Ser Trp Val Arg Gln Ala Pro Gly Gln Gly Leu Glu Trp Ile
            35                  40                  45

Gly Gly Ile Ile Pro Ile Phe Asp Thr Gly Asn Ser Ala Gln Ser Phe
        50                  55                  60

```
Gln Gly Arg Val Thr Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                 85                  90                  95

Ala Ser Ser Arg Ile Tyr Asp Ala Asn Arg Gln Ala Val Pro Tyr
            100                 105                 110

Tyr Asp Met Asp Val Trp Gly Gln Gly Thr Met Val Thr Val Ser Ser
        115                 120                 125
```

<210> SEQ ID NO 103
<211> LENGTH: 5
<212> TYPE: PRT
<213> ORGANISM: Homo sapiens
<220> FEATURE:
<223> OTHER INFORMATION: 1126F1 VH CDR1 amino acid sequence

<400> SEQUENCE: 103

```
Thr Tyr Gly Ile Ser
 1               5
```

<210> SEQ ID NO 104
<211> LENGTH: 17
<212> TYPE: PRT
<213> ORGANISM: Homo sapiens
<220> FEATURE:
<223> OTHER INFORMATION: 1126F1 VH CDR2 amino acid sequence

<400> SEQUENCE: 104

```
Gly Ile Ile Pro Ile Phe Asp Thr Gly Asn Ser Ala Gln Ser Phe Gln
 1               5                  10                  15

Gly
```

<210> SEQ ID NO 105
<211> LENGTH: 19
<212> TYPE: PRT
<213> ORGANISM: Homo sapiens
<220> FEATURE:
<223> OTHER INFORMATION: 1126F1 VH CDR3 amino acid sequence

<400> SEQUENCE: 105

```
Ser Ser Arg Ile Tyr Asp Ala Asn Arg Gln Ala Val Pro Tyr Tyr Asp
 1               5                  10                  15

Met Asp Val
```

<210> SEQ ID NO 106
<211> LENGTH: 330
<212> TYPE: DNA
<213> ORGANISM: Homo sapiens
<220> FEATURE:
<223> OTHER INFORMATION: 1126F1 VL nucleotide sequence

<400> SEQUENCE: 106

```
caggctgtgc tgactcagcc gtcctcggtg tctacgcccc caggacagat ggtcaccatc      60
tcctgctctg gaagcagctc cgacattggg aataattatg tatcgtggta ccagcagctc     120
ccaggaacag cccccaaact cctcatttat gacaataata gcgaccctca agggattcct     180
gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                       330
```

<210> SEQ ID NO 107

```
<211> LENGTH: 110
<212> TYPE: PRT
<213> ORGANISM: Homo sapiens
<220> FEATURE:
<223> OTHER INFORMATION: 1126F1 VL amino acid sequence

<400> SEQUENCE: 107

Gln Ala Val Leu Thr Gln Pro Ser Ser Val Ser Thr Pro Pro Gly Gln
1               5                   10                  15

Met Val Thr Ile Ser Cys Ser Gly Ser Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 108
<211> LENGTH: 13
<212> TYPE: PRT
<213> ORGANISM: Homo sapiens
<220> FEATURE:
<223> OTHER INFORMATION: 1126F1 VL CDR1 amino acid sequence

<400> SEQUENCE: 108

Ser Gly Ser Ser Ser Asp Ile Gly Asn Asn Tyr Val Ser
1               5                   10

<210> SEQ ID NO 109
<211> LENGTH: 7
<212> TYPE: PRT
<213> ORGANISM: Homo sapiens
<220> FEATURE:
<223> OTHER INFORMATION: 1126F1 VL CDR2 amino acid sequence

<400> SEQUENCE: 109

Asp Asn Asn Lys Arg Pro Ser
1               5

<210> SEQ ID NO 110
<211> LENGTH: 11
<212> TYPE: PRT
<213> ORGANISM: Homo sapiens
<220> FEATURE:
<223> OTHER INFORMATION: 1126F1 VL CDR3 amino acid sequence

<400> SEQUENCE: 110

Gly Thr Trp Asp Ser Ser Leu Ser Ala Trp Val
1               5                   10

<210> SEQ ID NO 111
<211> LENGTH: 385
<212> TYPE: DNA
<213> ORGANISM: Homo sapiens
<220> FEATURE:
<223> OTHER INFORMATION: 1126G5 VH nucleotide sequence

<400> SEQUENCE: 111
gaggtgcagc tggtgcagtc tggggctgag gtgaagaagc ctgggtcctc ggtgaaggtc      60
```

```
tcctgcaagg cttctggagg caccttcagc acctatggta tctcatgggt gcgacaggcc    120
cctggacaag gccttgagtg gataggaggg attattccta tctttgacac aggcaactct    180
gcacagagct tccagggcag agtcacgatt accgcggacg aatccacgag cacagcctac    240
atggaggtga gcagcctgag atctgacgac acggccgtat attattgtgc aagttcaagt    300
cgtatctacg acttcacgtc cggcctcgct ccctactacg atatggatgt ctggggccag    360
gggacaatgg tcaccgtctc ctcag                                          385
```

<210> SEQ ID NO 112
<211> LENGTH: 128
<212> TYPE: PRT
<213> ORGANISM: Homo sapiens
<220> FEATURE:
<223> OTHER INFORMATION: 1126G5 VH amino acid sequence

<400> SEQUENCE: 112

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Phe Thr Ser Gly Leu Ala Pro Tyr
            100                 105                 110

Tyr Asp Met Asp Val Trp Gly Gln Gly Thr Met Val Thr Val Ser Ser
        115                 120                 125

<210> SEQ ID NO 113
<211> LENGTH: 5
<212> TYPE: PRT
<213> ORGANISM: Homo sapiens
<220> FEATURE:
<223> OTHER INFORMATION: 1126G5 VH CDR1 amino acid sequence

<400> SEQUENCE: 113

Thr Tyr Gly Ile Ser
1               5

<210> SEQ ID NO 114
<211> LENGTH: 17
<212> TYPE: PRT
<213> ORGANISM: Homo sapiens
<220> FEATURE:
<223> OTHER INFORMATION: 1126G5 VH CDR2 amino acid sequence

<400> SEQUENCE: 114

Gly Ile Ile Pro Ile Phe Asp Thr Gly Asn Ser Ala Gln Ser Phe Gln
1               5                   10                  15

Gly

<210> SEQ ID NO 115
<211> LENGTH: 19
<212> TYPE: PRT

```
<213> ORGANISM: Homo sapiens
<220> FEATURE:
<223> OTHER INFORMATION: 1126G5 VH CDR3 amino acid sequence

<400> SEQUENCE: 115

Ser Ser Arg Ile Tyr Asp Phe Thr Ser Gly Leu Ala Pro Tyr Tyr Asp
1               5                   10                  15

Met Asp Val

<210> SEQ ID NO 116
<211> LENGTH: 330
<212> TYPE: DNA
<213> ORGANISM: Homo sapiens
<220> FEATURE:
<223> OTHER INFORMATION: 1126G5 VL nucleotide sequence

<400> SEQUENCE: 116
caggctgtgc tgactcagcc gtcctcagtg tctacgcccc caggacagaa ggtcaccatc     60
tcctgctctg gaagcagctc aacattggg aataattatg tatcgtggta ccagcagctc    120
ccaggaacag ccccaaaact cctcatttat gacaataata gcgacccc agggattcct     180 gaccgattct ctggctccaa gtctggcacg tcagccaccc tgggcatcac cggactccag    240
actggggacg aggccgatta ttactgcgga acatgggata gcagcctgag tacttgggtg    300
ttcggcggag ggaccaagct gaccgtccta                                      330

<210> SEQ ID NO 117
<211> LENGTH: 110
<212> TYPE: PRT
<213> ORGANISM: Homo sapiens
<220> FEATURE:
<223> OTHER INFORMATION: 1126G5 VL amino acid sequence

<400> SEQUENCE: 117

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Pro Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Thr Trp Val Phe Gly Gly Gly Thr Lys Leu Thr Val Leu
            100                 105                 110

<210> SEQ ID NO 118
<211> LENGTH: 13
<212> TYPE: PRT
<213> ORGANISM: Homo sapiens
<220> FEATURE:
<223> OTHER INFORMATION: 1126G5 VL CDR1 amino acid sequence

<400> SEQUENCE: 118

Ser Gly Ser Ser Ser Asn Ile Gly Asn Asn Tyr Val Ser
1               5                   10

<210> SEQ ID NO 119
```

```
<211> LENGTH: 7
<212> TYPE: PRT
<213> ORGANISM: Homo sapiens
<220> FEATURE:
<223> OTHER INFORMATION: 1126G5 VL CDR2 amino acid sequence

<400> SEQUENCE: 119

Asp Asn Asn Lys Arg Pro Pro
1               5

<210> SEQ ID NO 120
<211> LENGTH: 11
<212> TYPE: PRT
<213> ORGANISM: Homo sapiens
<220> FEATURE:
<223> OTHER INFORMATION: 1126G5 VL CDR3 amino acid sequence

<400> SEQUENCE: 120

Gly Thr Trp Asp Ser Ser Leu Ser Thr Trp Val
1               5                   10

<210> SEQ ID NO 121
<211> LENGTH: 386
<212> TYPE: DNA
<213> ORGANISM: Homo sapiens
<220> FEATURE:
<223> OTHER INFORMATION: 1126H5 VH nucleotide sequence

<400> SEQUENCE: 121
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggaggg attattccta tctttgacgc aggcaactct     180
gcacagagct tccagggcag agtcacgatt accgcggacg aatccacgag cacagcccac     240
atggaggtga gcagcctgag atctgaagac acggccgtat attattgtgc aagttcaagt     300
cgtatctacg accaccacat ccagaagggg ggttactacg atatggatgt ctggggccag     360
gggacaatgg tcaccgtctc ctcagg                                          386

<210> SEQ ID NO 122
<211> LENGTH: 128
<212> TYPE: PRT
<213> ORGANISM: Homo sapiens
<220> FEATURE:
<223> OTHER INFORMATION: 1126H5 VH amino acid sequence

<400> SEQUENCE: 122

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Ala Gly Asn Ser Ala Gln Ser Phe
    50                  55                  60

Gln Gly Arg Val Thr Ile Thr Ala Asp Glu Ser Thr Ser Thr Ala His
65                  70                  75                  80

Met Glu Val Ser Ser Leu Arg Ser Glu Asp Thr Ala Val Tyr Tyr Cys
                85                  90                  95

Ala Ser Ser Arg Ile Tyr Asp His His Ile Gln Lys Gly Gly Tyr
            100                 105                 110
```

Tyr Asp Met Asp Val Trp Gly Gln Gly Thr Met Val Thr Val Ser Ser
        115                 120                 125

<210> SEQ ID NO 123
<211> LENGTH: 5
<212> TYPE: PRT
<213> ORGANISM: Homo sapiens
<220> FEATURE:
<223> OTHER INFORMATION: 1126H5 VH CDR1 amino acid sequence

<400> SEQUENCE: 123

Thr Tyr Gly Ile Ser
1               5

<210> SEQ ID NO 124
<211> LENGTH: 17
<212> TYPE: PRT
<213> ORGANISM: Homo sapiens
<220> FEATURE:
<223> OTHER INFORMATION: 1126H5 VH CDR2 amino acid sequence

<400> SEQUENCE: 124

Gly Ile Ile Pro Ile Phe Asp Ala Gly Asn Ser Ala Gln Ser Phe Gln
1               5                   10                  15

Gly

<210> SEQ ID NO 125
<211> LENGTH: 19
<212> TYPE: PRT
<213> ORGANISM: Homo sapiens
<220> FEATURE:
<223> OTHER INFORMATION: 1126H5 VH CDR3 amino acid sequence

<400> SEQUENCE: 125

Ser Ser Arg Ile Tyr Asp His His Ile Gln Lys Gly Gly Tyr Tyr Asp
1               5                   10                  15

Met Asp Val

<210> SEQ ID NO 126
<211> LENGTH: 331
<212> TYPE: DNA
<213> ORGANISM: Homo sapiens
<220> FEATURE:
<223> OTHER INFORMATION: 1126H5 VL nucleotide sequence

<400> SEQUENCE: 126
caggctgtgc tgactcagcc gtcctcagtg tctacgcccc aggacagaa ggtcaccatc     60
tcctgctctg gaagcagctc caacattggg aataattatg tatcgtggta ccagcagctc    120
ccaggaacag cccccaaact cctcatttat gacaataata gcgaccctc agggattcct    180
gaccgattct ctggctccaa gtccggcacg tcagccaccc tgggcatcac cggactccag    240
actggggacg aggccgatta ttactgcgga acatgggata gcagcctgag tgcttgggtg    300
ttcggcggag ggaccaagct gaccgtccct a                                   331

<210> SEQ ID NO 127
<211> LENGTH: 110
<212> TYPE: PRT
<213> ORGANISM: Homo sapiens
<220> FEATURE:
<223> OTHER INFORMATION: 1126H5 VL amino acid sequence

<400> SEQUENCE: 127

Gln Ala Val Leu Thr Gln Pro Ser Ser Val Ser Thr Pro Pro Gly Gln

```
                 1               5                  10                  15
Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 128
<211> LENGTH: 13
<212> TYPE: PRT
<213> ORGANISM: Homo sapiens
<220> FEATURE:
<223> OTHER INFORMATION: 1126H5 VL CDR1 amino acid sequence

<400> SEQUENCE: 128

Ser Gly Ser Ser Asn Ile Gly Asn Asn Tyr Val Ser
1               5                   10

<210> SEQ ID NO 129
<211> LENGTH: 7
<212> TYPE: PRT
<213> ORGANISM: Homo sapiens
<220> FEATURE:
<223> OTHER INFORMATION: 1126H5 VL CDR2 amino acid sequence

<400> SEQUENCE: 129

Asp Asn Asn Lys Arg Pro Ser
1               5

<210> SEQ ID NO 130
<211> LENGTH: 11
<212> TYPE: PRT
<213> ORGANISM: Homo sapiens
<220> FEATURE:
<223> OTHER INFORMATION: 1126H5 VL CDR3 amino acid sequence

<400> SEQUENCE: 130

Gly Thr Trp Asp Ser Ser Leu Ser Ala Trp Val
1               5                   10

<210> SEQ ID NO 131
<211> LENGTH: 378
<212> TYPE: DNA
<213> ORGANISM: Homo sapiens
<220> FEATURE:
<223> OTHER INFORMATION: 1127D9 VH nucleotide sequence

<400> SEQUENCE: 131
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggagga attattccta tctttgacac aggcaactct     180
gcacagagct tccagggcag agtcacgatt accgcggacg aatcaacgag cacagcctac     240
atggaggtga gcagcctgag atctgacgac acggccgtat attactgtgc tagttcaagt     300
```

```
cgtatctacg actaccacac catagcctac tacgatatgg atgtctgggg ccaggggaca    360
atggtcaccg tctcctca                                                  378
```

<210> SEQ ID NO 132
<211> LENGTH: 126
<212> TYPE: PRT
<213> ORGANISM: Homo sapiens
<220> FEATURE:
<223> OTHER INFORMATION: 1127D9 VH amino acid sequence

<400> SEQUENCE: 132

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Tyr His Thr Ile Ala Tyr Tyr Asp
            100                 105                 110

Met Asp Val Trp Gly Gln Gly Thr Met Val Thr Val Ser Ser
        115                 120                 125
```

<210> SEQ ID NO 133
<211> LENGTH: 5
<212> TYPE: PRT
<213> ORGANISM: Homo sapiens
<220> FEATURE:
<223> OTHER INFORMATION: 1127D9 VH CDR1 amino acid sequence

<400> SEQUENCE: 133

```
Thr Tyr Gly Ile Ser
1               5
```

<210> SEQ ID NO 134
<211> LENGTH: 17
<212> TYPE: PRT
<213> ORGANISM: Homo sapiens
<220> FEATURE:
<223> OTHER INFORMATION: 1127D9 VH CDR2 amino acid sequence

<400> SEQUENCE: 134

```
Gly Ile Ile Pro Ile Phe Asp Thr Gly Asn Ser Ala Gln Ser Phe Gln
1               5                   10                  15

Gly
```

<210> SEQ ID NO 135
<211> LENGTH: 17
<212> TYPE: PRT
<213> ORGANISM: Homo sapiens
<220> FEATURE:
<223> OTHER INFORMATION: 1127D9 VH CDR3 amino acid sequence

<400> SEQUENCE: 135

```
Ser Ser Arg Ile Tyr Asp Tyr His Thr Ile Ala Tyr Tyr Asp Met Asp
1               5                   10                  15
```

Val

```
<210> SEQ ID NO 136
<211> LENGTH: 330
<212> TYPE: DNA
<213> ORGANISM: Homo sapiens
<220> FEATURE:
<223> OTHER INFORMATION: 1127D9 VL nucleotide sequence

<400> SEQUENCE: 136
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag ccccaaact cctcatttat gacaataata gcgaccctc agggattcct       180 gaccgattct ccggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 137
<211> LENGTH: 110
<212> TYPE: PRT
<213> ORGANISM: Homo sapiens
<220> FEATURE:
<223> OTHER INFORMATION: 1127D9 VL amino acid sequence

<400> SEQUENCE: 137

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 138
<211> LENGTH: 13
<212> TYPE: PRT
<213> ORGANISM: Homo sapiens
<220> FEATURE:
<223> OTHER INFORMATION: 1127D9 VL CDR1 amino acid sequence

<400> SEQUENCE: 138

Ser Gly Ser Ser Ser Asn Ile Gly Asn Asn Tyr Val Ser
1               5                   10

<210> SEQ ID NO 139
<211> LENGTH: 7
<212> TYPE: PRT
<213> ORGANISM: Homo sapiens
<220> FEATURE:
<223> OTHER INFORMATION: 1127D9 VL CDR2 amino acid sequence

<400> SEQUENCE: 139

Asp Asn Asn Lys Arg Pro Ser
```

<210> SEQ ID NO 140
<211> LENGTH: 11
<212> TYPE: PRT
<213> ORGANISM: Homo sapiens
<220> FEATURE:
<223> OTHER INFORMATION: 1127D9 VL CDR3 amino acid sequence

<400> SEQUENCE: 140

Gly Thr Trp Asp Ser Ser Leu Ser Ala Trp Val
1               5                   10

<210> SEQ ID NO 141
<211> LENGTH: 384
<212> TYPE: DNA
<213> ORGANISM: Homo sapiens
<220> FEATURE:
<223> OTHER INFORMATION: 1127F9 VH nucleotide sequence

<400> SEQUENCE: 141
gaggtgcagc tggtgcagtc tggggctgag gtgaagaagc ctgggtcctc ggtgaaggtc    60
tcctgcaagg cttctggagg caccttcagc acctatggta tctcatgggt gcgacaggcc   120
cctggacaag gacttgagtg gataggaggg attattccta tctttgacac aggcaattct   180
gcacagagct tccagggcag agtcacgatt accgcggacg aatccacgag cacagcctac   240
atgaaggtga gcagcctgag atctgacgac acggccgtat attattgcgc aagttcaagt   300
cgtatctacg actacatccc cggcatgcga ccctactacg atatggatgt ctggggccag   360
gggacaatgg tcaccgtctc ctca                                          384

<210> SEQ ID NO 142
<211> LENGTH: 128
<212> TYPE: PRT
<213> ORGANISM: Homo sapiens
<220> FEATURE:
<223> OTHER INFORMATION: 1127F9 VH amino acid sequence

<400> SEQUENCE: 142

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Lys Val Ser Ser Leu Arg Ser Asp Asp Thr Ala Val Tyr Tyr Cys
                85                  90                  95

Ala Ser Ser Ser Arg Ile Tyr Asp Tyr Ile Pro Gly Met Arg Pro Tyr
            100                 105                 110

Tyr Asp Met Asp Val Trp Gly Gln Gly Thr Met Val Thr Val Ser Ser
        115                 120                 125

<210> SEQ ID NO 143
<211> LENGTH: 5
<212> TYPE: PRT
<213> ORGANISM: Homo sapiens
<220> FEATURE:

<223> OTHER INFORMATION: 1127F9 VH CDR1 amino acid sequence

<400> SEQUENCE: 143

Thr Tyr Gly Ile Ser
1               5

<210> SEQ ID NO 144
<211> LENGTH: 17
<212> TYPE: PRT
<213> ORGANISM: Homo sapiens
<220> FEATURE:
<223> OTHER INFORMATION: 1127F9 VH CDR2 amino acid sequence

<400> SEQUENCE: 144

Gly Ile Ile Pro Ile Phe Asp Thr Gly Asn Ser Ala Gln Ser Phe Gln
1               5                   10                  15

Gly

<210> SEQ ID NO 145
<211> LENGTH: 19
<212> TYPE: PRT
<213> ORGANISM: Homo sapiens
<220> FEATURE:
<223> OTHER INFORMATION: 1127F9 VH CDR3 amino acid sequence

<400> SEQUENCE: 145

Ser Ser Arg Ile Tyr Asp Tyr Ile Pro Gly Met Arg Pro Tyr Tyr Asp
1               5                   10                  15

Met Asp Val

<210> SEQ ID NO 146
<211> LENGTH: 330
<212> TYPE: DNA
<213> ORGANISM: Homo sapiens
<220> FEATURE:
<223> OTHER INFORMATION: 1127F9 VL nucleotide sequence

<400> SEQUENCE: 146
caggctgtgc tgactcagcc gtcctcagtg tctacgcccc caggacagaa ggtcaccatc      60
tcctgctctg gaaacagctc caacattggg aataattacg tatcgtggta ccagcagctc     120
ccaggaacag cccccaaact ccttatttat gacaataata gcgaccctca gggattcct     180 gaccgattct ctggctccag gtctggcacg ttagccaccc tgggcatcac cggactccag     240
actggggacg aggccgatta ttactgcggt acatgggata gcagcctgag tgcttgggtg     300
ttcggcggag ggaccaagct gaccgtccta                                      330

<210> SEQ ID NO 147
<211> LENGTH: 110
<212> TYPE: PRT
<213> ORGANISM: Homo sapiens
<220> FEATURE:
<223> OTHER INFORMATION: 1127F9 VL amino acid sequence

<400> SEQUENCE: 147

Gln Ala Val Leu Thr Gln Pro Ser Ser Val Ser Thr Pro Pro Gly Gln
1               5                   10                  15

Lys Val Thr Ile Ser Cys Ser Gly Asn Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser

```
                50                  55                  60
Gly Ser Arg Ser Gly Thr Leu Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
            100                 105                 110
```

<210> SEQ ID NO 148
<211> LENGTH: 13
<212> TYPE: PRT
<213> ORGANISM: Homo sapiens
<220> FEATURE:
<223> OTHER INFORMATION: 1127F9 VL CDR1 amino acid sequence

<400> SEQUENCE: 148

```
Ser Gly Asn Ser Ser Asn Ile Gly Asn Asn Tyr Val Ser
 1               5                  10
```

<210> SEQ ID NO 149
<211> LENGTH: 7
<212> TYPE: PRT
<213> ORGANISM: Homo sapiens
<220> FEATURE:
<223> OTHER INFORMATION: 1127F9 VL CDR2 amino acid sequence

<400> SEQUENCE: 149

```
Asp Asn Asn Lys Arg Pro Ser
 1               5
```

<210> SEQ ID NO 150
<211> LENGTH: 11
<212> TYPE: PRT
<213> ORGANISM: Homo sapiens
<220> FEATURE:
<223> OTHER INFORMATION: 1127F9 VL CDR3 amino acid sequence

<400> SEQUENCE: 150

```
Gly Thr Trp Asp Ser Ser Leu Ser Ala Trp Val
 1               5                  10
```

<210> SEQ ID NO 151
<211> LENGTH: 384
<212> TYPE: DNA
<213> ORGANISM: Homo sapiens
<220> FEATURE:
<223> OTHER INFORMATION: 1131D7 VH nucleotide sequence

<400> SEQUENCE: 151

```
gaggtgcagc tggtgcagtc tggggctgag gtgaagaagc ctgggtcctc ggtgaaggtc    60
tcctgcaagg cttctggagg caccttcagc acctatggta tctcatgggt gcgacaggcc   120
cctggacaag gacttgagtg gataggaggg attattccta tctttgacac aggcaactct   180
gcacagagct tccagggcag agtcacgatt accgcggacg aatccacgag cacagcctac   240
atggaggtga gcagcctgag atctgacgac acggccgtat attattgtgc aagttcaagt   300
cgtatctacg acttcaactc gagcctgatc gcctactacg atatggatgt ctggggccag   360
gggacaatgg tcaccgtctc ctca                                          384
```

<210> SEQ ID NO 152
<211> LENGTH: 128
<212> TYPE: PRT
<213> ORGANISM: Homo sapiens

```
<220> FEATURE:
<223> OTHER INFORMATION: 1131D7 VH amino acid sequence

<400> SEQUENCE: 152
```

| Glu | Val | Gln | Leu | Val | Gln | Ser | Gly | Ala | Glu | Val | Lys | Lys | Pro | Gly | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Val | Lys | Val | Ser | Cys | Lys | Ala | Ser | Gly | Gly | Thr | Phe | Ser | Thr | Tyr |
|     |     |     | 20  |     |     |     |     | 25  |     |     |     |     | 30  |     |     |

| Gly | Ile | Ser | Trp | Val | Arg | Gln | Ala | Pro | Gly | Gln | Gly | Leu | Glu | Trp | Ile |
|     |     | 35  |     |     |     |     | 40  |     |     |     |     | 45  |     |     |     |

| Gly | Gly | Ile | Ile | Pro | Ile | Phe | Asp | Thr | Gly | Asn | Ser | Ala | Gln | Ser | Phe |
|     | 50  |     |     |     |     | 55  |     |     |     |     | 60  |     |     |     |     |

| Gln | Gly | Arg | Val | Thr | Ile | Thr | Ala | Asp | Glu | Ser | Thr | Ser | Thr | Ala | Tyr |
| 65  |     |     |     |     | 70  |     |     |     |     | 75  |     |     |     |     | 80  |

| Met | Glu | Val | Ser | Ser | Leu | Arg | Ser | Asp | Asp | Thr | Ala | Val | Tyr | Tyr | Cys |
|     |     |     |     | 85  |     |     |     |     | 90  |     |     |     |     | 95  |     |

| Ala | Ser | Ser | Arg | Ile | Tyr | Asp | Phe | Asn | Ser | Ser | Leu | Ile | Ala | Tyr | Tyr |
|     |     |     | 100 |     |     |     |     | 105 |     |     |     |     | 110 |     |     |

| Tyr | Asp | Met | Asp | Val | Trp | Gly | Gln | Gly | Thr | Met | Val | Thr | Val | Ser | Ser |
|     |     | 115 |     |     |     |     | 120 |     |     |     |     | 125 |     |     |     |

```
<210> SEQ ID NO 153
<211> LENGTH: 5
<212> TYPE: PRT
<213> ORGANISM: Homo sapiens
<220> FEATURE:
<223> OTHER INFORMATION: 1131D7 VH CDR1 amino acid sequence

<400> SEQUENCE: 153
```

| Thr | Tyr | Gly | Ile | Ser |
|-----|-----|-----|-----|-----|
| 1   |     |     |     | 5   |

```
<210> SEQ ID NO 154
<211> LENGTH: 17
<212> TYPE: PRT
<213> ORGANISM: Homo sapiens
<220> FEATURE:
<223> OTHER INFORMATION: 1131D7 VH CDR2 amino acid sequence

<400> SEQUENCE: 154
```

| Gly | Ile | Ile | Pro | Ile | Phe | Asp | Thr | Gly | Asn | Ser | Ala | Gln | Ser | Phe | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly

```
<210> SEQ ID NO 155
<211> LENGTH: 19
<212> TYPE: PRT
<213> ORGANISM: Homo sapiens
<220> FEATURE:
<223> OTHER INFORMATION: 1131D7 VH CDR3 amino acid sequence

<400> SEQUENCE: 155
```

| Ser | Ser | Arg | Ile | Tyr | Asp | Phe | Asn | Ser | Ser | Leu | Ile | Ala | Tyr | Tyr | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Met Asp Val

```
<210> SEQ ID NO 156
<211> LENGTH: 330
<212> TYPE: DNA
<213> ORGANISM: Homo sapiens
<220> FEATURE:
<223> OTHER INFORMATION: 1131D7 VL nucleotide sequence
```

-continued

<400> SEQUENCE: 156

```
caggctgtgc tgactcagcc gtcctcagtg tctacgcccc caggacagaa ggtcaccatc     60
tcctgctcag gaagcagctc caacattggg aataattatg tatcgtggta ccagcagctc    120
ccaggaactg cccccaaact cctcatttat gacaataata gcgaccctca gggattcct     180
gaccgattct ctggctccaa gtctggcacg tcagccactc tgggcatcac cggactccag    240
actgggacg agaccgatta ttactgcgga acatgggata gcagcctgag tgcttgggtg     300
ttcagcggag ggaccaagct gaccgtccta                                     330
```

<210> SEQ ID NO 157
<211> LENGTH: 110
<212> TYPE: PRT
<213> ORGANISM: Homo sapiens
<220> FEATURE:
<223> OTHER INFORMATION: 1131D7 VL amino acid sequence

<400> SEQUENCE: 157

```
Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Thr Asp Tyr Tyr Cys Gly Thr Trp Asp Ser Ser Leu
                85                  90                  95

Ser Ala Trp Val Phe Ser Gly Gly Thr Lys Leu Thr Val Leu
            100                 105                 110
```

<210> SEQ ID NO 158
<211> LENGTH: 13
<212> TYPE: PRT
<213> ORGANISM: Homo sapiens
<220> FEATURE:
<223> OTHER INFORMATION: 1131D7 VL CDR1 amino acid sequence

<400> SEQUENCE: 158

```
Ser Gly Ser Ser Ser Asn Ile Gly Asn Asn Tyr Val Ser
1               5                   10
```

<210> SEQ ID NO 159
<211> LENGTH: 7
<212> TYPE: PRT
<213> ORGANISM: Homo sapiens
<220> FEATURE:
<223> OTHER INFORMATION: 1131D7 VL CDR2 amino acid sequence

<400> SEQUENCE: 159

```
Asp Asn Asn Lys Arg Pro Ser
1               5
```

<210> SEQ ID NO 160
<211> LENGTH: 11
<212> TYPE: PRT
<213> ORGANISM: Homo sapiens
<220> FEATURE:
<223> OTHER INFORMATION: 1131D7 VL CDR3 amino acid sequence

<400> SEQUENCE: 160

Gly Thr Trp Asp Ser Ser Leu Ser Ala Trp Val
1               5                   10

<210> SEQ ID NO 161
<211> LENGTH: 384
<212> TYPE: DNA
<213> ORGANISM: Homo sapiens
<220> FEATURE:
<223> OTHER INFORMATION: 1131H2 VH nucleotide sequence

<400> SEQUENCE: 161

```
gaagtgcagc tggtgcagtc tggggctgag gtgaagaagc ctgggtccac ggtgaaggtc    60
tcctgcaagg cttctggagg caccttcagc acctatggta tctcatgggt gcgacaggcc   120
cctggacaag gacttgagtg gatagggggg attattccta tctttgacac aggcaactct   180
gcacagagct tccagggcag agtcacgatt accgcggacg aatccacgag cacagcctac   240
atggaggtga gcagcctgag atctgacgac acggccgtat attattgtgc aagctcaagt   300
cgtatctacg acttgaaccc ctccctcact gcctactacg atatggatgt ctggggccag   360
gggacaatgg tcaccgtctc ctca                                          384
```

<210> SEQ ID NO 162
<211> LENGTH: 128
<212> TYPE: PRT
<213> ORGANISM: Homo sapiens
<220> FEATURE:
<223> OTHER INFORMATION: 1131H2 VH amino acid sequence

<400> SEQUENCE: 162

Glu Val Gln Leu Val Gln Ser Gly Ala Glu Val Lys Lys Pro Gly Ser
1               5                   10                  15

Thr Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 163
<211> LENGTH: 5
<212> TYPE: PRT
<213> ORGANISM: Homo sapiens
<220> FEATURE:
<223> OTHER INFORMATION: 1131H2 VH CDR1 amino acid sequence

<400> SEQUENCE: 163

Thr Tyr Gly Ile Ser
1               5

<210> SEQ ID NO 164

```
<211> LENGTH: 17
<212> TYPE: PRT
<213> ORGANISM: Homo sapiens
<220> FEATURE:
<223> OTHER INFORMATION: 1131H2 VH CDR2 amino acid sequence

<400> SEQUENCE: 164

Gly Ile Ile Pro Ile Phe Asp Thr Gly Asn Ser Ala Gln Ser Phe Gln
1               5                   10                  15

Gly

<210> SEQ ID NO 165
<211> LENGTH: 19
<212> TYPE: PRT
<213> ORGANISM: Homo sapiens
<220> FEATURE:
<223> OTHER INFORMATION: 1131H2 VH CDR3 amino acid sequence

<400> SEQUENCE: 165

Ser Ser Arg Ile Tyr Asp Leu Asn Pro Ser Leu Thr Ala Tyr Tyr Asp
1               5                   10                  15

Met Asp Val

<210> SEQ ID NO 166
<211> LENGTH: 330
<212> TYPE: DNA
<213> ORGANISM: Homo sapiens
<220> FEATURE:
<223> OTHER INFORMATION: 1131H2 VL nucleotide sequence

<400> SEQUENCE: 166
caggctgtgc tgactcagcc gtcctcagtg tctacgcccc cgggacagaa ggtcaccatc        60
tcctgctctg gaaccagctc aacattggg aataattatg tatcgtggta ccagcagctc       120
ccaggaacgg cccccaaact cctcatttat gacaataata gcgaccctc agggattcct       180 gaccgattct ctggctccaa gtctggcacg tcagccaccc tgggcatcac cggactccag       240
actggggacg aggccgatta ttactgcgga acatgggata gcagcctgag tgcttgggtg       300
ttcggcggag ggaccaagct gaccgtccta                                       330

<210> SEQ ID NO 167
<211> LENGTH: 110
<212> TYPE: PRT
<213> ORGANISM: Homo sapiens
<220> FEATURE:
<223> OTHER INFORMATION: 1131H2 VL amino acid sequence

<400> SEQUENCE: 167

Gln Ala Val Leu Thr Gln Pro Ser Ser Val Ser Thr Pro Pro Gly Gln
1               5                   10                  15

Lys Val Thr Ile Ser Cys Ser Gly Thr Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
```

<210> SEQ ID NO 168
<211> LENGTH: 13
<212> TYPE: PRT
<213> ORGANISM: Homo sapiens
<220> FEATURE:
<223> OTHER INFORMATION: 1131H2 VL CDR1 amino acid sequence

<400> SEQUENCE: 168

Ser Gly Thr Ser Ser Asn Ile Gly Asn Asn Tyr Val Ser
1               5                   10

<210> SEQ ID NO 169
<211> LENGTH: 7
<212> TYPE: PRT
<213> ORGANISM: Homo sapiens
<220> FEATURE:
<223> OTHER INFORMATION: 1131H2 VL CDR2 amino acid sequence

<400> SEQUENCE: 169

Asp Asn Asn Lys Arg Pro Ser
1               5

<210> SEQ ID NO 170
<211> LENGTH: 11
<212> TYPE: PRT
<213> ORGANISM: Homo sapiens
<220> FEATURE:
<223> OTHER INFORMATION: 1131H2 VL CDR3 amino acid sequence

<400> SEQUENCE: 170

Gly Thr Trp Asp Ser Ser Leu Ser Ala Trp Val
1               5                   10

<210> SEQ ID NO 171
<211> LENGTH: 384
<212> TYPE: DNA
<213> ORGANISM: Homo sapiens
<220> FEATURE:
<223> OTHER INFORMATION: 1132A9 VH nucleotide sequence

<400> SEQUENCE: 171
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggccaag gacttgagtg gataggaggg attattccta tctttggcac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttcgagcc gtcgctgatt tattactacg atatggatgt ctggggccag     360
gggacaatgg tcaccgtctc ctca                                            384

<210> SEQ ID NO 172
<211> LENGTH: 128
<212> TYPE: PRT
<213> ORGANISM: Homo sapiens
<220> FEATURE:
<223> OTHER INFORMATION: 1132A9 VH amino acid sequence

<400> SEQUENCE: 172

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr

```
                    20                  25                  30
Gly Ile Ser Trp Val Arg Gln Ala Pro Gly Gln Gly Leu Glu Trp Ile
                35                  40                  45

Gly Gly Ile Ile Pro Ile Phe Gly Thr Gly Asn Ser Ala Gln Ser Phe
        50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Phe Glu Pro Ser Leu Ile Tyr Tyr
            100                 105                 110

Tyr Asp Met Asp Val Trp Gly Gln Gly Thr Met Val Thr Val Ser Ser
            115                 120                 125

<210> SEQ ID NO 173
<211> LENGTH: 5
<212> TYPE: PRT
<213> ORGANISM: Homo sapiens
<220> FEATURE:
<223> OTHER INFORMATION: 1132A9 VH CDR1 amino acid sequence

<400> SEQUENCE: 173

Thr Tyr Gly Ile Ser
1               5

<210> SEQ ID NO 174
<211> LENGTH: 17
<212> TYPE: PRT
<213> ORGANISM: Homo sapiens
<220> FEATURE:
<223> OTHER INFORMATION: 1132A9 VH CDR2 amino acid sequence

<400> SEQUENCE: 174

Gly Ile Ile Pro Ile Phe Gly Thr Gly Asn Ser Ala Gln Ser Phe Gln
1               5                   10                  15

Gly

<210> SEQ ID NO 175
<211> LENGTH: 19
<212> TYPE: PRT
<213> ORGANISM: Homo sapiens
<220> FEATURE:
<223> OTHER INFORMATION: 1132A9 VH CDR3 amino acid sequence

<400> SEQUENCE: 175

Ser Ser Arg Ile Tyr Asp Phe Glu Pro Ser Leu Ile Tyr Tyr Tyr Asp
1               5                   10                  15

Met Asp Val

<210> SEQ ID NO 176
<211> LENGTH: 330
<212> TYPE: DNA
<213> ORGANISM: Homo sapiens
<220> FEATURE:
<223> OTHER INFORMATION: 1132A9 VL nucleotide sequence

<400> SEQUENCE: 176
caggctgtgc tgactcagcc gtcctcagtg tctacgcccc caggacagaa ggtcaccatc    60
tcctgctctg gaagcagctc caacattggg aataattatg tatcgtggta ccagcagctc   120
ccaggaacag cccccaaact cctcatttat gacaataata gcgaccctca gggatccct    180
```

```
gaccgattct ctggctccaa gtctggcacg tcagccaccc tgggcatcac cggactccag    240
actggggacg aggccgatta ttactgcgga acatgggata gcagcctgag tgcttgggtg    300
ttcggcggag ggaccaagct gaccgtccta                                     330
```

<210> SEQ ID NO 177
<211> LENGTH: 110
<212> TYPE: PRT
<213> ORGANISM: Homo sapiens
<220> FEATURE:
<223> OTHER INFORMATION: 1132A9 VL amino acid sequence

<400> SEQUENCE: 177

```
Gln Ala Val Leu Thr Gln Pro Ser Ser Val Ser Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 178
<211> LENGTH: 13
<212> TYPE: PRT
<213> ORGANISM: Homo sapiens
<220> FEATURE:
<223> OTHER INFORMATION: 1132A9 VL CDR1 amino acid sequence

<400> SEQUENCE: 178

```
Ser Gly Ser Ser Ser Asn Ile Gly Asn Asn Tyr Val Ser
1               5                   10
```

<210> SEQ ID NO 179
<211> LENGTH: 7
<212> TYPE: PRT
<213> ORGANISM: Homo sapiens
<220> FEATURE:
<223> OTHER INFORMATION: 1132A9 VL CDR2 amino acid sequence

<400> SEQUENCE: 179

```
Asp Asn Asn Lys Arg Pro Ser
1               5
```

<210> SEQ ID NO 180
<211> LENGTH: 11
<212> TYPE: PRT
<213> ORGANISM: Homo sapiens
<220> FEATURE:
<223> OTHER INFORMATION: 1132A9 VL CDR3 amino acid sequence

<400> SEQUENCE: 180

```
Gly Thr Trp Asp Ser Ser Leu Ser Ala Trp Val
1               5                   10
```

<210> SEQ ID NO 181
<211> LENGTH: 384

<212> TYPE: DNA
<213> ORGANISM: Homo sapiens
<220> FEATURE:
<223> OTHER INFORMATION: 1132H9 VH nucleotide sequence

<400> SEQUENCE: 181

```
gaggtgcagc tggtgcagtc tggggctgag gtgaagaagc ctgggtcctc ggtgaaggtc      60
tcctgcaagg cttctggggg caccttcagc acctatggta tctcatgggt gcgacaggcc     120
cctggacaag acttgagtg gatagggggg attattccta tctttgacac aggcaactct     180
gcacagagct tccagggtag agtcacgatt accgcggacg agtccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc ctca                                             384
```

<210> SEQ ID NO 182
<211> LENGTH: 128
<212> TYPE: PRT
<213> ORGANISM: Homo sapiens
<220> FEATURE:
<223> OTHER INFORMATION: 1132H9 VH amino acid sequence

<400> SEQUENCE: 182

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125
```

<210> SEQ ID NO 183
<211> LENGTH: 5
<212> TYPE: PRT
<213> ORGANISM: Homo sapiens
<220> FEATURE:
<223> OTHER INFORMATION: 1132H9 VH CDR1 amino acid sequence

<400> SEQUENCE: 183

```
Thr Tyr Gly Ile Ser
1               5
```

<210> SEQ ID NO 184
<211> LENGTH: 17
<212> TYPE: PRT
<213> ORGANISM: Homo sapiens
<220> FEATURE:
<223> OTHER INFORMATION: 1132H9 VH CDR2 amino acid sequence

<400> SEQUENCE: 184

Gly Ile Ile Pro Ile Phe Asp Thr Gly Asn Ser Ala Gln Ser Phe Gln

```
<210> SEQ ID NO 185
<211> LENGTH: 19
<212> TYPE: PRT
<213> ORGANISM: Homo sapiens
<220> FEATURE:
<223> OTHER INFORMATION: 1132H9 VH CDR3 amino acid sequence

<400> SEQUENCE: 185

Ser Ser Arg Ile Tyr Asp Leu Asn Pro Ser Leu Thr Ala Tyr Tyr Asp
1               5                   10                  15

Met Asp Val

<210> SEQ ID NO 186
<211> LENGTH: 330
<212> TYPE: DNA
<213> ORGANISM: Homo sapiens
<220> FEATURE:
<223> OTHER INFORMATION: 1132H9 VL nucleotide sequence

<400> SEQUENCE: 186
caggctgtgc tgactcagcc gtcctcagtg tctacgcccc caggacagaa ggtcaccatc      60
tcctgctctg gaagcagctc cgacattggg aataattatg tgtcgtggta ccagcagctc     120
ccaggaacag ccccccaaact cctcatttat gacaataata agcgacccac agggattcct    180
gaccgattct ccggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                       330

<210> SEQ ID NO 187
<211> LENGTH: 110
<212> TYPE: PRT
<213> ORGANISM: Homo sapiens
<220> FEATURE:
<223> OTHER INFORMATION: 1132H9 VL amino acid sequence

<400> SEQUENCE: 187

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asp Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Thr Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 188
<211> LENGTH: 13
<212> TYPE: PRT
<213> ORGANISM: Homo sapiens
<220> FEATURE:
<223> OTHER INFORMATION: 1132H9 VL CDR1 amino acid sequence
```

-continued

<400> SEQUENCE: 188

Ser Gly Ser Ser Ser Asp Ile Gly Asn Asn Tyr Val Ser
1               5                   10

<210> SEQ ID NO 189
<211> LENGTH: 7
<212> TYPE: PRT
<213> ORGANISM: Homo sapiens
<220> FEATURE:
<223> OTHER INFORMATION: 1132H9 VL CDR2 amino acid sequence

<400> SEQUENCE: 189

Asp Asn Asn Lys Arg Pro Thr
1               5

<210> SEQ ID NO 190
<211> LENGTH: 11
<212> TYPE: PRT
<213> ORGANISM: Homo sapiens
<220> FEATURE:
<223> OTHER INFORMATION: 1132H9 VL CDR3 amino acid sequence

<400> SEQUENCE: 190

Gly Thr Trp Asp Ser Ser Leu Ser Ala Trp Val
1               5                   10

<210> SEQ ID NO 191
<211> LENGTH: 384
<212> TYPE: DNA
<213> ORGANISM: Homo sapiens
<220> FEATURE:
<223> OTHER INFORMATION: 1133C11 VH nucleotide sequence

<400> SEQUENCE: 191
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc ctca                                             384

<210> SEQ ID NO 192
<211> LENGTH: 128
<212> TYPE: PRT
<213> ORGANISM: Homo sapiens
<220> FEATURE:
<223> OTHER INFORMATION: 1133C11 VH amino acid sequence

<400> SEQUENCE: 192

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr

```
                65                  70                  75                  80
Met Glu Val Ser Ser Leu Arg Ser Asp Asp Thr Ala Val Tyr Tyr Cys
                    85                  90                  95
Ala Ser Ser Arg Ile Tyr Asp Leu Asn Pro Ser Leu Thr Ala Tyr
                    100                 105                 110
Tyr Asp Met Asp Val Trp Gly Gln Gly Thr Met Val Thr Val Ser Ser
        115                 120                 125

<210> SEQ ID NO 193
<211> LENGTH: 5
<212> TYPE: PRT
<213> ORGANISM: Homo sapiens
<220> FEATURE:
<223> OTHER INFORMATION: 1133C11 VH CDR1 amino acid sequence

<400> SEQUENCE: 193

Thr Tyr Gly Ile Ser
1               5

<210> SEQ ID NO 194
<211> LENGTH: 17
<212> TYPE: PRT
<213> ORGANISM: Homo sapiens
<220> FEATURE:
<223> OTHER INFORMATION: 1133C11 VH CDR2 amino acid sequence

<400> SEQUENCE: 194

Gly Ile Ile Pro Ile Phe Asp Thr Gly Asn Ser Ala Gln Ser Phe Gln
1               5                   10                  15
Gly

<210> SEQ ID NO 195
<211> LENGTH: 19
<212> TYPE: PRT
<213> ORGANISM: Homo sapiens
<220> FEATURE:
<223> OTHER INFORMATION: 1133C11 VH CDR3 amino acid sequence

<400> SEQUENCE: 195

Ser Ser Arg Ile Tyr Asp Leu Asn Pro Ser Leu Thr Ala Tyr Tyr Asp
1               5                   10                  15
Met Asp Val

<210> SEQ ID NO 196
<211> LENGTH: 330
<212> TYPE: DNA
<213> ORGANISM: Homo sapiens
<220> FEATURE:
<223> OTHER INFORMATION: 1133C11 VL nucleotide sequence

<400> SEQUENCE: 196
caggctgtgc tgactcagcc gtcctcagtg tctacgcccc caggacagaa ggtcaccatc      60
tcctgctctg gaagcagctc caacattggg ataattatg tatcgtggta ccagcagctc     120
ccaggaacag ccccccaaact cctcatttat gacaataata gcgaccctca agggattcct    180
gaccgattct ctggctccaa gtctggcacg tcagccaccc tgggcatcac cggactccag    240
actggggacg aggccgatta ttactgcgga acatgggata gcagcctgag tgcttgggtg    300
tttggcggag ggaccaagct gaccgtccta                                       330

<210> SEQ ID NO 197
<211> LENGTH: 110
```

```
<212> TYPE: PRT
<213> ORGANISM: Homo sapiens
<220> FEATURE:
<223> OTHER INFORMATION: 1133C11 VL amino acid sequence

<400> SEQUENCE: 197

Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 198
<211> LENGTH: 13
<212> TYPE: PRT
<213> ORGANISM: Homo sapiens
<220> FEATURE:
<223> OTHER INFORMATION: 1133C11 VL CDR1 amino acid sequence

<400> SEQUENCE: 198

Ser Gly Ser Ser Ser Asn Ile Gly Asn Asn Tyr Val Ser
1               5                   10

<210> SEQ ID NO 199
<211> LENGTH: 7
<212> TYPE: PRT
<213> ORGANISM: Homo sapiens
<220> FEATURE:
<223> OTHER INFORMATION: 1133C11 VL CDR2 amino acid sequence

<400> SEQUENCE: 199

Asp Asn Asn Lys Arg Pro Ser
1               5

<210> SEQ ID NO 200
<211> LENGTH: 11
<212> TYPE: PRT
<213> ORGANISM: Homo sapiens
<220> FEATURE:
<223> OTHER INFORMATION: 1133C11 VL CDR3 amino acid sequence

<400> SEQUENCE: 200

Gly Thr Trp Asp Ser Ser Leu Ser Ala Trp Val
1               5                   10

<210> SEQ ID NO 201
<211> LENGTH: 384
<212> TYPE: DNA
<213> ORGANISM: Homo sapiens
<220> FEATURE:
<223> OTHER INFORMATION: 1134D9 VH nucleotide sequence

<400> SEQUENCE: 201
gaggtgcagc tggtgcagtc tggggctgag gtgaagaagc ctgggtcctc ggtgaaggtc    60
```

```
tcctgcaagg cttctggagg caccttcagc acctatggaa tctcatgggt gcgacaggcc    120
cctggacaag gacttgagtg gatagggggg attattccta tcttcgacac aggcaactct    180
gcacagagct tccagggcag agtcgcgatt accgcggacg aatccacgag cacagcctac    240
atggaggtga gcagcctgag atctgacgat acggccgtat attattgtgc aagttcaagt    300
cgtatctacg acttgaaccc ctccctcact gcctactacg atatggatgt ctggggccag    360
gggacaatgg tcaccgtctc ctca                                          384
```

<210> SEQ ID NO 202
<211> LENGTH: 128
<212> TYPE: PRT
<213> ORGANISM: Homo sapiens
<220> FEATURE:
<223> OTHER INFORMATION: 1134D9 VH amino acid sequence

<400> SEQUENCE: 202

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Ala Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 203
<211> LENGTH: 5
<212> TYPE: PRT
<213> ORGANISM: Homo sapiens
<220> FEATURE:
<223> OTHER INFORMATION: 1134D9 VH CDR1 amino acid sequence

<400> SEQUENCE: 203

Thr Tyr Gly Ile Ser
1               5

<210> SEQ ID NO 204
<211> LENGTH: 17
<212> TYPE: PRT
<213> ORGANISM: Homo sapiens
<220> FEATURE:
<223> OTHER INFORMATION: 1134D9 VH CDR2 amino acid sequence

<400> SEQUENCE: 204

Gly Ile Ile Pro Ile Phe Asp Thr Gly Asn Ser Ala Gln Ser Phe Gln
1               5                   10                  15

Gly

<210> SEQ ID NO 205
<211> LENGTH: 18
<212> TYPE: PRT
<213> ORGANISM: Homo sapiens
<220> FEATURE:
<223> OTHER INFORMATION: 1134D9 VH CDR3 amino acid sequence

<400> SEQUENCE: 205

Ser Arg Ile Tyr Asp Leu Asn Pro Ser Leu Thr Ala Tyr Tyr Asp Met
1               5                   10                  15

Asp Val

<210> SEQ ID NO 206
<211> LENGTH: 330
<212> TYPE: DNA
<213> ORGANISM: Homo sapiens
<220> FEATURE:
<223> OTHER INFORMATION: 1134D9 VL nucleotide sequence

<400> SEQUENCE: 206
caggctgtgc tgactcagcc gtcctcagtg tctacgcccc caggacagaa ggtcaccatc     60
tcctgctctg gaagcagctc aacattggg aataattatg tatcgtggta ccagcagctc    120
ccaggaacag cccccaaaact cctcatttat gacaataata gcgaccctc agggattcct    180 gaccgattct ctggctccaa gtctggcacg tcagccaccc tgggcatcac cggactccag    240
actggggacg aggccgatta ttactgcgga acatgggata gcggcctgag tgcttgggtg    300
ttcggcggag ggaccaagct gaccgtccta                                     330

<210> SEQ ID NO 207
<211> LENGTH: 110
<212> TYPE: PRT
<213> ORGANISM: Homo sapiens
<220> FEATURE:
<223> OTHER INFORMATION: 1134D9 VL amino acid sequence

<400> SEQUENCE: 207

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Gly Leu
                85                  90                  95

Ser Ala Trp Val Phe Gly Gly Gly Thr Lys Leu Thr Val Leu
            100                 105                 110

<210> SEQ ID NO 208
<211> LENGTH: 13
<212> TYPE: PRT
<213> ORGANISM: Homo sapiens
<220> FEATURE:
<223> OTHER INFORMATION: 1134D9 VL CDR1 amino acid sequence

<400> SEQUENCE: 208

Ser Gly Ser Ser Ser Asn Ile Gly Asn Asn Tyr Val Ser
1               5                   10

<210> SEQ ID NO 209
<211> LENGTH: 7

<212> TYPE: PRT
<213> ORGANISM: Homo sapiens
<220> FEATURE:
<223> OTHER INFORMATION: 1134D9 VL CDR2 amino acid sequence

<400> SEQUENCE: 209

Asp Asn Asn Lys Arg Pro Ser
1               5

<210> SEQ ID NO 210
<211> LENGTH: 11
<212> TYPE: PRT
<213> ORGANISM: Homo sapiens
<220> FEATURE:
<223> OTHER INFORMATION: 1134D9 VL CDR3 amino acid sequence

<400> SEQUENCE: 210

Gly Thr Trp Asp Ser Gly Leu Ser Ala Trp Val
1               5                   10

<210> SEQ ID NO 211
<211> LENGTH: 384
<212> TYPE: DNA
<213> ORGANISM: Homo sapiens
<220> FEATURE:
<223> OTHER INFORMATION: 1145D1 VH nucleotide sequence

<400> SEQUENCE: 211
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggaggg attattccta tctttgacac aagcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttccggac cctctacagc acctactacg atatggatgt ctggggccag     360
gggacaatgg tcaccgtctc ctca                                            384

<210> SEQ ID NO 212
<211> LENGTH: 128
<212> TYPE: PRT
<213> ORGANISM: Homo sapiens
<220> FEATURE:
<223> OTHER INFORMATION: 1145D1 VH amino acid sequence

<400> SEQUENCE: 212

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Ser Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Phe Arg Thr Leu Tyr Ser Thr Tyr
            100                 105                 110

Tyr Asp Met Asp Val Trp Gly Gln Gly Thr Met Val Thr Val Ser Ser

<210> SEQ ID NO 213
<211> LENGTH: 5
<212> TYPE: PRT
<213> ORGANISM: Homo sapiens
<220> FEATURE:
<223> OTHER INFORMATION: 1145D1 VH CDR1 amino acid sequence

<400> SEQUENCE: 213

Thr Tyr Gly Ile Ser
1               5

<210> SEQ ID NO 214
<211> LENGTH: 17
<212> TYPE: PRT
<213> ORGANISM: Homo sapiens
<220> FEATURE:
<223> OTHER INFORMATION: 1145D1 VH CDR2 amino acid sequence

<400> SEQUENCE: 214

Gly Ile Ile Pro Ile Phe Asp Thr Ser Asn Ser Ala Gln Ser Phe Gln
1               5                   10                  15

Gly

<210> SEQ ID NO 215
<211> LENGTH: 19
<212> TYPE: PRT
<213> ORGANISM: Homo sapiens
<220> FEATURE:
<223> OTHER INFORMATION: 1145D1 VH CDR3 amino acid sequence

<400> SEQUENCE: 215

Ser Ser Arg Ile Tyr Asp Phe Arg Thr Leu Tyr Ser Thr Tyr Tyr Asp
1               5                   10                  15

Met Asp Val

<210> SEQ ID NO 216
<211> LENGTH: 330
<212> TYPE: DNA
<213> ORGANISM: Homo sapiens
<220> FEATURE:
<223> OTHER INFORMATION: 1145D1 VL nucleotide sequence

<400> SEQUENCE: 216
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag ccccaaaact cctcatttat gacaataata gcgaccctc agggatttct      180 gaccgattct ctggctccaa gtctggcacg tcagccaccc tgggcatcgc cggactccag     240
actggggacg aggccgatta ttactgcgga acatgggata gcagcctgag tgcttgggtg     300
ttcggcggag ggaccaagct gaccgtccta                                      330

<210> SEQ ID NO 217
<211> LENGTH: 110
<212> TYPE: PRT
<213> ORGANISM: Homo sapiens
<220> FEATURE:
<223> OTHER INFORMATION: 1145D1 VL amino acid sequence

<400> SEQUENCE: 217

Gln Ala Val Leu Thr Gln Pro Ser Ser Val Ser Thr Pro Pro Gly Gln
1               5                   10                  15

```
Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Ser Asp Arg Phe Ser
        50                  55                  60

Gly Ser Lys Ser Gly Thr Ser Ala Thr Leu Gly Ile Ala Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
                100                 105                 110

<210> SEQ ID NO 218
<211> LENGTH: 13
<212> TYPE: PRT
<213> ORGANISM: Homo sapiens
<220> FEATURE:
<223> OTHER INFORMATION: 1145D1 VL CDR1 amino acid sequence

<400> SEQUENCE: 218

Ser Gly Ser Ser Ser Asn Ile Gly Asn Asn Tyr Val Ser
1               5                   10

<210> SEQ ID NO 219
<211> LENGTH: 7
<212> TYPE: PRT
<213> ORGANISM: Homo sapiens
<220> FEATURE:
<223> OTHER INFORMATION: 1145D1 VL CDR2 amino acid sequence

<400> SEQUENCE: 219

Asp Asn Asn Lys Arg Pro Ser
1               5

<210> SEQ ID NO 220
<211> LENGTH: 11
<212> TYPE: PRT
<213> ORGANISM: Homo sapiens
<220> FEATURE:
<223> OTHER INFORMATION: 1145D1 VL CDR3 amino acid sequence

<400> SEQUENCE: 220

Gly Thr Trp Asp Ser Ser Leu Ser Ala Trp Val
1               5                   10

<210> SEQ ID NO 221
<211> LENGTH: 384
<212> TYPE: DNA
<213> ORGANISM: Homo sapiens
<220> FEATURE:
<223> OTHER INFORMATION: 1146D7 VH nucleotide sequence

<400> SEQUENCE: 221
gaggtgcagc tggtgcagtc tgggctgag gtgaagaagc ctgggtcctc ggtgaaggtc      60
tcctgcaagg cttctggagg caccttcagc acctatggta tctcatgggt gcgacaggcc     120
cctggacaag gacttgagtg gatgggggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
```

-continued

```
gggacaatgg tcaccgtctc ctca                                          384
```

<210> SEQ ID NO 222
<211> LENGTH: 128
<212> TYPE: PRT
<213> ORGANISM: Homo sapiens
<220> FEATURE:
<223> OTHER INFORMATION: 1146D7 VH amino acid sequence

<400> SEQUENCE: 222

```
Glu Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125
```

<210> SEQ ID NO 223
<211> LENGTH: 5
<212> TYPE: PRT
<213> ORGANISM: Homo sapiens
<220> FEATURE:
<223> OTHER INFORMATION: 1146D7 VH CDR1 amino acid sequence

<400> SEQUENCE: 223

```
Thr Tyr Gly Ile Ser
1               5
```

<210> SEQ ID NO 224
<211> LENGTH: 17
<212> TYPE: PRT
<213> ORGANISM: Homo sapiens
<220> FEATURE:
<223> OTHER INFORMATION: 1146D7 VH CDR2 amino acid sequence

<400> SEQUENCE: 224

```
Gly Ile Ile Pro Ile Phe Asp Thr Gly Asn Ser Ala Gln Ser Phe Gln
1               5                   10                  15

Gly
```

<210> SEQ ID NO 225
<211> LENGTH: 19
<212> TYPE: PRT
<213> ORGANISM: Homo sapiens
<220> FEATURE:
<223> OTHER INFORMATION: 1146D7 VH CDR3 amino acid sequence

<400> SEQUENCE: 225

```
Ser Ser Arg Ile Tyr Asp Leu Asn Pro Ser Leu Thr Ala Tyr Tyr Asp
1               5                   10                  15

Met Asp Val
```

-continued

<210> SEQ ID NO 226
<211> LENGTH: 330
<212> TYPE: DNA
<213> ORGANISM: Homo sapiens
<220> FEATURE:
<223> OTHER INFORMATION: 1146D7 VL nucleotide sequence

<400> SEQUENCE: 226

```
caggctgtgc tgactcagcc gtcctcagtg tctacgcccc caggacagga ggtcaccatc      60
tcctgctctg gaagcagcac caacattggg aataattatg tatcgtggta ccagcagctc     120
ccaggaacag cccccaaact cctcatttat gacaataata gcgaccctca agggattcct     180
gaccgattct ctggctccaa gtctggcacg tcagccaccc tgggcatcac cggactccag     240 actgggacg aggccgatta ttactgcgga acatgggata gcagcctgag tgcttgggtg     300
ttcggcggag ggaccaagct gaccgtccta                                      330
```

<210> SEQ ID NO 227
<211> LENGTH: 110
<212> TYPE: PRT
<213> ORGANISM: Homo sapiens
<220> FEATURE:
<223> OTHER INFORMATION: 1146D7 VL amino acid sequence

<400> SEQUENCE: 227

```
Gln Ala Val Leu Thr Gln Pro Ser Ser Val Ser Thr Pro Pro Gly Gln
 1               5                  10                  15

Glu Val Thr Ile Ser Cys Ser Gly Ser Ser Thr Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 228
<211> LENGTH: 13
<212> TYPE: PRT
<213> ORGANISM: Homo sapiens
<220> FEATURE:
<223> OTHER INFORMATION: 1146D7 VL CDR1 amino acid sequence

<400> SEQUENCE: 228

```
Ser Gly Ser Ser Thr Asn Ile Gly Asn Asn Tyr Val Ser
 1               5                  10
```

<210> SEQ ID NO 229
<211> LENGTH: 7
<212> TYPE: PRT
<213> ORGANISM: Homo sapiens
<220> FEATURE:
<223> OTHER INFORMATION: 1146D7 VL CDR2 amino acid sequence

<400> SEQUENCE: 229

```
Asp Asn Asn Lys Arg Pro Ser
 1               5
```

<210> SEQ ID NO 230
<211> LENGTH: 11
<212> TYPE: PRT
<213> ORGANISM: Homo sapiens
<220> FEATURE:
<223> OTHER INFORMATION: 1146D7 VL CDR3 amino acid sequence

<400> SEQUENCE: 230

Gly Thr Trp Asp Ser Ser Leu Ser Ala Trp Val
1               5                   10

<210> SEQ ID NO 231
<211> LENGTH: 384
<212> TYPE: DNA
<213> ORGANISM: Homo sapiens
<220> FEATURE:
<223> OTHER INFORMATION: 1147D2 VH nucleotide sequence

<400> SEQUENCE: 231
gaggtgcagc tggtgcagtc tggggctgag gtgaagaagc ctgggtcctc ggtgaggatc      60
tcctgcaagg cttctggagg caccttcagc acctatggtg tctcatgggt gcgacaggcc    120
cctggacaag acttgagtg gataggaggg attattccta tctttgacac aggcaactct     180
gcacagagct tccagggcag agtcacgatt accgcggacg aatccacgag cacagcctac    240
atggaggtga gcagcctgag atctgacgac acggccgtat attattgtgc aagttcgagt    300
cgtatctacg acttgaaccc ctccctcact gcctactacg atatggatgt ctggggccag    360
gggacaatgg tcaccgtctc ctca                                           384

<210> SEQ ID NO 232
<211> LENGTH: 128
<212> TYPE: PRT
<213> ORGANISM: Homo sapiens
<220> FEATURE:
<223> OTHER INFORMATION: 1147D2 VH amino acid sequence

<400> SEQUENCE: 232

Glu Val Gln Leu Val Gln Ser Gly Ala Glu Val Lys Lys Pro Gly Ser
1               5                   10                  15

Ser Val Arg Ile Ser Cys Lys Ala Ser Gly Gly Thr Phe Ser Thr Tyr
                20                  25                  30

Gly Val Ser Trp Val Arg Gln Ala Pro Gly Gln Gly Leu Glu Trp Ile
            35                  40                  45

Gly Gly Ile Ile Pro Ile Phe Asp Thr Gly Asn Ser Ala Gln Ser Phe
        50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
                100                 105                 110

Tyr Asp Met Asp Val Trp Gly Gln Gly Thr Met Val Thr Val Ser Ser
            115                 120                 125

<210> SEQ ID NO 233
<211> LENGTH: 5
<212> TYPE: PRT
<213> ORGANISM: Homo sapiens
<220> FEATURE:
<223> OTHER INFORMATION: 1147D2 VH CDR1 amino acid sequence

<400> SEQUENCE: 233

Thr Tyr Gly Val Ser
1               5

<210> SEQ ID NO 234
<211> LENGTH: 17
<212> TYPE: PRT
<213> ORGANISM: Homo sapiens
<220> FEATURE:
<223> OTHER INFORMATION: 1147D2 VH CDR2 amino acid sequence

<400> SEQUENCE: 234

Gly Ile Ile Pro Ile Phe Asp Thr Gly Asn Ser Ala Gln Ser Phe Gln
1               5                   10                  15

Gly

<210> SEQ ID NO 235
<211> LENGTH: 19
<212> TYPE: PRT
<213> ORGANISM: Homo sapiens
<220> FEATURE:
<223> OTHER INFORMATION: 1147D2 VH CDR3 amino acid sequence

<400> SEQUENCE: 235

Ser Ser Arg Ile Tyr Asp Leu Asn Pro Ser Leu Thr Ala Tyr Tyr Asp
1               5                   10                  15

Met Asp Val

<210> SEQ ID NO 236
<211> LENGTH: 330
<212> TYPE: DNA
<213> ORGANISM: Homo sapiens
<220> FEATURE:
<223> OTHER INFORMATION: 1147D2 VL nucleotide sequence

<400> SEQUENCE: 236
caggctgtgc tgactcagcc gtcctcagtg tctacgcccc caggacagaa ggtcaccatc      60
tcctgctctg gaagcagctc aacattggg aacaattatg tatcgtggta ccagcagctc     120
ccaggaacag cccccaaact cctcatttat gacaataata gcgaccctc aggggttcct      180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 237
<211> LENGTH: 110
<212> TYPE: PRT
<213> ORGANISM: Homo sapiens
<220> FEATURE:
<223> OTHER INFORMATION: 1147D2 VL amino acid sequence

<400> SEQUENCE: 237

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 238
<211> LENGTH: 13
<212> TYPE: PRT
<213> ORGANISM: Homo sapiens
<220> FEATURE:
<223> OTHER INFORMATION: 1147D2 VL CDR1 amino acid sequence

<400> SEQUENCE: 238

Ser Gly Ser Ser Ser Asn Ile Gly Asn Asn Tyr Val Ser
1               5                   10

<210> SEQ ID NO 239
<211> LENGTH: 7
<212> TYPE: PRT
<213> ORGANISM: Homo sapiens
<220> FEATURE:
<223> OTHER INFORMATION: 1147D2 VL CDR2 amino acid sequence

<400> SEQUENCE: 239

Asp Asn Asn Lys Arg Pro Ser
1               5

<210> SEQ ID NO 240
<211> LENGTH: 11
<212> TYPE: PRT
<213> ORGANISM: Homo sapiens
<220> FEATURE:
<223> OTHER INFORMATION: 1147D2 VL CDR3 amino acid sequence

<400> SEQUENCE: 240

Gly Thr Trp Asp Ser Ser Leu Ser Ala Trp Val
1               5                   10

<210> SEQ ID NO 241
<211> LENGTH: 384
<212> TYPE: DNA
<213> ORGANISM: Homo sapiens
<220> FEATURE:
<223> OTHER INFORMATION: 1147G9 VH nucleotide sequence

<400> SEQUENCE: 241
gaggtgcagc tggtgcagtc tggggctgag gtgaagaagc ctgggtcctc ggtgaaggtc      60
tcctgcaagg cttctggagg caccttcagc gcctatggta tctcatgggt gcgacaggcc     120
cctggacaag gacttgagtg gataggaggg attattccta tctttaacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc ctca                                            384

<210> SEQ ID NO 242
<211> LENGTH: 126
<212> TYPE: PRT
<213> ORGANISM: Homo sapiens
<220> FEATURE:

<223> OTHER INFORMATION: 1147G9 VH amino acid sequence

<400> SEQUENCE: 242

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asn Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val
        115                 120                 125

<210> SEQ ID NO 243
<211> LENGTH: 5
<212> TYPE: PRT
<213> ORGANISM: Homo sapiens
<220> FEATURE:
<223> OTHER INFORMATION: 1147G9 VH CDR1 amino acid sequence

<400> SEQUENCE: 243

Ala Tyr Gly Ile Ser
1               5

<210> SEQ ID NO 244
<211> LENGTH: 17
<212> TYPE: PRT
<213> ORGANISM: Homo sapiens
<220> FEATURE:
<223> OTHER INFORMATION: 1147G9 VH CDR2 amino acid sequence

<400> SEQUENCE: 244

Gly Ile Ile Pro Ile Phe Asn Thr Gly Asn Ser Ala Gln Ser Phe Gln
1               5                   10                  15

Gly

<210> SEQ ID NO 245
<211> LENGTH: 19
<212> TYPE: PRT
<213> ORGANISM: Homo sapiens
<220> FEATURE:
<223> OTHER INFORMATION: 1147G9 VH CDR3 amino acid sequence

<400> SEQUENCE: 245

Ser Ser Arg Ile Tyr Asp Leu Asn Pro Ser Leu Thr Ala Tyr Tyr Asp
1               5                   10                  15

Met Asp Val

<210> SEQ ID NO 246
<211> LENGTH: 330
<212> TYPE: DNA
<213> ORGANISM: Homo sapiens
<220> FEATURE:
<223> OTHER INFORMATION: 1147G9 VL nucleotide sequence -continued

<400> SEQUENCE: 246

```
caggctgtgc tgactcagcc gtcctcagtg tctacgcccc cagggcagaa ggtcaccgtc    60
tcctgctcag gaagcagctc caacattggg aataattatg tatcgtggta ccagcagctc   120
ccaggtacag cccccaaact cctcatttat gacaataata gcgaccctca agggattcct   180
gaccgattct ctggctccaa gtctggcacg tcagccaccc tgggcatcac cggactccag   240 actgggacg aggccgatta ttactgcgga acatgggata gcagcctgag tgcttgggtg   300
ttcggcggag ggaccaagct gaccgtccta                                    330
```

<210> SEQ ID NO 247
<211> LENGTH: 110
<212> TYPE: PRT
<213> ORGANISM: Homo sapiens
<220> FEATURE:
<223> OTHER INFORMATION: 1147G9 VL amino acid sequence

<400> SEQUENCE: 247

```
Gln Ala Val Leu Thr Gln Pro Ser Ser Val Ser Thr Pro Pro Gly Gln
1               5                   10                  15

Lys Val Thr Val Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 248
<211> LENGTH: 13
<212> TYPE: PRT
<213> ORGANISM: Homo sapiens
<220> FEATURE:
<223> OTHER INFORMATION: 1147G9 VL CDR1 amino acid sequence

<400> SEQUENCE: 248

```
Ser Gly Ser Ser Ser Asn Ile Gly Asn Asn Tyr Val Ser
1               5                   10
```

<210> SEQ ID NO 249
<211> LENGTH: 7
<212> TYPE: PRT
<213> ORGANISM: Homo sapiens
<220> FEATURE:
<223> OTHER INFORMATION: 1147G9 VL CDR2 amino acid sequence

<400> SEQUENCE: 249

```
Asp Asn Asn Lys Arg Pro Ser
1               5
```

<210> SEQ ID NO 250
<211> LENGTH: 11
<212> TYPE: PRT
<213> ORGANISM: Homo sapiens
<220> FEATURE:
<223> OTHER INFORMATION: 1147G9 VL CDR3 amino acid sequence -continued

```
<400> SEQUENCE: 250

Gly Thr Trp Asp Ser Ser Leu Ser Ala Trp Val
1               5                   10

<210> SEQ ID NO 251
<211> LENGTH: 384
<212> TYPE: DNA
<213> ORGANISM: Homo sapiens
<220> FEATURE:
<223> OTHER INFORMATION: 1150F1 VH nucleotide sequence

<400> SEQUENCE: 251
gaggtgcagc tggtgcagtc tggggctgag gtgaagaagc ctgggtcctc ggtgaaggtc      60
tcctgcaagg cttccggagg taccttcagc acctatggta tctcatgggt gcgacaggcc     120
cctggacaag gacttgagtg gatggggggg attattccta tctttgacac aggcaactct     180
gcacagagct tccaggacag agtcacgatt accgcggacg aatccacgag cacagcctac     240
atggaggtgg gcagcctgag atctgacgac acagccgtat attattgtgc aagttcaagt     300
cgtatctacg acttgaaccc ctccctcact gcctactacg atatggatgt ctggggccac     360
gggacaatgg tcaccgtctc ctca                                            384

<210> SEQ ID NO 252
<211> LENGTH: 128
<212> TYPE: PRT
<213> ORGANISM: Homo sapiens
<220> FEATURE:
<223> OTHER INFORMATION: 1150F1 VH amino acid sequence

<400> SEQUENCE: 252

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Asp Arg Val Thr Ile Thr Ala Asp Glu Ser Thr Ser Thr Ala Tyr
65                  70                  75                  80

Met Glu Val Gly Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly His Gly Thr Met Val Thr Val Ser Ser
        115                 120                 125

<210> SEQ ID NO 253
<211> LENGTH: 5
<212> TYPE: PRT
<213> ORGANISM: Homo sapiens
<220> FEATURE:
<223> OTHER INFORMATION: 1150F1 VH CDR1 amino acid sequence

<400> SEQUENCE: 253

Thr Tyr Gly Ile Ser
1               5

<210> SEQ ID NO 254
<211> LENGTH: 17
```

```
<212> TYPE: PRT
<213> ORGANISM: Homo sapiens
<220> FEATURE:
<223> OTHER INFORMATION: 1150F1 VH CDR2 amino acid sequence

<400> SEQUENCE: 254

Gly Ile Ile Pro Ile Phe Asp Thr Gly Asn Ser Ala Gln Ser Phe Gln
1               5                   10                  15

Asp

<210> SEQ ID NO 255
<211> LENGTH: 19
<212> TYPE: PRT
<213> ORGANISM: Homo sapiens
<220> FEATURE:
<223> OTHER INFORMATION: 1150F1 VH CDR3 amino acid sequence

<400> SEQUENCE: 255

Ser Ser Arg Ile Tyr Asp Leu Asn Pro Ser Leu Thr Ala Tyr Tyr Asp
1               5                   10                  15

Met Asp Val

<210> SEQ ID NO 256
<211> LENGTH: 330
<212> TYPE: DNA
<213> ORGANISM: Homo sapiens
<220> FEATURE:
<223> OTHER INFORMATION: 1150F1 VL nucleotide sequence

<400> SEQUENCE: 256
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag ccccccaaact cctcatttat gacaataata gcgaccctc agggattcct     180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 257
<211> LENGTH: 110
<212> TYPE: PRT
<213> ORGANISM: Homo sapiens
<220> FEATURE:
<223> OTHER INFORMATION: 1150F1 VL amino acid sequence

<400> SEQUENCE: 257

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 258
<211> LENGTH: 13
<212> TYPE: PRT
<213> ORGANISM: Homo sapiens
<220> FEATURE:
<223> OTHER INFORMATION: 1150F1 VL CDR1 amino acid sequence

<400> SEQUENCE: 258

Ser Gly Ser Ser Ser Asn Ile Gly Asn Asn Tyr Val Ser
1               5                   10

<210> SEQ ID NO 259
<211> LENGTH: 7
<212> TYPE: PRT
<213> ORGANISM: Homo sapiens
<220> FEATURE:
<223> OTHER INFORMATION: 1150F1 VL CDR2 amino acid sequence

<400> SEQUENCE: 259

Asp Asn Asn Lys Arg Pro Ser
1               5

<210> SEQ ID NO 260
<211> LENGTH: 11
<212> TYPE: PRT
<213> ORGANISM: Homo sapiens
<220> FEATURE:
<223> OTHER INFORMATION: 1150F1 VL CDR3 amino acid sequence

<400> SEQUENCE: 260

Gly Thr Trp Asp Ser Ser Leu Ser Ala Trp Val
1               5                   10

<210> SEQ ID NO 261
<211> LENGTH: 384
<212> TYPE: DNA
<213> ORGANISM: Homo sapiens
<220> FEATURE:
<223> OTHER INFORMATION: 1152H5 VH nucleotide sequence

<400> SEQUENCE: 261
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gactcgtgtg gataggaggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acatgatctc gtccttgcaa ccctactacg atatggatgt ctggggccag     360
gggacaatgg tcaccgtctc ctca                                            384

<210> SEQ ID NO 262
<211> LENGTH: 128
<212> TYPE: PRT
<213> ORGANISM: Homo sapiens
<220> FEATURE:
<223> OTHER INFORMATION: 1152H5 VH amino acid sequence

<400> SEQUENCE: 262

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

```
Gly Ile Ser Trp Val Arg Gln Ala Pro Gly Gln Gly Leu Val Trp Ile
            35                  40                  45

Gly Gly Ile Ile Pro Ile Phe Asp Thr Gly Asn Ser Ala Gln Ser Phe
        50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Met Ile Ser Ser Leu Gln Pro Tyr
                100                 105                 110             Tyr

Tyr Asp Met Asp Val Trp Gly Gln Gly Thr Met Val Thr Val Ser Ser
            115                 120                 125
```

<210> SEQ ID NO 263
<211> LENGTH: 5
<212> TYPE: PRT
<213> ORGANISM: Homo sapiens
<220> FEATURE:
<223> OTHER INFORMATION: 1152H5 VH CDR1 amino acid sequence

<400> SEQUENCE: 263

```
Thr Tyr Gly Ile Ser
1               5
```

<210> SEQ ID NO 264
<211> LENGTH: 17
<212> TYPE: PRT
<213> ORGANISM: Homo sapiens
<220> FEATURE:
<223> OTHER INFORMATION: 1152H5 VH CDR2 amino acid sequence

<400> SEQUENCE: 264

```
Gly Ile Ile Pro Ile Phe Asp Thr Gly Asn Ser Ala Gln Ser Phe Gln
1               5                   10                  15

Gly
```

<210> SEQ ID NO 265
<211> LENGTH: 19
<212> TYPE: PRT
<213> ORGANISM: Homo sapiens
<220> FEATURE:
<223> OTHER INFORMATION: 1152H5 VH CDR3 amino acid sequence

<400> SEQUENCE: 265

```
Ser Ser Arg Ile Tyr Asp Met Ile Ser Ser Leu Gln Pro Tyr Tyr Asp
1               5                   10                  15

Met Asp Val
```

<210> SEQ ID NO 266
<211> LENGTH: 330
<212> TYPE: DNA
<213> ORGANISM: Homo sapiens
<220> FEATURE:
<223> OTHER INFORMATION: 1152H5 VL nucleotide sequence

<400> SEQUENCE: 266

```
caggctgtgc tgactcagcc gtcctcagtg tctacgcccc caggacagaa ggccaccatc      60
tcctgctctg gaagcagctc caacattggg aataattatg tatcgtggta ccagcagctc     120
ccaggaacag ccccaaaact cctcatttat gacaataata gcgaccctc agggattcct     180 gaccgattct ctggctccaa gtctggcacg tcagccaccc tgggcatcac cggactccag     240
```

-continued

```
actgggacg aggccgatta ttactgcgga acatgggata gcagcctgag tgcttgggtg    300
ttcggcggag ggaccaagct gaccgtccta                                    330
```

<210> SEQ ID NO 267
<211> LENGTH: 110
<212> TYPE: PRT
<213> ORGANISM: Homo sapiens
<220> FEATURE:
<223> OTHER INFORMATION: 1152H5 VL amino acid sequence

<400> SEQUENCE: 267

```
Gln Ala Val Leu Thr Gln Pro Ser Ser Val Ser Thr Pro Pro Gly Gln
1               5                   10                  15

Lys Ala Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 268
<211> LENGTH: 13
<212> TYPE: PRT
<213> ORGANISM: Homo sapiens
<220> FEATURE:
<223> OTHER INFORMATION: 1152H5 VL CDR1 amino acid sequence

<400> SEQUENCE: 268

```
Ser Gly Ser Ser Ser Asn Ile Gly Asn Asn Tyr Val Ser
1               5                   10
```

<210> SEQ ID NO 269
<211> LENGTH: 7
<212> TYPE: PRT
<213> ORGANISM: Homo sapiens
<220> FEATURE:
<223> OTHER INFORMATION: 1152H5 VL CDR2 amino acid sequence

<400> SEQUENCE: 269

```
Asp Asn Asn Lys Arg Pro Ser
1               5
```

<210> SEQ ID NO 270
<211> LENGTH: 11
<212> TYPE: PRT
<213> ORGANISM: Homo sapiens
<220> FEATURE:
<223> OTHER INFORMATION: 1152H5 VL CDR3 amino acid sequence

<400> SEQUENCE: 270

```
Gly Thr Trp Asp Ser Ser Leu Ser Ala Trp Val
1               5                   10
```

<210> SEQ ID NO 271
<211> LENGTH: 384
<212> TYPE: DNA

-continued

<213> ORGANISM: Homo sapiens
<220> FEATURE:
<223> OTHER INFORMATION: 1155H1 VH nucleotide sequence

<400> SEQUENCE: 271

```
gaggtgcagc tggtgcagtc tggggctgag gtgaagaagc ctgggtcctc ggtgaaggtc    60
tcctgcaagg cttctggagg caccttcagc acctacggta tctcatgggt gcgacaggcc   120
cctggacaag gacttgagtg gataggaggg attattccta tctttgacac aggcaactct   180
gcacagagct tccagggcag agtcacgatt accgcggacg aatccacgag cacagcctac   240
atggaggtga gcagcctgag atctgacgac acggccgtat attattgtgc aagttcaagt   300
cgtatctacg acttccacct ggcgaacaag ggctactacg atatggatgt ctggggccag   360
gggacaatgg tcaccgtctc ctca                                         384
```

<210> SEQ ID NO 272
<211> LENGTH: 128
<212> TYPE: PRT
<213> ORGANISM: Homo sapiens
<220> FEATURE:
<223> OTHER INFORMATION: 1155H1 VH amino acid sequence

<400> SEQUENCE: 272

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Phe His Leu Ala Asn Lys Gly Tyr
            100                 105                 110

Tyr Asp Met Asp Val Trp Gly Gln Gly Thr Met Val Thr Val Ser Ser
        115                 120                 125

<210> SEQ ID NO 273
<211> LENGTH: 5
<212> TYPE: PRT
<213> ORGANISM: Homo sapiens
<220> FEATURE:
<223> OTHER INFORMATION: 1155H1 VH CDR1 amino acid sequence

<400> SEQUENCE: 273

Thr Tyr Gly Ile Ser
1               5

<210> SEQ ID NO 274
<211> LENGTH: 17
<212> TYPE: PRT
<213> ORGANISM: Homo sapiens
<220> FEATURE:
<223> OTHER INFORMATION: 1155H1 VH CDR2 amino acid sequence

<400> SEQUENCE: 274

Gly Ile Ile Pro Ile Phe Asp Thr Gly Asn Ser Ala Gln Ser Phe Gln
1               5                   10                  15

Gly

<210> SEQ ID NO 275
<211> LENGTH: 19
<212> TYPE: PRT
<213> ORGANISM: Homo sapiens
<220> FEATURE:
<223> OTHER INFORMATION: 1155H1 VH CDR3 amino acid sequence

<400> SEQUENCE: 275

Ser Ser Arg Ile Tyr Asp Phe His Leu Ala Asn Lys Gly Tyr Tyr Asp
1               5                   10                  15

Met Asp Val

<210> SEQ ID NO 276
<211> LENGTH: 330
<212> TYPE: DNA
<213> ORGANISM: Homo sapiens
<220> FEATURE:
<223> OTHER INFORMATION: 1155H1 VL nucleotide sequence

<400> SEQUENCE: 276
caggctgtgc tgactcagcc gtcctcagtg tctacgcccc caggacagaa ggccaccatc     60
tcctgctctg gaagcagctc caacattggg aataattatg tatcgtggta ccagcagctc    120
ccaggaacag cccccaaact cctcatttat gacaataata gcgaccctca gggattcct     180 gaccgattct ctggctccaa gtctggcacg tcagccaccc tggacatcac cggactccag    240
actggggacg aggccgatta ttactgcgga acatgggata gcagcctgag tgcttgggtg    300
ttcggcggag ggaccaagct gaccgtccta                                     330

<210> SEQ ID NO 277
<211> LENGTH: 110
<212> TYPE: PRT
<213> ORGANISM: Homo sapiens
<220> FEATURE:
<223> OTHER INFORMATION: 1155H1 VL amino acid sequence

<400> SEQUENCE: 277

Gln Ala Val Leu Thr Gln Pro Ser Ser Val Ser Thr Pro Pro Gly Gln
1               5                   10                  15

Lys Ala Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 278
<211> LENGTH: 13
<212> TYPE: PRT
<213> ORGANISM: Homo sapiens
<220> FEATURE:
<223> OTHER INFORMATION: 1155H1 VL CDR1 amino acid sequence

<400> SEQUENCE: 278

Ser Gly Ser Ser Ser Asn Ile Gly Asn Asn Tyr Val Ser
1               5                   10

<210> SEQ ID NO 279
<211> LENGTH: 7
<212> TYPE: PRT
<213> ORGANISM: Homo sapiens
<220> FEATURE:
<223> OTHER INFORMATION: 1155H1 VL CDR2 amino acid sequence

<400> SEQUENCE: 279

Asp Asn Asn Lys Arg Pro Ser
1               5

<210> SEQ ID NO 280
<211> LENGTH: 11
<212> TYPE: PRT
<213> ORGANISM: Homo sapiens
<220> FEATURE:
<223> OTHER INFORMATION: 1155H1 VL CDR3 amino acid sequence

<400> SEQUENCE: 280

Gly Thr Trp Asp Ser Ser Leu Ser Ala Trp Val
1               5                   10

<210> SEQ ID NO 281
<211> LENGTH: 384
<212> TYPE: DNA
<213> ORGANISM: Homo sapiens
<220> FEATURE:
<223> OTHER INFORMATION: 1158A1 VH nucleotide sequence

<400> SEQUENCE: 281

```
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggaggg attattccta tctttggcac aggcaactct     180
gcacagagct tccagggcag agtcacgatt accgcggatg aatccacgag cacagcctac     240
atggaggtga gcagcctgag atctgacgac acggccgtat attattgtgc aagttcaagt     300
cgtatctacg accaccacaa ccacgtgggg ggatactacg atatggatgt ctggggccag     360
gggacaatgg tcaccgtctc ctca                                            384
```

<210> SEQ ID NO 282
<211> LENGTH: 128
<212> TYPE: PRT
<213> ORGANISM: Homo sapiens
<220> FEATURE:
<223> OTHER INFORMATION: 1158A1 VH amino acid sequence

<400> SEQUENCE: 282

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Gly Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

```
Met Glu Val Ser Ser Leu Arg Ser Asp Asp Thr Ala Val Tyr Tyr Cys
                85                  90                  95

Ala Ser Ser Arg Ile Tyr Asp His His Asn His Val Gly Gly Tyr
        100                 105                 110

Tyr Asp Met Asp Val Trp Gly Gln Gly Thr Met Val Thr Val Ser Ser
        115                 120                 125

<210> SEQ ID NO 283
<211> LENGTH: 5
<212> TYPE: PRT
<213> ORGANISM: Homo sapiens
<220> FEATURE:
<223> OTHER INFORMATION: 1158A1 VH CDR1 amino acid sequence

<400> SEQUENCE: 283

Thr Tyr Gly Ile Ser
1               5

<210> SEQ ID NO 284
<211> LENGTH: 17
<212> TYPE: PRT
<213> ORGANISM: Homo sapiens
<220> FEATURE:
<223> OTHER INFORMATION: 1158A1 VH CDR2 amino acid sequence

<400> SEQUENCE: 284

Gly Ile Ile Pro Ile Phe Gly Thr Gly Asn Ser Ala Gln Ser Phe Gln
1               5                   10                  15

Gly

<210> SEQ ID NO 285
<211> LENGTH: 19
<212> TYPE: PRT
<213> ORGANISM: Homo sapiens
<220> FEATURE:
<223> OTHER INFORMATION: 1158A1 VH CDR3 amino acid sequence

<400> SEQUENCE: 285

Ser Ser Arg Ile Tyr Asp His His Asn His Val Gly Gly Tyr Tyr Asp
1               5                   10                  15

Met Asp Val

<210> SEQ ID NO 286
<211> LENGTH: 330
<212> TYPE: DNA
<213> ORGANISM: Homo sapiens
<220> FEATURE:
<223> OTHER INFORMATION: 1158A1 VL nucleotide sequence

<400> SEQUENCE: 286
caggctgtgc tgactcagcc gtcctcagtg tctacgcccc caggacagaa ggtcaccatc      60
tcctgctctg gaagcagctc aacattggga ataattatg catcgtggta ccagcagctc     120
ccaggaacag cccccaaact cctcatttat gacaataata gcgaccctc agggattcct     180 gaccgattct ctggctccaa gtctggcacg tcagccaccc tgggcatcac cggactccag     240 actgggacg aggccgatta ttactgcgga acatgggatg cagcctgag tgcttgggtg      300 ttcggcggag ggaccaagct gaccgtccta                                      330

<210> SEQ ID NO 287
<211> LENGTH: 110
<212> TYPE: PRT
```

<213> ORGANISM: Homo sapiens
<220> FEATURE:
<223> OTHER INFORMATION: 1158A1 VL amino acid sequence

<400> SEQUENCE: 287

```
Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Ala Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Ser Leu
                85                  90                  95

Ser Ala Trp Val Phe Gly Gly Gly Thr Lys Leu Thr Val Leu
            100                 105                 110
```

<210> SEQ ID NO 288
<211> LENGTH: 13
<212> TYPE: PRT
<213> ORGANISM: Homo sapiens
<220> FEATURE:
<223> OTHER INFORMATION: 1158A1 VL CDR1 amino acid sequence

<400> SEQUENCE: 288

```
Ser Gly Ser Ser Ser Asn Ile Gly Asn Asn Tyr Ala Ser
1               5                   10
```

<210> SEQ ID NO 289
<211> LENGTH: 7
<212> TYPE: PRT
<213> ORGANISM: Homo sapiens
<220> FEATURE:
<223> OTHER INFORMATION: 1158A1 VL CDR2 amino acid sequence

<400> SEQUENCE: 289

```
Asp Asn Asn Lys Arg Pro Ser
1               5
```

<210> SEQ ID NO 290
<211> LENGTH: 11
<212> TYPE: PRT
<213> ORGANISM: Homo sapiens
<220> FEATURE:
<223> OTHER INFORMATION: 1158A1 VL CDR3 amino acid sequence

<400> SEQUENCE: 290

```
Gly Thr Trp Asp Gly Ser Leu Ser Ala Trp Val
1               5                   10
```

<210> SEQ ID NO 291
<211> LENGTH: 384
<212> TYPE: DNA
<213> ORGANISM: Homo sapiens
<220> FEATURE:
<223> OTHER INFORMATION: 1160E3 VH nucleotide sequence

<400> SEQUENCE: 291

```
gaggtgcagc tggtgcagtc tggggctgag gtgaagaagc ctgggtcctc ggcgaaggtc      60
tcctgcaagg cttctggagg caccttcagc acctatggta tctcatgggt gcgacaggcc     120
```

```
cctggacaag gacttgagtg gataggggggg attattccta tctttgacac aggcaactct    180
gcacagagct tccagggcag agtcacgatt accgcgacg  aatccacgag cacagcctac    240
atggaggtga gcagcctgag atctgacgac acggccgtat attattgtgc aagttcaagt    300
cgtatctacg acttgaaccc ctccctcact gcctactacg atatggatgt ctggggccag    360
gggacaatgg tcaccgtctc gagt                                            384
```

```
<210> SEQ ID NO 292
<211> LENGTH: 128
<212> TYPE: PRT
<213> ORGANISM: Homo sapiens
<220> FEATURE:
<223> OTHER INFORMATION: 1160E3 VH amino acid sequence

<400> SEQUENCE: 292

Glu Val Gln Leu Val Gln Ser Gly Ala Glu Val Lys Lys Pro Gly Ser
1               5                   10                  15

Ser Ala Lys Val Ser Cys Lys Ala Ser Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125
```

```
<210> SEQ ID NO 293
<211> LENGTH: 5
<212> TYPE: PRT
<213> ORGANISM: Homo sapiens
<220> FEATURE:
<223> OTHER INFORMATION: 1160E3 VH CDR1 amino acid sequence

<400> SEQUENCE: 293

Thr Tyr Gly Ile Ser
1               5
```

```
<210> SEQ ID NO 294
<211> LENGTH: 17
<212> TYPE: PRT
<213> ORGANISM: Homo sapiens
<220> FEATURE:
<223> OTHER INFORMATION: 1160E3 VH CDR2 amino acid sequence

<400> SEQUENCE: 294

Gly Ile Ile Pro Ile Phe Asp Thr Gly Asn Ser Ala Gln Ser Phe Gln
1               5                   10                  15

Gly
```

```
<210> SEQ ID NO 295
<211> LENGTH: 19
<212> TYPE: PRT
<213> ORGANISM: Homo sapiens
<220> FEATURE:
```

<223> OTHER INFORMATION: 1160E3 VH CDR3 amino acid sequence

<400> SEQUENCE: 295

Ser Ser Arg Ile Tyr Asp Leu Asn Pro Ser Leu Thr Ala Tyr Tyr Asp
1               5                   10                  15

Met Asp Val

<210> SEQ ID NO 296
<211> LENGTH: 327
<212> TYPE: DNA
<213> ORGANISM: Homo sapiens
<220> FEATURE:
<223> OTHER INFORMATION: 1160E3 VL nucleotide sequence

<400> SEQUENCE: 296
caggctgtgc tgactcagcc gtcctcagtg tctacgcccc caggacagaa ggtcaccatc      60
tcctgctctg gaagcaactc caacattggg aataattatg tatcgtggta ccagcagctc     120
ccaggaacag cccccaaact cctcatttat gacaataata gcgaccctca gggattcct     180 gaccgattct ctggctccaa gtctggcacg tcagccaccc tgggcatcac cggactccag     240
actggggacg aggccgatta ttactgcgga acgtgggata gcagcctgag tgcttgggtg     300
ttcggcggag ggaccaagct gaccgtc                                          327

<210> SEQ ID NO 297
<211> LENGTH: 109
<212> TYPE: PRT
<213> ORGANISM: Homo sapiens
<220> FEATURE:
<223> OTHER INFORMATION: 1160E3 VL amino acid sequence

<400> SEQUENCE: 297

Gln Ala Val Leu Thr Gln Pro Ser Ser Val Ser Thr Pro Pro Gly Gln
1               5                   10                  15

Lys Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 298
<211> LENGTH: 13
<212> TYPE: PRT
<213> ORGANISM: Homo sapiens
<220> FEATURE:
<223> OTHER INFORMATION: 1160E3 VL CDR1 amino acid sequence

<400> SEQUENCE: 298

Ser Gly Ser Asn Ser Asn Ile Gly Asn Asn Tyr Val Ser
1               5                   10

<210> SEQ ID NO 299
<211> LENGTH: 7
<212> TYPE: PRT

<213> ORGANISM: Homo sapiens
<220> FEATURE:
<223> OTHER INFORMATION: 1160E3 VL CDR2 amino acid sequence

<400> SEQUENCE: 299

Asp Asn Asn Lys Arg Pro Ser
1               5

<210> SEQ ID NO 300
<211> LENGTH: 11
<212> TYPE: PRT
<213> ORGANISM: Homo sapiens
<220> FEATURE:
<223> OTHER INFORMATION: 1160E3 VL CDR3 amino acid sequence

<400> SEQUENCE: 300

Gly Thr Trp Asp Ser Ser Leu Ser Ala Trp Val
1               5                   10

<210> SEQ ID NO 301
<211> LENGTH: 384
<212> TYPE: DNA
<213> ORGANISM: Homo sapiens
<220> FEATURE:
<223> OTHER INFORMATION: 1165D4 VH nucleotide sequence

<400> SEQUENCE: 301
gaggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag acttgagtg gataggaggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc ctca                                            384

<210> SEQ ID NO 302
<211> LENGTH: 128
<212> TYPE: PRT
<213> ORGANISM: Homo sapiens
<220> FEATURE:
<223> OTHER INFORMATION: 1165D4 VH amino acid sequence

<400> SEQUENCE: 302

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 303
<211> LENGTH: 5
<212> TYPE: PRT
<213> ORGANISM: Homo sapiens
<220> FEATURE:
<223> OTHER INFORMATION: 1165D4 VH CDR1 amino acid sequence

<400> SEQUENCE: 303

Thr Tyr Gly Ile Ser
1               5

<210> SEQ ID NO 304
<211> LENGTH: 17
<212> TYPE: PRT
<213> ORGANISM: Homo sapiens
<220> FEATURE:
<223> OTHER INFORMATION: 1165D4 VH CDR2 amino acid sequence

<400> SEQUENCE: 304

Gly Ile Ile Pro Ile Phe Asp Thr Gly Asn Ser Ala Gln Ser Phe Gln
1               5                   10                  15

Gly

<210> SEQ ID NO 305
<211> LENGTH: 19
<212> TYPE: PRT
<213> ORGANISM: Homo sapiens
<220> FEATURE:
<223> OTHER INFORMATION: 1165D4 VH CDR3 amino acid sequence

<400> SEQUENCE: 305

Ser Ser Arg Ile Tyr Asp Leu Asn Pro Ser Leu Thr Ala Tyr Tyr Asp
1               5                   10                  15

Met Asp Val

<210> SEQ ID NO 306
<211> LENGTH: 330
<212> TYPE: DNA
<213> ORGANISM: Homo sapiens
<220> FEATURE:
<223> OTHER INFORMATION: 1165D4 VL nucleotide sequence

<400> SEQUENCE: 306
caggctgtgc tgactcagcc gtcctcagtg tctacgcccc caggacagaa ggtcaccatc      60
tcctgctctg gaagcagctc caacattgag aataattatg tatcgtggta ccagcagctc     120
ccaggaacag ccccccaaact cctcatttat gacaataata gcgaccctc agggattcct     180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 307
<211> LENGTH: 110
<212> TYPE: PRT
<213> ORGANISM: Homo sapiens
<220> FEATURE:
<223> OTHER INFORMATION: 1165D4 VL amino acid sequence

<400> SEQUENCE: 307

Gln Ala Val Leu Thr Gln Pro Ser Ser Val Ser Thr Pro Pro Gly Gln
1               5                   10                  15

```
Lys Val Thr Ile Ser Cys Ser Gly Ser Ser Asn Ile Glu Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
            100                 105                 110

<210> SEQ ID NO 308
<211> LENGTH: 13
<212> TYPE: PRT
<213> ORGANISM: Homo sapiens
<220> FEATURE:
<223> OTHER INFORMATION: 1165D4 VL CDR1 amino acid sequence

<400> SEQUENCE: 308

Ser Gly Ser Ser Ser Asn Ile Glu Asn Asn Tyr Val Ser
1               5                   10

<210> SEQ ID NO 309
<211> LENGTH: 7
<212> TYPE: PRT
<213> ORGANISM: Homo sapiens
<220> FEATURE:
<223> OTHER INFORMATION: 1165D4 VL CDR2 amino acid sequence

<400> SEQUENCE: 309

Asp Asn Asn Lys Arg Pro Ser
1               5

<210> SEQ ID NO 310
<211> LENGTH: 11
<212> TYPE: PRT
<213> ORGANISM: Homo sapiens
<220> FEATURE:
<223> OTHER INFORMATION: 1165D4 VL CDR3 amino acid sequence

<400> SEQUENCE: 310

Gly Thr Trp Asp Ser Ser Leu Ser Ala Trp Val
1               5                   10

<210> SEQ ID NO 311
<211> LENGTH: 384
<212> TYPE: DNA
<213> ORGANISM: Homo sapiens
<220> FEATURE:
<223> OTHER INFORMATION: 1175H8 VH nucleotide sequence

<400> SEQUENCE: 311
gaggtgcagc tggtgcagtc tggggctgag gtgaagaagc ctgggtcctc ggtgaaggtc      60
tcctgcaagg cttctggagg cacccttcag acctatggta tctcatgggt gcgacaggcc     120
cctggacaaa gacttgagtg gataggaggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acgcgaccac cggcctgact ccgtactacg atatggatgt ctggggccag     360
```
gggacaatgg tcaccgtctc ctca                                              384

```
<210> SEQ ID NO 312
<211> LENGTH: 128
<212> TYPE: PRT
<213> ORGANISM: Homo sapiens
<220> FEATURE:
<223> OTHER INFORMATION: 1175H8 VH amino acid sequence

<400> SEQUENCE: 312
```

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Arg Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Ala Thr Thr Gly Leu Thr Pro Tyr
            100                 105                 110

Tyr Asp Met Asp Val Trp Gly Gln Gly Thr Met Val Thr Val Ser Ser
            115                 120                 125

```
<210> SEQ ID NO 313
<211> LENGTH: 5
<212> TYPE: PRT
<213> ORGANISM: Homo sapiens
<220> FEATURE:
<223> OTHER INFORMATION: 1175H8 VH CDR1 amino acid sequence

<400> SEQUENCE: 313
```

Thr Tyr Gly Ile Ser
1               5

```
<210> SEQ ID NO 314
<211> LENGTH: 17
<212> TYPE: PRT
<213> ORGANISM: Homo sapiens
<220> FEATURE:
<223> OTHER INFORMATION: 1175H8 VH CDR2 amino acid sequence

<400> SEQUENCE: 314
```

Gly Ile Ile Pro Ile Phe Asp Thr Gly Asn Ser Ala Gln Ser Phe Gln
1               5                   10                  15

Gly

```
<210> SEQ ID NO 315
<211> LENGTH: 19
<212> TYPE: PRT
<213> ORGANISM: Homo sapiens
<220> FEATURE:
<223> OTHER INFORMATION: 1175H8 VH CDR3 amino acid sequence

<400> SEQUENCE: 315
```

Ser Ser Arg Ile Tyr Asp Ala Thr Thr Gly Leu Thr Pro Tyr Tyr Asp
1               5                   10                  15

Met Asp Val

<210> SEQ ID NO 316
<211> LENGTH: 330
<212> TYPE: DNA
<213> ORGANISM: Homo sapiens
<220> FEATURE:
<223> OTHER INFORMATION: 1175H8 VL nucleotide sequence

<400> SEQUENCE: 316

```
caggctgtgc tgactcagcc gtcctcagtg tctacgcccc caggacagaa ggtcaccatc    60
tcctgctctg gaagcagctc caacattggg aataattatg tatcgtggta ccagcagctc   120
ccaggaacag cccccaaact cctcatttat gacaataata gcgaccctca gggattcct    180
gaccgattct ctggctccaa gtctggcacg tcagccaccc tgggcatcac cggactccgg   240
actgggacg aggccgatta ttactgcgga acatgggata gcagcctgag tgcttgggtg    300
ttcggcggag ggaccaagct gaccgtccta                                    330
```

<210> SEQ ID NO 317
<211> LENGTH: 110
<212> TYPE: PRT
<213> ORGANISM: Homo sapiens
<220> FEATURE:
<223> OTHER INFORMATION: 1175H8 VL amino acid sequence

<400> SEQUENCE: 317

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 318
<211> LENGTH: 13
<212> TYPE: PRT
<213> ORGANISM: Homo sapiens
<220> FEATURE:
<223> OTHER INFORMATION: 1175H8 VL CDR1 amino acid sequence

<400> SEQUENCE: 318

Ser Gly Ser Ser Ser Asn Ile Gly Asn Asn Tyr Val Ser
1               5                   10

<210> SEQ ID NO 319
<211> LENGTH: 7
<212> TYPE: PRT
<213> ORGANISM: Homo sapiens
<220> FEATURE:
<223> OTHER INFORMATION: 1175H8 VL CDR2 amino acid sequence

<400> SEQUENCE: 319

Asp Asn Asn Lys Arg Pro Ser
1               5

<210> SEQ ID NO 320
<211> LENGTH: 11
<212> TYPE: PRT
<213> ORGANISM: Homo sapiens
<220> FEATURE:
<223> OTHER INFORMATION: 1175H8 VL CDR3 amino acid sequence

<400> SEQUENCE: 320

Gly Thr Trp Asp Ser Ser Leu Ser Ala Trp Val
1               5                   10

<210> SEQ ID NO 321
<211> LENGTH: 384
<212> TYPE: DNA
<213> ORGANISM: Homo sapiens
<220> FEATURE:
<223> OTHER INFORMATION: 1211G10 VH nucleotide sequence

<400> SEQUENCE: 321
gaggtgcagc tggtgcagtc tggggctgag gtgaggaagc ctgggtcctc ggtgaaggtc      60
tcctgcaagg cttatggagg caccttcagc acctatggta tctcatgggt gcgacaggcc     120
cctggacaag gacttgagtg ggtaggaggg attattccta tctttgacac acgcaactct     180
gcacagagct tccagggcag agtcacgatt accgcggacg aatccacgag cacagcctac     240
atggaggtga gcagcctgag atctgacgac acggccgtat attattgtgc gagttcaagt     300
cgtatctacg acatggtctc cacgctcatc ccctactacg atatggatgt ctggggccag     360
gggacaatgg tcaccgtctc ctca                                            384

<210> SEQ ID NO 322
<211> LENGTH: 128
<212> TYPE: PRT
<213> ORGANISM: Homo sapiens
<220> FEATURE:
<223> OTHER INFORMATION: 1211G10 VH amino acid sequence

<400> SEQUENCE: 322

Glu Val Gln Leu Val Gln Ser Gly Ala Glu Val Arg Lys Pro Gly Ser
1               5                   10                  15

Ser Val Lys Val Ser Cys Lys Ala Tyr Gly Gly Thr Phe Ser Thr Tyr
                20                  25                  30

Gly Ile Ser Trp Val Arg Gln Ala Pro Gly Gln Gly Leu Glu Trp Val
            35                  40                  45

Gly Gly Ile Ile Pro Ile Phe Asp Thr Arg Asn Ser Ala Gln Ser Phe
        50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Met Val Ser Thr Leu Ile Pro Tyr
                100                 105                 110

Tyr Asp Met Asp Val Trp Gly Gln Gly Thr Met Val Thr Val Ser Ser
            115                 120                 125

<210> SEQ ID NO 323
<211> LENGTH: 5
<212> TYPE: PRT
<213> ORGANISM: Homo sapiens
<220> FEATURE:
<223> OTHER INFORMATION: 1211G10 VH CDR1 amino acid sequence

<400> SEQUENCE: 323

Thr Tyr Gly Ile Ser
1               5

<210> SEQ ID NO 324
<211> LENGTH: 17
<212> TYPE: PRT
<213> ORGANISM: Homo sapiens
<220> FEATURE:
<223> OTHER INFORMATION: 1211G10 VH CDR2 amino acid sequence

<400> SEQUENCE: 324

Gly Ile Ile Pro Ile Phe Asp Thr Arg Asn Ser Ala Gln Ser Phe Gln
1               5                   10                  15

Gly

<210> SEQ ID NO 325
<211> LENGTH: 19
<212> TYPE: PRT
<213> ORGANISM: Homo sapiens
<220> FEATURE:
<223> OTHER INFORMATION: 1211G10 VH CDR3 amino acid sequence

<400> SEQUENCE: 325

Ser Ser Arg Ile Tyr Asp Met Val Ser Thr Leu Ile Pro Tyr Tyr Asp
1               5                   10                  15

Met Asp Val

<210> SEQ ID NO 326
<211> LENGTH: 330
<212> TYPE: DNA
<213> ORGANISM: Homo sapiens
<220> FEATURE:
<223> OTHER INFORMATION: 1211G10 VL nucleotide sequence

<400> SEQUENCE: 326
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag cccccaaact cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 327
<211> LENGTH: 110
<212> TYPE: PRT
<213> ORGANISM: Homo sapiens
<220> FEATURE:
<223> OTHER INFORMATION: 1211G10 VL amino acid sequence

<400> SEQUENCE: 327

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 328
<211> LENGTH: 13
<212> TYPE: PRT
<213> ORGANISM: Homo sapiens
<220> FEATURE:
<223> OTHER INFORMATION: 1211G10 VL CDR1 amino acid sequence

<400> SEQUENCE: 328

Ser Gly Ser Ser Ser Asn Ile Gly Asn Asn Tyr Val Ser
1               5                   10

<210> SEQ ID NO 329
<211> LENGTH: 7
<212> TYPE: PRT
<213> ORGANISM: Homo sapiens
<220> FEATURE:
<223> OTHER INFORMATION: 1211G10 VL CDR2 amino acid sequence

<400> SEQUENCE: 329

Asp Asn Asn Lys Arg Pro Ser
1               5

<210> SEQ ID NO 330
<211> LENGTH: 11
<212> TYPE: PRT
<213> ORGANISM: Homo sapiens
<220> FEATURE:
<223> OTHER INFORMATION: 1211G10 VL CDR3 amino acid sequence

<400> SEQUENCE: 330

Gly Thr Trp Asp Ser Ser Leu Ser Ala Trp Val
1               5                   10

<210> SEQ ID NO 331
<211> LENGTH: 378
<212> TYPE: DNA
<213> ORGANISM: Homo sapiens
<220> FEATURE:
<223> OTHER INFORMATION: 1214A1 VH nucleotide sequence

<400> SEQUENCE: 331
gaggtgcagc tggtgcagtc tggggctgag gtgaagaagc ctgggtcctc ggtgagggtc      60
tcctgcaagg cttctggagg caccttcagc acctatggta tctcatgggt gcgacaggcc     120
cctggacaag gacttgagtg gataggaggg attattccta tctttgacac aggcaactct     180
gcgcagagct tccagggcag agtcacgatt accgcggacg aatccacgag cacagcctac     240
atggaggtga gcagcctgag atctgacgac acggccgtat attattgtgc aagttcaagt     300
cgtatctacg acgcccacct gcaagcctac tacgatatgg atgtctgggg ccaggggaca     360
atggtcaccg tctcctca                                                   378

<210> SEQ ID NO 332
<211> LENGTH: 126
<212> TYPE: PRT
<213> ORGANISM: Homo sapiens
<220> FEATURE:
<223> OTHER INFORMATION: 1214A1 VH amino acid sequence -continued

<400> SEQUENCE: 332

Glu Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Ala His Leu Gln Ala Tyr Tyr Asp
            100                 105                 110

Met Asp Val Trp Gly Gln Gly Thr Met Val Thr Val Ser Ser
        115                 120                 125

<210> SEQ ID NO 333
<211> LENGTH: 5
<212> TYPE: PRT
<213> ORGANISM: Homo sapiens
<220> FEATURE:
<223> OTHER INFORMATION: 1214A1 VH CDR1 amino acid sequence

<400> SEQUENCE: 333

Thr Tyr Gly Ile Ser
1               5

<210> SEQ ID NO 334
<211> LENGTH: 17
<212> TYPE: PRT
<213> ORGANISM: Homo sapiens
<220> FEATURE:
<223> OTHER INFORMATION: 1214A1 VH CDR2 amino acid sequence

<400> SEQUENCE: 334

Gly Ile Ile Pro Ile Phe Asp Thr Gly Asn Ser Ala Gln Ser Phe Gln
1               5                   10                  15

Gly

<210> SEQ ID NO 335
<211> LENGTH: 17
<212> TYPE: PRT
<213> ORGANISM: Homo sapiens
<220> FEATURE:
<223> OTHER INFORMATION: 1214A1 VH CDR3 amino acid sequence

<400> SEQUENCE: 335

Ser Ser Arg Ile Tyr Asp Ala His Leu Gln Ala Tyr Tyr Asp Met Asp
1               5                   10                  15

Val

<210> SEQ ID NO 336
<211> LENGTH: 330
<212> TYPE: DNA
<213> ORGANISM: Homo sapiens
<220> FEATURE:
<223> OTHER INFORMATION: 1214A1 VL nucleotide sequence

<400> SEQUENCE: 336

```
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag cccccaaact cctcatttat gacaacaata gcgaccccc agggattcct      180 gaccgattct ctggctccaa gtctggcacg tcagccaccc tgggcatcac cggactccag     240
actggggacg aggccgatta ttactgcgga acacgggata gcagcctgag tgcttgggtg     300
ttcggcggag ggaccaagct gaccgtccta                                      330
```

<210> SEQ ID NO 337
<211> LENGTH: 110
<212> TYPE: PRT
<213> ORGANISM: Homo sapiens
<220> FEATURE:
<223> OTHER INFORMATION: 1214A1 VL amino acid sequence

<400> SEQUENCE: 337

```
Gln Ala Val Leu Thr Gln Pro Ser Ser Val Ser Thr Pro Pro Gly Gln
1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Pro Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Arg Asp Ser Ser Leu
                85                  90                  95

Ser Ala Trp Val Phe Gly Gly Gly Thr Lys Leu Thr Val Leu
            100                 105                 110
```

<210> SEQ ID NO 338
<211> LENGTH: 13
<212> TYPE: PRT
<213> ORGANISM: Homo sapiens
<220> FEATURE:
<223> OTHER INFORMATION: 1214A1 VL CDR1 amino acid sequence

<400> SEQUENCE: 338

```
Ser Gly Ser Ser Ser Asn Ile Gly Asn Asn Tyr Val Ser
1               5                  10
```

<210> SEQ ID NO 339
<211> LENGTH: 7
<212> TYPE: PRT
<213> ORGANISM: Homo sapiens
<220> FEATURE:
<223> OTHER INFORMATION: 1214A1 VL CDR2 amino acid sequence

<400> SEQUENCE: 339

```
Asp Asn Asn Lys Arg Pro Pro
1               5
```

<210> SEQ ID NO 340
<211> LENGTH: 11
<212> TYPE: PRT
<213> ORGANISM: Homo sapiens
<220> FEATURE:
<223> OTHER INFORMATION: 1214A1 VL CDR3 amino acid sequence

<400> SEQUENCE: 340

Gly Thr Arg Asp Ser Ser Leu Ser Ala Trp Val
1               5                   10

<210> SEQ ID NO 341
<211> LENGTH: 384
<212> TYPE: DNA
<213> ORGANISM: Homo sapiens
<220> FEATURE:
<223> OTHER INFORMATION: 1214D10 VH nucleotide sequence

<400> SEQUENCE: 341

```
gaggtgcagc tggtgcagtc tggggctgag gcgaagaagc ctgggtcctc ggtgaaggtc     60
tcctgcaagg cttctggagg caccttcagc acctatggta tctcatgggt gcgacaggcc    120
cctggacgag gacttgagtg gataggaggg attattccta tctttgacac aggcaactct    180
gcacagagct tccagggcag agtcgcgatt accgcgacg aatccacgag cacagcctac    240
atggaggtga gcagcctgag atctgacgac acggccgtat attattgtgc aagttcaagt    300
cgtatctacg acgcgcactt gaaccaccac ggctactacg atatggatgt ctggggccag    360
gggacaatgg tcaccgtctc ctca                                           384
```

<210> SEQ ID NO 342
<211> LENGTH: 128
<212> TYPE: PRT
<213> ORGANISM: Homo sapiens
<220> FEATURE:
<223> OTHER INFORMATION: 1214D10 VH amino acid sequence

<400> SEQUENCE: 342

Glu Val Gln Leu Val Gln Ser Gly Ala Glu Ala Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Arg Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Ala Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Ala His Leu Asn His His Gly Tyr
            100                 105                 110

Tyr Asp Met Asp Val Trp Gly Gln Gly Thr Met Val Thr Val Ser Ser
        115                 120                 125

<210> SEQ ID NO 343
<211> LENGTH: 5
<212> TYPE: PRT
<213> ORGANISM: Homo sapiens
<220> FEATURE:
<223> OTHER INFORMATION: 1214D10 VH CDR1 amino acid sequence

<400> SEQUENCE: 343

Thr Tyr Gly Ile Ser
1               5

<210> SEQ ID NO 344
<211> LENGTH: 17
<212> TYPE: PRT

<213> ORGANISM: Homo sapiens
<220> FEATURE:
<223> OTHER INFORMATION: 1214D10 VH CDR2 amino acid sequence

<400> SEQUENCE: 344

Gly Ile Ile Pro Ile Phe Asp Thr Gly Asn Ser Ala Gln Ser Phe Gln
1               5                   10                  15

Gly

<210> SEQ ID NO 345
<211> LENGTH: 19
<212> TYPE: PRT
<213> ORGANISM: Homo sapiens
<220> FEATURE:
<223> OTHER INFORMATION: 1214D10 VH CDR3 amino acid sequence

<400> SEQUENCE: 345

Ser Ser Arg Ile Tyr Asp Ala His Leu Asn His His Gly Tyr Tyr Asp
1               5                   10                  15

Met Asp Val

<210> SEQ ID NO 346
<211> LENGTH: 330
<212> TYPE: DNA
<213> ORGANISM: Homo sapiens
<220> FEATURE:
<223> OTHER INFORMATION: 1214D10 VL nucleotide sequence

<400> SEQUENCE: 346
caggctgtgc tgactcagcc gtcctcagtg tccacgcccc caggacagaa ggtcaccatc        60
tcctgctctg gaagcagctc caacattggg aataattatg tatcgtggta ccagcagctc       120
ccaggaacag cccccaaact cctcatttat gacaataata gcgaccctca gggattcct        180 gaccgattct ctggctccaa gtctggcacg tcagccaccc tgggcatcac cggactccag       240 gctgggacg aggccgatta ttactgcgga acatgggata gcagcctgag cgcttgggtg        300
ttcggcggag ggaccaagct gaccgtccta                                         330

<210> SEQ ID NO 347
<211> LENGTH: 110
<212> TYPE: PRT
<213> ORGANISM: Homo sapiens
<220> FEATURE:
<223> OTHER INFORMATION: 1214D10 VL amino acid sequence

<400> SEQUENCE: 347

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Ala Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 348
<211> LENGTH: 13
<212> TYPE: PRT
<213> ORGANISM: Homo sapiens
<220> FEATURE:
<223> OTHER INFORMATION: 1214D10 VL CDR1 amino acid sequence

<400> SEQUENCE: 348

Ser Gly Ser Ser Ser Asn Ile Gly Asn Asn Tyr Val Ser
1               5                   10

<210> SEQ ID NO 349
<211> LENGTH: 7
<212> TYPE: PRT
<213> ORGANISM: Homo sapiens
<220> FEATURE:
<223> OTHER INFORMATION: 1214D10 VL CDR2 amino acid sequence

<400> SEQUENCE: 349

Asp Asn Asn Lys Arg Pro Ser
1               5

<210> SEQ ID NO 350
<211> LENGTH: 11
<212> TYPE: PRT
<213> ORGANISM: Homo sapiens
<220> FEATURE:
<223> OTHER INFORMATION: 1214D10 VL CDR3 amino acid sequence

<400> SEQUENCE: 350

Gly Thr Trp Asp Ser Ser Leu Ser Ala Trp Val
1               5                   10

<210> SEQ ID NO 351
<211> LENGTH: 384
<212> TYPE: DNA
<213> ORGANISM: Homo sapiens
<220> FEATURE:
<223> OTHER INFORMATION: 1218H5 VH nucleotide sequence

<400> SEQUENCE: 351
gaggtgcagc tggtgcagtc tggggctgtg gtgaagaagc ctgggtcctc ggtgaaggtc      60
tcctgcaagg cttctggagg caccttcagc acctatggta tctcatgggt gcgacaggcc    120
cctggacaag gacttgagtg gatagggggg attattccta tctttgacac aggcagctct    180
gcacagagct tccagggcag agtcacgatt accgcggacg aatccacgag cacagcctac    240
atggaggtga gcagcttgag atctgacgac acggccgtat attattgtgc aagttcaagt    300
cgcatctacg acttgaaccc ctccctcact gcctactacg atatggatgt ctggggccag    360
gggacaatgg tcaccgtctc ctca                                            384

<210> SEQ ID NO 352
<211> LENGTH: 128
<212> TYPE: PRT
<213> ORGANISM: Homo sapiens
<220> FEATURE:
<223> OTHER INFORMATION: 1218H5 VH amino acid sequence

<400> SEQUENCE: 352

Glu Val Gln Leu Val Gln Ser Gly Ala Val Val Lys Lys Pro Gly Ser
1               5                   10                  15

Ser Val Lys Val Ser Cys Lys Ala Ser Gly Gly Thr Phe Ser Thr Tyr
            20                  25                  30

-continued

Gly Ile Ser Trp Val Arg Gln Ala Pro Gly Gln Gly Leu Glu Trp Ile
            35                  40                  45

Gly Gly Ile Ile Pro Ile Phe Asp Thr Gly Ser Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
                100                 105                 110

Tyr Asp Met Asp Val Trp Gly Gln Gly Thr Met Val Thr Val Ser Ser
        115                 120                 125

<210> SEQ ID NO 353
<211> LENGTH: 5
<212> TYPE: PRT
<213> ORGANISM: Homo sapiens
<220> FEATURE:
<223> OTHER INFORMATION: 1218H5 VH CDR1 amino acid sequence

<400> SEQUENCE: 353

Thr Tyr Gly Ile Ser
1               5

<210> SEQ ID NO 354
<211> LENGTH: 17
<212> TYPE: PRT
<213> ORGANISM: Homo sapiens
<220> FEATURE:
<223> OTHER INFORMATION: 1218H5 VH CDR2 amino acid sequence

<400> SEQUENCE: 354

Gly Ile Ile Pro Ile Phe Asp Thr Gly Ser Ser Ala Gln Ser Phe Gln
1               5                   10                  15

Gly

<210> SEQ ID NO 355
<211> LENGTH: 19
<212> TYPE: PRT
<213> ORGANISM: Homo sapiens
<220> FEATURE:
<223> OTHER INFORMATION: 1218H5 VH CDR3 amino acid sequence

<400> SEQUENCE: 355

Ser Ser Arg Ile Tyr Asp Leu Asn Pro Ser Leu Thr Ala Tyr Tyr Asp
1               5                   10                  15

Met Asp Val

<210> SEQ ID NO 356
<211> LENGTH: 330
<212> TYPE: DNA
<213> ORGANISM: Homo sapiens
<220> FEATURE:
<223> OTHER INFORMATION: 1218H5 VL nucleotide sequence

<400> SEQUENCE: 356
caggctgtgc tgactcagcc gtcctcagtg tctacgcccc caggacagaa ggtcaccatc      60
tcctgctctg gaagcagctc caacactggg aataattatg tatcgtggta ccagcagctc     120
tcaggaacag ccccccaaact cctcatttat gacaataata agcgaccctc agggattcct     180
gaccgattct ctggctccaa gtctggcacg tcagccaccc tgggcatcac cggactccag     240

```
actggggacg aggccgatta ttactgcgga acatgggata gcagcctgag tgcttgggtg      300
ttcggcggag ggaccaagct gaccgtccta                                       330
```

<210> SEQ ID NO 357
<211> LENGTH: 110
<212> TYPE: PRT
<213> ORGANISM: Homo sapiens
<220> FEATURE:
<223> OTHER INFORMATION: 1218H5 VL amino acid sequence

<400> SEQUENCE: 357

```
Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Thr Gly Asn Asn
            20                  25                  30

Tyr Val Ser Trp Tyr Gln Gln Leu Ser Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 358
<211> LENGTH: 13
<212> TYPE: PRT
<213> ORGANISM: Homo sapiens
<220> FEATURE:
<223> OTHER INFORMATION: 1218H5 VL CDR1 amino acid sequence

<400> SEQUENCE: 358

```
Ser Gly Ser Ser Ser Asn Thr Gly Asn Asn Tyr Val Ser
1               5                   10
```

<210> SEQ ID NO 359
<211> LENGTH: 7
<212> TYPE: PRT
<213> ORGANISM: Homo sapiens
<220> FEATURE:
<223> OTHER INFORMATION: 1218H5 VL CDR2 amino acid sequence

<400> SEQUENCE: 359

```
Asp Asn Asn Lys Arg Pro Ser
1               5
```

<210> SEQ ID NO 360
<211> LENGTH: 11
<212> TYPE: PRT
<213> ORGANISM: Homo sapiens
<220> FEATURE:
<223> OTHER INFORMATION: 1218H5 VL CDR3 amino acid sequence

<400> SEQUENCE: 360

```
Gly Thr Trp Asp Ser Ser Leu Ser Ala Trp Val
1               5                   10
```

<210> SEQ ID NO 361
<211> LENGTH: 384
<212> TYPE: DNA
<213> ORGANISM: Homo sapiens
<220> FEATURE:
<223> OTHER INFORMATION: 1230H7 VH nucleotide sequence

<400> SEQUENCE: 361

```
gagatgcagc tggtgcagtc tggggctgag gtgaagaagc ctgggtcctc ggtgaaggtc      60
tcctgcaagg cttctggagg cacctttcagt acctatggta tctcatgggt gcgacaggcc    120
cctggacaag gacttgagtg gataggaggg attattccta tctttgacac aggcaactct    180
gcacagagct tccagggcag agtcacgatt accgcggacg aatccacgag cacagcctac    240
atggaggtga gcagcctgag atctgacgac acggccgtat attattgtgc aagttcaagt    300
cgtatctatg acttcaactc cgccctcata tcctactacg atatggatgt ctggggccag    360
gggacaatgg tcaccgtctc gagt                                            384
```

<210> SEQ ID NO 362
<211> LENGTH: 128
<212> TYPE: PRT
<213> ORGANISM: Homo sapiens
<220> FEATURE:
<223> OTHER INFORMATION: 1230H7 VH amino acid sequence

<400> SEQUENCE: 362

```
Glu Met Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Thr Tyr
            20                  25                  30
Gly Ile Ser Trp Val Arg Gln Ala Pro Gly Gln Gly Leu Glu Trp Ile
        35                  40                  45
Gly Gly Ile Ile Pro Ile Phe Asp Thr Gly Asn Ser Ala Gln Ser Phe
    50                  55                  60
Gln Gly Arg Val Thr Ile Thr Ala Asp Glu Ser Thr Ser Thr Ala Tyr
65                  70                  75                  80
Met Glu Val Ser Ser Leu Arg Ser Asp Asp Thr Ala Val Tyr Tyr Cys
                85                  90                  95
Ala Ser Ser Ser Arg Ile Tyr Asp Phe Asn Ser Ala Leu Ile Ser Tyr
            100                 105                 110
Tyr Asp Met Asp Val Trp Gly Gln Gly Thr Met Val Thr Val Ser Ser
        115                 120                 125
```

<210> SEQ ID NO 363
<211> LENGTH: 5
<212> TYPE: PRT
<213> ORGANISM: Homo sapiens
<220> FEATURE:
<223> OTHER INFORMATION: 1230H7 VH CDR1 amino acid sequence

<400> SEQUENCE: 363

```
Thr Tyr Gly Ile Ser
1               5
```

<210> SEQ ID NO 364
<211> LENGTH: 17
<212> TYPE: PRT
<213> ORGANISM: Homo sapiens
<220> FEATURE:
<223> OTHER INFORMATION: 1230H7 VH CDR2 amino acid sequence

<400> SEQUENCE: 364

```
Gly Ile Ile Pro Ile Phe Asp Thr Gly Asn Ser Ala Gln Ser Phe Gln
1               5                   10                  15
```

Gly

<210> SEQ ID NO 365
<211> LENGTH: 19
<212> TYPE: PRT
<213> ORGANISM: Homo sapiens
<220> FEATURE:
<223> OTHER INFORMATION: 1230H7 VH CDR3 amino acid sequence

<400> SEQUENCE: 365

Ser Ser Arg Ile Tyr Asp Phe Asn Ser Ala Leu Ile Ser Tyr Tyr Asp
1               5                   10                  15

Met Asp Val

<210> SEQ ID NO 366
<211> LENGTH: 327
<212> TYPE: DNA
<213> ORGANISM: Homo sapiens
<220> FEATURE:
<223> OTHER INFORMATION: 1230H7 VL nucleotide sequence

<400> SEQUENCE: 366
caagctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag cccccaaact cctcatttat gacaataata gcgaccctca gggattcct     180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtc                                         327

<210> SEQ ID NO 367
<211> LENGTH: 109
<212> TYPE: PRT
<213> ORGANISM: Homo sapiens
<220> FEATURE:
<223> OTHER INFORMATION: 1230H7 VL amino acid sequence

<400> SEQUENCE: 367

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 368
<211> LENGTH: 13
<212> TYPE: PRT
<213> ORGANISM: Homo sapiens
<220> FEATURE:
<223> OTHER INFORMATION: 1230H7 VL CDR1 amino acid sequence

<400> SEQUENCE: 368

<210> SEQ ID NO 369
<211> LENGTH: 7
<212> TYPE: PRT
<213> ORGANISM: Homo sapiens
<220> FEATURE:
<223> OTHER INFORMATION: 1230H7 VL CDR2 amino acid sequence

<400> SEQUENCE: 369

Ser Gly Ser Ser Ser Asn Ile Gly Asn Asn Tyr Val Ser
1               5                   10

<210> SEQ ID NO 369
<211> LENGTH: 7
<212> TYPE: PRT
<213> ORGANISM: Homo sapiens
<220> FEATURE:
<223> OTHER INFORMATION: 1230H7 VL CDR2 amino acid sequence

<400> SEQUENCE: 369

Asp Asn Asn Lys Arg Pro Ser
1               5

<210> SEQ ID NO 370
<211> LENGTH: 11
<212> TYPE: PRT
<213> ORGANISM: Homo sapiens
<220> FEATURE:
<223> OTHER INFORMATION: 1230H7 VL CDR3 amino acid sequence

<400> SEQUENCE: 370

Gly Thr Trp Asp Ser Ser Leu Ser Ala Trp Val
1               5                   10

<210> SEQ ID NO 371
<211> LENGTH: 375
<212> TYPE: DNA
<213> ORGANISM: Homo sapiens
<220> FEATURE:
<223> OTHER INFORMATION: 1227H8 VH nucleotide sequence

<400> SEQUENCE: 371

```
cagatgcagc tggtgcagtc tggggctgag gtgaagaaga ccgggtcctc agtgaaggtt      60
tcctgcaagg cttccggaca cacccttcgcc taccactacc tacactgggt gcgacaggcc    120
cctggacagg gcttgagtg gatgggaggg atcatccctat tctttggtac aacaaactac    180
gcacagaggt tccaggacag agtcacgatt acagcggacg agtccactag cacagcctac    240
atggagttga gcagtctgag atctgaggac acggccgtct attactgtgc gagtgctgat    300
tacgcttggg agagttacca gccgccccag atcaacggtg tgtggggcag agggacaatg    360
gtcaccgtct cctca                                                     375
```

<210> SEQ ID NO 372
<211> LENGTH: 125
<212> TYPE: PRT
<213> ORGANISM: Homo sapiens
<220> FEATURE:
<223> OTHER INFORMATION: 1227H8 VH amino acid sequence

<400> SEQUENCE: 372

Gln Met Gln Leu Val Gln Ser Gly Ala Glu Val Lys Lys Thr Gly Ser
1               5                   10                  15

Ser Val Lys Val Ser Cys Lys Ala Ser Gly His Thr Phe Ala Tyr His
                20                  25                  30

Tyr Leu His Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Arg Phe
        50                  55                  60

Gln Asp Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Ser Ala Asp Tyr Ala Trp Glu Ser Tyr Gln Pro Pro Gln Ile Asn
            100                 105                 110

Gly Val Trp Gly Arg Gly Thr Met Val Thr Val Ser Ser
        115                 120                 125

<210> SEQ ID NO 373
<211> LENGTH: 5
<212> TYPE: PRT
<213> ORGANISM: Homo sapiens
<220> FEATURE:
<223> OTHER INFORMATION: 1227H8 VH CDR1 amino acid sequence

<400> SEQUENCE: 373

Tyr His Tyr Leu His
1               5

<210> SEQ ID NO 374
<211> LENGTH: 17
<212> TYPE: PRT
<213> ORGANISM: Homo sapiens
<220> FEATURE:
<223> OTHER INFORMATION: 1227H8 VH CDR2 amino acid sequence

<400> SEQUENCE: 374

Gly Ile Ile Pro Ile Phe Gly Thr Thr Asn Tyr Ala Gln Arg Phe Gln
1               5                   10                  15

Asp

<210> SEQ ID NO 375
<211> LENGTH: 16
<212> TYPE: PRT
<213> ORGANISM: Homo sapiens
<220> FEATURE:
<223> OTHER INFORMATION: 1227H8 VH CDR3 amino acid sequence

<400> SEQUENCE: 375

Ala Asp Tyr Ala Trp Glu Ser Tyr Gln Pro Pro Gln Ile Asn Gly Val
1               5                   10                  15

<210> SEQ ID NO 376
<211> LENGTH: 330
<212> TYPE: DNA
<213> ORGANISM: Homo sapiens
<220> FEATURE:
<223> OTHER INFORMATION: 1227H8 VL nucleotide sequence

<400> SEQUENCE: 376
cagtctgtgc tgacgcagcc gccctcagtg tctgcggccc caggacagaa ggtcaccatt      60
acctgctctg gaagcacctc caacattggg aataactatg tctcctggta ccaacagcac     120
ccaggcaaag cccccaaact catgatttat gatgtcagta gcggccctca gggggtccct     180
gaccgattct ctggctccaa gtctggcaac tcagcctccc tggacatcag tgggctccag     240
tctgaggatg aggctgatta ttactgtgca gcatgggatg acagcctgag tgaattttc      300 ttcggaactg ggaccaagct gaccgtccta                                      330

<210> SEQ ID NO 377
<211> LENGTH: 110
<212> TYPE: PRT
<213> ORGANISM: Homo sapiens
<220> FEATURE:
<223> OTHER INFORMATION: 1227H8 VL amino acid sequence
```

<400> SEQUENCE: 377

Gln Ser Val Leu Thr Gln Pro Pro Ser Val Ser Ala Ala Pro Gly Gln
1               5                   10                  15

Lys Val Thr Ile Thr Cys Ser Gly Ser Thr Ser Asn Ile Gly Asn Asn
            20                  25                  30

Tyr Val Ser Trp Tyr Gln Gln His Pro Gly Lys Ala Pro Lys Leu Met
        35                  40                  45

Ile Tyr Asp Val Ser Lys Arg Pro Ser Gly Val Pro Asp Arg Phe Ser
    50                  55                  60

Gly Ser Lys Ser Gly Asn Ser Ala Ser Leu Asp Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Glu Phe Phe Phe Gly Thr Gly Thr Lys Leu Thr Val Leu
            100                 105                 110

<210> SEQ ID NO 378
<211> LENGTH: 13
<212> TYPE: PRT
<213> ORGANISM: Homo sapiens
<220> FEATURE:
<223> OTHER INFORMATION: 1227H8 VL CDR1 amino acid sequence

<400> SEQUENCE: 378

Ser Gly Ser Thr Ser Asn Ile Gly Asn Asn Tyr Val Ser
1               5                   10

<210> SEQ ID NO 379
<211> LENGTH: 7
<212> TYPE: PRT
<213> ORGANISM: Homo sapiens
<220> FEATURE:
<223> OTHER INFORMATION: 1227H8 VL CDR2 amino acid sequence

<400> SEQUENCE: 379

Asp Val Ser Lys Arg Pro Ser
1               5

<210> SEQ ID NO 380
<211> LENGTH: 11
<212> TYPE: PRT
<213> ORGANISM: Homo sapiens
<220> FEATURE:
<223> OTHER INFORMATION: 1227H8 VL CDR3 amino acid sequence

<400> SEQUENCE: 380

Ala Ala Trp Asp Asp Ser Leu Ser Glu Phe Phe
1               5                   10

<210> SEQ ID NO 381
<211> LENGTH: 375
<212> TYPE: DNA
<213> ORGANISM: Homo sapiens
<220> FEATURE:
<223> OTHER INFORMATION: 1230D8 VH nucleotide sequence

<400> SEQUENCE: 381
cagatgcagc tggtgcagtc tggggctgag gtgaagaaga ccgggtcctc agtgaaggtt      60
tcctgcaagg cttccggata caccttcccc taccactacc tacactgggt gcgacaggcc    120
cctggacaag ggcttgagtg gatgggaggg atcatcccta tctttggtac aacaaactac    180

```
gcacagaggt tccaggacag agtcacgatt accgcggacg agtccaccag cacagcctac      240
atggagttta gcagtctgag atctgaggac acggccgtct attactgtgc gagtgctgat      300
tacgtttggg agagttatca cccggccacg tccttgagtc tctggggcag agggacaatg      360
gtcaccgtct cctca                                                       375
```

```
<210> SEQ ID NO 382
<211> LENGTH: 125
<212> TYPE: PRT
<213> ORGANISM: Homo sapiens
<220> FEATURE:
<223> OTHER INFORMATION: 1230D8 VH amino acid sequence

<400> SEQUENCE: 382

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Pro Tyr His
            20                  25                  30

Tyr Leu His Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Arg Phe
    50                  55                  60

Gln Asp Arg Val Thr Ile Thr Ala Asp Glu Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Ala Ser Ala Asp Tyr Val Trp Glu Ser Tyr His Pro Ala Thr Ser Leu
            100                 105                 110

Ser Leu Trp Gly Arg Gly Thr Met Val Thr Val Ser Ser
        115                 120                 125

<210> SEQ ID NO 383
<211> LENGTH: 5
<212> TYPE: PRT
<213> ORGANISM: Homo sapiens
<220> FEATURE:
<223> OTHER INFORMATION: 1230D8 VH CDR1 amino acid sequence

<400> SEQUENCE: 383

Tyr His Tyr Leu His
1               5

<210> SEQ ID NO 384
<211> LENGTH: 17
<212> TYPE: PRT
<213> ORGANISM: Homo sapiens
<220> FEATURE:
<223> OTHER INFORMATION: 1230D8 VH CDR2 amino acid sequence

<400> SEQUENCE: 384

Gly Ile Ile Pro Ile Phe Gly Thr Thr Asn Tyr Ala Gln Arg Phe Gln
1               5                   10                  15

Asp

<210> SEQ ID NO 385
<211> LENGTH: 16
<212> TYPE: PRT
<213> ORGANISM: Homo sapiens
<220> FEATURE:
<223> OTHER INFORMATION: 1230D8 VH CDR3 amino acid sequence

<400> SEQUENCE: 385
```

Ala Asp Tyr Val Trp Glu Ser Tyr His Pro Ala Thr Ser Leu Ser Leu
1               5                   10                  15

<210> SEQ ID NO 386
<211> LENGTH: 330
<212> TYPE: DNA
<213> ORGANISM: Homo sapiens
<220> FEATURE:
<223> OTHER INFORMATION: 1230D8 VL nucleotide sequence

<400> SEQUENCE: 386

```
cagtctgtgc tgacgcagcc gccctcagtg tctgcggccc caggacagaa ggtcaccatt    60
tcctgccctg gaagcacctc caacattggg aataactatg tctcctggta ccaacagcgc   120
ccaggcaaag cccccaaact catgatttat gatgtcagta agcggccctc agggtccct    180 gaccgattct ctggctccaa gtctggcaac tcagcctccc tggacatcag tgagctccag   240
tctgaggatg aggctgatta ttactgtgca gcatgggatg acagcctgag tgaatttctc   300
ttcggaactg ggaccaagct gaccgtccta                                     330
```

<210> SEQ ID NO 387
<211> LENGTH: 110
<212> TYPE: PRT
<213> ORGANISM: Homo sapiens
<220> FEATURE:
<223> OTHER INFORMATION: 1230D8 VL amino acid sequence

<400> SEQUENCE: 387

Gln Ser Val Leu Thr Gln Pro Pro Ser Val Ala Ala Pro Gly Gln
1               5                   10                  15

Lys Val Thr Ile Ser Cys Pro Gly Ser Thr Ser Asn Ile Gly Asn Asn
                20                  25                  30

Tyr Val Ser Trp Tyr Gln Gln Arg Pro Gly Lys Ala Pro Lys Leu Met
            35                  40                  45

Ile Tyr Asp Val Ser Lys Arg Pro Ser Gly Val Pro Asp Arg Phe Ser
        50                  55                  60

Gly Ser Lys Ser Gly Asn Ser Ala Ser Leu Asp Ile Ser Glu Leu Gln
65                  70                  75                  80

Ser Glu Asp Glu Ala Asp Tyr Tyr Cys Ala Ala Trp Asp Asp Ser Leu
                85                  90                  95

Ser Glu Phe Leu Phe Gly Thr Gly Thr Lys Leu Thr Val Leu
            100                 105                 110

<210> SEQ ID NO 388
<211> LENGTH: 13
<212> TYPE: PRT
<213> ORGANISM: Homo sapiens
<220> FEATURE:
<223> OTHER INFORMATION: 1230D8 VL CDR1 amino acid sequence

<400> SEQUENCE: 388

Pro Gly Ser Thr Ser Asn Ile Gly Asn Asn Tyr Val Ser
1               5                   10

<210> SEQ ID NO 389
<211> LENGTH: 7
<212> TYPE: PRT
<213> ORGANISM: Homo sapiens
<220> FEATURE:
<223> OTHER INFORMATION: 1230D8 VL CDR2 amino acid sequence

<400> SEQUENCE: 389

Asp Val Ser Lys Arg Pro Ser
1               5

<210> SEQ ID NO 390
<211> LENGTH: 11
<212> TYPE: PRT
<213> ORGANISM: Homo sapiens
<220> FEATURE:
<223> OTHER INFORMATION: 1230D8 VL CDR3 amino acid sequence

<400> SEQUENCE: 390

Ala Ala Trp Asp Asp Ser Leu Ser Glu Phe Leu
1               5                   10

<210> SEQ ID NO 391
<211> LENGTH: 384
<212> TYPE: DNA
<213> ORGANISM: Homo sapiens
<220> FEATURE:
<223> OTHER INFORMATION: 1252A5 VH nucleotide sequence

<400> SEQUENCE: 391
caggtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gatgggaggg attattccta tctttgacac aggcaactct     180
gcacagagct tccagggcag agtcacgatt accgcggacg aatccacgag cacagcctac     240
atggagctga gcagcctgag atctgaagac acggccgtat attattgtgc acgttcaagt     300
cgtatctacg acctgaaccc gtccctgacc gcctactacg atatggatgt ctggggccag     360
gggacaatgg tcaccgtctc gagt                                            384

<210> SEQ ID NO 392
<211> LENGTH: 128
<212> TYPE: PRT
<213> ORGANISM: Homo sapiens
<220> FEATURE:
<223> OTHER INFORMATION: 1252A5 VH amino acid sequence

<400> SEQUENCE: 392

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 393
<211> LENGTH: 5
<212> TYPE: PRT

```
<213> ORGANISM: Homo sapiens
<220> FEATURE:
<223> OTHER INFORMATION: 1252A5 VH CDR1 amino acid sequence

<400> SEQUENCE: 393

Thr Tyr Gly Ile Ser
1               5

<210> SEQ ID NO 394
<211> LENGTH: 17
<212> TYPE: PRT
<213> ORGANISM: Homo sapiens
<220> FEATURE:
<223> OTHER INFORMATION: 1252A5 VH CDR2 amino acid sequence

<400> SEQUENCE: 394

Gly Ile Ile Pro Ile Phe Asp Thr Gly Asn Ser Ala Gln Ser Phe Gln
1               5                   10                  15

Gly

<210> SEQ ID NO 395
<211> LENGTH: 19
<212> TYPE: PRT
<213> ORGANISM: Homo sapiens
<220> FEATURE:
<223> OTHER INFORMATION: 1252A5 VH CDR3 amino acid sequence

<400> SEQUENCE: 395

Ser Ser Arg Ile Tyr Asp Leu Asn Pro Ser Leu Thr Ala Tyr Tyr Asp
1               5                   10                  15

Met Asp Val

<210> SEQ ID NO 396
<211> LENGTH: 330
<212> TYPE: DNA
<213> ORGANISM: Homo sapiens
<220> FEATURE:
<223> OTHER INFORMATION: 1252A5 VL nucleotide sequence

<400> SEQUENCE: 396
cagtctgtgc tgactcagcc gccgtcagtg tctgcggccc caggacagaa ggtcaccatc      60
tcctgctctg gaagcagctc aacattggg aataattatg tatcgtggta ccagcagctc     120
ccaggaacag ccccccaaact cctcatttat gacaataata gcgaccctc agggattcct     180 gaccgattct ctggctccaa gtctggcacg tcagccaccc tgggcatcac cggactccag     240 actgggacg aggccgatta ttactgcgga acatgggata gcagcctgag tgcttgggtg     300
ttcggcggag ggaccaagct gaccgtccta                                      330

<210> SEQ ID NO 397
<211> LENGTH: 110
<212> TYPE: PRT
<213> ORGANISM: Homo sapiens
<220> FEATURE:
<223> OTHER INFORMATION: 1252A5 VL amino acid sequence

<400> SEQUENCE: 397

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45
```

Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 398
<211> LENGTH: 13
<212> TYPE: PRT
<213> ORGANISM: Homo sapiens
<220> FEATURE:
<223> OTHER INFORMATION: 1252A5 VL CDR1 amino acid sequence

<400> SEQUENCE: 398

Ser Gly Ser Ser Ser Asn Ile Gly Asn Asn Tyr Val Ser
 1               5                  10

<210> SEQ ID NO 399
<211> LENGTH: 7
<212> TYPE: PRT
<213> ORGANISM: Homo sapiens
<220> FEATURE:
<223> OTHER INFORMATION: 1252A5 VL CDR2 amino acid sequence

<400> SEQUENCE: 399

Asp Asn Asn Lys Arg Pro Ser
 1               5

<210> SEQ ID NO 400
<211> LENGTH: 11
<212> TYPE: PRT
<213> ORGANISM: Homo sapiens
<220> FEATURE:
<223> OTHER INFORMATION: 1252A5 VL CDR3 amino acid sequence

<400> SEQUENCE: 400

Gly Thr Trp Asp Ser Ser Leu Ser Ala Trp Val
 1               5                  10

<210> SEQ ID NO 401
<211> LENGTH: 384
<212> TYPE: DNA
<213> ORGANISM: Homo sapiens
<220> FEATURE:
<223> OTHER INFORMATION: G1152H5 VH nucleotide sequence

<400> SEQUENCE: 401
caggtgcagc tggtgcagtc tggggctgag gtgaagaagc ctgggtcctc ggtgaaggtc     60
tcctgcaagg cttctggagg caccttcagc acctatggta tctcatgggt gcgacaggcc    120
cctggacaag gacttgagtg gatgggaggg attattccta tctttgacac aggcaactct    180
gcacagagct tccagggcag agtcacgatt accgcggacg aatccacgag cacagcctac    240
atggagctga gcagcctgag atctgaagac acggccgtat attattgtgc acgttcaagt    300
cgtatctacg acatgatctc gtccttgcaa ccctactacg atatggatgt ctggggccag    360
gggacaatgg tcaccgtctc ctca                                           384

<210> SEQ ID NO 402
<211> LENGTH: 128

<212> TYPE: PRT
<213> ORGANISM: Homo sapiens
<220> FEATURE:
<223> OTHER INFORMATION: G1152H5 VH amino acid sequence

<400> SEQUENCE: 402

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Met Ile Ser Ser Leu Gln Pro Tyr
            100                 105                 110

Tyr Asp Met Asp Val Trp Gly Gln Gly Thr Met Val Thr Val Ser Ser
        115                 120                 125

<210> SEQ ID NO 403
<211> LENGTH: 5
<212> TYPE: PRT
<213> ORGANISM: Homo sapiens
<220> FEATURE:
<223> OTHER INFORMATION: G1152H5 VH CDR1 amino acid sequence

<400> SEQUENCE: 403

Thr Tyr Gly Ile Ser
1               5

<210> SEQ ID NO 404
<211> LENGTH: 17
<212> TYPE: PRT
<213> ORGANISM: Homo sapiens
<220> FEATURE:
<223> OTHER INFORMATION: G1152H5 VH CDR2 amino acid sequence

<400> SEQUENCE: 404

Gly Ile Ile Pro Ile Phe Asp Thr Gly Asn Ser Ala Gln Ser Phe Gln
1               5                   10                  15

Gly

<210> SEQ ID NO 405
<211> LENGTH: 19
<212> TYPE: PRT
<213> ORGANISM: Homo sapiens
<220> FEATURE:
<223> OTHER INFORMATION: G1152H5 VH CDR3 amino acid sequence

<400> SEQUENCE: 405

Ser Ser Arg Ile Tyr Asp Met Ile Ser Ser Leu Gln Pro Tyr Tyr Asp
1               5                   10                  15

Met Asp Val

<210> SEQ ID NO 406
<211> LENGTH: 330
<212> TYPE: DNA
<213> ORGANISM: Homo sapiens
<220> FEATURE:
<223> OTHER INFORMATION: G1152H5 VL nucleotide sequence

<400> SEQUENCE: 406

```
cagtctgtgc tgactcagcc gccgtcagtg tctgcggccc caggacagaa ggtcaccatc      60
tcctgctctg gaagcagctc caacattggg aataattatg tatcgtggta ccagcagctc     120
ccaggaacag cccccaaact cctcatttat gacaataata agcgaccctc agggattcct     180
gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                       330
```

<210> SEQ ID NO 407
<211> LENGTH: 110
<212> TYPE: PRT
<213> ORGANISM: Homo sapiens
<220> FEATURE:
<223> OTHER INFORMATION: G1152H5 VL amino acid sequence

<400> SEQUENCE: 407

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 408
<211> LENGTH: 13
<212> TYPE: PRT
<213> ORGANISM: Homo sapiens
<220> FEATURE:
<223> OTHER INFORMATION: G1152H5 VL CDR1 amino acid sequence

<400> SEQUENCE: 408

```
Ser Gly Ser Ser Ser Asn Ile Gly Asn Asn Tyr Val Ser
1               5                   10
```

<210> SEQ ID NO 409
<211> LENGTH: 7
<212> TYPE: PRT
<213> ORGANISM: Homo sapiens
<220> FEATURE:
<223> OTHER INFORMATION: G1152H5 VL CDR2 amino acid sequence

<400> SEQUENCE: 409

```
Asp Asn Asn Lys Arg Pro Ser
1               5
```

<210> SEQ ID NO 410
<211> LENGTH: 11
<212> TYPE: PRT
<213> ORGANISM: Homo sapiens
<220> FEATURE:
<223> OTHER INFORMATION: G1152H5 VL CDR3 amino acid sequence

<400> SEQUENCE: 410

Gly Thr Trp Asp Ser Ser Leu Ser Ala Trp Val
1               5                   10

<210> SEQ ID NO 411
<211> LENGTH: 385
<212> TYPE: DNA
<213> ORGANISM: Homo sapiens
<220> FEATURE:
<223> OTHER INFORMATION: G1165D4 VH nucleotide sequence

<400> SEQUENCE: 411
caggtgcagc tggtgcagtc tggggctgag gtgaagaagc ctgggtcctc ggtgaaggtc      60
tcctgcaagg cttctggagg caccttcagc acctatggta tctcatgggt gcgacaggcc    120
cctggacaag gacttgagtg gatgggaggg attattccta tctttgacac aggcaactct    180
gcacagagct tccagggcag agtcacgatt accgcggacg aatccacgag cacagcctac    240
atggagctga gcagcctgag atctgaagac acggccgtat attattgtgc acgttcaagt    300
cgtatctacg acctgaaccc gtccctgacc gcctactacg atatggatgt ctggggccag    360
gggacaatgg tcaccgtctc gagtg                                          385

<210> SEQ ID NO 412
<211> LENGTH: 128
<212> TYPE: PRT
<213> ORGANISM: Homo sapiens
<220> FEATURE:
<223> OTHER INFORMATION: G1165D4 VH amino acid sequence

<400> SEQUENCE: 412

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 413
<211> LENGTH: 5
<212> TYPE: PRT
<213> ORGANISM: Homo sapiens
<220> FEATURE:
<223> OTHER INFORMATION: G1165D4 VH CDR1 amino acid sequence

<400> SEQUENCE: 413

Thr Tyr Gly Ile Ser
1               5

```
<210> SEQ ID NO 414
<211> LENGTH: 17
<212> TYPE: PRT
<213> ORGANISM: Homo sapiens
<220> FEATURE:
<223> OTHER INFORMATION: G1165D4 VH CDR2 amino acid sequence

<400> SEQUENCE: 414

Gly Ile Ile Pro Ile Phe Asp Thr Gly Asn Ser Ala Gln Ser Phe Gln
1               5                   10                  15

Gly

<210> SEQ ID NO 415
<211> LENGTH: 18
<212> TYPE: PRT
<213> ORGANISM: Homo sapiens
<220> FEATURE:
<223> OTHER INFORMATION: G1165D4 VH CDR3 amino acid sequence

<400> SEQUENCE: 415

Ser Arg Ile Tyr Asp Leu Asn Pro Ser Leu Thr Ala Tyr Tyr Asp Met
1               5                   10                  15

Asp Val

<210> SEQ ID NO 416
<211> LENGTH: 330
<212> TYPE: DNA
<213> ORGANISM: Homo sapiens
<220> FEATURE:
<223> OTHER INFORMATION: G1165D4 VL nucleotide sequence

<400> SEQUENCE: 416
cagtctgtgc tgactcagcc gccgtcagtg tctgcggccc caggacagaa ggtcaccatc      60
tcctgctctg gaagcagctc caacattgag aataattatg tatcgtggta ccagcagctc     120
ccaggaacag cccccaaact cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtccta                                      330

<210> SEQ ID NO 417
<211> LENGTH: 109
<212> TYPE: PRT
<213> ORGANISM: Homo sapiens
<220> FEATURE:
<223> OTHER INFORMATION: G1165D4 VL amino acid sequence

<400> SEQUENCE: 417

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95
```

-continued

Ser Ala Trp Val Phe Gly Gly Gly Thr Lys Leu Thr Val
            100                 105

<210> SEQ ID NO 418
<211> LENGTH: 13
<212> TYPE: PRT
<213> ORGANISM: Homo sapiens
<220> FEATURE:
<223> OTHER INFORMATION: G1165D4 VL CDR1 amino acid sequence

<400> SEQUENCE: 418

Ser Gly Ser Ser Ser Asn Ile Glu Asn Asn Tyr Val Ser
1               5                   10

<210> SEQ ID NO 419
<211> LENGTH: 7
<212> TYPE: PRT
<213> ORGANISM: Homo sapiens
<220> FEATURE:
<223> OTHER INFORMATION: G1165D4 VL CDR2 amino acid sequence

<400> SEQUENCE: 419

Asp Asn Asn Lys Arg Pro Ser
1               5

<210> SEQ ID NO 420
<211> LENGTH: 11
<212> TYPE: PRT
<213> ORGANISM: Homo sapiens
<220> FEATURE:
<223> OTHER INFORMATION: G1165D4 VL CDR3 amino acid sequence

<400> SEQUENCE: 420

Gly Thr Trp Asp Ser Ser Leu Ser Ala Trp Val
1               5                   10

<210> SEQ ID NO 421
<211> LENGTH: 384
<212> TYPE: DNA
<213> ORGANISM: Homo sapiens
<220> FEATURE:
<223> OTHER INFORMATION: G1230H7 VH nucleotide sequence

<400> SEQUENCE: 421
caggtgcagc tggtgcagtc tggggctgag gtgaagaagc ctgggtcctc ggtgaaggtc      60
tcctgcaagg cttctggagg caccttcagc acctatggta tctcatgggt gcgacaggcc    120
cctggacaag gacttgagtg gatgggaggg attattccta tctttgacac aggcaactct    180
gcacagagct tccagggcag agtcacgatt accgcggacg aatccacgag cacagcctac    240
atggagctga gcagcctgag atctgaagac acggccgtat attattgtgc acgttcaagt    300
cgtatctatg acttcaactc cgccctcata tcctactacg atatggatgt ctggggccag    360
ggaacaatgg tcaccgtctc ctca                                            384

<210> SEQ ID NO 422
<211> LENGTH: 128
<212> TYPE: PRT
<213> ORGANISM: Homo sapiens
<220> FEATURE:
<223> OTHER INFORMATION: G1230H7 VH amino acid sequence

<400> SEQUENCE: 422

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Phe Asn Ser Ala Leu Ile Ser Tyr
            100                 105                 110

Tyr Asp Met Asp Val Trp Gly Gln Gly Thr Met Val Thr Val Ser Ser
        115                 120                 125

<210> SEQ ID NO 423
<211> LENGTH: 5
<212> TYPE: PRT
<213> ORGANISM: Homo sapiens
<220> FEATURE:
<223> OTHER INFORMATION: G1230H7 VH CDR1 amino acid sequence

<400> SEQUENCE: 423

Thr Tyr Gly Ile Ser
1               5

<210> SEQ ID NO 424
<211> LENGTH: 17
<212> TYPE: PRT
<213> ORGANISM: Homo sapiens
<220> FEATURE:
<223> OTHER INFORMATION: G1230H7 VH CDR2 amino acid sequence

<400> SEQUENCE: 424

Gly Ile Ile Pro Ile Phe Asp Thr Gly Asn Ser Ala Gln Ser Phe Gln
1               5                   10                  15

Gly

<210> SEQ ID NO 425
<211> LENGTH: 19
<212> TYPE: PRT
<213> ORGANISM: Homo sapiens
<220> FEATURE:
<223> OTHER INFORMATION: G1230H7 VH CDR3 amino acid sequence

<400> SEQUENCE: 425

Ser Ser Arg Ile Tyr Asp Phe Asn Ser Ala Leu Ile Ser Tyr Tyr Asp
1               5                   10                  15

Met Asp Val

<210> SEQ ID NO 426
<211> LENGTH: 330
<212> TYPE: DNA
<213> ORGANISM: Homo sapiens
<220> FEATURE:
<223> OTHER INFORMATION: G1230H7 VL nucleotide sequence

<400> SEQUENCE: 426
cagtctgtgc tgactcagcc gccgtcagtg tctgcggccc caggacagaa ggtcaccatc      60
tcctgctctg gaagcagctc caacattggg aataattatg tatcgtggta ccagcagctc     120
```

```
ccaggaacag ccccccaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggata gcagcctgag tgcttgggtg    300
ttcggcggag ggaccaagct gaccgtccta                                     330
```

<210> SEQ ID NO 427
<211> LENGTH: 110
<212> TYPE: PRT
<213> ORGANISM: Homo sapiens
<220> FEATURE:
<223> OTHER INFORMATION: G1230H7 VL amino acid sequence

<400> SEQUENCE: 427

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 428
<211> LENGTH: 13
<212> TYPE: PRT
<213> ORGANISM: Homo sapiens
<220> FEATURE:
<223> OTHER INFORMATION: G1230H7 VL CDR1 amino acid sequence

<400> SEQUENCE: 428

```
Ser Gly Ser Ser Ser Asn Ile Gly Asn Asn Tyr Val Ser
1               5                   10
```

<210> SEQ ID NO 429
<211> LENGTH: 7
<212> TYPE: PRT
<213> ORGANISM: Homo sapiens
<220> FEATURE:
<223> OTHER INFORMATION: G1230H7 VL CDR2 amino acid sequence

<400> SEQUENCE: 429

```
Asp Asn Asn Lys Arg Pro Ser
1               5
```

<210> SEQ ID NO 430
<211> LENGTH: 11
<212> TYPE: PRT
<213> ORGANISM: Homo sapiens
<220> FEATURE:
<223> OTHER INFORMATION: G1230H7 VL CDR3 amino acid sequence

<400> SEQUENCE: 430

```
Gly Thr Trp Asp Ser Ser Leu Ser Ala Trp Val
1               5                   10
```

<210> SEQ ID NO 431
<211> LENGTH: 384
<212> TYPE: DNA
<213> ORGANISM: Homo sapiens
<220> FEATURE:
<223> OTHER INFORMATION: 1147A3 VH nucleotide sequence

<400> SEQUENCE: 431

```
gaagtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gatagggggg attattccta tctttgacgc aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatga tcaccgtctc gagt                                            384
```

<210> SEQ ID NO 432
<211> LENGTH: 128
<212> TYPE: PRT
<213> ORGANISM: Homo sapiens
<220> FEATURE:
<223> OTHER INFORMATION: 1147A3 VH amino acid sequence

<400> SEQUENCE: 432

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Ala Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Ile Thr Val Ser Ser
        115                 120                 125

<210> SEQ ID NO 433
<211> LENGTH: 5
<212> TYPE: PRT
<213> ORGANISM: Homo sapiens
<220> FEATURE:
<223> OTHER INFORMATION: 1147A3 VH CDR1 amino acid sequence

<400> SEQUENCE: 433

Thr Tyr Gly Ile Ser
1               5

<210> SEQ ID NO 434
<211> LENGTH: 17
<212> TYPE: PRT
<213> ORGANISM: Homo sapiens
<220> FEATURE:
<223> OTHER INFORMATION: 1147A3 VH CDR2 amino acid sequence

<400> SEQUENCE: 434

Gly Ile Ile Pro Ile Phe Asp Ala Gly Asn Ser Ala Gln Ser Phe Gln
1               5                   10                  15

Gly

<210> SEQ ID NO 435
<211> LENGTH: 19
<212> TYPE: PRT
<213> ORGANISM: Homo sapiens
<220> FEATURE:
<223> OTHER INFORMATION: 1147A3 VH CDR3 amino acid sequence

<400> SEQUENCE: 435

Ser Ser Arg Ile Tyr Asp Leu Asn Pro Ser Leu Thr Ala Tyr Tyr Asp
1               5                   10                  15

Met Asp Val

<210> SEQ ID NO 436
<211> LENGTH: 327
<212> TYPE: DNA
<213> ORGANISM: Homo sapiens
<220> FEATURE:
<223> OTHER INFORMATION: 1147A3 VL nucleotide sequence

<400> SEQUENCE: 436
caggctgtgc tgacccagcc gtcctcagtg tctacgcccc caggacagaa ggtcaccatc     60
tcctgctctg gaggcagctc caacattggg aataattatg tatcgtggta ccggcagctc    120
ccaggaacag cccccaaact cctcatttat gacaataata gcgaccctca gggattcct    180 gaccgattct ctggctccaa gtctggcgcg tcagccaccc tgggcatcac cggactccag    240
actggggacg aggccgatta ttactgcgga acatgggata gcagcctgag tgcttgggtg    300
ttcggcggag ggaccaagct gaccgtc                                        327

<210> SEQ ID NO 437
<211> LENGTH: 109
<212> TYPE: PRT
<213> ORGANISM: Homo sapiens
<220> FEATURE:
<223> OTHER INFORMATION: 1147A3 VL amino acid sequence

<400> SEQUENCE: 437

Gln Ala Val Leu Thr Gln Pro Ser Ser Val Ser Thr Pro Pro Gly Gln
1               5                   10                  15

Lys Val Thr Ile Ser Cys Ser Gly Gly Ser Ser Asn Ile Gly Asn Asn
                20                  25                  30

Tyr Val Ser Trp Tyr Arg Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Ala Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 438
<211> LENGTH: 13
<212> TYPE: PRT
<213> ORGANISM: Homo sapiens

```
<220> FEATURE:
<223> OTHER INFORMATION: 1147A3 VL CDR1 amino acid sequence

<400> SEQUENCE: 438

Ser Gly Gly Ser Ser Asn Ile Gly Asn Asn Tyr Val Ser
1               5                   10

<210> SEQ ID NO 439
<211> LENGTH: 7
<212> TYPE: PRT
<213> ORGANISM: Homo sapiens
<220> FEATURE:
<223> OTHER INFORMATION: 1147A3 VL CDR2 amino acid sequence

<400> SEQUENCE: 439

Asp Asn Asn Lys Arg Pro Ser
1               5

<210> SEQ ID NO 440
<211> LENGTH: 11
<212> TYPE: PRT
<213> ORGANISM: Homo sapiens
<220> FEATURE:
<223> OTHER INFORMATION: 1147A3 VL CDR3 amino acid sequence

<400> SEQUENCE: 440

Gly Thr Trp Asp Ser Ser Leu Ser Ala Trp Val
1               5                   10

<210> SEQ ID NO 441
<211> LENGTH: 384
<212> TYPE: DNA
<213> ORGANISM: Homo sapiens
<220> FEATURE:
<223> OTHER INFORMATION: 1147F2 VH nucleotide sequence

<400> SEQUENCE: 441
gaagtgcagc tggtgcagtc tggggctgag gtgaagaagc ctgggtcctc ggtgaaggtc        60
tcctgcaagg cttctggagg caccttcagc acctatggca tctcatgggt gcgacaggcc      120
cctggacaag acttgagtg gataggaggg gttattccta tctttgacac aggtaactct       180
gcacagagct tccagggcag agtcacgatt accgcggacg aatccacgag cacagcctac      240
atggaggtga gcagcctgag atctgatgac acggccgtat attattgtgc aagttcaaat      300
cgtatctacg acttgaaccc ctccctcact gcctactacg atatggacgt ctggggccag      360
gggacaatgg tcaccgtctc gagt                                              384

<210> SEQ ID NO 442
<211> LENGTH: 128
<212> TYPE: PRT
<213> ORGANISM: Homo sapiens
<220> FEATURE:
<223> OTHER INFORMATION: 1147F2 VH amino acid sequence

<400> SEQUENCE: 442

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Val Ile Pro Ile Phe Asp Thr Gly Asn Ser Ala Gln Ser Phe
    50                  55                  60
```

Gln Gly Arg Val Thr Ile Thr Ala Asp Glu Ser Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Asn Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 443
<211> LENGTH: 5
<212> TYPE: PRT
<213> ORGANISM: Homo sapiens
<220> FEATURE:
<223> OTHER INFORMATION: 1147F2 VH CDR1 amino acid sequence

<400> SEQUENCE: 443

Thr Tyr Gly Ile Ser
1               5

<210> SEQ ID NO 444
<211> LENGTH: 17
<212> TYPE: PRT
<213> ORGANISM: Homo sapiens
<220> FEATURE:
<223> OTHER INFORMATION: 1147F2 VH CDR2 amino acid sequence

<400> SEQUENCE: 444

Gly Val Ile Pro Ile Phe Asp Thr Gly Asn Ser Ala Gln Ser Phe Gln
1               5                   10                  15

Gly

<210> SEQ ID NO 445
<211> LENGTH: 19
<212> TYPE: PRT
<213> ORGANISM: Homo sapiens
<220> FEATURE:
<223> OTHER INFORMATION: 1147F2 VH CDR3 amino acid sequence

<400> SEQUENCE: 445

Ser Asn Arg Ile Tyr Asp Leu Asn Pro Ser Leu Thr Ala Tyr Tyr Asp
1               5                   10                  15

Met Asp Val

<210> SEQ ID NO 446
<211> LENGTH: 327
<212> TYPE: DNA
<213> ORGANISM: Homo sapiens
<220> FEATURE:
<223> OTHER INFORMATION: 1147F2 VL nucleotide sequence

<400> SEQUENCE: 446
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag cccccaaact cctcatttat gacaataata agcgaccctc agggattcct     180
gaccgattct ctggctccaa gtctggcacg tcagccaccc tggacatcac cggactccag     240
actggggacg aggccgatta ttactgcgga acatgggata gcagcctgag cgcttgggta     300
ttcggcggag ggaccaagct gaccgtc                                         327

-continued

<210> SEQ ID NO 447
<211> LENGTH: 109
<212> TYPE: PRT
<213> ORGANISM: Homo sapiens
<220> FEATURE:
<223> OTHER INFORMATION: 1147F2 VL amino acid sequence

<400> SEQUENCE: 447

```
Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105
```

<210> SEQ ID NO 448
<211> LENGTH: 13
<212> TYPE: PRT
<213> ORGANISM: Homo sapiens
<220> FEATURE:
<223> OTHER INFORMATION: 1147F2 VL CDR1 amino acid sequence

<400> SEQUENCE: 448

```
Ser Gly Ser Ser Ser Asn Ile Gly Asn Asn Tyr Val Ser
1               5                   10
```

<210> SEQ ID NO 449
<211> LENGTH: 7
<212> TYPE: PRT
<213> ORGANISM: Homo sapiens
<220> FEATURE:
<223> OTHER INFORMATION: 1147F2 VL CDR2 amino acid sequence

<400> SEQUENCE: 449

```
Asp Asn Asn Lys Arg Pro Ser
1               5
```

<210> SEQ ID NO 450
<211> LENGTH: 10
<212> TYPE: PRT
<213> ORGANISM: Homo sapiens
<220> FEATURE:
<223> OTHER INFORMATION: 1147F2 VL CDR3 amino acid sequence

<400> SEQUENCE: 450

```
Gly Thr Trp Asp Ser Ser Leu Ser Ala Trp
1               5                   10
```

<210> SEQ ID NO 451
<211> LENGTH: 384
<212> TYPE: DNA
<213> ORGANISM: Homo sapiens
<220> FEATURE:
<223> OTHER INFORMATION: 1149D9 VH nucleotide sequence

<400> SEQUENCE: 451

```
gaagtgcagc tggtgcagtc tggggctgag gtgaaaaagc ctgggtcctc ggtgaaggtc      60
tcctgcaagg cttctggagg caccttcagc acctatggta tctcatgggt gcgacagacc     120
cctggacaag gacttgagtg gataggggg attattccta tctttgacac aggcaactcc      180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc gagt                                            384
```

<210> SEQ ID NO 452
<211> LENGTH: 128
<212> TYPE: PRT
<213> ORGANISM: Homo sapiens
<220> FEATURE:
<223> OTHER INFORMATION: 1149D9 VH amino acid sequence

<400> SEQUENCE: 452

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Thr Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 453
<211> LENGTH: 5
<212> TYPE: PRT
<213> ORGANISM: Homo sapiens
<220> FEATURE:
<223> OTHER INFORMATION: 1149D9 VH CDR1 amino acid sequence

<400> SEQUENCE: 453

Thr Tyr Gly Ile Ser
1               5

<210> SEQ ID NO 454
<211> LENGTH: 17
<212> TYPE: PRT
<213> ORGANISM: Homo sapiens
<220> FEATURE:
<223> OTHER INFORMATION: 1149D9 VH CDR2 amino acid sequence

<400> SEQUENCE: 454

Gly Ile Ile Pro Ile Phe Asp Thr Gly Asn Ser Ala Gln Ser Phe Gln
1               5                   10                  15

Gly

<210> SEQ ID NO 455
<211> LENGTH: 19

```
<212> TYPE: PRT
<213> ORGANISM: Homo sapiens
<220> FEATURE:
<223> OTHER INFORMATION: 1149D9 VH CDR3 amino acid sequence

<400> SEQUENCE: 455

Ser Ser Arg Ile Tyr Asp Leu Asn Pro Ser Leu Thr Ala Tyr Tyr Asp
1               5                   10                  15

Met Asp Val

<210> SEQ ID NO 456
<211> LENGTH: 327
<212> TYPE: DNA
<213> ORGANISM: Homo sapiens
<220> FEATURE:
<223> OTHER INFORMATION: 1149D9 VL nucleotide sequence

<400> SEQUENCE: 456
caggctgtgc tgactcagcc gtcctcagtg tctacgcccc caggacagaa ggtcaccatc      60
tcctgctctg gaagcagctc caacattggg aataattatg tatcgtggta ccagcagctc     120
ccaggaacag cccccaaact cctcatttac gacaataata gcgaccctca gggattcct     180 gaccgattct ccggctccaa gtctggcacg tcagccaccc tgggcatcac cggactccag     240
actggggacg aggccgatta ttactgcgga gcatgggata gcagcctgag tgcttgggtg     300
ttcggcggag ggaccaagct gaccgtc                                          327

<210> SEQ ID NO 457
<211> LENGTH: 109
<212> TYPE: PRT
<213> ORGANISM: Homo sapiens
<220> FEATURE:
<223> OTHER INFORMATION: 1149D9 VL amino acid sequence

<400> SEQUENCE: 457

Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Ser Ser Leu
                85                  90                  95

Ser Ala Trp Val Phe Gly Gly Gly Thr Lys Leu Thr Val
            100                 105

<210> SEQ ID NO 458
<211> LENGTH: 13
<212> TYPE: PRT
<213> ORGANISM: Homo sapiens
<220> FEATURE:
<223> OTHER INFORMATION: 1149D9 VL CDR1 amino acid sequence

<400> SEQUENCE: 458

Ser Gly Ser Ser Ser Asn Ile Gly Asn Asn Tyr Val Ser
1               5                   10
```

```
<210> SEQ ID NO 459
<211> LENGTH: 7
<212> TYPE: PRT
<213> ORGANISM: Homo sapiens
<220> FEATURE:
<223> OTHER INFORMATION: 1149D9 VL CDR2 amino acid sequence

<400> SEQUENCE: 459

Asp Asn Asn Lys Arg Pro Ser
1               5

<210> SEQ ID NO 460
<211> LENGTH: 11
<212> TYPE: PRT
<213> ORGANISM: Homo sapiens
<220> FEATURE:
<223> OTHER INFORMATION: 1149D9 VL CDR3 amino acid sequence

<400> SEQUENCE: 460

Gly Ala Trp Asp Ser Ser Leu Ser Ala Trp Val
1               5                   10

<210> SEQ ID NO 461
<211> LENGTH: 384
<212> TYPE: DNA
<213> ORGANISM: Homo sapiens
<220> FEATURE:
<223> OTHER INFORMATION: 1150D9 VH nucleotide sequence

<400> SEQUENCE: 461
gaagtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gatagggggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaacgg tcaccgtctc gagt                                            384

<210> SEQ ID NO 462
<211> LENGTH: 128
<212> TYPE: PRT
<213> ORGANISM: Homo sapiens
<220> FEATURE:
<223> OTHER INFORMATION: 1150D9 VH amino acid sequence

<400> SEQUENCE: 462

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110
```

Tyr Asp Met Asp Val Trp Gly Gln Gly Thr Thr Val Thr Val Ser Ser
            115                 120                 125

<210> SEQ ID NO 463
<211> LENGTH: 5
<212> TYPE: PRT
<213> ORGANISM: Homo sapiens
<220> FEATURE:
<223> OTHER INFORMATION: 1150D9 VH CDR1 amino acid sequence

<400> SEQUENCE: 463

Thr Tyr Gly Ile Ser
1               5

<210> SEQ ID NO 464
<211> LENGTH: 17
<212> TYPE: PRT
<213> ORGANISM: Homo sapiens
<220> FEATURE:
<223> OTHER INFORMATION: 1150D9 VH CDR2 amino acid sequence

<400> SEQUENCE: 464

Gly Ile Ile Pro Ile Phe Asp Thr Gly Asn Ser Ala Gln Ser Phe Gln
1               5                   10                  15

Gly

<210> SEQ ID NO 465
<211> LENGTH: 18
<212> TYPE: PRT
<213> ORGANISM: Homo sapiens
<220> FEATURE:
<223> OTHER INFORMATION: 1150D9 VH CDR3 amino acid sequence

<400> SEQUENCE: 465

Ser Arg Ile Tyr Asp Leu Asn Pro Ser Leu Thr Ala Tyr Tyr Asp Met
1               5                   10                  15

Asp Val

<210> SEQ ID NO 466
<211> LENGTH: 327
<212> TYPE: DNA
<213> ORGANISM: Homo sapiens
<220> FEATURE:
<223> OTHER INFORMATION: 1150D9 VL nucleotide sequence

<400> SEQUENCE: 466
caggctgtgc tgactcagcc gtcctcagtg ccaacgcccc caggacagaa ggtcaccatc      60
tcctgctctg gaagcagctc aacattggg gataattatg tatcgtggta ccagcagctc     120
ccaggaacag cccccaaact cctcatttat gacaataata gcgaccctc agggattcct     180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtc                                          327

<210> SEQ ID NO 467
<211> LENGTH: 109
<212> TYPE: PRT
<213> ORGANISM: Homo sapiens
<220> FEATURE:
<223> OTHER INFORMATION: 1150D9 VL amino acid sequence

<400> SEQUENCE: 467

Gln Ala Val Leu Thr Gln Pro Ser Ser Val Pro Thr Pro Pro Gly Gln
1               5                   10                  15

Lys Val Thr Ile Ser Cys Ser Gly Ser Ser Asn Ile Gly Asp Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 468
<211> LENGTH: 13
<212> TYPE: PRT
<213> ORGANISM: Homo sapiens
<220> FEATURE:
<223> OTHER INFORMATION: 1150D9 VL CDR1 amino acid sequence

<400> SEQUENCE: 468

Ser Gly Ser Ser Asn Ile Gly Asp Asn Tyr Val Ser
1               5                   10

<210> SEQ ID NO 469
<211> LENGTH: 7
<212> TYPE: PRT
<213> ORGANISM: Homo sapiens
<220> FEATURE:
<223> OTHER INFORMATION: 1150D9 VL CDR2 amino acid sequence

<400> SEQUENCE: 469

Asp Asn Asn Lys Arg Pro Ser
1               5

<210> SEQ ID NO 470
<211> LENGTH: 11
<212> TYPE: PRT
<213> ORGANISM: Homo sapiens
<220> FEATURE:
<223> OTHER INFORMATION: 1150D9 VL CDR3 amino acid sequence

<400> SEQUENCE: 470

Gly Thr Trp Asp Ser Ser Leu Ser Ala Trp Val
1               5                   10

<210> SEQ ID NO 471
<211> LENGTH: 384
<212> TYPE: DNA
<213> ORGANISM: Homo sapiens
<220> FEATURE:
<223> OTHER INFORMATION: 1150G8 VH nucleotide sequence

<400> SEQUENCE: 471
gaagtgcagc tggtgcagtc tggggctgag gtgaagaagc ctgggtcctc ggcgaaggtc        60
tcctgcaagg cttctggagg caccttcagc acctatggta tctcatgggt gcgacaggcc       120
cctggacaag gacttgagtg gataggggg attattccta tctttgacac aggcaactct       180
gcacagagct tccagggcag agtcacgatt accgcgacg agtccacgag cacagcctac       240
atggaggtga gcagcctgag atctgacgac acggccgtat attattgtgc aagttcaagt       300

```
cgtatctacg acttgaaccc ctccctcact gcctactacg atatggatgt ctggggccag    360
gggacaatgg tcaccgtctc gagt                                           384
```

<210> SEQ ID NO 472
<211> LENGTH: 128
<212> TYPE: PRT
<213> ORGANISM: Homo sapiens
<220> FEATURE:
<223> OTHER INFORMATION: 1150G8 VH amino acid sequence

<400> SEQUENCE: 472

```
Glu Val Gln Leu Val Gln Ser Gly Ala Glu Val Lys Lys Pro Gly Ser
1               5                   10                  15

Ser Ala Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125
```

<210> SEQ ID NO 473
<211> LENGTH: 5
<212> TYPE: PRT
<213> ORGANISM: Homo sapiens
<220> FEATURE:
<223> OTHER INFORMATION: 1150G8 VH CDR1 amino acid sequence

<400> SEQUENCE: 473

```
Thr Tyr Gly Ile Ser
1               5
```

<210> SEQ ID NO 474
<211> LENGTH: 17
<212> TYPE: PRT
<213> ORGANISM: Homo sapiens
<220> FEATURE:
<223> OTHER INFORMATION: 1150G8 VH CDR2 amino acid sequence

<400> SEQUENCE: 474

```
Gly Ile Ile Pro Ile Phe Asp Thr Gly Asn Ser Ala Gln Ser Phe Gln
1               5                   10                  15

Gly
```

<210> SEQ ID NO 475
<211> LENGTH: 19
<212> TYPE: PRT
<213> ORGANISM: Homo sapiens
<220> FEATURE:
<223> OTHER INFORMATION: 1150G8 VH CDR3 amino acid sequence

<400> SEQUENCE: 475

```
Ser Ser Arg Ile Tyr Asp Leu Asn Pro Ser Leu Thr Ala Tyr Tyr Asp
1               5                   10                  15
```

Met Asp Val

<210> SEQ ID NO 476
<211> LENGTH: 327
<212> TYPE: DNA
<213> ORGANISM: Homo sapiens
<220> FEATURE:
<223> OTHER INFORMATION: 1150G8 VL nucleotide sequence

<400> SEQUENCE: 476

```
caggctgtgc tgactcagcc gtcctcagtg tctacgcccc caggacagaa ggtcaccatc     60
tcctgctctg gaggcagctc caacattggg aataattatg tatcgtggta ccagcagctc    120
ccaggaacag ccccaaaact cctcatttat gacaataata gcgaccctc agggattcct     180 gaccgattct ctggctccaa gtccggcacg tcagccaccc tgggcatcac cggactccag    240
actggggacg aggccgatta ttattgcgga acatgggata gcagcctgag tgcttgggtg    300
ttcggcggag ggaccaagct gaccgtc                                        327
```

<210> SEQ ID NO 477
<211> LENGTH: 109
<212> TYPE: PRT
<213> ORGANISM: Homo sapiens
<220> FEATURE:
<223> OTHER INFORMATION: 1150G8 VL amino acid sequence

<400> SEQUENCE: 477

```
Gln Ala Val Leu Thr Gln Pro Ser Ser Val Ser Thr Pro Pro Gly Gln
1               5                   10                  15

Lys Val Thr Ile Ser Cys Ser Gly Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105
```

<210> SEQ ID NO 478
<211> LENGTH: 13
<212> TYPE: PRT
<213> ORGANISM: Homo sapiens
<220> FEATURE:
<223> OTHER INFORMATION: 1150G8 VL CDR1 amino acid sequence

<400> SEQUENCE: 478

```
Ser Gly Gly Ser Ser Asn Ile Gly Asn Asn Tyr Val Ser
1               5                   10
```

<210> SEQ ID NO 479
<211> LENGTH: 7
<212> TYPE: PRT
<213> ORGANISM: Homo sapiens
<220> FEATURE:
<223> OTHER INFORMATION: 1150G8 VL CDR2 amino acid sequence

<400> SEQUENCE: 479

Asp Asn Asn Lys Arg Pro Ser
1               5

<210> SEQ ID NO 480
<211> LENGTH: 11
<212> TYPE: PRT
<213> ORGANISM: Homo sapiens
<220> FEATURE:
<223> OTHER INFORMATION: 1150G8 VL CDR3 amino acid sequence

<400> SEQUENCE: 480

Gly Thr Trp Asp Ser Ser Leu Ser Ala Trp Val
1               5                   10

<210> SEQ ID NO 481
<211> LENGTH: 384
<212> TYPE: DNA
<213> ORGANISM: Homo sapiens
<220> FEATURE:
<223> OTHER INFORMATION: 1152D5 VH nucleotide sequence

<400> SEQUENCE: 481
gaagtgcagc tggtgcagtc cggggctgag gtgaagaagc ctgggtcctc ggtgaaggtc      60
tcctgcaagg cctctggagg caccttcagc acctatggta tctcatgggt gcgacaggcc     120
cctggacaag aacttgagtg gataggaggg attattccta tctttgacac aggcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc gagt                                            384

<210> SEQ ID NO 482
<211> LENGTH: 128
<212> TYPE: PRT
<213> ORGANISM: Homo sapiens
<220> FEATURE:
<223> OTHER INFORMATION: 1152D5 VH amino acid sequence

<400> SEQUENCE: 482

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Glu Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 483
<211> LENGTH: 5
<212> TYPE: PRT
<213> ORGANISM: Homo sapiens

```
<220> FEATURE:
<223> OTHER INFORMATION: 1152D5 VH CDR1 amino acid sequence

<400> SEQUENCE: 483

Thr Tyr Gly Ile Ser
1               5

<210> SEQ ID NO 484
<211> LENGTH: 17
<212> TYPE: PRT
<213> ORGANISM: Homo sapiens
<220> FEATURE:
<223> OTHER INFORMATION: 1152D5 VH CDR2 amino acid sequence

<400> SEQUENCE: 484

Gly Ile Ile Pro Ile Phe Asp Thr Gly Asn Ser Ala Gln Ser Phe Gln
1               5                   10                  15

Gly

<210> SEQ ID NO 485
<211> LENGTH: 19
<212> TYPE: PRT
<213> ORGANISM: Homo sapiens
<220> FEATURE:
<223> OTHER INFORMATION: 1152D5 VH CDR3 amino acid sequence

<400> SEQUENCE: 485

Ser Ser Arg Ile Tyr Asp Leu Asn Pro Ser Leu Thr Ala Tyr Tyr Asp
1               5                   10                  15

Met Asp Val

<210> SEQ ID NO 486
<211> LENGTH: 327
<212> TYPE: DNA
<213> ORGANISM: Homo sapiens
<220> FEATURE:
<223> OTHER INFORMATION: 1152D5 VL nucleotide sequence

<400> SEQUENCE: 486
caggctgtgc tgactcagcc gtcctcagtg tctacgcccc caggacagaa ggtcaccatc      60
tcctgctctg gaagcagctc caacactggg aataattatg tatcgtggta ccagcagctc     120
ccaggagcag cccccaaact cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtc                                         327

<210> SEQ ID NO 487
<211> LENGTH: 109
<212> TYPE: PRT
<213> ORGANISM: Homo sapiens
<220> FEATURE:
<223> OTHER INFORMATION: 1152D5 VL amino acid sequence

<400> SEQUENCE: 487

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Thr Gly Asn Asn
            20                  25                  30

Tyr Val Ser Trp Tyr Gln Gln Leu Pro Gly Ala Ala Pro Lys Leu Leu
        35                  40                  45
```

```
Ile Tyr Asp Asn Asn Lys Arg Pro Ser Gly Ile Pro Asp Arg Phe Ser
        50                  55                  60
Gly Ser Lys Ser Gly Thr Ser Ala Thr Leu Gly Ile Thr Gly Leu Gln
 65                  70                  75                  80
Thr Gly Asp Glu Ala Asp Tyr Tyr Cys Gly Thr Trp Asp Ser Ser Leu
                 85                  90                  95
Ser Ala Trp Val Phe Gly Gly Gly Thr Lys Leu Thr Val
            100                 105
```

<210> SEQ ID NO 488
<211> LENGTH: 13
<212> TYPE: PRT
<213> ORGANISM: Homo sapiens
<220> FEATURE:
<223> OTHER INFORMATION: 1152D5 VL CDR1 amino acid sequence

<400> SEQUENCE: 488

```
Ser Gly Ser Ser Ser Asn Thr Gly Asn Asn Tyr Val Ser
 1               5                  10
```

<210> SEQ ID NO 489
<211> LENGTH: 7
<212> TYPE: PRT
<213> ORGANISM: Homo sapiens
<220> FEATURE:
<223> OTHER INFORMATION: 1152D5 VL CDR2 amino acid sequence

<400> SEQUENCE: 489

```
Asp Asn Asn Lys Arg Pro Ser
 1               5
```

<210> SEQ ID NO 490
<211> LENGTH: 11
<212> TYPE: PRT
<213> ORGANISM: Homo sapiens
<220> FEATURE:
<223> OTHER INFORMATION: 1152D5 VL CDR3 amino acid sequence

<400> SEQUENCE: 490

```
Gly Thr Trp Asp Ser Ser Leu Ser Ala Trp Val
 1               5                  10
```

<210> SEQ ID NO 491
<211> LENGTH: 384
<212> TYPE: DNA
<213> ORGANISM: Homo sapiens
<220> FEATURE:
<223> OTHER INFORMATION: 1152G10 VH nucleotide sequence

<400> SEQUENCE: 491

```
caagagcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gataggaggg attattccta tctttgacac agtcaactct     180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc gagt                                            384
```

<210> SEQ ID NO 492
<211> LENGTH: 128
<212> TYPE: PRT

<213> ORGANISM: Homo sapiens
<220> FEATURE:
<223> OTHER INFORMATION: 1152G10 VH amino acid sequence

<400> SEQUENCE: 492

```
Gln Glu Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Val Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125
```

<210> SEQ ID NO 493
<211> LENGTH: 5
<212> TYPE: PRT
<213> ORGANISM: Homo sapiens
<220> FEATURE:
<223> OTHER INFORMATION: 1152G10 VH CDR1 amino acid sequence

<400> SEQUENCE: 493

```
Thr Tyr Gly Ile Ser
1               5
```

<210> SEQ ID NO 494
<211> LENGTH: 17
<212> TYPE: PRT
<213> ORGANISM: Homo sapiens
<220> FEATURE:
<223> OTHER INFORMATION: 1152G10 VH CDR2 amino acid sequence

<400> SEQUENCE: 494

```
Gly Ile Ile Pro Ile Phe Asp Thr Val Asn Ser Ala Gln Ser Phe Gln
1               5                   10                  15

Gly
```

<210> SEQ ID NO 495
<211> LENGTH: 19
<212> TYPE: PRT
<213> ORGANISM: Homo sapiens
<220> FEATURE:
<223> OTHER INFORMATION: 1152G10 VH CDR3 amino acid sequence

<400> SEQUENCE: 495

```
Ser Ser Arg Ile Tyr Asp Leu Asn Pro Ser Leu Thr Ala Tyr Tyr Asp
1               5                   10                  15

Met Asp Val
```

<210> SEQ ID NO 496
<211> LENGTH: 327
<212> TYPE: DNA
<213> ORGANISM: Homo sapiens
<220> FEATURE:

<223> OTHER INFORMATION: 1152G10 VL nucleotide sequence

<400> SEQUENCE: 496

```
caggctgtgc tgactcagcc gtcctcagtg tctacgcccc caggacagaa ggtcaccatc    60
tcctgctctg gaagcagccc caacattggg aataattatg tatcgtggta ccagcagctc   120
ccaggaacag ccccagact cctcatttat gacaataata gcgaccctc agggtccct     180
gaccgattct ctggctccaa gtctggcacg tcagccaccc tgggcatcac cggactccag   240
actggggacg aggccgatta ttactgcgga acatgggata gcagcctgag tgcctgggtg   300
ttcggcggag ggaccaagct gaccgtc                                        327
```

<210> SEQ ID NO 497
<211> LENGTH: 109
<212> TYPE: PRT
<213> ORGANISM: Homo sapiens
<220> FEATURE:
<223> OTHER INFORMATION: 1152G10 VL amino acid sequence

<400> SEQUENCE: 497

```
Gln Ala Val Leu Thr Gln Pro Ser Ser Val Ser Thr Pro Pro Gly Gln
1               5                   10                  15
Lys Val Thr Ile Ser Cys Ser Gly Ser Ser Pro Asn Ile Gly Asn Asn
            20                  25                  30
Tyr Val Ser Trp Tyr Gln Gln Leu Pro Gly Thr Ala Pro Arg Leu Leu
        35                  40                  45
Ile Tyr Asp Asn Asn Lys Arg Pro Ser Gly Val Pro Asp Arg Phe Ser
    50                  55                  60
Gly Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Ser Ser Leu
                85                  90                  95
Ser Ala Trp Val Phe Gly Gly Gly Thr Lys Leu Thr Val
            100                 105
```

<210> SEQ ID NO 498
<211> LENGTH: 13
<212> TYPE: PRT
<213> ORGANISM: Homo sapiens
<220> FEATURE:
<223> OTHER INFORMATION: 1152G10 VL CDR1 amino acid sequence

<400> SEQUENCE: 498

```
Ser Gly Ser Ser Pro Asn Ile Gly Asn Asn Tyr Val Ser
1               5                   10
```

<210> SEQ ID NO 499
<211> LENGTH: 7
<212> TYPE: PRT
<213> ORGANISM: Homo sapiens
<220> FEATURE:
<223> OTHER INFORMATION: 1152G10 VL CDR2 amino acid sequence

<400> SEQUENCE: 499

```
Asp Asn Asn Lys Arg Pro Ser
1               5
```

<210> SEQ ID NO 500
<211> LENGTH: 11
<212> TYPE: PRT
<213> ORGANISM: Homo sapiens
<220> FEATURE:

<223> OTHER INFORMATION: 1152G10 VL CDR3 amino acid sequence

<400> SEQUENCE: 500

Gly Thr Trp Asp Ser Ser Leu Ser Ala Trp Val
1               5                   10

<210> SEQ ID NO 501
<211> LENGTH: 384
<212> TYPE: DNA
<213> ORGANISM: Homo sapiens
<220> FEATURE:
<223> OTHER INFORMATION: 1156G6 VH nucleotide sequence

<400> SEQUENCE: 501
gaagtgcagc tggtgcagtc tggggctgag gtgaagaagc ctgggtcctc ggtgaaggtc       60
tcctgcaagg cttctggagg caccttcagc acctatggta tctcatgggt gcgacaggcc     120
cctggacaag gacttgagtg gataggggg attattccta tctttgacac aggcagctct      180
gcacagagct tccagggcag agtcacgatt accgcggacg aatccacgag cacagcctac     240
atggaggtga gcagcctgag atctgacgac acggccgtat attattgtgc aagttcaagt     300
cgtatctacg acttgaaccc ctccctcact gcctactacg atatggatgt ctggggccag     360
gggacaatgg tcaccgtctc gagt                                            384

<210> SEQ ID NO 502
<211> LENGTH: 128
<212> TYPE: PRT
<213> ORGANISM: Homo sapiens
<220> FEATURE:
<223> OTHER INFORMATION: 1156G6 VH amino acid sequence

<400> SEQUENCE: 502

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Gly Ile Ser Trp Val Arg Gln Ala Pro Gly Gln Gly Leu Glu Trp Ile
            35                  40                  45

Gly Gly Ile Ile Pro Ile Phe Asp Thr Gly Ser Ser Ala Gln Ser Phe
        50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
                100                 105                 110

Tyr Asp Met Asp Val Trp Gly Gln Gly Thr Met Val Thr Val Ser Ser
            115                 120                 125

<210> SEQ ID NO 503
<211> LENGTH: 5
<212> TYPE: PRT
<213> ORGANISM: Homo sapiens
<220> FEATURE:
<223> OTHER INFORMATION: 1156G6 VH CDR1 amino acid sequence

<400> SEQUENCE: 503

Thr Tyr Gly Ile Ser
1               5

<210> SEQ ID NO 504
<211> LENGTH: 17
<212> TYPE: PRT
<213> ORGANISM: Homo sapiens
<220> FEATURE:
<223> OTHER INFORMATION: 1156G6 VH CDR2 amino acid sequence

<400> SEQUENCE: 504

Gly Ile Ile Pro Ile Phe Asp Thr Gly Ser Ser Ala Gln Ser Phe Gln
1               5                   10                  15

Gly

<210> SEQ ID NO 505
<211> LENGTH: 19
<212> TYPE: PRT
<213> ORGANISM: Homo sapiens
<220> FEATURE:
<223> OTHER INFORMATION: 1156G6 VH CDR3 amino acid sequence

<400> SEQUENCE: 505

Ser Ser Arg Ile Tyr Asp Leu Asn Pro Ser Leu Thr Ala Tyr Tyr Asp
1               5                   10                  15

Met Asp Val

<210> SEQ ID NO 506
<211> LENGTH: 327
<212> TYPE: DNA
<213> ORGANISM: Homo sapiens
<220> FEATURE:
<223> OTHER INFORMATION: 1156G6 VL nucleotide sequence

<400> SEQUENCE: 506
caggctgtgc tgactcagcc gtcctcagtg tctacgcccc caggacagaa ggtcaccatc      60
tcctgctctg gaagcaactc caacattggg aataattatg tatcgtggta ccagcagctc     120
ccaggaacag ccccaaaact cctcatttat gacaataata gcgaccctc agggattcct      180 gaccgattct ctggctccaa gtctggcacg tcagccaccc tgggcatcac cggactccag     240
actggggacg aggccgatta ttactgcgga acgtgggata gcagcctgag tgcttgggtg     300
ttcggcggag ggaccaagct gaccgtc                                         327

<210> SEQ ID NO 507
<211> LENGTH: 109
<212> TYPE: PRT
<213> ORGANISM: Homo sapiens
<220> FEATURE:
<223> OTHER INFORMATION: 1156G6 VL amino acid sequence

<400> SEQUENCE: 507

Gln Ala Val Leu Thr Gln Pro Ser Ser Val Ser Thr Pro Pro Gly Gln
1               5                   10                  15

Lys Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 508
<211> LENGTH: 13
<212> TYPE: PRT
<213> ORGANISM: Homo sapiens
<220> FEATURE:
<223> OTHER INFORMATION: 1156G6 VL CDR1 amino acid sequence

<400> SEQUENCE: 508

Ser Gly Ser Asn Ser Asn Ile Gly Asn Asn Tyr Val Ser
1               5                   10

<210> SEQ ID NO 509
<211> LENGTH: 7
<212> TYPE: PRT
<213> ORGANISM: Homo sapiens
<220> FEATURE:
<223> OTHER INFORMATION: 1156G6 VL CDR2 amino acid sequence

<400> SEQUENCE: 509

Asp Asn Asn Lys Arg Pro Ser
1               5

<210> SEQ ID NO 510
<211> LENGTH: 11
<212> TYPE: PRT
<213> ORGANISM: Homo sapiens
<220> FEATURE:
<223> OTHER INFORMATION: 1156G6 VL CDR3 amino acid sequence

<400> SEQUENCE: 510

Gly Thr Trp Asp Ser Ser Leu Ser Ala Trp Val
1               5                   10

<210> SEQ ID NO 511
<211> LENGTH: 384
<212> TYPE: DNA
<213> ORGANISM: Homo sapiens
<220> FEATURE:
<223> OTHER INFORMATION: 1215A06 VH nucleotide sequence
<220> FEATURE:
<221> NAME/KEY: modified_base
<222> LOCATION: (1)..(28)
<223> OTHER INFORMATION: a, c, t or g
<220> FEATURE:
<221> NAME/KEY: modified_base
<222> LOCATION: (333)..(333)
<223> OTHER INFORMATION: a, c, t or g

<400> SEQUENCE: 511
nnnnnnnnnn nnnnnnnnnn nnnnnnnnag gtgaagaagc ctgggtcctc ggtgaaggtc     60
tcctgcaagg cttctggagg caccttcagc acctatggta tctcatgggt gcgacaggcc    120
cctggacaag gacttgagtg gataggaggg attattccta tctttaacac aggcaactct    180
gcacagagct tccaaggcag agtcacgatt accgcggatg aatccacgag cacagcctac    240
atggaggtga gcagcctgag atctgacgac acggccgtat attattgtgc aagttcaagt    300
cgtatctacg acttgaaccc ctccctcact gcntactacg atatggatgt ctggggccag    360
gggacaatgg tcaccgtctc gagt                                           384

<210> SEQ ID NO 512
<211> LENGTH: 128
<212> TYPE: PRT
<213> ORGANISM: Homo sapiens

```
<220> FEATURE:
<223> OTHER INFORMATION: 1215A06 VH amino acid sequence
<220> FEATURE:
<221> NAME/KEY: MOD_RES
<222> LOCATION: (1)..(10)
<223> OTHER INFORMATION: Any amino acid

<400> SEQUENCE: 512

Xaa Xaa Xaa Xaa Xaa Xaa Xaa Xaa Xaa Xaa Val Lys Lys Pro Gly Ser
 1               5                  10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asn Thr Gly Asn Ser Ala Gln Ser Phe
    50                  55                  60

Gln Gly Arg Val Thr Ile Thr Ala Asp Glu Ser Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 513
<211> LENGTH: 5
<212> TYPE: PRT
<213> ORGANISM: Homo sapiens
<220> FEATURE:
<223> OTHER INFORMATION: 1215A06 VH CDR1 amino acid sequence

<400> SEQUENCE: 513

Thr Tyr Gly Ile Ser
 1               5

<210> SEQ ID NO 514
<211> LENGTH: 17
<212> TYPE: PRT
<213> ORGANISM: Homo sapiens
<220> FEATURE:
<223> OTHER INFORMATION: 1215A06 VH CDR2 amino acid sequence

<400> SEQUENCE: 514

Gly Ile Ile Pro Ile Phe Asn Thr Gly Asn Ser Ala Gln Ser Phe Gln
 1               5                  10                  15

Gly

<210> SEQ ID NO 515
<211> LENGTH: 19
<212> TYPE: PRT
<213> ORGANISM: Homo sapiens
<220> FEATURE:
<223> OTHER INFORMATION: 1215A06 VH CDR3 amino acid sequence

<400> SEQUENCE: 515

Ser Ser Arg Ile Tyr Asp Leu Asn Pro Ser Leu Thr Ala Tyr Tyr Asp
 1               5                  10                  15

Met Asp Val

<210> SEQ ID NO 516
<211> LENGTH: 327
```

```
<212> TYPE: DNA
<213> ORGANISM: Homo sapiens
<220> FEATURE:
<223> OTHER INFORMATION: 1215A06 VL nucleotide sequence

<400> SEQUENCE: 516
caggctgtgc tgacccagcc gtcctcagtg tctacgcccc caggacagaa ggtcaccatc      60
tcctgctctg gaagcagctc caacattggg aataattatg tatcgtggta ccagcggctc     120
ccaggaacag cccccaaact cctcatttat gacaataata gcgaccctc agggattcct      180 gaccgattct ctggctccaa gtctggcacg tcagccaccc tgggcatcac cggactccag     240 actgggacg aggccgatta ttactgcgga acatgggata gcagcctgag tgcttgggtg       300
ttcggcggag ggaccaagct gaccgtc                                         327

<210> SEQ ID NO 517
<211> LENGTH: 109
<212> TYPE: PRT
<213> ORGANISM: Homo sapiens
<220> FEATURE:
<223> OTHER INFORMATION: 1215A06 VL amino acid sequence

<400> SEQUENCE: 517

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Arg Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 518
<211> LENGTH: 13
<212> TYPE: PRT
<213> ORGANISM: Homo sapiens
<220> FEATURE:
<223> OTHER INFORMATION: 1215A06 VL CDR1 amino acid sequence

<400> SEQUENCE: 518

Ser Gly Ser Ser Ser Asn Ile Gly Asn Asn Tyr Val Ser
1               5                   10

<210> SEQ ID NO 519
<211> LENGTH: 7
<212> TYPE: PRT
<213> ORGANISM: Homo sapiens
<220> FEATURE:
<223> OTHER INFORMATION: 1215A06 VL CDR2 amino acid sequence

<400> SEQUENCE: 519

Asp Asn Asn Lys Arg Pro Ser
1               5

<210> SEQ ID NO 520
<211> LENGTH: 11
```

```
<212> TYPE: PRT
<213> ORGANISM: Homo sapiens
<220> FEATURE:
<223> OTHER INFORMATION: 1215A06 VL CDR3 amino acid sequence

<400> SEQUENCE: 520

Gly Thr Trp Asp Ser Ser Leu Ser Ala Trp Val
1               5                   10

<210> SEQ ID NO 521
<211> LENGTH: 384
<212> TYPE: DNA
<213> ORGANISM: Homo sapiens
<220> FEATURE:
<223> OTHER INFORMATION: 1219D9 VH nucleotide sequence

<400> SEQUENCE: 521
gaagtgcagc tggtgcagtc tggggctgag gtgaagaagc ctgggtcctc ggtgaaggtc      60
tcctgcaagg cttctggagg caccttcagc acctatggta tctcatgggt gcgacaggcc     120
cctggacaag gacttgagtg gatagaaggg attattccta tctttgacac aggcaactct     180
gcacagagct tccagggcag agtcacgatt accgcggacg aatccacgag cacagcctac     240
atggaggtga gcagcctgag atctgacgac acggccgtat actattgtgc aagttcaagt     300
cgtatctacg acttgaaccc ctccctcact gcctactacg atatggatgt ctggggccag     360
gggacaatgg tcaccgtctc gggt                                            384

<210> SEQ ID NO 522
<211> LENGTH: 128
<212> TYPE: PRT
<213> ORGANISM: Homo sapiens
<220> FEATURE:
<223> OTHER INFORMATION: 1219D9 VH amino acid sequence

<400> SEQUENCE: 522

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Gly
        115                 120                 125

<210> SEQ ID NO 523
<211> LENGTH: 5
<212> TYPE: PRT
<213> ORGANISM: Homo sapiens
<220> FEATURE:
<223> OTHER INFORMATION: 1219D9 VH CDR1 amino acid sequence

<400> SEQUENCE: 523

Thr Tyr Gly Ile Ser
```

<210> SEQ ID NO 524
<211> LENGTH: 17
<212> TYPE: PRT
<213> ORGANISM: Homo sapiens
<220> FEATURE:
<223> OTHER INFORMATION: 1219D9 VH CDR2 amino acid sequence

<400> SEQUENCE: 524

Gly Ile Ile Pro Ile Phe Asp Thr Gly Asn Ser Ala Gln Ser Phe Gln
1               5                   10                  15

Gly

<210> SEQ ID NO 525
<211> LENGTH: 19
<212> TYPE: PRT
<213> ORGANISM: Homo sapiens
<220> FEATURE:
<223> OTHER INFORMATION: 1219D9 VH CDR3 amino acid sequence

<400> SEQUENCE: 525

Ser Ser Arg Ile Tyr Asp Leu Asn Pro Ser Leu Thr Ala Tyr Tyr Asp
1               5                   10                  15

Met Asp Val

<210> SEQ ID NO 526
<211> LENGTH: 327
<212> TYPE: DNA
<213> ORGANISM: Homo sapiens
<220> FEATURE:
<223> OTHER INFORMATION: 1219D9 VL nucleotide sequence

<400> SEQUENCE: 526
caggctgtgc tgactcagcc gtcctcagta tctacgcccc caggacagaa ggtcaccatc      60
tcctgctctg gaagcaggtc aacattggg aataattatg tatcgtggta ccagcagctc     120
ccaggaacag ccccccaaact cctcatttat gacaataata gcgaccctc agggattcct     180 gaccgattct ctggctccaa gtctggcacg tcagccaccc tgggcatcac cggactccag     240
actggggacg aggccgatta ttactgcgga acatgggata gcagcctgag tgcttgggtg     300
ttcggcggag ggaccaagct gaccgtc                                         327

<210> SEQ ID NO 527
<211> LENGTH: 109
<212> TYPE: PRT
<213> ORGANISM: Homo sapiens
<220> FEATURE:
<223> OTHER INFORMATION: 1219D9 VL amino acid sequence

<400> SEQUENCE: 527

Gln Ala Val Leu Thr Gln Pro Ser Ser Val Ser Thr Pro Pro Gly Gln
1               5                   10                  15

Lys Val Thr Ile Ser Cys Ser Gly Ser Arg Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

```
            Thr Gly Asp Glu Ala Asp Tyr Tyr Cys Gly Thr Trp Asp Ser Ser Leu
                        85                  90                  95
            Ser Ala Trp Val Phe Gly Gly Thr Lys Leu Thr Val
                    100                 105
```

<210> SEQ ID NO 528
<211> LENGTH: 13
<212> TYPE: PRT
<213> ORGANISM: Homo sapiens
<220> FEATURE:
<223> OTHER INFORMATION: 1219D9 VL CDR1 amino acid sequence

<400> SEQUENCE: 528

```
Ser Gly Ser Arg Ser Asn Ile Gly Asn Asn Tyr Val Ser
1               5                   10
```

<210> SEQ ID NO 529
<211> LENGTH: 7
<212> TYPE: PRT
<213> ORGANISM: Homo sapiens
<220> FEATURE:
<223> OTHER INFORMATION: 1219D9 VL CDR2 amino acid sequence

<400> SEQUENCE: 529

```
Asp Asn Asn Lys Arg Pro Ser
1               5
```

<210> SEQ ID NO 530
<211> LENGTH: 11
<212> TYPE: PRT
<213> ORGANISM: Homo sapiens
<220> FEATURE:
<223> OTHER INFORMATION: 1219D9 VL CDR3 amino acid sequence

<400> SEQUENCE: 530

```
Gly Thr Trp Asp Ser Ser Leu Ser Ala Trp Val
1               5                   10
```

<210> SEQ ID NO 531
<211> LENGTH: 7
<212> TYPE: PRT
<213> ORGANISM: Homo sapiens

<400> SEQUENCE: 531

```
Leu Asn Pro Ser Leu Thr Ala
1               5
```

<210> SEQ ID NO 532
<211> LENGTH: 7
<212> TYPE: PRT
<213> ORGANISM: Homo sapiens

<400> SEQUENCE: 532

```
Phe Asn Ser Ala Leu Ile Ser
1               5
```

<210> SEQ ID NO 533
<211> LENGTH: 7
<212> TYPE: PRT
<213> ORGANISM: Homo sapiens

<400> SEQUENCE: 533

```
Met Ile Ser Ser Leu Gln Pro
1               5
```

```
<210> SEQ ID NO 534
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer FDTETSEQ24

<400> SEQUENCE: 534
tttgtcgtct ttccagacgt tagt                                              24

<210> SEQ ID NO 535
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer PUCreverse

<400> SEQUENCE: 535
agcggataac aatttcacac agg                                               23

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer Lseq

<400> SEQUENCE: 536
gattacgcca agctttggag c                                                 21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer MYC Seq 10

<400> SEQUENCE: 537
ctcttctgag atgagttttt g                                                 21
```